US012447028B2

(12) United States Patent
Abdou et al.

(10) Patent No.: US 12,447,028 B2
(45) **Date of Patent: *Oct. 21, 2025**

(54) DEVICES AND METHODS FOR SPINAL IMPLANTATION

(71) Applicant: Samy Abdou, San Diego, CA (US)

(72) Inventors: Samy Abdou, San Diego, CA (US); Brian Bowman, Carlsbad, CA (US); Colin Murphy, San Diego, CA (US)

(73) Assignee: Samy Abdou, San Diego, CA (US)

( * ) Notice: Subject to any disclaimer, the term of this patent is extended or adjusted under 35 U.S.C. 154(b) by 740 days.

This patent is subject to a terminal disclaimer.

(21) Appl. No.: 17/352,051

(22) Filed: Jun. 18, 2021

(65) Prior Publication Data

US 2022/0110765 A1 Apr. 14, 2022

Related U.S. Application Data

(63) Continuation of application No. 16/590,300, filed on Oct. 1, 2019, now Pat. No. 11,179,248.
(Continued)

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4425* (2013.01); *A61F 2002/30153* (2013.01);
(Continued)

(58) Field of Classification Search
CPC .... A61F 2/4611; A61F 2/4423; A61F 2/4603; A61F 2002/4615
See application file for complete search history.

(56) References Cited

U.S. PATENT DOCUMENTS 167,625 A 9/1875 Charles
203,512 A 5/1878 Nicholas
(Continued)

FOREIGN PATENT DOCUMENTS

AU 2006214001 B2 5/2011
AU 2011213872 A1 9/2011
(Continued)

OTHER PUBLICATIONS

Abstract for French Patent Publication FR2781359, Published Jan. 28, 2000, entitled: "Osteosynthesis Frame for Spinal Surgery has Rod with Clamps to Hold Cross Bars with Anchor Screws". Accession No. 9867555 (Derwent Information Ltd.).
(Continued)

*Primary Examiner* — Brian A Dukert
(74) *Attorney, Agent, or Firm* — Patent Beach PC

(57) ABSTRACT

Methods and apparatus for providing correction of one or more maladies or conditions of the spinal column of a living being. In one embodiment, the apparatus includes an implant delivery instrument and an implant for use therewith. In one variant, the implant delivery instrument includes a non-detachable distraction member for distraction of the disc space and a track for slidable delivery of an implant to the distracted disc space. In another variant, the implant delivery instrument includes a detachable distraction member for distraction of the disc space and a track for slidable delivery of an implant to the distracted disc space. In the latter variant, the distraction member is co-implanted in the disc space with the implant.

7 Claims, 43 Drawing Sheets

Related U.S. Application Data

(60) Provisional application No. 62/766,123, filed on Oct. 2, 2018, provisional application No. 62/766,127, filed on Oct. 2, 2018.

(52) U.S. Cl.
CPC ... *A61F 2002/30263* (2013.01); *A61F 2/4603* (2013.01); *A61F 2002/4615* (2013.01)

(56) References Cited

U.S. PATENT DOCUMENTS 203,624 A 5/1878 Josias
229,347 A 6/1880 Shepherd
267,269 A 11/1882 John
824,983 A 7/1906 Charles
944,725 A 12/1909 Ferguson, Jr.
1,015,890 A 1/1912 Hyde
1,156,440 A 10/1915 Smith
1,213,599 A 1/1917 Dow
1,785,709 A 12/1930 Harry et al.
2,248,054 A 7/1941 Becker
2,329,398 A 9/1943 Duffy
2,370,407 A 2/1945 McCartney
2,574,352 A 11/1951 Senter
2,677,369 A 5/1954 Knowles
2,774,350 A 12/1956 Cleveland, Jr. et al.
3,025,853 A 3/1962 Mason
3,037,596 A 6/1962 Fordyce
3,072,423 A 1/1963 Charlton
3,073,584 A 1/1963 Henry et al.
3,090,386 A 5/1963 William et al.
3,236,141 A 2/1966 Smith
3,242,922 A 3/1966 Thomas
3,260,412 A 7/1966 Larkin
3,277,555 A 10/1966 Kutash
3,374,786 A 3/1968 Callender, Jr. et al.
3,383,769 A 5/1968 Davis
3,384,077 A 5/1968 Gauthier
3,426,364 A 2/1969 Lumb, V et al.
3,604,487 A 9/1971 Gilbert
3,648,691 A 3/1972 Lumb et al.
3,659,595 A 5/1972 Haboush
3,695,259 A 10/1972 Yost et al.
3,708,883 A 1/1973 Flander et al.
3,741,205 A 6/1973 Markolf et al.
3,749,088 A 7/1973 Kohlmann et al.
3,791,380 A 2/1974 Dawidowski et al.
3,795,981 A 3/1974 Franklin et al.
3,805,219 A 4/1974 Bright et al.
3,825,992 A 7/1974 Troeger et al.
3,858,578 A 1/1975 Milo
3,865,105 A 2/1975 Lode
3,867,728 A 2/1975 Stubstad et al.
3,892,232 A 7/1975 Neufeld
3,965,890 A 6/1976 Gauthier
4,009,712 A 3/1977 Burstein et al.
4,037,592 A 7/1977 Kronner
4,047,524 A 9/1977 Hall
4,074,542 A 2/1978 Hankosky et al.
4,135,506 A 1/1979 Ulrich
4,143,883 A 3/1979 Paynter
4,165,746 A 8/1979 Burgin
4,175,555 A 11/1979 Herbert
4,237,875 A 12/1980 Termanini
4,254,763 A 3/1981 Mccready et al.
4,289,123 A 9/1981 Dunn
4,309,777 A 1/1982 Patil
4,349,921 A 9/1982 Kuntz et al.
4,399,813 A 8/1983 Barber
4,409,974 A 10/1983 Freedland
4,432,358 A 2/1984 Fixel
4,448,181 A 5/1984 Ishikawa et al.
4,448,191 A 5/1984 Rodnyansky et al.
4,488,543 A 12/1984 Tornier
4,493,317 A 1/1985 Klaue
4,494,535 A 1/1985 Haig
4,503,848 A 3/1985 Caspar et al.
4,545,374 A 10/1985 Jacobson et al.
4,554,914 A 11/1985 Kapp et al.
4,561,432 A 12/1985 Mazor
4,569,662 A 2/1986 Dragan
4,570,618 A 2/1986 Wu
4,580,563 A 4/1986 Gross
4,604,995 A 8/1986 Stephens et al.
4,611,581 A 9/1986 Steffee
4,611,582 A 9/1986 Duff
4,612,920 A 9/1986 Lower
4,632,101 A 12/1986 Freedland
4,636,217 A 1/1987 Ogilvie et al.
4,653,481 A 3/1987 Howland et al.
4,655,462 A 4/1987 Balsells
4,655,629 A 4/1987 Flaherty
4,655,778 A 4/1987 Koeneman
4,664,305 A 5/1987 Blake, III et al.
4,697,582 A 10/1987 William
4,699,076 A 10/1987 Curtis et al.
4,702,230 A 10/1987 Pelta
4,711,232 A 12/1987 Fischer et al.
4,714,469 A 12/1987 Kenna
4,722,331 A 2/1988 Fox
4,747,394 A 5/1988 Watanabe
4,747,395 A 5/1988 Brief
4,756,711 A 7/1988 Mai et al.
4,759,766 A 7/1988 Buettner-Janz et al.
4,759,769 A 7/1988 Hedman et al.
4,773,402 A 9/1988 Asher et al.
4,787,908 A 11/1988 Wyss et al.
4,790,303 A 12/1988 Steffee
4,791,918 A 12/1988 Von
4,794,918 A 1/1989 Wolter
4,820,305 A 4/1989 Harms et al.
4,834,757 A 5/1989 Brantigan
4,867,404 A 9/1989 Harrington et al.
4,874,389 A 10/1989 Downey
4,877,020 A 10/1989 Vich
4,881,525 A 11/1989 Williams
4,887,595 A 12/1989 Heinig et al.
4,898,156 A 2/1990 Gatturna et al.
4,899,761 A 2/1990 Brown et al.
4,903,692 A 2/1990 Reese
4,904,110 A 2/1990 Klein
4,907,577 A 3/1990 Wu
4,911,718 A 3/1990 Lee et al.
4,913,134 A 4/1990 Luque
4,932,975 A 6/1990 Main et al.
4,934,352 A 6/1990 Sullivan, Jr.
4,938,769 A 7/1990 Shaw
4,944,757 A 7/1990 Martinez et al.
4,946,378 A 8/1990 Hirayama et al.
4,946,468 A 8/1990 Li
4,949,707 A 8/1990 LeVahn et al.
4,955,908 A 9/1990 Frey et al.
4,957,495 A 9/1990 Kluger
4,957,497 A 9/1990 Hoogland et al.
4,961,740 A 10/1990 Ray et al.
4,963,152 A 10/1990 Hofmann et al.
4,964,403 A 10/1990 Karas et al.
4,969,886 A 11/1990 Cziffer et al.
4,969,887 A 11/1990 Sodhi
4,973,332 A 11/1990 Kummer
4,997,123 A 3/1991 Backus et al.
4,997,432 A 3/1991 Keller
5,002,550 A 3/1991 Li
5,002,576 A 3/1991 Fuhrmann et al.
5,007,880 A 4/1991 Walker
5,007,910 A 4/1991 Anapliotis et al.
5,011,484 A 4/1991 Breard
5,015,247 A 5/1991 Michelson
5,026,373 A 6/1991 Ray et al.
5,052,711 A 10/1991 Pirkey et al.
5,055,104 A 10/1991 Ray
5,061,271 A 10/1991 Van
5,071,437 A 12/1991 Steffee

(56) References Cited

U.S. PATENT DOCUMENTS

| | | | |
|---|---|---|---|
| 5,084,049 | A | 1/1992 | Asher et al. |
| 5,087,266 | A | 2/1992 | Connell et al. |
| 5,092,866 | A | 3/1992 | Breard et al. |
| 5,092,893 | A | 3/1992 | Smith |
| 5,098,435 | A | 3/1992 | Stednitz et al. |
| 5,116,336 | A | 5/1992 | Frigg |
| 5,122,130 | A | 6/1992 | Keller |
| 5,122,131 | A | 6/1992 | Tsou |
| 5,127,914 | A | 7/1992 | Calderale et al. |
| 5,129,899 | A | 7/1992 | Small et al. |
| 5,131,904 | A | 7/1992 | Markoll |
| 5,133,717 | A | 7/1992 | Chopin |
| 5,147,360 | A | 9/1992 | Dubousset |
| 5,147,361 | A | 9/1992 | Ojima et al. |
| 5,152,303 | A | 10/1992 | Allen |
| 5,167,662 | A | 12/1992 | Hayes et al. |
| 5,176,680 | A | 1/1993 | Vignaud et al. |
| 5,180,381 | A | 1/1993 | Aust et al. |
| 5,180,393 | A | 1/1993 | Commarmond |
| 5,192,327 | A | 3/1993 | Brantigan |
| 5,207,679 | A | 5/1993 | Li |
| 5,222,954 | A | 6/1993 | Baker et al. |
| 5,226,766 | A | 7/1993 | Lasner |
| 5,234,431 | A | 8/1993 | Keller |
| 5,234,432 | A | 8/1993 | Brown |
| 5,234,447 | A | 8/1993 | Kaster et al. |
| 5,236,460 | A | 8/1993 | Barber |
| 5,242,444 | A | 9/1993 | Macmillan |
| 5,242,445 | A | 9/1993 | Ashman |
| 5,246,442 | A | 9/1993 | Ashman et al. |
| 5,246,458 | A | 9/1993 | Graham |
| 5,250,055 | A | 10/1993 | Moore et al. |
| 5,252,016 | A | 10/1993 | Schmid et al. |
| 5,254,118 | A | 10/1993 | Mirkovic |
| 5,258,031 | A | 11/1993 | Salib et al. |
| 5,261,907 | A | 11/1993 | Vignaud et al. |
| 5,261,909 | A | 11/1993 | Sutterlin et al. |
| 5,261,910 | A | 11/1993 | Warden et al. |
| 5,261,911 | A | 11/1993 | Carl |
| 5,261,914 | A | 11/1993 | Warren |
| 5,275,600 | A | 1/1994 | Allard et al. |
| 5,275,601 | A | 1/1994 | Gogolewski et al. |
| 5,281,222 | A | 1/1994 | Allard et al. |
| 5,282,801 | A | 2/1994 | Sherman |
| 5,282,862 | A | 2/1994 | Baker et al. |
| 5,290,312 | A | 3/1994 | Kojimoto et al. |
| 5,300,074 | A | 4/1994 | Frigg |
| 5,304,178 | A | 4/1994 | Stahurski |
| 5,306,307 | A | 4/1994 | Senter et al. |
| 5,312,405 | A | 5/1994 | Korotko et al. |
| 5,324,290 | A | 6/1994 | Zdeblick et al. |
| 5,324,292 | A | 6/1994 | Meyers |
| 5,330,468 | A | 7/1994 | Burkhart |
| 5,330,473 | A | 7/1994 | Howland |
| 5,334,205 | A | 8/1994 | Cain |
| 5,335,418 | A | 8/1994 | Krivec |
| 5,336,225 | A | 8/1994 | Zang |
| 5,336,226 | A | 8/1994 | Mcdaniel et al. |
| 5,342,394 | A | 8/1994 | Matsuno et al. |
| 5,344,421 | A | 9/1994 | Crook |
| 5,344,422 | A | 9/1994 | Frigg |
| 5,346,493 | A | 9/1994 | Stahurski et al. |
| 5,350,380 | A | 9/1994 | Goble et al. |
| 5,352,226 | A | 10/1994 | Lin |
| 5,352,231 | A | 10/1994 | Brumfield et al. |
| 5,354,292 | A | 10/1994 | Braeuer et al. |
| 5,356,410 | A | 10/1994 | Pennig |
| 5,358,289 | A | 10/1994 | Banker et al. |
| 5,360,429 | A | 11/1994 | Jeanson et al. |
| 5,360,431 | A | 11/1994 | Puno et al. |
| 5,361,766 | A | 11/1994 | Nichols et al. |
| 5,364,399 | A | 11/1994 | Lowery et al. |
| 5,366,455 | A | 11/1994 | Dove et al. |
| 5,370,697 | A | 12/1994 | Baumgartner |
| 5,372,599 | A | 12/1994 | Martins |
| 5,374,267 | A | 12/1994 | Siegal |
| 5,375,823 | A | 12/1994 | Navas |
| 5,380,324 | A | 1/1995 | Mueller et al. |
| 5,385,583 | A | 1/1995 | Cotrel |
| 5,387,176 | A | 2/1995 | Markoll |
| 5,387,213 | A | 2/1995 | Breard et al. |
| 5,395,371 | A | 3/1995 | Miller et al. |
| 5,397,363 | A | 3/1995 | Gelbard |
| 5,397,364 | A | 3/1995 | Kozak et al. |
| 5,403,316 | A | 4/1995 | Ashman |
| 5,413,576 | A | 5/1995 | Rivard |
| 5,415,661 | A | 5/1995 | Holmes |
| 5,417,712 | A | 5/1995 | Whittaker et al. |
| 5,423,816 | A | 6/1995 | Lin |
| 5,423,818 | A | 6/1995 | Van et al. |
| 5,423,819 | A | 6/1995 | Small et al. |
| 5,423,826 | A | 6/1995 | Coates et al. |
| 5,425,772 | A | 6/1995 | Brantigan |
| 5,425,773 | A | 6/1995 | Boyd et al. |
| 5,427,418 | A | 6/1995 | Watts |
| 5,429,639 | A | 7/1995 | Judet |
| 5,431,658 | A | 7/1995 | Moskovich |
| 5,437,669 | A | 8/1995 | Yuan et al. |
| 5,437,670 | A | 8/1995 | Sherman et al. |
| 5,437,672 | A | 8/1995 | Alleyne |
| 5,437,674 | A | 8/1995 | Worcel et al. |
| 5,439,339 | A | 8/1995 | Batchelor |
| 5,439,463 | A | 8/1995 | Lin |
| 5,443,467 | A | 8/1995 | Biedermann et al. |
| 5,443,514 | A | 8/1995 | Steffee |
| 5,449,257 | A | 9/1995 | Giannuzzi |
| 5,453,073 | A | 9/1995 | Markoll |
| 5,456,714 | A | 10/1995 | Owen |
| 5,458,638 | A | 10/1995 | Kuslich et al. |
| 5,466,237 | A | 11/1995 | Byrd, III et al. |
| 5,468,241 | A | 11/1995 | Metz-Stavenhagen et al. |
| 5,472,452 | A | 12/1995 | Trott |
| 5,474,551 | A | 12/1995 | Finn et al. |
| 5,474,555 | A | 12/1995 | Puno et al. |
| 5,476,462 | A | 12/1995 | Allard et al. |
| 5,476,464 | A | 12/1995 | Metz-Stavenhagen et al. |
| 5,478,342 | A | 12/1995 | Kohrs |
| 5,480,401 | A | 1/1996 | Navas |
| 5,484,437 | A | 1/1996 | Michelson |
| 5,484,440 | A | 1/1996 | Allard |
| 5,486,174 | A | 1/1996 | Fournet-Fayard et al. |
| 5,486,176 | A | 1/1996 | Hildebrand et al. |
| 5,487,742 | A | 1/1996 | Cotrel |
| 5,489,307 | A | 2/1996 | Kuslich et al. |
| 5,489,308 | A | 2/1996 | Kuslich et al. |
| 5,490,750 | A | 2/1996 | Gundy |
| 5,496,318 | A | 3/1996 | Howland et al. |
| 5,496,321 | A | 3/1996 | Puno et al. |
| 5,499,892 | A | 3/1996 | Reed |
| 5,505,731 | A | 4/1996 | Tornier |
| 5,507,745 | A | 4/1996 | Logroscino et al. |
| 5,507,754 | A | 4/1996 | Green et al. |
| 5,507,816 | A | 4/1996 | Bullivant |
| 5,512,038 | A | 4/1996 | O'Neal et al. |
| 5,514,180 | A | 5/1996 | Heggeness et al. |
| 5,520,690 | A | 5/1996 | Errico et al. |
| 5,522,899 | A | 6/1996 | Michelson |
| 5,527,314 | A | 6/1996 | Brumfield et al. |
| 5,531,747 | A | 7/1996 | Ray |
| 5,531,751 | A | 7/1996 | Schultheiss et al. |
| 5,534,001 | A | 7/1996 | Schlapfer et al. |
| 5,534,002 | A | 7/1996 | Brumfield et al. |
| 5,534,027 | A | 7/1996 | Hodorek |
| 5,540,688 | A | 7/1996 | Navas |
| 5,545,163 | A | 8/1996 | Miller et al. |
| 5,545,164 | A | 8/1996 | Howland |
| 5,545,165 | A | 8/1996 | Harms et al. |
| 5,545,179 | A | 8/1996 | Williamson, IV |
| 5,549,607 | A | 8/1996 | Olson et al. |
| 5,549,612 | A | 8/1996 | Yapp et al. |
| 5,554,157 | A | 9/1996 | Errico et al. |
| 5,556,431 | A | 9/1996 | Buettner-Janz |
| 5,558,674 | A | 9/1996 | Heggeness et al. |
| 5,562,660 | A | 10/1996 | Grob |

(56) References Cited

U.S. PATENT DOCUMENTS 5,562,661 A 10/1996 Yoshimi et al.
5,562,662 A 10/1996 Brumfield et al.
5,562,663 A 10/1996 Wisnewski et al.
5,562,737 A 10/1996 Graf
5,562,738 A 10/1996 Boyd et al.
5,569,247 A 10/1996 Morrison
5,569,248 A 10/1996 Mathews
5,569,250 A 10/1996 Sarver et al.
5,569,251 A 10/1996 Baker et al.
5,569,252 A 10/1996 Justin et al.
5,575,792 A 11/1996 Errico et al.
5,578,033 A 11/1996 Errico et al.
5,578,034 A 11/1996 Estes
5,582,612 A 12/1996 Lin
5,584,833 A 12/1996 Fournet-Fayard et al.
5,584,834 A 12/1996 Errico et al.
5,586,984 A 12/1996 Errico et al.
5,591,166 A 1/1997 Bernhardt et al.
5,599,279 A 2/1997 Slotman et al.
5,601,553 A 2/1997 Trebing et al.
5,603,714 A 2/1997 Kaneda et al.
5,607,304 A 3/1997 Bailey et al.
5,607,425 A 3/1997 Rogozinski
5,607,426 A 3/1997 Ralph et al.
5,607,428 A 3/1997 Lin
5,609,593 A 3/1997 Errico et al.
5,609,594 A 3/1997 Errico et al.
5,609,634 A 3/1997 Voydeville
5,609,635 A 3/1997 Michelson
5,609,636 A 3/1997 Kohrs et al.
5,609,637 A 3/1997 Biedermann et al.
5,611,800 A 3/1997 Davis et al.
5,616,142 A 4/1997 Yuan et al.
5,620,169 A 4/1997 Payne
5,620,443 A 4/1997 Gertzbein et al.
5,628,740 A 5/1997 Mullane
5,630,817 A 5/1997 Rokegem et al.
5,641,256 A 6/1997 Gundy
5,643,260 A 7/1997 Doherty
5,643,261 A 7/1997 Schaefer et al.
5,643,262 A 7/1997 Metz-Stavenhagen et al.
5,643,321 A 7/1997 McDevitt
5,645,544 A 7/1997 Tai et al.
5,645,599 A 7/1997 Samani
5,647,873 A 7/1997 Errico et al.
5,649,931 A 7/1997 Bryant et al.
5,653,763 A 8/1997 Errico et al.
5,662,652 A 9/1997 Schaefer et al.
5,662,653 A 9/1997 Songer et al.
5,665,049 A 9/1997 Markoll
5,667,513 A 9/1997 Torrie et al.
5,669,868 A 9/1997 Markoll
5,669,909 A 9/1997 Zdeblick et al.
5,669,911 A 9/1997 Errico et al.
5,669,912 A 9/1997 Spetzler
5,672,175 A 9/1997 Martin
5,672,176 A 9/1997 Biedermann et al.
5,674,294 A 10/1997 Bainville et al.
5,674,296 A 10/1997 Bryan et al.
5,676,666 A 10/1997 Oxland et al.
5,676,697 A 10/1997 McDonald
5,676,701 A 10/1997 Yuan et al.
5,676,703 A 10/1997 Gelbard
5,681,311 A 10/1997 Foley et al.
5,681,312 A 10/1997 Yuan et al.
5,681,313 A 10/1997 Diez
5,681,319 A 10/1997 Biedermann et al.
5,683,390 A 11/1997 Metz-Stavenhagen et al.
5,683,391 A 11/1997 Boyd
5,683,392 A 11/1997 Richelsoph et al.
5,683,394 A 11/1997 Rinner
5,683,464 A 11/1997 Wagner et al.
5,688,275 A 11/1997 Koros et al.
5,690,630 A 11/1997 Errico et al.
5,697,929 A 12/1997 Mellinger
5,702,451 A 12/1997 Biedermann et al.
5,704,936 A 1/1998 Mazel
5,707,372 A 1/1998 Errico et al.
5,709,686 A 1/1998 Talos et al.
5,711,709 A 1/1998 McCoy
5,713,672 A 2/1998 Lu
5,713,898 A 2/1998 Stuecker et al.
5,713,899 A 2/1998 Marnay et al.
5,713,900 A 2/1998 Benzel et al.
5,713,904 A 2/1998 Errico et al.
5,716,356 A 2/1998 Biedermann et al.
5,716,357 A 2/1998 Rogozinski
5,720,751 A 2/1998 Jackson
5,722,976 A 3/1998 Brown
5,722,977 A 3/1998 Wilhelmy
5,723,013 A 3/1998 Jeanson et al.
5,725,527 A 3/1998 Biedermann et al.
5,725,528 A 3/1998 Errico et al.
5,725,582 A 3/1998 Bevan et al.
5,728,046 A 3/1998 Mayer et al.
5,728,098 A 3/1998 Sherman et al.
5,733,284 A 3/1998 Martin
5,733,285 A 3/1998 Errico et al.
5,733,286 A 3/1998 Errico et al.
5,733,290 A 3/1998 McCue et al.
5,735,853 A 4/1998 Olerud
5,738,685 A 4/1998 Halm et al.
5,741,254 A 4/1998 Henry et al.
5,741,261 A 4/1998 Moskovitz et al.
5,746,743 A 5/1998 Greenberg
5,749,916 A 5/1998 Richelsoph
5,749,968 A 5/1998 Melanson et al.
5,752,957 A 5/1998 Ralph et al.
5,755,660 A 5/1998 Tyagi
5,755,732 A 5/1998 Green et al.
5,766,252 A 6/1998 Henry et al.
5,772,583 A 6/1998 Wright et al.
5,776,135 A 7/1998 Errico et al.
5,776,199 A 7/1998 Michelson
5,782,830 A 7/1998 Farris
5,782,832 A 7/1998 Larsen et al.
5,782,833 A 7/1998 Haider
5,782,919 A 7/1998 Zdeblick et al.
5,792,044 A 8/1998 Foley et al.
5,795,289 A 8/1998 Wyttenbach
5,795,291 A 8/1998 Koros et al.
5,795,584 A 8/1998 Totakura et al.
5,797,911 A 8/1998 Sherman et al.
5,800,433 A 9/1998 Benzel et al.
5,800,435 A 9/1998 Errico et al.
5,800,547 A 9/1998 Schaefer et al.
5,807,403 A 9/1998 Beyar et al.
5,810,818 A 9/1998 Errico et al.
5,810,819 A 9/1998 Errico et al.
5,817,094 A 10/1998 Errico et al.
5,833,418 A 11/1998 Shoji
5,836,948 A 11/1998 Zucherman et al.
5,842,966 A 12/1998 Markoll
5,846,192 A 12/1998 Teixido
5,860,977 A 1/1999 Zucherman et al.
5,863,293 A 1/1999 Richelsoph
5,865,848 A 2/1999 Baker
5,873,878 A 2/1999 Harms et al.
5,876,402 A 3/1999 Errico et al.
5,876,404 A 3/1999 Zucherman et al.
5,879,350 A 3/1999 Sherman et al.
5,879,351 A 3/1999 Viart
5,882,298 A 3/1999 Sharratt
5,882,350 A 3/1999 Ralph et al.
5,882,351 A 3/1999 Fox
5,884,702 A 3/1999 Yokley et al.
5,885,286 A 3/1999 Sherman et al.
5,888,197 A 3/1999 Mulac et al.
5,888,222 A 3/1999 Coates et al.
5,888,224 A 3/1999 Beckers et al.
5,888,226 A 3/1999 Rogozinski
5,890,271 A 4/1999 Bromley et al.
5,891,145 A 4/1999 Morrison et al.
5,893,831 A 4/1999 Koros et al.

(56) References Cited

U.S. PATENT DOCUMENTS

| | | | |
|---|---|---|---|
| 5,899,425 | A | 5/1999 | Corey, Jr. et al. |
| 5,899,904 | A | 5/1999 | Errico et al. |
| 5,899,905 | A | 5/1999 | Errico et al. |
| 5,902,231 | A | 5/1999 | Foley et al. |
| 5,902,233 | A | 5/1999 | Farley et al. |
| 5,902,304 | A | 5/1999 | Walker et al. |
| 5,904,683 | A | 5/1999 | Pohndorf et al. |
| RE36,221 | E | 6/1999 | Breard et al. |
| 5,908,382 | A | 6/1999 | Koros et al. |
| 5,910,141 | A | 6/1999 | Morrison et al. |
| 5,928,139 | A | 7/1999 | Koros et al. |
| 5,928,231 | A | 7/1999 | Klein et al. |
| 5,928,233 | A | 7/1999 | Apfelbaum et al. |
| 5,931,777 | A | 8/1999 | Sava |
| 5,938,663 | A | 8/1999 | Petreto |
| 5,941,885 | A | 8/1999 | Jackson |
| 5,944,465 | A | 8/1999 | Janitzki |
| 5,944,658 | A | 8/1999 | Koros et al. |
| 5,947,967 | A | 9/1999 | Barker |
| 5,947,970 | A | 9/1999 | Schmelzeisen et al. |
| 5,951,553 | A | 9/1999 | Betz et al. |
| 5,951,558 | A | 9/1999 | Fiz |
| 5,954,722 | A | 9/1999 | Bono |
| 5,954,725 | A | 9/1999 | Sherman et al. |
| 5,961,516 | A | 10/1999 | Graf |
| 5,961,517 | A | 10/1999 | Biedermann et al. |
| 5,961,518 | A | 10/1999 | Errico et al. |
| 5,964,760 | A | 10/1999 | Richelsoph |
| 5,964,762 | A | 10/1999 | Biedermann et al. |
| 5,964,763 | A | 10/1999 | Incavo et al. |
| 5,967,970 | A | 10/1999 | Cowan et al. |
| 5,967,972 | A | 10/1999 | Santilli et al. |
| 5,971,987 | A | 10/1999 | Huxel et al. |
| 5,976,135 | A | 11/1999 | Sherman et al. |
| 5,976,140 | A | 11/1999 | Haas |
| 5,976,146 | A | 11/1999 | Ogawa et al. |
| 5,976,186 | A | 11/1999 | Bao et al. |
| 5,980,522 | A | 11/1999 | Koros et al. |
| 5,984,865 | A | 11/1999 | Farley et al. |
| 5,984,923 | A | 11/1999 | Breard |
| 5,984,967 | A | 11/1999 | Zdeblick et al. |
| 5,993,385 | A | 11/1999 | Johnston et al. |
| 5,993,449 | A | 11/1999 | Schlaepfer et al. |
| 5,997,539 | A | 12/1999 | Errico et al. |
| 6,001,098 | A | 12/1999 | Metz-Stavenhagen et al. |
| 6,001,130 | A | 12/1999 | Bryan et al. |
| 6,004,326 | A | 12/1999 | Castro et al. |
| 6,004,349 | A | 12/1999 | Jackson |
| 6,010,503 | A | 1/2000 | Richelsoph et al. |
| 6,010,692 | A | 1/2000 | Goldberg et al. |
| 6,016,727 | A | 1/2000 | Morgan |
| 6,017,342 | A | 1/2000 | Rinner |
| 6,017,344 | A | 1/2000 | Errico et al. |
| 6,019,759 | A | 2/2000 | Rogozinski |
| 6,019,792 | A | 2/2000 | Cauthen |
| 6,022,350 | A | 2/2000 | Ganem |
| 6,022,376 | A | 2/2000 | Assell et al. |
| 6,030,388 | A | 2/2000 | Yoshimi et al. |
| 6,033,170 | A | 3/2000 | Gold |
| 6,033,406 | A | 3/2000 | Mathews |
| 6,033,436 | A | 3/2000 | Steinke et al. |
| 6,039,740 | A | 3/2000 | Olerud |
| 6,039,761 | A | 3/2000 | Li et al. |
| D422,705 | S | 4/2000 | Koros et al. |
| 6,045,555 | A | 4/2000 | Smith et al. |
| 6,045,579 | A | 4/2000 | Hochshuler et al. |
| 6,048,302 | A | 4/2000 | Markoll |
| 6,048,342 | A | 4/2000 | Zucherman et al. |
| 6,048,343 | A | 4/2000 | Mathis et al. |
| 6,050,997 | A | 4/2000 | Mullane |
| 6,053,917 | A | 4/2000 | Sherman et al. |
| 6,059,785 | A | 5/2000 | Schavan et al. |
| 6,059,786 | A | 5/2000 | Jackson |
| 6,063,089 | A | 5/2000 | Errico et al. |
| 6,063,090 | A | 5/2000 | Schlaepfer |
| 6,066,174 | A | 5/2000 | Farris |
| 6,066,175 | A | 5/2000 | Henderson et al. |
| 6,068,630 | A | 5/2000 | Zucherman et al. |
| 6,071,310 | A | 6/2000 | Picha et al. |
| 6,074,343 | A | 6/2000 | Nathanson et al. |
| 6,074,390 | A | 6/2000 | Zucherman et al. |
| 6,074,391 | A | 6/2000 | Metz-Stavenhagen et al. |
| 6,077,262 | A | 6/2000 | Schlaepfer et al. |
| 6,080,193 | A | 6/2000 | Hochshuler et al. |
| 6,083,224 | A | 7/2000 | Gertzbein et al. |
| 6,083,225 | A | 7/2000 | Winslow et al. |
| 6,083,624 | A | 7/2000 | Hiura |
| 6,086,588 | A | 7/2000 | Ameil et al. |
| 6,086,589 | A | 7/2000 | Kuslich et al. |
| 6,086,613 | A | 7/2000 | Camino et al. |
| 6,090,110 | A | 7/2000 | Metz-Stavenhagen |
| 6,090,111 | A | 7/2000 | Nichols |
| 6,090,113 | A | 7/2000 | Le et al. |
| 6,093,205 | A | 7/2000 | McLeod et al. |
| 6,096,060 | A | 8/2000 | Fitts et al. |
| 6,099,528 | A | 8/2000 | Saurat |
| 6,099,531 | A | 8/2000 | Bonutti |
| 6,102,912 | A | 8/2000 | Cazin et al. |
| 6,102,913 | A | 8/2000 | Jackson |
| 6,110,172 | A | 8/2000 | Jackson |
| 6,110,173 | A | 8/2000 | Thomas, Jr. |
| 6,111,164 | A | 8/2000 | Rainey et al. |
| 6,113,599 | A | 9/2000 | Landsberger |
| 6,113,601 | A | 9/2000 | Tatar |
| 6,113,638 | A | 9/2000 | Williams et al. |
| 6,117,135 | A | 9/2000 | Schlaepfer |
| 6,117,137 | A | 9/2000 | Halm et al. |
| 6,119,631 | A | 9/2000 | Markoll |
| 6,120,502 | A | 9/2000 | Michelson |
| 6,123,706 | A | 9/2000 | Lange |
| 6,123,707 | A | 9/2000 | Wagner |
| 6,126,689 | A | 10/2000 | Brett |
| 6,132,370 | A | 10/2000 | Furnish et al. |
| 6,132,430 | A | 10/2000 | Wagner |
| 6,132,431 | A | 10/2000 | Nilsson et al. |
| 6,132,432 | A | 10/2000 | Richelsoph |
| 6,132,434 | A | 10/2000 | Sherman et al. |
| 6,132,464 | A | 10/2000 | Martin |
| 6,136,000 | A | 10/2000 | Louis et al. |
| 6,136,002 | A | 10/2000 | Shih et al. |
| 6,139,316 | A | 10/2000 | Sachdeva et al. |
| 6,139,493 | A | 10/2000 | Koros et al. |
| 6,139,549 | A | 10/2000 | Keller |
| 6,143,032 | A | 11/2000 | Schafer et al. |
| 6,143,033 | A | 11/2000 | Paul et al. |
| 6,146,044 | A | 11/2000 | Calvet |
| 6,146,383 | A | 11/2000 | Studer et al. |
| 6,146,422 | A | 11/2000 | Lawson |
| 6,149,650 | A | 11/2000 | Michelson |
| 6,152,927 | A | 11/2000 | Farris et al. |
| 6,156,037 | A | 12/2000 | Lehuec et al. |
| 6,159,210 | A | 12/2000 | Voor |
| 6,159,211 | A | 12/2000 | Boriani et al. |
| 6,159,215 | A | 12/2000 | Urbahns et al. |
| 6,159,244 | A | 12/2000 | Suddaby |
| 6,162,252 | A | 12/2000 | Kuras et al. |
| 6,174,311 | B1 | 1/2001 | Branch et al. |
| 6,176,882 | B1 | 1/2001 | Biedermann et al. |
| 6,179,838 | B1 | 1/2001 | Fiz |
| 6,179,873 | B1 | 1/2001 | Zientek |
| 6,179,874 | B1 | 1/2001 | Cauthen |
| 6,183,472 | B1 | 2/2001 | Lutz |
| 6,183,473 | B1 | 2/2001 | Ashman |
| 6,186,005 | B1 | 2/2001 | Leidl |
| 6,186,718 | B1 | 2/2001 | Fogard |
| 6,187,005 | B1 | 2/2001 | Brace et al. |
| 6,193,720 | B1 | 2/2001 | Yuan et al. |
| 6,193,721 | B1 | 2/2001 | Michelson |
| 6,193,757 | B1 | 2/2001 | Foley et al. |
| 6,197,033 | B1 | 3/2001 | Haid, Jr. et al. |
| 6,200,322 | B1 | 3/2001 | Branch et al. |
| 6,206,826 | B1 | 3/2001 | Mathews et al. |
| 6,206,879 | B1 | 3/2001 | Marnay et al. |
| 6,206,922 | B1 | 3/2001 | Zdeblick et al. |

(56) References Cited

U.S. PATENT DOCUMENTS

| | | | |
|---|---|---|---|
| 6,206,923 | B1 | 3/2001 | Boyd et al. |
| D440,311 | S | 4/2001 | Michelson |
| 6,210,376 | B1 | 4/2001 | Grayson |
| 6,210,412 | B1 | 4/2001 | Michelson |
| 6,210,413 | B1 | 4/2001 | Justis et al. |
| 6,214,005 | B1 | 4/2001 | Benzel et al. |
| 6,214,012 | B1 | 4/2001 | Karpman et al. |
| 6,221,077 | B1 | 4/2001 | Rinner et al. |
| RE37,161 | E | 5/2001 | Michelson et al. |
| 6,224,545 | B1 | 5/2001 | Cocchia et al. |
| 6,224,595 | B1 | 5/2001 | Michelson |
| 6,224,596 | B1 | 5/2001 | Jackson |
| 6,224,598 | B1 | 5/2001 | Jackson |
| 6,224,602 | B1 | 5/2001 | Hayes |
| 6,224,607 | B1 | 5/2001 | Michelson |
| 6,226,548 | B1 | 5/2001 | Foley et al. |
| 6,228,022 | B1 | 5/2001 | Friesem et al. |
| 6,228,085 | B1 | 5/2001 | Theken et al. |
| 6,231,575 | B1 | 5/2001 | Krag |
| 6,234,705 | B1 | 5/2001 | Troxell |
| 6,235,028 | B1 | 5/2001 | Brumfield et al. |
| 6,235,034 | B1 | 5/2001 | Bray |
| 6,235,726 | B1 | 5/2001 | Burns et al. |
| 6,238,396 | B1 | 5/2001 | Lombardo |
| 6,241,729 | B1 | 6/2001 | Estes et al. |
| 6,241,730 | B1 | 6/2001 | Alby |
| 6,241,769 | B1 | 6/2001 | Nicholson et al. |
| 6,241,770 | B1 | 6/2001 | Michelson |
| 6,245,072 | B1 | 6/2001 | Zdeblick et al. |
| 6,245,108 | B1 | 6/2001 | Biscup |
| 6,248,104 | B1 | 6/2001 | Chopin et al. |
| 6,248,105 | B1 | 6/2001 | Schlaepfer et al. |
| 6,248,106 | B1 | 6/2001 | Ferree |
| 6,248,107 | B1 | 6/2001 | Foley et al. |
| 6,248,110 | B1 | 6/2001 | Reiley et al. |
| 6,250,984 | B1 | 6/2001 | Jin et al. |
| 6,251,112 | B1 | 6/2001 | Jackson |
| 6,251,140 | B1 | 6/2001 | Marino et al. |
| 6,254,146 | B1 | 7/2001 | Church |
| 6,254,602 | B1 | 7/2001 | Justis |
| 6,254,603 | B1 | 7/2001 | Gertzbein et al. |
| 6,258,089 | B1 | 7/2001 | Campbell et al. |
| 6,258,125 | B1 | 7/2001 | Paul et al. |
| 6,261,287 | B1 | 7/2001 | Metz-Stavenhagen |
| 6,261,291 | B1 | 7/2001 | Talaber et al. |
| 6,264,656 | B1 | 7/2001 | Michelson |
| 6,267,764 | B1 | 7/2001 | Elberg |
| 6,267,765 | B1 | 7/2001 | Taylor et al. |
| 6,270,498 | B1 | 8/2001 | Michelson |
| 6,273,888 | B1 | 8/2001 | Justis |
| 6,273,889 | B1 | 8/2001 | Richelsoph |
| 6,277,122 | B1 | 8/2001 | McGahan et al. |
| 6,277,149 | B1 | 8/2001 | Boyle et al. |
| 6,280,442 | B1 | 8/2001 | Barker et al. |
| 6,280,445 | B1 | 8/2001 | Morrison et al. |
| D448,081 | S | 9/2001 | Koros et al. |
| 6,283,967 | B1 | 9/2001 | Troxell et al. |
| 6,287,308 | B1 | 9/2001 | Betz et al. |
| 6,287,309 | B1 | 9/2001 | Baccelli et al. |
| 6,287,311 | B1 | 9/2001 | Sherman et al. |
| 6,290,703 | B1 | 9/2001 | Ganem |
| 6,293,949 | B1 | 9/2001 | Justis et al. |
| 6,294,202 | B1 | 9/2001 | Burns et al. |
| D449,692 | S | 10/2001 | Michelson |
| 6,296,642 | B1 | 10/2001 | Morrison et al. |
| 6,296,643 | B1 | 10/2001 | Hopf et al. |
| 6,296,664 | B1 | 10/2001 | Middleton |
| 6,299,613 | B1 | 10/2001 | Ogilvie et al. |
| 6,302,843 | B1 | 10/2001 | Lees et al. |
| 6,302,888 | B1 | 10/2001 | Mellinger et al. |
| 6,302,914 | B1 | 10/2001 | Michelson |
| 6,304,178 | B1 | 10/2001 | Hayashida |
| 6,306,136 | B1 | 10/2001 | Baccelli |
| 6,306,137 | B2 | 10/2001 | Troxell |
| 6,306,170 | B2 | 10/2001 | Ray |
| 6,309,391 | B1 | 10/2001 | Crandall et al. |
| 6,312,431 | B1 | 11/2001 | Asfora |
| 6,315,564 | B1 | 11/2001 | Levisman |
| 6,315,779 | B1 | 11/2001 | Morrison et al. |
| 6,317,957 | B1 | 11/2001 | Gregor et al. |
| 6,319,002 | B1 | 11/2001 | Pond |
| 6,319,257 | B1 | 11/2001 | Carignan et al. |
| 6,322,500 | B1 | 11/2001 | Sikora et al. |
| RE37,479 | E | 12/2001 | Kuslich |
| 6,331,179 | B1 | 12/2001 | Freid et al. |
| 6,332,882 | B1 | 12/2001 | Zucherman et al. |
| 6,340,345 | B1 | 1/2002 | Lees et al. |
| 6,342,074 | B1 | 1/2002 | Simpson |
| 6,344,057 | B1 | 2/2002 | Rabbe et al. |
| 6,348,058 | B1 | 2/2002 | Melkent et al. |
| 6,348,071 | B1 | 2/2002 | Steffee et al. |
| 6,350,283 | B1 | 2/2002 | Michelson |
| 6,355,038 | B1 | 3/2002 | Pisharodi |
| 6,355,039 | B1 | 3/2002 | Troussel et al. |
| 6,355,040 | B1 | 3/2002 | Richelsoph et al. |
| 6,360,750 | B1 | 3/2002 | Gerber et al. |
| 6,361,258 | B1 | 3/2002 | Heesch |
| RE37,665 | E | 4/2002 | Ralph |
| 6,364,880 | B1 | 4/2002 | Michelson |
| 6,364,881 | B1 | 4/2002 | Apgar et al. |
| 6,364,883 | B1 | 4/2002 | Santilli |
| 6,368,320 | B1 | 4/2002 | Le et al. |
| 6,368,321 | B1 | 4/2002 | Jackson |
| 6,368,350 | B1 | 4/2002 | Erickson et al. |
| 6,371,957 | B1 | 4/2002 | Amrein et al. |
| 6,371,987 | B1 | 4/2002 | Weiland et al. |
| 6,371,988 | B1 | 4/2002 | Pafford et al. |
| 6,375,655 | B1 | 4/2002 | Zdeblick et al. |
| 6,375,681 | B1 | 4/2002 | Truscott |
| 6,379,355 | B1 | 4/2002 | Zucherman et al. |
| 6,379,357 | B1 | 4/2002 | Bernstein et al. |
| 6,387,130 | B1 | 5/2002 | Stone et al. |
| 6,389,391 | B1 | 5/2002 | Terauchi |
| 6,395,031 | B1 | 5/2002 | Foley et al. |
| 6,395,035 | B2 | 5/2002 | Bresina et al. |
| 6,398,783 | B1 | 6/2002 | Michelson |
| 6,402,749 | B1 | 6/2002 | Ashman |
| 6,402,750 | B1 | 6/2002 | Atkinson et al. |
| 6,402,751 | B1 | 6/2002 | Hoeck et al. |
| 6,402,752 | B2 | 6/2002 | Schaffler-Wachter et al. |
| 6,402,756 | B1 | 6/2002 | Ralph et al. |
| 6,402,757 | B1 | 6/2002 | Moore, III et al. |
| 6,402,785 | B1 | 6/2002 | Zdeblick et al. |
| 6,406,478 | B1 | 6/2002 | Kuo |
| 6,409,765 | B1 | 6/2002 | Bianchi et al. |
| 6,412,999 | B1 | 7/2002 | Pierpont |
| 6,413,258 | B1 | 7/2002 | Bernhardt, Jr. |
| 6,413,259 | B1 | 7/2002 | Lyons et al. |
| 6,413,278 | B1 | 7/2002 | Marchosky |
| 6,416,465 | B2 | 7/2002 | Brau |
| 6,416,515 | B1 | 7/2002 | Wagner |
| 6,419,676 | B1 | 7/2002 | Zucherman et al. |
| 6,419,677 | B2 | 7/2002 | Zucherman et al. |
| 6,419,703 | B1 | 7/2002 | Fallin et al. |
| 6,419,704 | B1 | 7/2002 | Ferree |
| 6,419,706 | B1 | 7/2002 | Graf |
| 6,423,063 | B1 | 7/2002 | Bonutti |
| 6,423,095 | B1 | 7/2002 | Hoeck et al. |
| 6,428,542 | B1 | 8/2002 | Michelson |
| 6,428,576 | B1 | 8/2002 | Haldimann |
| 6,432,108 | B1 | 8/2002 | Burgess et al. |
| 6,432,140 | B1 | 8/2002 | Lin |
| 6,440,133 | B1 | 8/2002 | Beale et al. |
| 6,440,137 | B1 | 8/2002 | Horvath et al. |
| 6,440,139 | B2 | 8/2002 | Michelson |
| 6,440,168 | B1 | 8/2002 | Cauthen |
| 6,440,169 | B1 | 8/2002 | Elberg et al. |
| 6,440,170 | B1 | 8/2002 | Jackson |
| 6,443,956 | B1 | 9/2002 | Ray |
| 6,443,989 | B1 | 9/2002 | Jackson |
| 6,447,440 | B1 | 9/2002 | Markoll |
| 6,447,443 | B1 | 9/2002 | Keogh et al. |
| 6,447,547 | B1 | 9/2002 | Michelson |
| 6,447,548 | B1 | 9/2002 | Ralph et al. |

(56) References Cited

U.S. PATENT DOCUMENTS

| | | | |
|---|---|---|---|
| 6,451,019 | B1 | 9/2002 | Zucherman et al. |
| 6,451,020 | B1 | 9/2002 | Zucherman et al. |
| 6,451,021 | B1 | 9/2002 | Ralph et al. |
| 6,454,769 | B2 | 9/2002 | Wagner et al. |
| 6,454,771 | B1 | 9/2002 | Michelson |
| 6,454,773 | B1 | 9/2002 | Sherman et al. |
| 6,458,159 | B1 | 10/2002 | Thalgott |
| 6,461,358 | B1 | 10/2002 | Faccioli et al. |
| 6,461,359 | B1 | 10/2002 | Tribus et al. |
| 6,468,310 | B1 | 10/2002 | Ralph et al. |
| 6,471,703 | B1 | 10/2002 | Ashman |
| 6,471,704 | B2 | 10/2002 | Gertzbein et al. |
| 6,471,705 | B1 | 10/2002 | Biedermann et al. |
| 6,471,724 | B2 | 10/2002 | Zdeblick et al. |
| 6,475,218 | B2 | 11/2002 | Gournay et al. |
| 6,478,796 | B2 | 11/2002 | Zucherman et al. |
| 6,478,798 | B1 | 11/2002 | Howland |
| 6,478,800 | B1 | 11/2002 | Fraser et al. |
| 6,478,801 | B1 | 11/2002 | Ralph et al. |
| 6,482,234 | B1 | 11/2002 | Weber et al. |
| 6,485,491 | B1 | 11/2002 | Farris et al. |
| 6,485,492 | B1 | 11/2002 | Halm et al. |
| 6,485,494 | B1 | 11/2002 | Haider |
| 6,485,517 | B1 | 11/2002 | Michelson |
| 6,485,518 | B1 | 11/2002 | Cornwall et al. |
| 6,488,681 | B2 | 12/2002 | Martin et al. |
| 6,497,726 | B1 | 12/2002 | Carter et al. |
| 6,500,205 | B1 | 12/2002 | Michelson |
| 6,503,250 | B2 | 1/2003 | Paul |
| 6,508,818 | B2 | 1/2003 | Steiner et al. |
| 6,508,839 | B1 | 1/2003 | Lambrecht et al. |
| 6,511,484 | B2 | 1/2003 | Torode et al. |
| 6,514,256 | B2 | 2/2003 | Zucherman et al. |
| 6,514,260 | B1 | 2/2003 | Zdeblick et al. |
| 6,517,580 | B1 | 2/2003 | Ramadan et al. |
| 6,520,962 | B1 | 2/2003 | Taylor et al. |
| 6,520,967 | B1 | 2/2003 | Cauthen |
| 6,520,996 | B1 | 2/2003 | Manasas et al. |
| 6,521,223 | B1 | 2/2003 | Calias et al. |
| 6,524,233 | B2 | 2/2003 | Markoll |
| 6,524,238 | B2 | 2/2003 | Velikaris et al. |
| 6,524,312 | B2 | 2/2003 | Landry et al. |
| 6,524,315 | B1 | 2/2003 | Selvitelli et al. |
| 6,527,773 | B1 | 3/2003 | Lin et al. |
| 6,527,803 | B1 | 3/2003 | Crozet et al. |
| 6,527,804 | B1 | 3/2003 | Gauchet et al. |
| 6,527,806 | B2 | 3/2003 | Ralph et al. |
| 6,530,929 | B1 | 3/2003 | Justis et al. |
| 6,531,146 | B2 | 3/2003 | Calhoun et al. |
| 6,533,786 | B1 | 3/2003 | Needham et al. |
| 6,537,276 | B2 | 3/2003 | Metz-Stavenhagen |
| 6,537,279 | B1 | 3/2003 | Michelson |
| 6,538,262 | B1 | 3/2003 | Crespi et al. |
| 6,539,826 | B2 | 4/2003 | Oesterle et al. |
| 6,540,749 | B2 | 4/2003 | Schaefer et al. |
| 6,540,785 | B1 | 4/2003 | Gill et al. |
| 6,547,790 | B2 | 4/2003 | Harkey, III et al. |
| 6,547,795 | B2 | 4/2003 | Schneiderman |
| 6,551,242 | B1 | 4/2003 | Furnish et al. |
| 6,551,320 | B2 | 4/2003 | Lieberman |
| 6,551,322 | B1 | 4/2003 | Lieberman |
| 6,551,323 | B2 | 4/2003 | Doubler et al. |
| 6,554,831 | B1 | 4/2003 | Rivard et al. |
| 6,554,832 | B2 | 4/2003 | Shluzas |
| 6,554,834 | B1 | 4/2003 | Crozet et al. |
| 6,554,863 | B2 | 4/2003 | Paul et al. |
| 6,558,386 | B1 | 5/2003 | Cragg |
| 6,558,387 | B2 | 5/2003 | Errico et al. |
| 6,558,390 | B2 | 5/2003 | Cragg |
| 6,558,423 | B1 | 5/2003 | Michelson |
| 6,558,424 | B2 | 5/2003 | Thalgott |
| 6,562,038 | B1 | 5/2003 | Morrison |
| 6,562,040 | B1 | 5/2003 | Wagner |
| 6,562,046 | B2 | 5/2003 | Sasso |
| 6,562,074 | B2 | 5/2003 | Gerbec et al. |
| 6,565,565 | B1 | 5/2003 | Yuan et al. |
| 6,565,567 | B1 | 5/2003 | Haider |
| 6,565,571 | B1 | 5/2003 | Jackowski et al. |
| 6,565,605 | B2 | 5/2003 | Goble et al. |
| 6,569,168 | B2 | 5/2003 | Lin |
| 6,572,618 | B1 | 6/2003 | Morrison |
| 6,575,899 | B1 | 6/2003 | Foley et al. |
| 6,575,981 | B1 | 6/2003 | Boyd et al. |
| 6,576,016 | B1 | 6/2003 | Hochshuler et al. |
| 6,579,291 | B1 | 6/2003 | Keith et al. |
| 6,579,319 | B2 | 6/2003 | Goble et al. |
| 6,582,431 | B1 | 6/2003 | Ray |
| 6,582,433 | B2 | 6/2003 | Yun |
| 6,582,436 | B2 | 6/2003 | Schlapfer et al. |
| 6,582,466 | B1 | 6/2003 | Gauchet |
| 6,585,740 | B2 | 7/2003 | Schlapfer et al. |
| 6,589,243 | B1 | 7/2003 | Viart et al. |
| 6,592,585 | B2 | 7/2003 | Lee et al. |
| 6,592,624 | B1 | 7/2003 | Fraser et al. |
| 6,595,992 | B1 | 7/2003 | Wagner et al. |
| 6,595,993 | B2 | 7/2003 | Donno et al. |
| 6,595,995 | B2 | 7/2003 | Zdeblick et al. |
| 6,599,240 | B2 | 7/2003 | Puchovsky et al. |
| 6,599,290 | B2 | 7/2003 | Bailey et al. |
| 6,599,292 | B1 | 7/2003 | Ray |
| 6,599,294 | B2 | 7/2003 | Fuss et al. |
| 6,599,295 | B1 | 7/2003 | Tornier et al. |
| 6,599,320 | B1 | 7/2003 | Kuslich et al. |
| 6,599,321 | B2 | 7/2003 | Hyde, Jr. |
| 6,602,254 | B2 | 8/2003 | Gertzbein et al. |
| 6,602,255 | B1 | 8/2003 | Campbell et al. |
| 6,602,256 | B1 | 8/2003 | Hayes |
| 6,602,257 | B1 | 8/2003 | Thramann |
| 6,605,089 | B1 | 8/2003 | Michelson |
| 6,607,530 | B1 | 8/2003 | Carl et al. |
| 6,607,558 | B2 | 8/2003 | Kuras |
| 6,610,063 | B2 | 8/2003 | Kumar et al. |
| 6,610,089 | B1 | 8/2003 | Liu et al. |
| 6,610,093 | B1 | 8/2003 | Pisharodi |
| 6,613,050 | B1 | 9/2003 | Wagner et al. |
| 6,613,089 | B1 | 9/2003 | Estes et al. |
| 6,613,091 | B1 | 9/2003 | Zdeblick et al. |
| 6,613,278 | B1 | 9/2003 | Mills et al. |
| 6,616,664 | B2 | 9/2003 | Walulik et al. |
| 6,616,665 | B2 | 9/2003 | Grafton et al. |
| 6,616,667 | B1 | 9/2003 | Steiger et al. |
| 6,616,669 | B2 | 9/2003 | Ogilvie et al. |
| 6,616,695 | B1 | 9/2003 | Crozet et al. |
| 6,620,163 | B1 | 9/2003 | Michelson |
| 6,622,344 | B1 | 9/2003 | Lu |
| 6,623,485 | B2 | 9/2003 | Doubler et al. |
| 6,626,347 | B2 | 9/2003 | Ng |
| 6,626,904 | B1 | 9/2003 | Jammet et al. |
| 6,626,906 | B1 | 9/2003 | Young |
| 6,626,907 | B2 | 9/2003 | Campbell et al. |
| 6,626,908 | B2 | 9/2003 | Cooper et al. |
| 6,635,059 | B2 | 10/2003 | Randall et al. |
| 6,635,060 | B2 | 10/2003 | Hanson et al. |
| 6,635,086 | B2 | 10/2003 | Lin |
| 6,635,087 | B2 | 10/2003 | Angelucci et al. |
| 6,638,276 | B2 | 10/2003 | Sharkey et al. |
| 6,638,310 | B2 | 10/2003 | Lin et al. |
| 6,641,583 | B2 | 11/2003 | Shluzas et al. |
| 6,641,585 | B2 | 11/2003 | Sato et al. |
| 6,641,586 | B2 | 11/2003 | Varieur |
| 6,641,614 | B1 | 11/2003 | Wagner et al. |
| 6,645,206 | B1 | 11/2003 | Zdeblick et al. |
| 6,645,207 | B2 | 11/2003 | Dixon et al. |
| 6,645,208 | B2 | 11/2003 | Apfelbaum et al. |
| 6,645,249 | B2 | 11/2003 | Ralph et al. |
| 6,648,885 | B1 | 11/2003 | Friesem |
| 6,648,887 | B2 | 11/2003 | Ashman |
| 6,648,888 | B1 | 11/2003 | Shluzas |
| 6,648,891 | B2 | 11/2003 | Kim |
| 6,648,894 | B2 | 11/2003 | Abdelgany et al. |
| 6,648,895 | B2 | 11/2003 | Burkus et al. |
| 6,648,917 | B2 | 11/2003 | Gerbec et al. |
| 6,652,525 | B1 | 11/2003 | Assaker et al. |
| 6,652,526 | B1 | 11/2003 | Arafiles |

(56) References Cited

U.S. PATENT DOCUMENTS 6,652,533 B2 11/2003 O'Neil
6,652,584 B2 11/2003 Michelson
6,652,586 B2 11/2003 Hunter et al.
6,652,765 B1 11/2003 Beaty
6,652,818 B1 11/2003 Mills et al.
6,656,179 B1 12/2003 Schaefer et al.
6,656,181 B2 12/2003 Dixon et al.
6,656,224 B2 12/2003 Middleton
6,660,004 B2 12/2003 Barker et al.
6,660,006 B2 12/2003 Markworth et al.
6,663,631 B2 12/2003 Kuntz
6,663,632 B1 12/2003 Frigg
6,663,635 B2 12/2003 Frigg et al.
6,663,642 B2 12/2003 Beyar et al.
6,665,555 B2 12/2003 Henderson et al.
6,666,612 B2 12/2003 Lorigny et al.
6,666,866 B2 12/2003 Martz et al.
6,666,867 B2 12/2003 Ralph et al.
6,666,890 B2 12/2003 Michelson
6,666,891 B2 12/2003 Boehm et al.
6,668,688 B2 12/2003 Zhao et al.
6,669,700 B1 12/2003 Farris et al.
6,669,730 B2 12/2003 Ralph et al.
6,673,073 B1 1/2004 Schaefer
6,673,113 B2 1/2004 Ralph et al.
6,673,362 B2 1/2004 Calhoun et al.
6,675,805 B1 1/2004 Graether
6,676,661 B1 1/2004 Martin et al.
6,676,703 B2 1/2004 Biscup
6,679,833 B2 1/2004 Smith et al.
6,679,883 B2 1/2004 Hawkes et al.
6,679,887 B2 1/2004 Nicholson et al.
6,679,915 B1 1/2004 Cauthen
6,682,529 B2 1/2004 Stahurski
6,682,530 B2 1/2004 Dixon et al.
6,682,533 B1 1/2004 Dinsdale et al.
6,682,562 B2 1/2004 Viart et al.
6,683,690 B1 1/2004 Tobias
6,685,705 B1 2/2004 Taylor
6,689,133 B2 2/2004 Morrison et al.
6,689,134 B2 2/2004 Ralph et al.
6,692,495 B1 2/2004 Zacouto
6,695,842 B2 2/2004 Zucherman et al.
6,695,843 B2 2/2004 Biedermann et al.
6,695,846 B2 2/2004 Richelsoph et al.
6,695,851 B2 2/2004 Zdeblick et al.
6,699,246 B2 3/2004 Zucherman et al.
6,699,247 B2 3/2004 Zucherman et al.
6,699,249 B2 3/2004 Schlaepfer et al.
6,702,814 B2 3/2004 Walulik et al.
6,706,045 B2 3/2004 Lin et al.
6,706,067 B2 3/2004 Shimp et al.
6,706,068 B2 3/2004 Ferree
6,706,070 B1 3/2004 Wagner et al.
6,706,922 B2 3/2004 Wolff et al.
6,709,389 B2 3/2004 Farascioni
6,709,458 B2 3/2004 Michelson
6,709,461 B2 3/2004 O'Neil et al.
6,712,795 B1 3/2004 Cohen
6,712,818 B1 3/2004 Michelson
6,712,819 B2 3/2004 Zucherman et al.
6,712,852 B1 3/2004 Chung et al.
6,716,212 B1 4/2004 Pickens
6,716,213 B2 4/2004 Shitoto
6,716,214 B1 4/2004 Jackson
6,716,247 B2 4/2004 Michelson
6,719,794 B2 4/2004 Gerber et al.
6,719,795 B1 4/2004 Cornwall et al.
6,723,043 B2 4/2004 Kleeman et al.
6,723,096 B1 4/2004 Dorchak et al.
6,723,100 B2 4/2004 Biedermann et al.
6,723,126 B1 4/2004 Berry
6,723,127 B2 4/2004 Ralph et al.
6,723,128 B2 4/2004 Uk
6,726,685 B2 4/2004 To et al.
6,726,687 B2 4/2004 Jackson
6,726,720 B2 4/2004 Ross et al.
6,730,093 B2 5/2004 Saint
6,730,126 B2 5/2004 Boehm, Jr. et al.
6,730,127 B2 5/2004 Michelson
6,733,444 B2 5/2004 Phillips
6,733,496 B2 5/2004 Sharkey et al.
6,733,502 B2 5/2004 Altarac et al.
6,733,531 B1 5/2004 Trieu
6,733,534 B2 5/2004 Sherman
6,733,535 B2 5/2004 Michelson
6,736,816 B2 5/2004 Ritland
6,736,817 B2 5/2004 Troxell et al.
6,736,820 B2 5/2004 Biedermann et al.
6,739,068 B1 5/2004 Rinner
6,740,086 B2 5/2004 Richelsoph
6,740,087 B2 5/2004 Knox
6,740,090 B1 5/2004 Cragg et al.
6,740,118 B2 5/2004 Eisermann et al.
6,743,231 B1 6/2004 Gray et al.
6,743,255 B2 6/2004 Ferree
6,743,256 B2 6/2004 Mason
6,743,257 B2 6/2004 Castro
6,746,449 B2 6/2004 Jones et al.
6,746,454 B2 6/2004 Winterbottom et al.
6,749,613 B1 6/2004 Conchy et al.
6,749,614 B2 6/2004 Teitelbaum et al.
6,749,635 B1 6/2004 Bryan
6,749,636 B2 6/2004 Michelson
6,752,832 B2 6/2004 Neumann
6,755,829 B1 6/2004 Bono et al.
6,755,830 B2 6/2004 Minfelde et al.
6,755,833 B1 6/2004 Paul et al.
6,755,835 B2 6/2004 Schultheiss et al.
6,755,836 B1 6/2004 Lewis
6,755,841 B2 6/2004 Fraser et al.
6,758,861 B2 7/2004 Ralph et al.
6,761,719 B2 7/2004 Justis et al.
6,761,720 B1 7/2004 Senegas
6,761,721 B2 7/2004 Burgess et al.
6,761,723 B2 7/2004 Buttermann et al.
6,761,738 B1 7/2004 Boyd
6,764,515 B2 7/2004 Ralph et al.
6,767,351 B2 7/2004 Orbay et al.
6,767,367 B1 7/2004 Michelson
6,770,074 B2 8/2004 Michelson
6,770,075 B2 8/2004 Howland
6,770,096 B2 8/2004 Bolger et al.
6,778,861 B1 8/2004 Liebrecht et al.
6,780,186 B2 8/2004 Errico et al.
6,780,192 B2 8/2004 McKay et al.
6,783,527 B2 8/2004 Drewry et al.
6,783,547 B2 8/2004 Castro
6,790,209 B2 9/2004 Beale et al.
6,790,210 B1 9/2004 Cragg et al.
6,793,658 B2 9/2004 Lehuec et al.
6,802,844 B2 10/2004 Ferree
6,805,697 B1 10/2004 Helm et al.
6,805,713 B1 10/2004 Carter et al.
6,805,714 B2 10/2004 Sutcliffe
6,808,493 B1 10/2004 Bookwalter et al.
6,808,537 B2 10/2004 Michelson
6,811,567 B2 11/2004 Reiley
6,814,737 B2 11/2004 Cauthen
6,821,277 B2 11/2004 Teitelbaum
6,824,565 B2 11/2004 Muhanna et al.
6,827,719 B2 12/2004 Ralph et al.
6,827,722 B1 12/2004 Schoenefeld
6,830,570 B1 12/2004 Frey et al.
6,830,571 B2 12/2004 Lenke et al.
6,830,589 B2 12/2004 Erickson
6,832,997 B2 12/2004 Uchida et al.
6,832,999 B2 12/2004 Ueyama et al.
6,835,196 B2 12/2004 Biedermann et al.
6,835,206 B2 12/2004 Jackson
6,837,884 B2 1/2005 Woloszko
6,837,889 B2 1/2005 Shluzas
6,840,940 B2 1/2005 Ralph et al.
6,843,791 B2 1/2005 Serhan

(56) References Cited

U.S. PATENT DOCUMENTS

| | | | |
|---|---|---|---|
| 6,849,076 | B2 | 2/2005 | Blunn et al. |
| 6,849,093 | B2 | 2/2005 | Michelson |
| 6,852,127 | B2 | 2/2005 | Varga et al. |
| 6,852,128 | B2 | 2/2005 | Lange |
| 6,852,129 | B2 | 2/2005 | Gerbec et al. |
| 6,855,147 | B2 | 2/2005 | Harrington et al. |
| 6,857,343 | B1 | 2/2005 | Easterbrooks et al. |
| 6,858,030 | B2 | 2/2005 | Martin et al. |
| 6,858,031 | B2 | 2/2005 | Morrison et al. |
| 6,860,850 | B2 | 3/2005 | Phillips et al. |
| 6,863,673 | B2 | 3/2005 | Gerbec et al. |
| 6,869,398 | B2 | 3/2005 | Obenchain et al. |
| 6,869,432 | B2 | 3/2005 | Schlapfer et al. |
| 6,869,433 | B2 | 3/2005 | Glascott |
| 6,872,208 | B1 | 3/2005 | McBride et al. |
| 6,875,211 | B2 | 4/2005 | Nichols et al. |
| 6,881,228 | B2 | 4/2005 | Zdeblick et al. |
| 6,884,241 | B2 | 4/2005 | Bertranou et al. |
| 6,884,242 | B2 | 4/2005 | Lehuec et al. |
| 6,884,243 | B2 | 4/2005 | Sellers |
| 6,885,243 | B2 | 4/2005 | Burstein et al. |
| D505,205 | S | 5/2005 | Freid |
| 6,887,242 | B2 | 5/2005 | Doubler et al. |
| 6,890,355 | B2 | 5/2005 | Michelson |
| 6,893,444 | B2 | 5/2005 | Orbay |
| 6,896,675 | B2 | 5/2005 | Leung et al. |
| 6,896,676 | B2 | 5/2005 | Zubok et al. |
| 6,896,677 | B1 | 5/2005 | Lin |
| 6,896,680 | B2 | 5/2005 | Michelson |
| 6,899,714 | B2 | 5/2005 | Vaughan |
| 6,899,716 | B2 | 5/2005 | Cragg |
| 6,902,566 | B2 | 6/2005 | Zucherman et al. |
| 6,902,580 | B2 | 6/2005 | Fallin et al. |
| 6,911,045 | B2 | 6/2005 | Shimp |
| 6,916,320 | B2 | 7/2005 | Michelson |
| 6,916,340 | B2 | 7/2005 | Metzger et al. |
| 6,918,910 | B2 | 7/2005 | Smith et al. |
| 6,918,911 | B2 | 7/2005 | Biedermann et al. |
| 6,921,403 | B2 | 7/2005 | Cragg et al. |
| 6,923,811 | B1 | 8/2005 | Carl et al. |
| 6,923,830 | B2 | 8/2005 | Michelson |
| 6,926,658 | B2 | 8/2005 | Farnan |
| 6,926,737 | B2 | 8/2005 | Jackson |
| 6,929,606 | B2 | 8/2005 | Ritland |
| 6,929,640 | B1 | 8/2005 | Underwood et al. |
| 6,932,817 | B2 | 8/2005 | Baynham et al. |
| 6,932,820 | B2 | 8/2005 | Osman |
| 6,936,071 | B1 | 8/2005 | Marnay et al. |
| 6,945,933 | B2 | 9/2005 | Branch et al. |
| 6,945,972 | B2 | 9/2005 | Frigg et al. |
| 6,945,973 | B2 | 9/2005 | Bray |
| 6,945,975 | B2 | 9/2005 | Dalton |
| 6,947,967 | B2 | 9/2005 | Ferris et al. |
| 6,949,100 | B1 | 9/2005 | Venturini |
| 6,949,105 | B2 | 9/2005 | Bryan et al. |
| 6,951,538 | B2 | 10/2005 | Ritland |
| 6,951,561 | B2 | 10/2005 | Warren et al. |
| 6,953,462 | B2 | 10/2005 | Lieberman |
| 6,953,477 | B2 | 10/2005 | Berry |
| 6,955,677 | B2 | 10/2005 | Dahners |
| 6,958,065 | B2 | 10/2005 | Ueyama et al. |
| 6,964,664 | B2 | 11/2005 | Freid et al. |
| 6,964,665 | B2 | 11/2005 | Thomas et al. |
| 6,964,666 | B2 | 11/2005 | Jackson |
| 6,964,667 | B2 | 11/2005 | Shaolian et al. |
| 6,964,687 | B1 | 11/2005 | Bernard et al. |
| 6,966,910 | B2 | 11/2005 | Ritland |
| 6,966,929 | B2 | 11/2005 | Mitchell |
| 6,972,019 | B2 | 12/2005 | Michelson |
| 6,972,035 | B2 | 12/2005 | Michelson |
| 6,974,460 | B2 | 12/2005 | Carbone et al. |
| 6,979,334 | B2 | 12/2005 | Dalton |
| 6,980,862 | B2 | 12/2005 | Fredricks et al. |
| 6,981,973 | B2 | 1/2006 | McKinley |
| 6,981,975 | B2 | 1/2006 | Michelson |
| 6,984,234 | B2 | 1/2006 | Bray |
| 6,984,245 | B2 | 1/2006 | McGahan et al. |
| 6,986,771 | B2 | 1/2006 | Paul et al. |
| 6,986,772 | B2 | 1/2006 | Michelson |
| 6,989,011 | B2 | 1/2006 | Paul et al. |
| 6,989,044 | B2 | 1/2006 | Zhang et al. |
| 6,991,632 | B2 | 1/2006 | Ritland |
| 6,991,654 | B2 | 1/2006 | Foley |
| 6,994,688 | B2 | 2/2006 | Brauckman et al. |
| 6,997,929 | B2 | 2/2006 | Manzi et al. |
| 6,997,941 | B2 | 2/2006 | Sharkey et al. |
| 7,001,385 | B2 | 2/2006 | Bonutti |
| 7,001,432 | B2 | 2/2006 | Keller et al. |
| 7,004,947 | B2 | 2/2006 | Shluzas et al. |
| RE39,035 | E | 3/2006 | Finn et al. |
| 7,008,422 | B2 | 3/2006 | Foley et al. |
| 7,008,424 | B2 | 3/2006 | Teitelbaum |
| 7,008,426 | B2 | 3/2006 | Paul |
| 7,008,453 | B1 | 3/2006 | Michelson |
| 7,011,619 | B1 | 3/2006 | Lewis et al. |
| 7,011,658 | B2 | 3/2006 | Young |
| 7,011,660 | B2 | 3/2006 | Sherman et al. |
| 7,014,608 | B2 | 3/2006 | Larson et al. |
| 7,014,633 | B2 | 3/2006 | Cragg |
| 7,018,378 | B2 | 3/2006 | Biedermann et al. |
| 7,018,379 | B2 | 3/2006 | Drewry et al. |
| 7,018,412 | B2 | 3/2006 | Ferreira et al. |
| 7,018,415 | B1 | 3/2006 | McKay |
| 7,018,416 | B2 | 3/2006 | Hanson et al. |
| 7,022,122 | B2 | 4/2006 | Amrein et al. |
| 7,025,716 | B1 | 4/2006 | Meloul et al. |
| 7,025,787 | B2 | 4/2006 | Bryan et al. |
| 7,029,472 | B1 | 4/2006 | Fortin |
| 7,029,475 | B2 | 4/2006 | Panjabi |
| 7,033,362 | B2 | 4/2006 | McGahan et al. |
| RE39,089 | E | 5/2006 | Ralph et al. |
| 7,037,339 | B2 | 5/2006 | Houfburg |
| 7,041,135 | B2 | 5/2006 | Michelson |
| 7,041,136 | B2 | 5/2006 | Goble et al. |
| 7,044,971 | B2 | 5/2006 | Suddaby |
| 7,048,736 | B2 | 5/2006 | Robinson et al. |
| 7,052,497 | B2 | 5/2006 | Sherman et al. |
| 7,056,321 | B2 | 6/2006 | Pagliuca et al. |
| 7,056,344 | B2 | 6/2006 | Huppert et al. |
| 7,060,066 | B2 | 6/2006 | Zhao et al. |
| 7,060,097 | B2 | 6/2006 | Fraser et al. |
| 7,063,702 | B2 | 6/2006 | Michelson |
| 7,066,062 | B2 | 6/2006 | Flesher |
| 7,066,937 | B2 | 6/2006 | Shluzas |
| 7,066,961 | B2 | 6/2006 | Michelson |
| 7,070,598 | B2 | 7/2006 | Lim et al. |
| 7,074,237 | B2 | 7/2006 | Goble et al. |
| 7,081,116 | B1 | 7/2006 | Carly |
| 7,083,621 | B2 | 8/2006 | Shaolian et al. |
| 7,083,622 | B2 | 8/2006 | Simonson |
| 7,083,625 | B2 | 8/2006 | Berry |
| 7,083,649 | B2 | 8/2006 | Zucherman et al. |
| 7,087,057 | B2 | 8/2006 | Konieczynski et al. |
| 7,087,058 | B2 | 8/2006 | Cragg |
| 7,087,083 | B2 | 8/2006 | Pasquet et al. |
| 7,090,674 | B2 | 8/2006 | Doubler et al. |
| 7,090,679 | B2 | 8/2006 | Saint-Martin et al. |
| 7,090,680 | B2 | 8/2006 | Bonati et al. |
| 7,094,242 | B2 | 8/2006 | Ralph et al. |
| 7,094,258 | B2 | 8/2006 | Lambrecht et al. |
| 7,097,648 | B1 | 8/2006 | Globerman et al. |
| 7,101,375 | B2 | 9/2006 | Zucherman et al. |
| 7,101,399 | B2 | 9/2006 | Errico et al. |
| 7,105,024 | B2 | 9/2006 | Richelsoph |
| 7,108,698 | B2 | 9/2006 | Robbins et al. |
| 7,112,206 | B2 | 9/2006 | Michelson |
| 7,118,576 | B2 | 10/2006 | Gitis et al. |
| 7,118,579 | B2 | 10/2006 | Michelson |
| 7,118,580 | B1 | 10/2006 | Beyersdorff et al. |
| 7,118,598 | B2 | 10/2006 | Michelson |
| 7,121,755 | B2 | 10/2006 | Schlapfer et al. |
| 7,122,629 | B2 | 10/2006 | Bejanin et al. |
| 7,125,410 | B2 | 10/2006 | Freudiger |
| 7,125,425 | B2 | 10/2006 | Simonton et al. |

(56) References Cited

U.S. PATENT DOCUMENTS 7,125,426 B2 10/2006 Moumene et al.
7,128,743 B2 10/2006 Metz-Stavenhagen
7,128,760 B2 10/2006 Michelson
7,128,761 B2 10/2006 Kuras et al.
7,137,985 B2 11/2006 Jahng
7,137,986 B2 11/2006 Troxell et al.
7,141,051 B2 11/2006 Janowski et al.
7,144,396 B2 12/2006 Shluzas
7,144,397 B2 12/2006 Lambrecht et al.
7,147,599 B2 12/2006 Phillips et al.
7,150,714 B2 12/2006 Myles
7,153,281 B2 12/2006 Holmes
7,153,325 B2 12/2006 Kim et al.
7,156,806 B2 1/2007 Dobrovolny
7,160,300 B2 1/2007 Jackson
7,163,538 B2 1/2007 Altarac et al.
7,163,539 B2 1/2007 Abdelgany et al.
7,163,558 B2 1/2007 Senegas et al.
7,163,561 B2 1/2007 Michelson
7,166,073 B2 1/2007 Ritland
7,166,107 B2 1/2007 Anderson
7,166,108 B2 1/2007 Mazda et al.
7,166,121 B2 1/2007 Reiley et al.
7,169,183 B2 1/2007 Liu et al.
7,179,261 B2 2/2007 Sicvol et al.
7,182,729 B2 2/2007 Abdelgany et al.
7,186,255 B2 3/2007 Baynham et al.
7,188,626 B2 3/2007 Foley et al.
7,198,644 B2 4/2007 Schultz et al.
7,201,751 B2 4/2007 Zucherman et al.
7,204,851 B2 4/2007 Trieu et al.
7,204,852 B2 4/2007 Marnay et al.
7,204,853 B2 4/2007 Gordon et al.
7,207,949 B2 4/2007 Miles et al.
7,207,991 B2 4/2007 Michelson
7,207,992 B2 4/2007 Ritland
7,211,085 B2 5/2007 Michelson
7,211,086 B2 5/2007 Biedermann et al.
7,211,087 B2 5/2007 Young
7,211,112 B2 5/2007 Baynham et al.
7,214,186 B2 5/2007 Ritland
7,214,227 B2 5/2007 Colleran et al.
7,217,291 B2 5/2007 Zucherman et al.
7,223,268 B2 5/2007 Biedermann
7,223,289 B2 5/2007 Trieu et al.
7,227,477 B2 6/2007 Ye
7,229,441 B2 6/2007 Trieu et al.
7,232,441 B2 6/2007 Altarac et al.
7,232,463 B2 6/2007 Falahee
7,232,464 B2 6/2007 Mathieu et al.
7,235,048 B2 6/2007 Rein et al.
7,235,105 B2 6/2007 Jackson
7,241,297 B2 7/2007 Shaolian et al.
7,250,052 B2 7/2007 Landry et al.
7,252,673 B2 8/2007 Lim
7,264,621 B2 9/2007 Coates et al.
7,270,665 B2 9/2007 Morrison et al.
7,273,496 B2 9/2007 Mitchell
7,276,081 B1 10/2007 Coates et al.
7,276,082 B2 10/2007 Zdeblick et al.
7,282,063 B2 10/2007 Cohen et al.
7,282,064 B2 10/2007 Chin
7,282,065 B2 10/2007 Kirschman
7,285,121 B2 10/2007 Braun et al.
7,291,149 B1 11/2007 Michelson
7,291,151 B2 11/2007 Alvarez
7,291,152 B2 11/2007 Abdou
7,291,153 B2 11/2007 Glascott
7,294,128 B2 11/2007 Alleyne et al.
7,294,129 B2 11/2007 Hawkins et al.
7,300,441 B2 11/2007 Haid et al.
7,303,563 B2 12/2007 Poyner et al.
7,306,603 B2 12/2007 Boehm, Jr. et al.
7,306,604 B2 12/2007 Carli
7,306,606 B2 12/2007 Sasing
7,306,628 B2 12/2007 Zucherman et al.
7,309,338 B2 12/2007 Cragg
7,311,734 B2 12/2007 Hoeck et al.
7,314,467 B2 1/2008 Howland
7,316,684 B1 1/2008 Baccelli et al.
7,316,714 B2 1/2008 Gordon et al.
7,318,817 B2 1/2008 Hamada
7,318,840 B2 1/2008 Mckay
7,322,979 B2 1/2008 Crandall et al.
7,326,216 B2 2/2008 Bertagnoli et al.
7,329,258 B2 2/2008 Studer
7,331,961 B2 2/2008 Abdou
7,331,995 B2 2/2008 Eisermann et al.
7,335,201 B2 2/2008 Doubler et al.
7,335,202 B2 2/2008 Matthis et al.
7,335,203 B2 2/2008 Winslow et al.
7,338,490 B2 3/2008 Ogilvie et al.
7,338,491 B2 3/2008 Baker et al.
7,338,527 B2 3/2008 Blatt et al.
7,341,587 B2 3/2008 Molz et al.
7,347,874 B2 3/2008 Disilvestro
7,361,179 B2 4/2008 Rousseau et al.
7,361,196 B2 4/2008 Fallin et al.
7,374,534 B2 5/2008 Dalton
7,377,921 B2 5/2008 Studer et al.
7,377,942 B2 5/2008 Berry
7,396,328 B2 7/2008 Penenberg
7,396,360 B2 7/2008 Lieberman
7,410,501 B2 8/2008 Michelson
7,419,505 B2 9/2008 Fleischmann et al.
7,431,735 B2 10/2008 Liu et al.
7,435,262 B2 10/2008 Michelson
7,442,209 B2 10/2008 Michelson
7,445,635 B2 11/2008 Fallin et al.
7,445,637 B2 11/2008 Taylor
7,455,639 B2 11/2008 Ritland
7,455,685 B2 11/2008 Justis
7,465,306 B2 12/2008 Pond, Jr. et al.
7,473,223 B2 1/2009 Fetzer
7,473,276 B2 1/2009 Aebi et al.
7,476,228 B2 1/2009 Abdou
7,476,238 B2 1/2009 Panjabi
7,479,160 B2 1/2009 Branch et al.
7,485,132 B1 2/2009 McBride et al.
7,491,205 B1 2/2009 Michelson
7,491,208 B2 2/2009 Pond, Jr. et al.
7,494,508 B2 2/2009 Zeegers
7,497,859 B2 3/2009 Zucherman et al.
7,503,918 B2 3/2009 Baccelli et al.
7,503,933 B2 3/2009 Michelson
7,520,888 B2 4/2009 Trieu
7,527,640 B2 5/2009 Ziolo et al.
7,534,265 B1 5/2009 Boyd et al.
7,537,565 B2 5/2009 Bass
7,537,616 B1 5/2009 Branch et al.
7,540,882 B2 6/2009 Michelson
7,547,308 B2 6/2009 Bertagnoli et al.
7,547,325 B2 6/2009 Biedermann et al.
7,556,639 B2 7/2009 Rothman et al.
7,559,930 B2 7/2009 Allard et al.
7,559,942 B2 7/2009 Paul et al.
7,563,274 B2 7/2009 Justis et al.
7,563,283 B2 7/2009 Kwak
7,566,345 B1 7/2009 Fallin et al.
7,569,014 B2 8/2009 Bass et al.
7,572,276 B2 8/2009 Lim et al.
7,575,580 B2 8/2009 Lim et al.
7,575,587 B2 8/2009 Rezach et al.
7,578,820 B2 8/2009 Moore et al.
7,578,822 B2 8/2009 Rezach et al.
7,578,834 B2 8/2009 Abdou et al.
7,578,849 B2 8/2009 Trieu
7,582,058 B1 9/2009 Miles et al.
7,582,107 B2 9/2009 Trail et al.
7,585,316 B2 9/2009 Trieu
7,588,537 B2 9/2009 Bass
7,588,579 B2 9/2009 Mommaerts
7,588,589 B2 9/2009 Falahee
7,588,593 B2 9/2009 Aferzon

(56) References Cited

U.S. PATENT DOCUMENTS 7,591,839 B2 9/2009 Biedermann et al.
7,591,851 B2 9/2009 Winslow et al.
7,594,919 B2 9/2009 Peterman
7,594,931 B2 9/2009 Louis et al.
7,594,932 B2 9/2009 Aferzon et al.
7,597,694 B2 10/2009 Lim et al.
7,601,166 B2 10/2009 Biedermann et al.
7,601,170 B2 10/2009 Winslow et al.
7,604,643 B2 10/2009 Ciccone et al.
7,604,654 B2 10/2009 Fallin et al.
7,611,518 B2 11/2009 Walder et al.
7,618,423 B1 11/2009 Valentine et al.
7,618,443 B2 11/2009 Abdou
7,618,455 B2 11/2009 Goble et al.
7,618,456 B2 11/2009 Mathieu et al.
7,621,912 B2 11/2009 Harms et al.
7,621,939 B2 11/2009 Zucherman et al.
7,621,940 B2 11/2009 Harms et al.
7,621,942 B2 11/2009 Piehl
7,621,953 B2 11/2009 Braddock et al.
7,621,955 B2 11/2009 Goble et al.
7,621,957 B2 11/2009 Errico et al.
7,625,379 B2 12/2009 Puno et al.
7,625,380 B2 * 12/2009 Drewry .................. A61F 2/447
606/90
7,625,393 B2 12/2009 Fallin et al.
7,625,396 B2 12/2009 Jackson
7,628,799 B2 12/2009 Richelsoph et al.
7,632,292 B2 12/2009 Sengupta et al.
7,635,366 B2 12/2009 Abdou
7,635,371 B2 12/2009 McGahan et al.
7,641,673 B2 1/2010 Le et al.
7,641,690 B2 1/2010 Abdou
7,641,693 B2 1/2010 Gutlin et al.
7,645,281 B2 1/2010 Marik
7,651,515 B2 1/2010 Mack et al.
7,654,954 B1 2/2010 Phillips et al.
7,655,026 B2 2/2010 Justis et al.
7,655,027 B2 2/2010 Michelson
7,655,028 B2 2/2010 Kirschman
7,655,042 B2 2/2010 Foley et al.
7,658,739 B2 2/2010 Shluzas
7,658,752 B2 2/2010 Labrom et al.
7,658,766 B2 2/2010 Melkent et al.
7,682,375 B2 3/2010 Ritland
7,682,396 B2 3/2010 Beaurain et al.
7,686,809 B2 3/2010 Triplett et al.
7,691,057 B2 4/2010 Miles et al.
7,691,129 B2 4/2010 Felix
7,695,496 B2 4/2010 Labrom et al.
7,695,498 B2 4/2010 Ritland
7,695,514 B2 4/2010 Kwak
7,695,516 B2 4/2010 Zeegers
7,695,517 B2 4/2010 Benzel et al.
7,704,271 B2 4/2010 Abdou
7,708,743 B2 5/2010 Anderson et al.
7,708,765 B2 5/2010 Carl et al.
7,722,618 B2 5/2010 Estes et al.
7,727,233 B2 6/2010 Blackwell et al.
7,727,280 B2 6/2010 McLuen
7,738,968 B2 6/2010 Bleich
7,744,635 B2 6/2010 Sweeney et al.
7,749,231 B2 7/2010 Bonvallet et al.
7,749,251 B2 7/2010 Obenchain et al.
7,749,252 B2 7/2010 Zucherman et al.
7,749,269 B2 7/2010 Peterman et al.
7,749,270 B2 7/2010 Peterman
7,749,274 B2 7/2010 Razian
7,753,844 B2 7/2010 Sharratt et al.
7,753,937 B2 7/2010 Chervitz et al.
7,753,938 B2 7/2010 Aschmann et al.
7,753,958 B2 7/2010 Gordon et al.
7,758,274 B2 7/2010 Paul
7,758,501 B2 7/2010 Frasier et al.
7,758,644 B2 7/2010 Trieu et al.
7,758,645 B2 7/2010 Studer et al.
7,758,648 B2 7/2010 Castleman et al.
7,763,074 B2 7/2010 Altarac et al.
7,763,078 B2 7/2010 Peterman et al.
7,766,918 B2 8/2010 Allard et al.
7,771,432 B2 8/2010 Schwab et al.
7,771,473 B2 8/2010 Thramann
7,771,475 B2 8/2010 Michelson
7,776,049 B1 8/2010 Curran et al.
7,776,067 B2 8/2010 Jackson
7,776,090 B2 8/2010 Winslow et al.
7,780,670 B2 8/2010 Bonutti
7,780,732 B2 8/2010 Abernathie et al.
7,789,914 B2 9/2010 Michelson
7,794,501 B2 9/2010 Edie et al.
7,799,053 B2 9/2010 Haid, Jr. et al.
7,799,081 B2 9/2010 McKinley
7,806,911 B2 10/2010 Peckham
7,806,913 B2 10/2010 Fanger et al.
7,811,326 B2 10/2010 Braddock, Jr. et al.
7,815,683 B2 10/2010 Melkent et al.
7,819,801 B2 10/2010 Miles et al.
7,819,903 B2 10/2010 Fraser et al.
7,824,445 B2 11/2010 Biro et al.
7,828,807 B2 11/2010 Lehuec et al.
7,828,847 B2 11/2010 Abdou
7,828,849 B2 11/2010 Lim
7,837,688 B2 11/2010 Boyer, II et al.
7,837,714 B2 11/2010 Drewry et al.
7,837,732 B2 11/2010 Zucherman et al.
7,837,734 B2 11/2010 Zucherman et al.
7,842,074 B2 11/2010 Abdou
7,846,186 B2 12/2010 Taylor
7,846,207 B2 12/2010 Lechmann et al.
7,850,608 B2 12/2010 Hamada
7,850,731 B2 12/2010 Brittan et al.
7,850,732 B2 12/2010 Heinz
7,850,733 B2 12/2010 Baynham et al.
7,854,752 B2 12/2010 Colleran et al.
7,857,818 B2 12/2010 Trieu et al.
7,857,833 B2 12/2010 Abdou
7,862,588 B2 1/2011 Abdou et al.
7,871,426 B2 1/2011 Chin et al.
7,875,034 B2 1/2011 Josse et al.
7,875,076 B2 1/2011 Mathieu et al.
7,875,078 B2 1/2011 Wysocki et al.
7,879,074 B2 2/2011 Kwak et al.
7,883,532 B2 2/2011 Biscup et al.
7,883,542 B2 2/2011 Zipnick et al.
7,887,591 B2 2/2011 Aebi et al.
7,892,173 B2 2/2011 Miles et al.
7,892,174 B2 2/2011 Hestad et al.
7,892,261 B2 2/2011 Bonutti
7,892,286 B2 2/2011 Michelson
7,901,409 B2 3/2011 Canaveral et al.
7,901,458 B2 3/2011 DeRidder et al.
7,905,840 B2 3/2011 Pimenta et al.
7,905,886 B1 3/2011 Curran et al.
7,909,829 B2 3/2011 Patel et al.
7,909,848 B2 3/2011 Patel et al.
7,909,870 B2 3/2011 Kraus
7,909,871 B2 3/2011 Abdou
7,914,558 B2 3/2011 Landry et al.
7,918,792 B2 4/2011 Drzyzga et al.
7,922,658 B2 4/2011 Cohen et al.
7,922,745 B2 4/2011 Hestad et al.
7,922,750 B2 4/2011 Trautwein et al.
7,927,337 B2 4/2011 Keller
7,931,589 B2 4/2011 Cohen et al.
7,931,674 B2 4/2011 Zucherman et al.
7,935,134 B2 5/2011 Reglos et al.
7,935,147 B2 5/2011 Wales
7,935,149 B2 5/2011 Michelson
7,938,848 B2 5/2011 Sweeney
7,946,982 B2 5/2011 Hamada
7,951,153 B2 5/2011 Abdou et al.
7,951,198 B2 5/2011 Sucec et al.
7,955,390 B2 6/2011 Fallin et al.
7,955,392 B2 6/2011 Dewey et al.

(56) References Cited

U.S. PATENT DOCUMENTS

| | | | |
|---|---|---|---|
| 7,959,564 | B2 | 6/2011 | Ritland |
| 7,959,677 | B2 | 6/2011 | Landry et al. |
| 7,972,363 | B2 | 7/2011 | Moskowitz et al. |
| 7,976,566 | B2 | 7/2011 | Michelson |
| 7,981,031 | B2 | 7/2011 | Frasier et al. |
| 7,985,258 | B2 | 7/2011 | Zdeblick et al. |
| 7,988,699 | B2 | 8/2011 | Martz et al. |
| 8,002,802 | B2 | 8/2011 | Abdou |
| 8,002,833 | B2 | 8/2011 | Fabris et al. |
| 8,002,842 | B2 | 8/2011 | Ronk |
| 8,012,207 | B2 | 9/2011 | Kim |
| 8,021,393 | B2 | 9/2011 | Seifert et al. |
| 8,021,401 | B2 | 9/2011 | Carl et al. |
| 8,021,429 | B2 | 9/2011 | Viker |
| 8,025,680 | B2 | 9/2011 | Hayes et al. |
| 8,025,697 | B2 | 9/2011 | McClellan, III et al. |
| 8,034,109 | B2 | 10/2011 | Zwirkoski |
| 8,034,110 | B2 | 10/2011 | Garner et al. |
| 8,038,716 | B2 | 10/2011 | Duggal et al. |
| 8,043,334 | B2 | 10/2011 | Fisher et al. |
| 8,043,343 | B2 | 10/2011 | Miller et al. |
| 8,043,376 | B2 | 10/2011 | Falahee |
| 8,043,380 | B1 | 10/2011 | Park et al. |
| 8,048,120 | B1 | 11/2011 | Fallin et al. |
| 8,062,299 | B2 | 11/2011 | McGahan et al. |
| 8,062,336 | B2 | 11/2011 | Triplett et al. |
| 8,062,337 | B2 | 11/2011 | Bruneau et al. |
| 8,066,710 | B2 | 11/2011 | Estes et al. |
| 8,066,714 | B2 | 11/2011 | Shipp et al. |
| 8,066,741 | B2 | 11/2011 | Fallin et al. |
| 8,066,742 | B2 | 11/2011 | Anderson et al. |
| 8,066,749 | B2 | 11/2011 | Winslow et al. |
| 8,070,749 | B2 | 12/2011 | Stern |
| 8,070,816 | B2 | 12/2011 | Taylor |
| 8,075,593 | B2 | 12/2011 | Hess |
| 8,075,618 | B2 | 12/2011 | Trieu et al. |
| 8,075,621 | B2 | 12/2011 | Michelson |
| 8,080,046 | B2 | 12/2011 | Suddaby |
| 8,083,798 | B2 | 12/2011 | Allard et al. |
| 8,097,018 | B2 | 1/2012 | Malandain et al. |
| 8,100,828 | B2 | 1/2012 | Frey et al. |
| 8,100,978 | B2 | 1/2012 | Bass |
| 8,105,358 | B2 | 1/2012 | Phan |
| 8,114,131 | B2 | 2/2012 | Kohm et al. |
| 8,123,807 | B2 | 2/2012 | Kim |
| 8,128,659 | B2 | 3/2012 | Ginsberg et al. |
| 8,128,664 | B2 | 3/2012 | Pasquet |
| 8,137,284 | B2 | 3/2012 | Miles et al. |
| 8,142,479 | B2 | 3/2012 | Hess |
| 8,157,840 | B2 | 4/2012 | Zucherman et al. |
| 8,163,026 | B2 | 4/2012 | Gray |
| 8,167,887 | B2 | 5/2012 | McLean |
| 8,167,908 | B2 | 5/2012 | Ely et al. |
| 8,167,915 | B2 | 5/2012 | Ferree et al. |
| 8,167,946 | B2 | 5/2012 | Michelson |
| 8,167,949 | B2 | 5/2012 | Tyber et al. |
| 8,172,855 | B2 | 5/2012 | Abdou |
| 8,182,423 | B2 | 5/2012 | Miles et al. |
| 8,192,358 | B2 | 6/2012 | Leahy |
| 8,197,488 | B2 | 6/2012 | Sorrenti et al. |
| 8,197,514 | B2 | 6/2012 | Maas et al. |
| 8,197,522 | B2 | 6/2012 | Park et al. |
| 8,206,420 | B2 | 6/2012 | Patel et al. |
| 8,216,312 | B2 | 7/2012 | Gray |
| 8,226,690 | B2 | 7/2012 | Altarac et al. |
| 8,231,623 | B1 | 7/2012 | Jordan |
| 8,241,329 | B2 | 8/2012 | Abdou |
| 8,241,330 | B2 | 8/2012 | Lamborne et al. |
| 8,241,359 | B2 | 8/2012 | Davis et al. |
| 8,241,362 | B2 | 8/2012 | Voorhies |
| 8,251,997 | B2 | 8/2012 | Michelson |
| 8,268,004 | B2 | 9/2012 | Castleman et al. |
| 8,273,005 | B2 | 9/2012 | Abdou et al. |
| 8,277,489 | B2 | 10/2012 | Saidha et al. |
| 8,287,569 | B1 | 10/2012 | Powell |
| 8,292,896 | B2 | 10/2012 | Abdou et al. |
| 8,303,629 | B1 | 11/2012 | Abdou |
| 8,303,630 | B2 | 11/2012 | Abdou et al. |
| 8,303,660 | B1 | 11/2012 | Abdou |
| 8,308,776 | B2 | 11/2012 | Abdou et al. |
| 8,308,804 | B2 | 11/2012 | Krueger |
| 8,343,046 | B2 | 1/2013 | Miles et al. |
| 8,343,190 | B1 | 1/2013 | Mueller et al. |
| 8,349,012 | B2 | 1/2013 | Mckay |
| 8,353,826 | B2 | 1/2013 | Weiman et al. |
| 8,361,108 | B2 | 1/2013 | Gold et al. |
| 8,382,801 | B2 | 2/2013 | Lamborne et al. |
| 8,388,660 | B1 | 3/2013 | Abdou |
| 8,388,687 | B2 | 3/2013 | Gimbel et al. |
| 8,397,522 | B2 | 3/2013 | Springer et al. |
| 8,398,689 | B2 | 3/2013 | Abdou |
| 8,403,959 | B2 | 3/2013 | Doellinger |
| 8,409,208 | B2 | 4/2013 | Abdou |
| 8,419,738 | B2 | 4/2013 | Smisson, III et al. |
| 8,419,772 | B2 | 4/2013 | Thompson et al. |
| 8,425,602 | B2 | 4/2013 | Guyer et al. |
| 8,435,268 | B2 | 5/2013 | Thompson et al. |
| 8,435,269 | B2 | 5/2013 | Woolley et al. |
| 8,439,953 | B2 | 5/2013 | Mitchell et al. |
| 8,454,621 | B2 | 6/2013 | Deridder et al. |
| 8,454,661 | B2 | 6/2013 | Rathbun et al. |
| 8,454,694 | B2 | 6/2013 | Armstrong et al. |
| 8,465,547 | B2 | 6/2013 | Melkent et al. |
| RE44,380 | E | 7/2013 | De et al. |
| 8,475,497 | B2 | 7/2013 | Grizzard |
| 8,480,712 | B1 | 7/2013 | Samuel et al. |
| 8,480,747 | B2 | 7/2013 | Melkent et al. |
| 8,486,147 | B2 | 7/2013 | De et al. |
| 8,491,471 | B2 | 7/2013 | Deshmukh et al. |
| 8,500,814 | B2 | 8/2013 | Abdou |
| 8,506,629 | B2 | 8/2013 | Weiland |
| 8,512,343 | B2 | 8/2013 | Dziedzic et al. |
| 8,529,611 | B2 | 9/2013 | Champagne et al. |
| 8,545,538 | B2 | 10/2013 | Abdou et al. |
| 8,562,650 | B2 | 10/2013 | Dace |
| 8,568,453 | B2 | 10/2013 | Abdou et al. |
| 8,574,267 | B2 | 11/2013 | Linares |
| 8,603,143 | B2 | 12/2013 | Robinson |
| 8,623,055 | B2 | 1/2014 | Abdou |
| 8,623,088 | B1 | 1/2014 | Tohmeh et al. |
| 8,636,655 | B1 | 1/2014 | Childs |
| 8,636,772 | B2 | 1/2014 | Schmierer et al. |
| 8,657,855 | B2 | 2/2014 | Zhang |
| 8,663,331 | B2 | 3/2014 | McClellan, III et al. |
| 8,673,013 | B2 | 3/2014 | Abdou |
| 8,685,065 | B1 | 4/2014 | Taber et al. |
| 8,685,093 | B2 | 4/2014 | Anderson et al. |
| 8,690,917 | B2 | 4/2014 | Suh et al. |
| 8,690,950 | B2 | 4/2014 | Refai et al. |
| 8,696,709 | B2 | 4/2014 | Dinville et al. |
| 8,696,751 | B2 | 4/2014 | Ashley et al. |
| 8,702,756 | B2 | 4/2014 | Reimels |
| 8,721,686 | B2 | 5/2014 | Gordon et al. |
| 8,721,689 | B2 | 5/2014 | Butler et al. |
| 8,764,806 | B2 | 7/2014 | Abdou |
| 8,771,318 | B2 | 7/2014 | Triplett et al. |
| 8,771,355 | B2 | 7/2014 | Abdou |
| 8,771,360 | B2 | 7/2014 | Jimenez et al. |
| 8,795,335 | B1 | 8/2014 | Abdou et al. |
| 8,795,375 | B2 | 8/2014 | Malberg |
| 8,801,757 | B2 | 8/2014 | Abdou et al. |
| 8,808,379 | B2 | 8/2014 | Abdou et al. |
| 8,827,900 | B1 | 9/2014 | Pimenta |
| 8,828,055 | B2 | 9/2014 | Blain et al. |
| 8,828,056 | B2 | 9/2014 | Buss et al. |
| 8,828,061 | B2 | 9/2014 | Scrantz et al. |
| 8,845,688 | B2 | 9/2014 | Abdou et al. |
| 8,845,696 | B1 | 9/2014 | Abdou |
| 8,845,701 | B2 | 9/2014 | Abdou |
| 8,845,728 | B1 | 9/2014 | Abdou |
| 8,870,920 | B2 | 10/2014 | Abdou et al. |
| 8,876,874 | B2 | 11/2014 | Abdou et al. |
| 8,876,904 | B2 | 11/2014 | Pimenta et al. |
| 8,900,137 | B1 | 12/2014 | Lovell et al. |

(56) References Cited

U.S. PATENT DOCUMENTS

| | | | |
|---|---|---|---|
| 8,906,092 | B2 | 12/2014 | Abdou |
| 8,911,441 | B2 | 12/2014 | Dace et al. |
| 8,940,019 | B2 | 1/2015 | Gordon et al. |
| 8,940,051 | B2 | 1/2015 | Gimbel et al. |
| 8,940,052 | B2 | 1/2015 | Lechmann et al. |
| 8,956,415 | B2 | 2/2015 | Cowan |
| 8,974,381 | B1 | 3/2015 | Lovell et al. |
| 8,974,461 | B2 | 3/2015 | Abdou |
| 8,998,905 | B2 | 4/2015 | Marik et al. |
| 9,005,248 | B2 | 4/2015 | Taber et al. |
| 9,011,538 | B2 | 4/2015 | Allard et al. |
| 9,044,280 | B1 | 6/2015 | Arambula et al. |
| 9,060,816 | B2 | 6/2015 | Abdou |
| 9,060,873 | B2 | 6/2015 | Abdou |
| 9,101,491 | B2 | 8/2015 | Rodgers et al. |
| 9,107,705 | B2 | 8/2015 | Abdou et al. |
| 9,113,853 | B1 | 8/2015 | Casey et al. |
| 9,135,059 | B2 | 9/2015 | Ballard et al. |
| 9,179,903 | B2 | 11/2015 | Cianfrani et al. |
| 9,198,767 | B2 | 12/2015 | Abdou |
| 9,211,147 | B2 | 12/2015 | Gordon et al. |
| 9,247,968 | B2 | 2/2016 | Taber et al. |
| 9,265,526 | B1 | 2/2016 | Abdou |
| 9,308,099 | B2 | 4/2016 | Triplett et al. |
| 9,314,350 | B1 | 4/2016 | Abdou |
| 9,320,506 | B2 | 4/2016 | Bertagnoli et al. |
| 9,320,610 | B2 | 4/2016 | Alheidt et al. |
| 9,320,617 | B2 | 4/2016 | Abdou et al. |
| 9,345,464 | B2 | 5/2016 | Abdou et al. |
| 9,364,338 | B2 | 6/2016 | Malberg |
| 9,375,239 | B2 | 6/2016 | Abdou |
| 9,408,596 | B2 | 8/2016 | Blain |
| 9,408,717 | B2 | 8/2016 | Perrow et al. |
| 9,445,918 | B1 | 9/2016 | Lin et al. |
| 9,451,940 | B2 | 9/2016 | Spann |
| 9,486,328 | B2 | 11/2016 | Jimenez et al. |
| 9,610,176 | B1 | 4/2017 | Abdou |
| 9,622,795 | B2 | 4/2017 | Reitblat et al. |
| 9,655,505 | B1 | 5/2017 | Gharib et al. |
| 9,675,389 | B2 | 6/2017 | Abdou |
| 9,687,356 | B1 | 6/2017 | Spangler et al. |
| 9,687,357 | B2 | 6/2017 | Bannigan et al. |
| 9,717,601 | B2 | 8/2017 | Miller |
| 9,730,737 | B2 | 8/2017 | Baynham et al. |
| 9,730,802 | B1 | 8/2017 | Harvey |
| 9,795,367 | B1 | 10/2017 | Lee et al. |
| 9,795,370 | B2 | 10/2017 | O'Connell et al. |
| RE46,647 | E | 12/2017 | Messerli et al. |
| 9,867,714 | B1 | 1/2018 | Abdou |
| 9,901,458 | B1 | 2/2018 | Abdou |
| 9,937,052 | B2 | 4/2018 | Abdou et al. |
| 10,092,330 | B2 | 10/2018 | Abdou et al. |
| 10,111,757 | B2 | 10/2018 | Abdou et al. |
| 10,166,018 | B2 | 1/2019 | Hunt et al. |
| 10,188,529 | B2 | 1/2019 | Abdou |
| 10,426,450 | B2 | 10/2019 | Vogel et al. |
| 10,470,892 | B2 | 11/2019 | Abdou |
| 10,543,107 | B2 | 1/2020 | Abdou |
| 10,548,740 | B1 | 2/2020 | Abdou |
| 10,575,961 | B1 | 3/2020 | Abdou |
| 10,610,380 | B2 | 4/2020 | Abdou |
| 10,695,105 | B2 | 6/2020 | Abdou |
| 10,744,000 | B1 | 8/2020 | Abdou |
| 10,857,003 | B1 | 12/2020 | Abdou |
| 10,857,004 | B2 | 12/2020 | Abdou |
| 10,918,498 | B2 | 2/2021 | Abdou |
| 10,945,861 | B2 | 3/2021 | Abdou |
| 10,973,648 | B1 | 4/2021 | Abdou |
| 11,006,982 | B2 | 5/2021 | Abdou |
| 11,058,548 | B1 | 7/2021 | Abdou |
| 11,096,799 | B2 | 8/2021 | Abdou |
| 11,179,248 | B2 | 11/2021 | Abdou et al. |
| 11,246,718 | B2 | 2/2022 | Abdou |
| 11,259,935 | B1 | 3/2022 | Abdou |
| 2001/0001129 | A1 | 5/2001 | McKay et al. |
| 2001/0012938 | A1 | 8/2001 | Zucherman et al. |
| 2001/0021850 | A1 | 9/2001 | Zucherman et al. |
| 2001/0031965 | A1 | 10/2001 | Zucherman et al. |
| 2001/0039452 | A1 | 11/2001 | Zucherman et al. |
| 2001/0047172 | A1 | 11/2001 | Foley et al. |
| 2001/0053914 | A1 | 12/2001 | Landry et al. |
| 2001/0056219 | A1 | 12/2001 | Brauckman et al. |
| 2002/0016595 | A1 | 2/2002 | Michelson |
| 2002/0019626 | A1 | 2/2002 | Sharkey et al. |
| 2002/0019637 | A1 | 2/2002 | Frey et al. |
| 2002/0026101 | A1 | 2/2002 | Bookwalter et al. |
| 2002/0032484 | A1 | 3/2002 | Hyde |
| 2002/0045899 | A1 | 4/2002 | Errico et al. |
| 2002/0045904 | A1 | 4/2002 | Fuss et al. |
| 2002/0045945 | A1 | 4/2002 | Liu et al. |
| 2002/0049394 | A1 | 4/2002 | Roy et al. |
| 2002/0049444 | A1 | 4/2002 | Knox |
| 2002/0049446 | A1 | 4/2002 | Harkey et al. |
| 2002/0055738 | A1 | 5/2002 | Lieberman |
| 2002/0055741 | A1 | 5/2002 | Schlapfer et al. |
| 2002/0058944 | A1 | 5/2002 | Michelson |
| 2002/0065558 | A1 | 5/2002 | Varga et al. |
| 2002/0077530 | A1 | 6/2002 | Velikaris et al. |
| 2002/0082602 | A1 | 6/2002 | Biedermann et al. |
| 2002/0082700 | A1 | 6/2002 | Bianchi et al. |
| 2002/0099386 | A1 | 7/2002 | Beger et al. |
| 2002/0111628 | A1 | 8/2002 | Ralph et al. |
| 2002/0120268 | A1 | 8/2002 | Berger |
| 2002/0128713 | A1 | 9/2002 | Ferree |
| 2002/0138146 | A1 | 9/2002 | Jackson |
| 2002/0143328 | A1 | 10/2002 | Shluzas et al. |
| 2002/0143332 | A1 | 10/2002 | Lin et al. |
| 2002/0143341 | A1 | 10/2002 | Biedermann et al. |
| 2002/0147449 | A1 | 10/2002 | Yun |
| 2002/0161368 | A1 | 10/2002 | Foley et al. |
| 2002/0165550 | A1 | 11/2002 | Frey et al. |
| 2002/0165612 | A1 | 11/2002 | Gerber et al. |
| 2002/0169450 | A1 | 11/2002 | Lange |
| 2002/0169453 | A1 | 11/2002 | Berger |
| 2002/0183748 | A1 | 12/2002 | Martin et al. |
| 2002/0183755 | A1 | 12/2002 | Michelson |
| 2002/0183761 | A1 | 12/2002 | Johnson et al. |
| 2002/0183848 | A1 | 12/2002 | Ray et al. |
| 2002/0188296 | A1 | 12/2002 | Michelson |
| 2003/0000350 | A1 | 1/2003 | Zhao et al. |
| 2003/0004572 | A1 | 1/2003 | Goble et al. |
| 2003/0014068 | A1 | 1/2003 | Bonutti et al. |
| 2003/0014123 | A1 | 1/2003 | Copf et al. |
| 2003/0018389 | A1 | 1/2003 | Castro et al. |
| 2003/0023240 | A1 | 1/2003 | Amrein et al. |
| 2003/0023243 | A1 | 1/2003 | Biedermann et al. |
| 2003/0023305 | A1 | 1/2003 | McKay |
| 2003/0023306 | A1 | 1/2003 | Liu et al. |
| 2003/0023308 | A1 | 1/2003 | Leroux et al. |
| 2003/0028251 | A1 | 2/2003 | Mathews |
| 2003/0040746 | A1 | 2/2003 | Mitchell et al. |
| 2003/0040798 | A1 | 2/2003 | Michelson |
| 2003/0045878 | A1 | 3/2003 | Petit et al. |
| 2003/0045935 | A1 | 3/2003 | Angelucci et al. |
| 2003/0055430 | A1 | 3/2003 | Kim |
| 2003/0060826 | A1 | 3/2003 | Foley et al. |
| 2003/0065330 | A1 | 4/2003 | Zucherman et al. |
| 2003/0065395 | A1 | 4/2003 | Ralph et al. |
| 2003/0065396 | A1 | 4/2003 | Michelson |
| 2003/0073997 | A1 | 4/2003 | Doubler et al. |
| 2003/0074001 | A1 | 4/2003 | Apfelbaum et al. |
| 2003/0074005 | A1 | 4/2003 | Roth et al. |
| 2003/0078583 | A1 | 4/2003 | Biedermann et al. |
| 2003/0078662 | A1 | 4/2003 | Ralph et al. |
| 2003/0078664 | A1 | 4/2003 | Ralph et al. |
| 2003/0083747 | A1 | 5/2003 | Winterbottom et al. |
| 2003/0088251 | A1 | 5/2003 | Braun et al. |
| 2003/0093153 | A1 | 5/2003 | Banick et al. |
| 2003/0094812 | A1 | 5/2003 | Balsells |
| 2003/0100896 | A1 | 5/2003 | Biedermann et al. |
| 2003/0105460 | A1 | 6/2003 | Crandall et al. |
| 2003/0109880 | A1 | 6/2003 | Shirado et al. |
| 2003/0114852 | A1 | 6/2003 | Biedermann et al. |
| 2003/0125741 | A1 | 7/2003 | Biedermann et al. |

(56) References Cited

U.S. PATENT DOCUMENTS

| | | | |
|---|---|---|---|
| 2003/0125742 | A1 | 7/2003 | Yuan et al. |
| 2003/0139813 | A1 | 7/2003 | Messerli et al. |
| 2003/0149341 | A1 | 8/2003 | Clifton |
| 2003/0149431 | A1 | 8/2003 | Varieur |
| 2003/0149432 | A1 | 8/2003 | Frigg et al. |
| 2003/0149484 | A1 | 8/2003 | Michelson |
| 2003/0153911 | A1 | 8/2003 | Shluzas |
| 2003/0153913 | A1 | 8/2003 | Altarac et al. |
| 2003/0163133 | A1 | 8/2003 | Altarac et al. |
| 2003/0163199 | A1 | 8/2003 | Boehm et al. |
| 2003/0167058 | A1 | 9/2003 | Shluzas |
| 2003/0171749 | A1 | 9/2003 | Le et al. |
| 2003/0171751 | A1 | 9/2003 | Ritland |
| 2003/0176862 | A1 | 9/2003 | Taylor et al. |
| 2003/0176864 | A1 | 9/2003 | Ueyama et al. |
| 2003/0176923 | A1 | 9/2003 | Keller et al. |
| 2003/0181975 | A1 | 9/2003 | Ishii et al. |
| 2003/0187436 | A1 | 10/2003 | Bolger et al. |
| 2003/0187510 | A1 | 10/2003 | Hyde |
| 2003/0191470 | A1 | 10/2003 | Ritland |
| 2003/0195518 | A1 | 10/2003 | Cragg |
| 2003/0195633 | A1 | 10/2003 | Hyde |
| 2003/0199873 | A1 | 10/2003 | Richelsoph |
| 2003/0199981 | A1 | 10/2003 | Ferree |
| 2003/0208202 | A1 | 11/2003 | Falahee |
| 2003/0208203 | A1 | 11/2003 | Lim et al. |
| 2003/0208204 | A1 | 11/2003 | Bailey et al. |
| 2003/0208273 | A1 | 11/2003 | Eisermann et al. |
| 2003/0212398 | A1 | 11/2003 | Jackson |
| 2003/0216735 | A1 | 11/2003 | Altarac et al. |
| 2003/0216736 | A1 | 11/2003 | Robinson et al. |
| 2003/0216737 | A1 | 11/2003 | Biscup |
| 2003/0217809 | A1 | 11/2003 | Morishige |
| 2003/0220642 | A1 | 11/2003 | Freudiger |
| 2003/0220643 | A1 | 11/2003 | Ferree |
| 2003/0225408 | A1 | 12/2003 | Nichols et al. |
| 2003/0229347 | A1 | 12/2003 | Sherman et al. |
| 2003/0233136 | A1 | 12/2003 | Williams et al. |
| 2003/0236472 | A1 | 12/2003 | Van et al. |
| 2003/0236572 | A1 | 12/2003 | Bertram |
| 2004/0002708 | A1 | 1/2004 | Ritland |
| 2004/0006342 | A1 | 1/2004 | Altarac et al. |
| 2004/0006391 | A1 | 1/2004 | Reiley |
| 2004/0010253 | A1 | 1/2004 | Morrison |
| 2004/0012938 | A1 | 1/2004 | Sylvester et al. |
| 2004/0018228 | A1 | 1/2004 | Fischell et al. |
| 2004/0019263 | A1 | 1/2004 | Jutras et al. |
| 2004/0030338 | A1 | 2/2004 | Paul |
| 2004/0030346 | A1 | 2/2004 | Frey et al. |
| 2004/0039387 | A1 | 2/2004 | Gause et al. |
| 2004/0044412 | A1 | 3/2004 | Lambrecht et al. |
| 2004/0049189 | A1 | 3/2004 | Le et al. |
| 2004/0049190 | A1 | 3/2004 | Biedermann et al. |
| 2004/0049271 | A1 | 3/2004 | Biedermann et al. |
| 2004/0049280 | A1 | 3/2004 | Cauthen |
| 2004/0054412 | A1 | 3/2004 | Gerbec et al. |
| 2004/0059318 | A1 | 3/2004 | Zhang et al. |
| 2004/0068261 | A1 | 4/2004 | Fourcault et al. |
| 2004/0068318 | A1 | 4/2004 | Coates et al. |
| 2004/0073215 | A1 | 4/2004 | Carli |
| 2004/0073216 | A1 | 4/2004 | Lieberman |
| 2004/0078079 | A1 | 4/2004 | Foley |
| 2004/0078082 | A1 | 4/2004 | Lange |
| 2004/0087947 | A1 | 5/2004 | Lim et al. |
| 2004/0087948 | A1 | 5/2004 | Suddaby |
| 2004/0087949 | A1 | 5/2004 | Bono et al. |
| 2004/0087952 | A1 | 5/2004 | Borgstrom et al. |
| 2004/0092930 | A1 | 5/2004 | Petit et al. |
| 2004/0092933 | A1 | 5/2004 | Shaolian et al. |
| 2004/0092934 | A1 | 5/2004 | Howland |
| 2004/0093083 | A1 | 5/2004 | Branch et al. |
| 2004/0097933 | A1 | 5/2004 | Lourdel et al. |
| 2004/0097935 | A1 | 5/2004 | Richelsoph et al. |
| 2004/0097940 | A1 | 5/2004 | Paul |
| 2004/0098129 | A1 | 5/2004 | Lin |
| 2004/0102780 | A1 | 5/2004 | West |
| 2004/0106927 | A1 | 6/2004 | Ruffner et al. |
| 2004/0106995 | A1 | 6/2004 | Le et al. |
| 2004/0106996 | A1 | 6/2004 | Liu et al. |
| 2004/0111136 | A1 | 6/2004 | Sharkey et al. |
| 2004/0111141 | A1 | 6/2004 | Brabec et al. |
| 2004/0116929 | A1 | 6/2004 | Barker et al. |
| 2004/0116965 | A1 | 6/2004 | Falkenberg |
| 2004/0122518 | A1 | 6/2004 | Rhoda |
| 2004/0127963 | A1 | 7/2004 | Uchida et al. |
| 2004/0127990 | A1 | 7/2004 | Bartish et al. |
| 2004/0127994 | A1 | 7/2004 | Kast et al. |
| 2004/0133207 | A1 | 7/2004 | Abdou |
| 2004/0138662 | A1 | 7/2004 | Landry et al. |
| 2004/0138671 | A1 | 7/2004 | Zander et al. |
| 2004/0143264 | A1 | 7/2004 | McAfee |
| 2004/0143265 | A1 | 7/2004 | Landry et al. |
| 2004/0143270 | A1 | 7/2004 | Zucherman et al. |
| 2004/0143332 | A1 | 7/2004 | Krueger et al. |
| 2004/0147928 | A1 | 7/2004 | Landry et al. |
| 2004/0147929 | A1 | 7/2004 | Biedermann et al. |
| 2004/0153065 | A1 | 8/2004 | Lim |
| 2004/0153070 | A1 | 8/2004 | Barker et al. |
| 2004/0158247 | A1 | 8/2004 | Sitiso et al. |
| 2004/0158254 | A1 | 8/2004 | Eisermann |
| 2004/0162558 | A1 | 8/2004 | Hegde et al. |
| 2004/0162560 | A1 | 8/2004 | Raynor et al. |
| 2004/0167520 | A1 | 8/2004 | Zucherman et al. |
| 2004/0167625 | A1 | 8/2004 | Beyar et al. |
| 2004/0167626 | A1 | 8/2004 | Geremakis et al. |
| 2004/0172022 | A1 | 9/2004 | Landry et al. |
| 2004/0172025 | A1 | 9/2004 | Drewry et al. |
| 2004/0172134 | A1 | 9/2004 | Berry |
| 2004/0176766 | A1 | 9/2004 | Shluzas |
| 2004/0181226 | A1 | 9/2004 | Michelson |
| 2004/0181285 | A1 | 9/2004 | Simonson |
| 2004/0186473 | A1 | 9/2004 | Cournoyer et al. |
| 2004/0186572 | A1 | 9/2004 | Lange et al. |
| 2004/0193151 | A1 | 9/2004 | To et al. |
| 2004/0193159 | A1 | 9/2004 | Zucherman et al. |
| 2004/0195089 | A1 | 10/2004 | O'Brien |
| 2004/0204712 | A1 | 10/2004 | Kolb et al. |
| 2004/0204713 | A1 | 10/2004 | Abdou |
| 2004/0210216 | A1 | 10/2004 | Farris et al. |
| 2004/0215190 | A1 | 10/2004 | Nguyen et al. |
| 2004/0220567 | A1 | 11/2004 | Eisermann et al. |
| 2004/0220670 | A1 | 11/2004 | Eisermann et al. |
| 2004/0220671 | A1 | 11/2004 | Ralph et al. |
| 2004/0225289 | A1 | 11/2004 | Biedermann et al. |
| 2004/0225291 | A1 | 11/2004 | Schwammberger et al. |
| 2004/0225364 | A1 | 11/2004 | Richelsoph et al. |
| 2004/0225365 | A1 | 11/2004 | Eisermann et al. |
| 2004/0225366 | A1 | 11/2004 | Eisermann et al. |
| 2004/0230309 | A1 | 11/2004 | DiMauro et al. |
| 2004/0236327 | A1 | 11/2004 | Paul et al. |
| 2004/0236328 | A1 | 11/2004 | Paul et al. |
| 2004/0236329 | A1 | 11/2004 | Panjabi |
| 2004/0236330 | A1 | 11/2004 | Purcell et al. |
| 2004/0236333 | A1 | 11/2004 | Lin |
| 2004/0236425 | A1 | 11/2004 | Huang |
| 2004/0243240 | A1 | 12/2004 | Beaurain et al. |
| 2004/0249377 | A1 | 12/2004 | Kaes et al. |
| 2004/0249379 | A1 | 12/2004 | Winslow et al. |
| 2004/0249380 | A1 | 12/2004 | Glascott |
| 2004/0249461 | A1 | 12/2004 | Ferree |
| 2004/0254574 | A1 | 12/2004 | Morrison et al. |
| 2004/0254575 | A1 | 12/2004 | Obenchain et al. |
| 2004/0260283 | A1 | 12/2004 | Wu et al. |
| 2004/0260291 | A1 | 12/2004 | Jensen |
| 2004/0267264 | A1 | 12/2004 | Konieczynski et al. |
| 2004/0267369 | A1 | 12/2004 | Lyons et al. |
| 2005/0004573 | A1 | 1/2005 | Abdou |
| 2005/0010227 | A1 | 1/2005 | Paul |
| 2005/0010291 | A1 | 1/2005 | Stinson et al. |
| 2005/0010301 | A1 | 1/2005 | Disilvestro et al. |
| 2005/0012506 | A1 | 1/2005 | Yudahira |
| 2005/0015149 | A1 | 1/2005 | Michelson |
| 2005/0021029 | A1 | 1/2005 | Trieu et al. |
| 2005/0021031 | A1 | 1/2005 | Foley et al. |

(56) References Cited

U.S. PATENT DOCUMENTS

| | | | |
|---|---|---|---|
| 2005/0021040 | A1 | 1/2005 | Bertagnoli |
| 2005/0021041 | A1 | 1/2005 | Michelson |
| 2005/0027296 | A1 | 2/2005 | Thramann et al. |
| 2005/0027360 | A1 | 2/2005 | Webb et al. |
| 2005/0033296 | A1 | 2/2005 | Bono et al. |
| 2005/0033298 | A1 | 2/2005 | Hawkes et al. |
| 2005/0033431 | A1 | 2/2005 | Gordon et al. |
| 2005/0033432 | A1 | 2/2005 | Gordon et al. |
| 2005/0033434 | A1 | 2/2005 | Berry |
| 2005/0038432 | A1 | 2/2005 | Shaolian et al. |
| 2005/0038511 | A1 | 2/2005 | Martz et al. |
| 2005/0043800 | A1 | 2/2005 | Paul et al. |
| 2005/0043802 | A1 | 2/2005 | Eisermann et al. |
| 2005/0049705 | A1 | 3/2005 | Hale et al. |
| 2005/0049708 | A1 | 3/2005 | Atkinson et al. |
| 2005/0055026 | A1 | 3/2005 | Biedermann et al. |
| 2005/0055031 | A1 | 3/2005 | Lim |
| 2005/0065514 | A1 | 3/2005 | Studer |
| 2005/0065515 | A1 | 3/2005 | Jahng |
| 2005/0065516 | A1 | 3/2005 | Jahng |
| 2005/0065517 | A1 | 3/2005 | Chin |
| 2005/0069701 | A1 | 3/2005 | Watanabe et al. |
| 2005/0070899 | A1 | 3/2005 | Doubler et al. |
| 2005/0070901 | A1 | 3/2005 | David |
| 2005/0070917 | A1 | 3/2005 | Justis |
| 2005/0071007 | A1 | 3/2005 | Malek |
| 2005/0075636 | A1 | 4/2005 | Gotzen |
| 2005/0080320 | A1 | 4/2005 | Lee et al. |
| 2005/0080415 | A1 | 4/2005 | Keyer et al. |
| 2005/0085812 | A1 | 4/2005 | Sherman et al. |
| 2005/0085813 | A1 | 4/2005 | Spitler et al. |
| 2005/0085815 | A1 | 4/2005 | Harms et al. |
| 2005/0085816 | A1 | 4/2005 | Michelson |
| 2005/0085909 | A1 | 4/2005 | Eisermann |
| 2005/0096652 | A1 | 5/2005 | Burton |
| 2005/0096653 | A1 | 5/2005 | Doubler et al. |
| 2005/0096654 | A1 | 5/2005 | Lin |
| 2005/0096745 | A1 | 5/2005 | Andre et al. |
| 2005/0107788 | A1 | 5/2005 | Beaurain et al. |
| 2005/0113830 | A1 | 5/2005 | Rezach et al. |
| 2005/0113833 | A1 | 5/2005 | Davison |
| 2005/0113927 | A1 | 5/2005 | Malek |
| 2005/0113928 | A1 | 5/2005 | Cragg et al. |
| 2005/0119663 | A1 | 6/2005 | Keyer et al. |
| 2005/0119747 | A1 | 6/2005 | Fabris et al. |
| 2005/0119748 | A1 | 6/2005 | Reiley et al. |
| 2005/0124991 | A1 | 6/2005 | Jahng |
| 2005/0125061 | A1 | 6/2005 | Zucherman et al. |
| 2005/0125066 | A1 | 6/2005 | McAfee |
| 2005/0126576 | A1 | 6/2005 | Ferree |
| 2005/0131404 | A1 | 6/2005 | Mazda et al. |
| 2005/0131406 | A1 | 6/2005 | Reiley et al. |
| 2005/0131407 | A1 | 6/2005 | Sicvol et al. |
| 2005/0131409 | A1 | 6/2005 | Chervitz et al. |
| 2005/0131413 | A1 | 6/2005 | O'Driscoll et al. |
| 2005/0131420 | A1 | 6/2005 | Techiera et al. |
| 2005/0131421 | A1 | 6/2005 | Anderson et al. |
| 2005/0137597 | A1 | 6/2005 | Butler et al. |
| 2005/0137604 | A1 | 6/2005 | Assell et al. |
| 2005/0143737 | A1 | 6/2005 | Pafford et al. |
| 2005/0143822 | A1 | 6/2005 | Paul |
| 2005/0143823 | A1 | 6/2005 | Boyd et al. |
| 2005/0149020 | A1 | 7/2005 | Jahng |
| 2005/0149023 | A1 | 7/2005 | Ritland |
| 2005/0149035 | A1 | 7/2005 | Pimenta et al. |
| 2005/0149188 | A1 | 7/2005 | Cook et al. |
| 2005/0149196 | A1 | 7/2005 | Zucherman et al. |
| 2005/0154389 | A1 | 7/2005 | Selover et al. |
| 2005/0154390 | A1 | 7/2005 | Biedermann et al. |
| 2005/0154391 | A1 | 7/2005 | Doherty et al. |
| 2005/0154461 | A1 | 7/2005 | Humphreys et al. |
| 2005/0159750 | A1 | 7/2005 | Doherty |
| 2005/0159756 | A1 | 7/2005 | Ray |
| 2005/0159813 | A1 | 7/2005 | Molz, IV |
| 2005/0159815 | A1 | 7/2005 | Kamimura et al. |
| 2005/0165396 | A1 | 7/2005 | Fortin et al. |
| 2005/0165398 | A1 | 7/2005 | Reiley |
| 2005/0165400 | A1 | 7/2005 | Fernandez |
| 2005/0165487 | A1 | 7/2005 | Muhanna et al. |
| 2005/0171540 | A1 | 8/2005 | Lim et al. |
| 2005/0171541 | A1 | 8/2005 | Boehm et al. |
| 2005/0171543 | A1 | 8/2005 | Timm et al. |
| 2005/0171608 | A1 | 8/2005 | Peterman et al. |
| 2005/0171609 | A1 | 8/2005 | Humphreys et al. |
| 2005/0171610 | A1 | 8/2005 | Humphreys et al. |
| 2005/0177156 | A1 | 8/2005 | Timm et al. |
| 2005/0177157 | A1 | 8/2005 | Jahng |
| 2005/0177163 | A1 | 8/2005 | Abdou et al. |
| 2005/0177164 | A1 | 8/2005 | Walters et al. |
| 2005/0177166 | A1 | 8/2005 | Timm et al. |
| 2005/0177167 | A1 | 8/2005 | Muckter |
| 2005/0177209 | A1 | 8/2005 | Leung et al. |
| 2005/0177210 | A1 | 8/2005 | Leung et al. |
| 2005/0177211 | A1 | 8/2005 | Leung et al. |
| 2005/0177240 | A1 | 8/2005 | Blain |
| 2005/0182401 | A1 | 8/2005 | Timm et al. |
| 2005/0182404 | A1 | 8/2005 | Lauryssen et al. |
| 2005/0187548 | A1 | 8/2005 | Butler et al. |
| 2005/0187555 | A1 | 8/2005 | Biedermann et al. |
| 2005/0187628 | A1 | 8/2005 | Michelson |
| 2005/0192571 | A1 | 9/2005 | Abdelgany |
| 2005/0192577 | A1 | 9/2005 | Mosca et al. |
| 2005/0192580 | A1 | 9/2005 | Dalton |
| 2005/0192589 | A1 | 9/2005 | Raymond et al. |
| 2005/0192671 | A1 | 9/2005 | Bao et al. |
| 2005/0197660 | A1 | 9/2005 | Haid et al. |
| 2005/0197702 | A1 | 9/2005 | Coppes et al. |
| 2005/0203511 | A1 | 9/2005 | Wilson-MacDonald et al. |
| 2005/0203512 | A1 | 9/2005 | Hawkins et al. |
| 2005/0203513 | A1 | 9/2005 | Jahng et al. |
| 2005/0203514 | A1 | 9/2005 | Jahng et al. |
| 2005/0203516 | A1 | 9/2005 | Biedermann et al. |
| 2005/0203517 | A1 | 9/2005 | Jahng et al. |
| 2005/0203518 | A1 | 9/2005 | Biedermann et al. |
| 2005/0203519 | A1 | 9/2005 | Harms et al. |
| 2005/0203533 | A1 | 9/2005 | Ferguson et al. |
| 2005/0203604 | A1 | 9/2005 | Brabec et al. |
| 2005/0203624 | A1 | 9/2005 | Serhan et al. |
| 2005/0209694 | A1 | 9/2005 | Loeb |
| 2005/0215999 | A1 | 9/2005 | Birkmeyer et al. |
| 2005/0216001 | A1 | 9/2005 | David |
| 2005/0216003 | A1 | 9/2005 | Biedermann et al. |
| 2005/0216083 | A1 | 9/2005 | Michelson |
| 2005/0222682 | A1 | 10/2005 | Link et al. |
| 2005/0222683 | A1 | 10/2005 | Berry |
| 2005/0228376 | A1 | 10/2005 | Boomer et al. |
| 2005/0228377 | A1 | 10/2005 | Chao et al. |
| 2005/0228395 | A1 | 10/2005 | Auxepaules et al. |
| 2005/0228400 | A1 | 10/2005 | Chao et al. |
| 2005/0228501 | A1 | 10/2005 | Miller et al. |
| 2005/0234449 | A1 | 10/2005 | Aferzon |
| 2005/0234450 | A1 | 10/2005 | Barker |
| 2005/0234451 | A1 | 10/2005 | Markworth |
| 2005/0234452 | A1 | 10/2005 | Malandain |
| 2005/0234453 | A1 | 10/2005 | Shaolian et al. |
| 2005/0234454 | A1 | 10/2005 | Chin |
| 2005/0234456 | A1 | 10/2005 | Malandain |
| 2005/0234555 | A1 | 10/2005 | Sutton et al. |
| 2005/0240181 | A1 | 10/2005 | Boomer et al. |
| 2005/0240183 | A1 | 10/2005 | Vaughan |
| 2005/0240265 | A1 | 10/2005 | Kuiper et al. |
| 2005/0240273 | A1 | 10/2005 | Khandkar et al. |
| 2005/0245928 | A1 | 11/2005 | Colleran et al. |
| 2005/0245930 | A1 | 11/2005 | Timm et al. |
| 2005/0251137 | A1 | 11/2005 | Ball |
| 2005/0251139 | A1 | 11/2005 | Roh |
| 2005/0251140 | A1 | 11/2005 | Shaolian et al. |
| 2005/0251141 | A1 | 11/2005 | Frigg et al. |
| 2005/0251258 | A1 | 11/2005 | Jackson |
| 2005/0256576 | A1 | 11/2005 | Moskowitz et al. |
| 2005/0256578 | A1 | 11/2005 | Blatt et al. |
| 2005/0260058 | A1 | 11/2005 | Cassagne, III |
| 2005/0261685 | A1 | 11/2005 | Fortin et al. |
| 2005/0261687 | A1 | 11/2005 | Garamszegi et al. |

(56) References Cited

U.S. PATENT DOCUMENTS

2005/0261768 A1 11/2005 Trieu
2005/0267470 A1 12/2005 McBride
2005/0267471 A1 12/2005 Biedermann et al.
2005/0267474 A1 12/2005 Dalton
2005/0267477 A1 12/2005 Jackson
2005/0267579 A1 12/2005 Reiley et al.
2005/0267580 A1 12/2005 Suddaby
2005/0273099 A1 12/2005 Baccelli et al.
2005/0273101 A1 12/2005 Schumacher
2005/0273120 A1 12/2005 Abdou et al.
2005/0273171 A1 12/2005 Gordon et al.
2005/0277919 A1 12/2005 Slivka et al.
2005/0277921 A1 12/2005 Eisermann et al.
2005/0277922 A1 12/2005 Trieu et al.
2005/0277923 A1 12/2005 Sweeney
2005/0277924 A1 12/2005 Roychowdhury
2005/0277925 A1 12/2005 Mujwid
2005/0277927 A1 12/2005 Guenther et al.
2005/0277928 A1 12/2005 Boschert
2005/0277931 A1 12/2005 Sweeney et al.
2005/0277934 A1 12/2005 Vardiman
2005/0278026 A1 12/2005 Gordon et al.
2005/0283152 A1 12/2005 Lindemann et al.
2005/0283153 A1 12/2005 Poyner et al.
2005/0283157 A1 12/2005 Coates et al.
2005/0283236 A1 12/2005 Razian
2005/0283238 A1 12/2005 Reiley
2005/0283241 A1 12/2005 Keller et al.
2005/0283244 A1 12/2005 Gordon et al.
2005/0283245 A1 12/2005 Gordon et al.
2005/0288669 A1 12/2005 Abdou et al.
2005/0288670 A1 12/2005 Panjabi et al.
2005/0288671 A1 12/2005 Yuan et al.
2005/0288672 A1 12/2005 Ferree
2005/0288673 A1 12/2005 Catbagan et al.
2006/0004357 A1 1/2006 Lee et al.
2006/0004359 A1 1/2006 Kramer et al.
2006/0004360 A1 1/2006 Kramer et al.
2006/0004363 A1 1/2006 Brockmeyer et al.
2006/0004367 A1 1/2006 Alamin et al.
2006/0004453 A1 1/2006 Bartish et al.
2006/0009767 A1 1/2006 Kiester
2006/0009768 A1 1/2006 Ritland
2006/0009769 A1 1/2006 Lieberman
2006/0009770 A1 1/2006 Speirs et al.
2006/0009775 A1 1/2006 Dec et al.
2006/0009780 A1 1/2006 Foley et al.
2006/0009846 A1 1/2006 Trieu et al.
2006/0015099 A1 1/2006 Cannon et al.
2006/0015104 A1 1/2006 Dalton
2006/0015181 A1 1/2006 Elberg
2006/0015183 A1 1/2006 Gilbert et al.
2006/0020342 A1 1/2006 Ferree et al.
2006/0024614 A1 2/2006 Williamson
2006/0025767 A1 2/2006 Khalili
2006/0025768 A1 2/2006 Iott et al.
2006/0025770 A1 2/2006 Schlapfer et al.
2006/0030839 A1 2/2006 Park et al.
2006/0030850 A1 2/2006 Keegan et al.
2006/0030943 A1 2/2006 Peterman
2006/0036240 A1 2/2006 Colleran et al.
2006/0036242 A1 2/2006 Nilsson et al.
2006/0036244 A1 2/2006 Spitler et al.
2006/0036246 A1 2/2006 Carl et al.
2006/0036250 A1 2/2006 Lange et al.
2006/0036252 A1 2/2006 Baynham et al.
2006/0036254 A1 2/2006 Lim
2006/0036255 A1 2/2006 Pond, Jr. et al.
2006/0036256 A1 2/2006 Carl et al.
2006/0036258 A1 2/2006 Zucherman et al.
2006/0036259 A1 2/2006 Carl et al.
2006/0036260 A1 2/2006 Runco et al.
2006/0036323 A1 2/2006 Carl et al.
2006/0036324 A1 2/2006 Sachs et al.
2006/0041259 A1 2/2006 Paul et al.
2006/0052780 A1 3/2006 Errico et al.
2006/0052783 A1 3/2006 Dant et al.
2006/0052784 A1 3/2006 Dant et al.
2006/0052786 A1 3/2006 Dant et al.
2006/0052870 A1 3/2006 Ferree
2006/0052872 A1 3/2006 Studer et al.
2006/0058788 A1 3/2006 Hammer et al.
2006/0058790 A1 3/2006 Carl et al.
2006/0058791 A1 3/2006 Broman et al.
2006/0058800 A1 3/2006 Ainsworth et al.
2006/0058878 A1 3/2006 Michelson
2006/0064090 A1 3/2006 Park
2006/0064091 A1 3/2006 Ludwig et al.
2006/0064092 A1 3/2006 Howland
2006/0064095 A1 3/2006 Senn et al.
2006/0069315 A1 3/2006 Miles et al.
2006/0069390 A1 3/2006 Frigg et al.
2006/0069436 A1 3/2006 Sutton et al.
2006/0069438 A1 3/2006 Zucherman et al.
2006/0074419 A1 4/2006 Taylor et al.
2006/0074445 A1 4/2006 Gerber et al.
2006/0074488 A1 4/2006 Abdou et al.
2006/0079894 A1 4/2006 Colleran et al.
2006/0079895 A1 4/2006 Mcleer
2006/0079896 A1 4/2006 Kwak et al.
2006/0079898 A1 4/2006 Ainsworth et al.
2006/0079899 A1 4/2006 Ritland
2006/0079903 A1 4/2006 Wong
2006/0079905 A1 4/2006 Beyar et al.
2006/0084844 A1 4/2006 Nehls
2006/0084976 A1 4/2006 Borgstrom et al.
2006/0084977 A1 4/2006 Lieberman
2006/0084981 A1 4/2006 Shluzas
2006/0084982 A1 4/2006 Kim
2006/0084983 A1 4/2006 Kim
2006/0084984 A1 4/2006 Kim
2006/0084985 A1 4/2006 Kim
2006/0084986 A1 4/2006 Grinberg et al.
2006/0084987 A1 4/2006 Kim
2006/0084988 A1 4/2006 Kim
2006/0084989 A1 4/2006 Dickinson et al.
2006/0084991 A1 4/2006 Borgstrom et al.
2006/0084993 A1 4/2006 Landry et al.
2006/0084995 A1 4/2006 Biedermann et al.
2006/0085069 A1 4/2006 Kim
2006/0085076 A1 4/2006 Krishna et al.
2006/0088398 A1 4/2006 Lund
2006/0089643 A1 4/2006 Mujwid
2006/0089644 A1 4/2006 Felix
2006/0089646 A1 4/2006 Bonutti
2006/0089647 A1 4/2006 Culbert et al.
2006/0089656 A1 4/2006 Allard et al.
2006/0089718 A1 4/2006 Zucherman et al.
2006/0095037 A1 5/2006 Jones et al.
2006/0106380 A1 5/2006 Colleran et al.
2006/0106381 A1 5/2006 Ferree et al.
2006/0106383 A1 5/2006 Biedermann et al.
2006/0106387 A1 5/2006 Fanger et al.
2006/0106395 A1 5/2006 Link et al.
2006/0106397 A1 5/2006 Lins
2006/0111714 A1 5/2006 Foley
2006/0111715 A1 5/2006 Jackson
2006/0111728 A1 5/2006 Abdou
2006/0116677 A1 6/2006 Burd et al.
2006/0116768 A1 6/2006 Krueger et al.
2006/0122597 A1 6/2006 Jones et al.
2006/0122599 A1 6/2006 Drewry et al.
2006/0122604 A1 6/2006 Gorhan et al.
2006/0122607 A1 6/2006 Kolb
2006/0122625 A1 6/2006 Truckai et al.
2006/0122701 A1 6/2006 Kiester
2006/0129147 A1 6/2006 Biedermann et al.
2006/0129149 A1 6/2006 Iott et al.
2006/0129239 A1 6/2006 Kwak
2006/0129244 A1 6/2006 Ensign
2006/0136060 A1 6/2006 Taylor
2006/0136062 A1 6/2006 Dinello et al.
2006/0142758 A1 6/2006 Petit
2006/0142760 A1 6/2006 McDonnell

(56) References Cited

U.S. PATENT DOCUMENTS

| | | | |
|---|---|---|---|
| 2006/0142761 | A1 | 6/2006 | Landry et al. |
| 2006/0142858 | A1 | 6/2006 | Colleran et al. |
| 2006/0149228 | A1 | 7/2006 | Schlapfer et al. |
| 2006/0149229 | A1 | 7/2006 | Kwak et al. |
| 2006/0149232 | A1 | 7/2006 | Sasing |
| 2006/0149234 | A1 | 7/2006 | De |
| 2006/0149238 | A1 | 7/2006 | Sherman et al. |
| 2006/0149240 | A1 | 7/2006 | Jackson |
| 2006/0149241 | A1 | 7/2006 | Richelsoph et al. |
| 2006/0149244 | A1 | 7/2006 | Amrein et al. |
| 2006/0149245 | A1 | 7/2006 | Sweeney |
| 2006/0149278 | A1 | 7/2006 | Abdou |
| 2006/0149284 | A1 | 7/2006 | McCormack et al. |
| 2006/0149385 | A1 | 7/2006 | McKay |
| 2006/0155277 | A1 | 7/2006 | Metz-Stavenhagen |
| 2006/0155278 | A1 | 7/2006 | Warnick |
| 2006/0155284 | A1 | 7/2006 | Doherty et al. |
| 2006/0161152 | A1 | 7/2006 | Ensign et al. |
| 2006/0161154 | A1 | 7/2006 | McAfee |
| 2006/0167454 | A1 | 7/2006 | Ludwig et al. |
| 2006/0167455 | A1 | 7/2006 | Clement et al. |
| 2006/0173454 | A1 | 8/2006 | Spitler et al. |
| 2006/0173456 | A1 | 8/2006 | Hawkes et al. |
| 2006/0178746 | A1 | 8/2006 | Bartish, Jr. et al. |
| 2006/0184112 | A1 | 8/2006 | Horn et al. |
| 2006/0184171 | A1 | 8/2006 | Biedermann et al. |
| 2006/0184180 | A1 | 8/2006 | Augostino et al. |
| 2006/0184247 | A1 | 8/2006 | Edidin et al. |
| 2006/0187562 | A1 | 8/2006 | Mounnarat et al. |
| 2006/0189983 | A1 | 8/2006 | Fallin et al. |
| 2006/0189984 | A1 | 8/2006 | Fallin et al. |
| 2006/0189985 | A1 | 8/2006 | Lewis |
| 2006/0189999 | A1 | 8/2006 | Zwirkoski |
| 2006/0190082 | A1 | 8/2006 | Keller et al. |
| 2006/0190083 | A1 | 8/2006 | Arnin et al. |
| 2006/0195089 | A1 | 8/2006 | Lehuec et al. |
| 2006/0195090 | A1 | 8/2006 | Suddaby |
| 2006/0195093 | A1 | 8/2006 | Jahng |
| 2006/0195096 | A1 | 8/2006 | Lee et al. |
| 2006/0195098 | A1 | 8/2006 | Schumacher |
| 2006/0195102 | A1 | 8/2006 | Malandain |
| 2006/0195192 | A1 | 8/2006 | Gordon et al. |
| 2006/0200121 | A1 | 9/2006 | Mowery |
| 2006/0200128 | A1 | 9/2006 | Mueller |
| 2006/0200130 | A1 | 9/2006 | Hawkins et al. |
| 2006/0200131 | A1 | 9/2006 | Chao et al. |
| 2006/0200132 | A1 | 9/2006 | Chao et al. |
| 2006/0200135 | A1 | 9/2006 | Sherman et al. |
| 2006/0200138 | A1 | 9/2006 | Michelson |
| 2006/0200139 | A1 | 9/2006 | Michelson |
| 2006/0200149 | A1 | 9/2006 | Hoy et al. |
| 2006/0210494 | A1 | 9/2006 | Rabiei et al. |
| 2006/0212033 | A1 | 9/2006 | Rothman et al. |
| 2006/0212034 | A1 | 9/2006 | Triplett et al. |
| 2006/0217710 | A1 | 9/2006 | Abdou |
| 2006/0217712 | A1 | 9/2006 | Mueller et al. |
| 2006/0217713 | A1 | 9/2006 | Serhan et al. |
| 2006/0217714 | A1 | 9/2006 | Serhan et al. |
| 2006/0217716 | A1 | 9/2006 | Baker et al. |
| 2006/0217719 | A1 | 9/2006 | Albert et al. |
| 2006/0217731 | A1 | 9/2006 | Gil et al. |
| 2006/0217809 | A1 | 9/2006 | Albert et al. |
| 2006/0224159 | A1 | 10/2006 | Anderson |
| 2006/0224241 | A1 | 10/2006 | Butler et al. |
| 2006/0229608 | A1 | 10/2006 | Foster et al. |
| 2006/0229609 | A1 | 10/2006 | Wang |
| 2006/0229610 | A1 | 10/2006 | Piehl |
| 2006/0229612 | A1 | 10/2006 | Rothman et al. |
| 2006/0229613 | A1 | 10/2006 | Timm et al. |
| 2006/0229614 | A1 | 10/2006 | Foley et al. |
| 2006/0229615 | A1 | 10/2006 | Abdou et al. |
| 2006/0229627 | A1 | 10/2006 | Hunt et al. |
| 2006/0229629 | A1 | 10/2006 | Manzi et al. |
| 2006/0229715 | A1 | 10/2006 | Istephanous et al. |
| 2006/0229729 | A1 | 10/2006 | Gordon et al. |
| 2006/0235387 | A1 | 10/2006 | Peterman |
| 2006/0235389 | A1 | 10/2006 | Albert et al. |
| 2006/0235391 | A1 | 10/2006 | Sutterlin, III |
| 2006/0235392 | A1 | 10/2006 | Hammer et al. |
| 2006/0235393 | A1 | 10/2006 | Bono et al. |
| 2006/0235403 | A1 | 10/2006 | Blain |
| 2006/0235411 | A1 | 10/2006 | Blain et al. |
| 2006/0235414 | A1 | 10/2006 | Lim et al. |
| 2006/0235426 | A1 | 10/2006 | Lim et al. |
| 2006/0235520 | A1 | 10/2006 | Pannu |
| 2006/0235532 | A1 | 10/2006 | Meunier et al. |
| 2006/0241593 | A1 | 10/2006 | Sherman et al. |
| 2006/0241595 | A1 | 10/2006 | Molz, IV et al. |
| 2006/0241599 | A1 | 10/2006 | Konieczynski et al. |
| 2006/0241600 | A1 | 10/2006 | Ensign et al. |
| 2006/0241601 | A1 | 10/2006 | Trautwein et al. |
| 2006/0241610 | A1 | 10/2006 | Lim et al. |
| 2006/0241614 | A1 | 10/2006 | Bruneau et al. |
| 2006/0241615 | A1 | 10/2006 | Melkent |
| 2006/0241641 | A1 | 10/2006 | Albans et al. |
| 2006/0241761 | A1 | 10/2006 | Gately |
| 2006/0241769 | A1 | 10/2006 | Gordon et al. |
| 2006/0241771 | A1 | 10/2006 | Gordon et al. |
| 2006/0247624 | A1 | 11/2006 | Banouskou et al. |
| 2006/0247630 | A1 | 11/2006 | Iott et al. |
| 2006/0247631 | A1 | 11/2006 | Ahn et al. |
| 2006/0247632 | A1 | 11/2006 | Winslow et al. |
| 2006/0247633 | A1 | 11/2006 | Winslow et al. |
| 2006/0247634 | A1 | 11/2006 | Warner et al. |
| 2006/0247635 | A1 | 11/2006 | Gordon et al. |
| 2006/0247636 | A1 | 11/2006 | Yuan et al. |
| 2006/0247637 | A1 | 11/2006 | Colleran et al. |
| 2006/0247640 | A1 | 11/2006 | Blackwell et al. |
| 2006/0247645 | A1 | 11/2006 | Wilcox et al. |
| 2006/0247655 | A1 | 11/2006 | Francis et al. |
| 2006/0247679 | A1 | 11/2006 | Peterman |
| 2006/0247772 | A1 | 11/2006 | McKay |
| 2006/0247778 | A1 | 11/2006 | Ferree et al. |
| 2006/0247779 | A1 | 11/2006 | Gordon et al. |
| 2006/0247781 | A1 | 11/2006 | Francis |
| 2006/0247782 | A1 | 11/2006 | Molz, IV et al. |
| 2006/0253198 | A1 | 11/2006 | Myint et al. |
| 2006/0253201 | A1 | 11/2006 | McLuen |
| 2006/0264933 | A1 | 11/2006 | Baker et al. |
| 2006/0264934 | A1 | 11/2006 | Fallin |
| 2006/0264935 | A1 | 11/2006 | White |
| 2006/0264936 | A1 | 11/2006 | Partin et al. |
| 2006/0264937 | A1 | 11/2006 | White |
| 2006/0264940 | A1 | 11/2006 | Hartmann |
| 2006/0264942 | A1 | 11/2006 | Lim et al. |
| 2006/0264962 | A1 | 11/2006 | Chin et al. |
| 2006/0265077 | A1 | 11/2006 | Zwirkoski |
| 2006/0269940 | A1 | 11/2006 | Li et al. |
| 2006/0271046 | A1 | 11/2006 | Kwak et al. |
| 2006/0276787 | A1 | 12/2006 | Zubok et al. |
| 2006/0276789 | A1 | 12/2006 | Jackson |
| 2006/0276791 | A1 | 12/2006 | Shluzas |
| 2006/0276792 | A1 | 12/2006 | Ensign et al. |
| 2006/0276793 | A1 | 12/2006 | Berry |
| 2006/0276803 | A1 | 12/2006 | Salerni |
| 2006/0276900 | A1 | 12/2006 | Carpenter |
| 2006/0282074 | A1 | 12/2006 | Renaud et al. |
| 2006/0282075 | A1 | 12/2006 | Labrom et al. |
| 2006/0282076 | A1 | 12/2006 | Labrom et al. |
| 2006/0282078 | A1 | 12/2006 | Labrom et al. |
| 2006/0282079 | A1 | 12/2006 | Labrom et al. |
| 2006/0287583 | A1 | 12/2006 | Mangiardi |
| 2006/0293662 | A1 | 12/2006 | Boyer, II et al. |
| 2007/0010889 | A1 | 1/2007 | Francis |
| 2007/0016218 | A1 | 1/2007 | Winslow et al. |
| 2007/0016298 | A1 | 1/2007 | Recoules-Arche et al. |
| 2007/0021836 | A1 | 1/2007 | Doty |
| 2007/0027542 | A1 | 2/2007 | Xu |
| 2007/0032790 | A1 | 2/2007 | Aschmann et al. |
| 2007/0039837 | A1 | 2/2007 | Hanina et al. |
| 2007/0043356 | A1 | 2/2007 | Timm et al. |
| 2007/0043442 | A1 | 2/2007 | Abernathie et al. |
| 2007/0049935 | A1 | 3/2007 | Edidin et al. |
| 2007/0050030 | A1 | 3/2007 | Kim |

(56) References Cited

U.S. PATENT DOCUMENTS

| | | | |
|---|---|---|---|
| 2007/0050032 | A1 | 3/2007 | Gittings et al. |
| 2007/0055236 | A1 | 3/2007 | Hudgins et al. |
| 2007/0055377 | A1 | 3/2007 | Hanson et al. |
| 2007/0067035 | A1 | 3/2007 | Falahee |
| 2007/0073111 | A1 | 3/2007 | Bass |
| 2007/0073398 | A1 | 3/2007 | Fabian et al. |
| 2007/0083266 | A1 | 4/2007 | Lang |
| 2007/0090238 | A1 | 4/2007 | Justis |
| 2007/0093817 | A1 | 4/2007 | Barrus et al. |
| 2007/0093823 | A1 | 4/2007 | Booth et al. |
| 2007/0093825 | A1 | 4/2007 | Ferree et al. |
| 2007/0093828 | A1 | 4/2007 | Abdou et al. |
| 2007/0093829 | A1 | 4/2007 | Abdou |
| 2007/0093901 | A1 | 4/2007 | Grotz et al. |
| 2007/0100212 | A1 | 5/2007 | Pimenta et al. |
| 2007/0100340 | A1 | 5/2007 | Lange et al. |
| 2007/0100341 | A1 | 5/2007 | Reglos et al. |
| 2007/0106298 | A1 | 5/2007 | Carli et al. |
| 2007/0106383 | A1 | 5/2007 | Abdou et al. |
| 2007/0108383 | A1 | 5/2007 | Combes et al. |
| 2007/0118121 | A1 | 5/2007 | Purcell et al. |
| 2007/0118122 | A1 | 5/2007 | Butler et al. |
| 2007/0118123 | A1 | 5/2007 | Strausbaugh et al. |
| 2007/0118132 | A1 | 5/2007 | Culbert et al. |
| 2007/0123867 | A1 | 5/2007 | Kirschman |
| 2007/0123869 | A1 | 5/2007 | Chin et al. |
| 2007/0123884 | A1 | 5/2007 | Abdou |
| 2007/0129804 | A1 | 6/2007 | Bentley et al. |
| 2007/0142916 | A1 | 6/2007 | Olson, Jr. et al. |
| 2007/0149978 | A1 | 6/2007 | Shezifi et al. |
| 2007/0151116 | A1 | 7/2007 | Malandain |
| 2007/0156233 | A1 | 7/2007 | Kapadia et al. |
| 2007/0161962 | A1 | 7/2007 | Edie et al. |
| 2007/0161992 | A1 | 7/2007 | Kwak et al. |
| 2007/0162000 | A1 | 7/2007 | Perkins |
| 2007/0162001 | A1 | 7/2007 | Chin et al. |
| 2007/0162005 | A1 | 7/2007 | Peterson et al. |
| 2007/0162127 | A1 | 7/2007 | Peterman et al. |
| 2007/0162133 | A1 | 7/2007 | Doubler et al. |
| 2007/0162138 | A1 | 7/2007 | Heinz |
| 2007/0167948 | A1 | 7/2007 | Abdou |
| 2007/0168036 | A1 | 7/2007 | Ainsworth et al. |
| 2007/0173831 | A1 | 7/2007 | Abdou |
| 2007/0173842 | A1 | 7/2007 | Abdou |
| 2007/0179493 | A1 | 8/2007 | Kim |
| 2007/0179500 | A1 | 8/2007 | Chin et al. |
| 2007/0179614 | A1 | 8/2007 | Heinz et al. |
| 2007/0185367 | A1 | 8/2007 | Abdou |
| 2007/0185376 | A1 | 8/2007 | Wilson et al. |
| 2007/0185489 | A1 | 8/2007 | Abdou |
| 2007/0191834 | A1 | 8/2007 | Bruneau et al. |
| 2007/0191861 | A1 | 8/2007 | Allard et al. |
| 2007/0191946 | A1 | 8/2007 | Heinz et al. |
| 2007/0191951 | A1 | 8/2007 | Branch, Jr. et al. |
| 2007/0191958 | A1 | 8/2007 | Abdou |
| 2007/0198090 | A1 | 8/2007 | Abdou |
| 2007/0208227 | A1 | 9/2007 | Smith et al. |
| 2007/0213597 | A1 | 9/2007 | Wooster |
| 2007/0213732 | A1 | 9/2007 | Khanna et al. |
| 2007/0225724 | A1 | 9/2007 | Edmond |
| 2007/0225726 | A1 | 9/2007 | Dye et al. |
| 2007/0225807 | A1 | 9/2007 | Phan et al. |
| 2007/0225808 | A1 | 9/2007 | Warnick |
| 2007/0225812 | A1 | 9/2007 | Gill |
| 2007/0233074 | A1 | 10/2007 | Anderson et al. |
| 2007/0233077 | A1 | 10/2007 | Khalili |
| 2007/0233082 | A1 | 10/2007 | Chin et al. |
| 2007/0233083 | A1 | 10/2007 | Abdou |
| 2007/0233084 | A1 | 10/2007 | Betz et al. |
| 2007/0233088 | A1 | 10/2007 | Edmond |
| 2007/0233089 | A1 | 10/2007 | Dipoto et al. |
| 2007/0233118 | A1 | 10/2007 | McLain |
| 2007/0233129 | A1 | 10/2007 | Bertagnoli et al. |
| 2007/0233247 | A1 | 10/2007 | Schwab |
| 2007/0233251 | A1 | 10/2007 | Abdou |
| 2007/0255389 | A1 | 11/2007 | Oberti et al. |
| 2007/0255415 | A1 | 11/2007 | Edie et al. |
| 2007/0260314 | A1 | 11/2007 | Biyani |
| 2007/0270812 | A1 | 11/2007 | Peckham |
| 2007/0270813 | A1 | 11/2007 | Garamszegi |
| 2007/0270824 | A1 | 11/2007 | Lim et al. |
| 2007/0270827 | A1 | 11/2007 | Lim et al. |
| 2007/0270838 | A1 | 11/2007 | Bruneau et al. |
| 2007/0270840 | A1 | 11/2007 | Chin et al. |
| 2007/0270874 | A1 | 11/2007 | Anderson |
| 2007/0270963 | A1 | 11/2007 | Melkent et al. |
| 2007/0270968 | A1 | 11/2007 | Baynham et al. |
| 2007/0274772 | A1 | 11/2007 | Tiberghien et al. |
| 2007/0276370 | A1 | 11/2007 | Altarac et al. |
| 2007/0282448 | A1 | 12/2007 | Abdou |
| 2007/0293949 | A1 | 12/2007 | Salerni et al. |
| 2007/0299445 | A1 | 12/2007 | Shadduck et al. |
| 2007/0299521 | A1 | 12/2007 | Glenn et al. |
| 2008/0009880 | A1 | 1/2008 | Warnick et al. |
| 2008/0015580 | A1 | 1/2008 | Chao |
| 2008/0015597 | A1 | 1/2008 | Whipple |
| 2008/0015698 | A1 | 1/2008 | Marino et al. |
| 2008/0021466 | A1 | 1/2008 | Shadduck et al. |
| 2008/0021559 | A1 | 1/2008 | Thramann |
| 2008/0027432 | A1 | 1/2008 | Strauss et al. |
| 2008/0027438 | A1 | 1/2008 | Abdou |
| 2008/0027458 | A1 | 1/2008 | Aikins et al. |
| 2008/0027544 | A1 | 1/2008 | Melkent |
| 2008/0027545 | A1 | 1/2008 | Zucherman et al. |
| 2008/0027550 | A1 | 1/2008 | Link et al. |
| 2008/0033440 | A1 | 2/2008 | Moskowitz et al. |
| 2008/0039837 | A1 | 2/2008 | Gambale |
| 2008/0039843 | A1 | 2/2008 | Abdou |
| 2008/0045963 | A1 | 2/2008 | Abdou |
| 2008/0045968 | A1 | 2/2008 | Yu et al. |
| 2008/0045983 | A1 | 2/2008 | To et al. |
| 2008/0051783 | A1 | 2/2008 | Null et al. |
| 2008/0051896 | A1 | 2/2008 | Suddaby |
| 2008/0058606 | A1 | 3/2008 | Miles et al. |
| 2008/0058810 | A1 | 3/2008 | Abdou |
| 2008/0065219 | A1 | 3/2008 | Dye |
| 2008/0065222 | A1 | 3/2008 | Hamada |
| 2008/0081951 | A1 | 4/2008 | Frasier et al. |
| 2008/0086080 | A1 | 4/2008 | Mastri et al. |
| 2008/0091211 | A1 | 4/2008 | Gately |
| 2008/0108993 | A1 | 5/2008 | Bennett et al. |
| 2008/0114401 | A1 | 5/2008 | Liu et al. |
| 2008/0114455 | A1 | 5/2008 | Lange et al. |
| 2008/0119853 | A1 | 5/2008 | Felt et al. |
| 2008/0119935 | A1 | 5/2008 | Alvarez |
| 2008/0125813 | A1 | 5/2008 | Erickson et al. |
| 2008/0125865 | A1 | 5/2008 | Abdelgany |
| 2008/0126813 | A1 | 5/2008 | Kawakami |
| 2008/0132951 | A1 | 6/2008 | Reiley et al. |
| 2008/0133012 | A1 | 6/2008 | McGuckin |
| 2008/0133014 | A1 | 6/2008 | Gately et al. |
| 2008/0133016 | A1 | 6/2008 | Heinz |
| 2008/0133017 | A1 | 6/2008 | Beyar et al. |
| 2008/0139879 | A1 | 6/2008 | Olson et al. |
| 2008/0140085 | A1 | 6/2008 | Gately et al. |
| 2008/0140125 | A1 | 6/2008 | Mitchell et al. |
| 2008/0140204 | A1 | 6/2008 | Heinz |
| 2008/0140207 | A1 | 6/2008 | Olmos et al. |
| 2008/0147123 | A1 | 6/2008 | Schermerhorn |
| 2008/0147190 | A1 | 6/2008 | Dewey et al. |
| 2008/0154308 | A1 | 6/2008 | Sherman et al. |
| 2008/0154374 | A1 | 6/2008 | Labrom |
| 2008/0161818 | A1 | 7/2008 | Kloss et al. |
| 2008/0161821 | A1 | 7/2008 | Heinz |
| 2008/0161853 | A1 | 7/2008 | Arnold et al. |
| 2008/0161856 | A1 | 7/2008 | Liu et al. |
| 2008/0167655 | A1 | 7/2008 | Wang et al. |
| 2008/0167657 | A1 | 7/2008 | Greenhalgh |
| 2008/0177271 | A1 | 7/2008 | Yeh |
| 2008/0177298 | A1 | 7/2008 | Zucherman et al. |
| 2008/0177306 | A1 | 7/2008 | Lamborne et al. |
| 2008/0177312 | A1 | 7/2008 | Perez-Cruet et al. |
| 2008/0177326 | A1 | 7/2008 | Thompson |
| 2008/0177391 | A1 | 7/2008 | Mitchell et al. |

(56) References Cited

U.S. PATENT DOCUMENTS

| | | | |
|---|---|---|---|
| 2008/0183204 | A1 | 7/2008 | Greenhalgh et al. |
| 2008/0183209 | A1 | 7/2008 | Robinson et al. |
| 2008/0183211 | A1 | 7/2008 | Lamborne et al. |
| 2008/0183218 | A1 | 7/2008 | Mueller et al. |
| 2008/0188898 | A1 | 8/2008 | Jackson |
| 2008/0188941 | A1 | 8/2008 | Grotz |
| 2008/0195152 | A1 | 8/2008 | Altarac et al. |
| 2008/0234735 | A1 | 9/2008 | Joshi |
| 2008/0243185 | A1 | 10/2008 | Felix et al. |
| 2008/0243186 | A1 | 10/2008 | Abdou |
| 2008/0243188 | A1 | 10/2008 | Walder et al. |
| 2008/0243189 | A1 | 10/2008 | Purcell et al. |
| 2008/0243255 | A1 | 10/2008 | Butler et al. |
| 2008/0249622 | A1 | 10/2008 | Gray |
| 2008/0249628 | A1 | 10/2008 | Altarac et al. |
| 2008/0262318 | A1 | 10/2008 | Gorek et al. |
| 2008/0262554 | A1 | 10/2008 | Hayes et al. |
| 2008/0269904 | A1 | 10/2008 | Voorhies |
| 2008/0281346 | A1 | 11/2008 | Greenhalgh et al. |
| 2008/0281358 | A1 | 11/2008 | Abdou |
| 2008/0281359 | A1 | 11/2008 | Abdou |
| 2008/0281424 | A1 | 11/2008 | Parry et al. |
| 2008/0281425 | A1 | 11/2008 | Thalgott et al. |
| 2008/0288073 | A1 | 11/2008 | Renganath et al. |
| 2008/0294199 | A1 | 11/2008 | Kohm et al. |
| 2008/0294200 | A1 | 11/2008 | Kohm et al. |
| 2008/0300598 | A1 | 12/2008 | Barreiro et al. |
| 2008/0300601 | A1 | 12/2008 | Fabian et al. |
| 2008/0300685 | A1 | 12/2008 | Carls et al. |
| 2008/0300686 | A1 | 12/2008 | Khoo |
| 2008/0306601 | A1 | 12/2008 | Dreyfuss |
| 2008/0312655 | A1 | 12/2008 | Kirschman et al. |
| 2008/0312692 | A1 | 12/2008 | Brennan et al. |
| 2008/0312741 | A1 | 12/2008 | Lee et al. |
| 2008/0312743 | A1 | 12/2008 | Vila et al. |
| 2008/0319487 | A1 | 12/2008 | Fielding et al. |
| 2008/0319549 | A1 | 12/2008 | Greenhalgh et al. |
| 2009/0012566 | A1 | 1/2009 | Fauth |
| 2009/0012623 | A1 | 1/2009 | Sack et al. |
| 2009/0024166 | A1 | 1/2009 | Carl et al. |
| 2009/0024217 | A1 | 1/2009 | Levy et al. |
| 2009/0030423 | A1 | 1/2009 | Puno |
| 2009/0030457 | A1 | 1/2009 | Janowski et al. |
| 2009/0030465 | A1 | 1/2009 | Altarac et al. |
| 2009/0030519 | A1 | 1/2009 | Falahee |
| 2009/0030520 | A1 | 1/2009 | Biedermann et al. |
| 2009/0036746 | A1 | 2/2009 | Blackwell et al. |
| 2009/0036927 | A1 | 2/2009 | Vestgaarden |
| 2009/0036929 | A1 | 2/2009 | Reglos et al. |
| 2009/0036988 | A1 | 2/2009 | Peckham |
| 2009/0048668 | A1 | 2/2009 | Wilson et al. |
| 2009/0054931 | A1 | 2/2009 | Metz-Stavenhagen |
| 2009/0062869 | A1 | 3/2009 | Claverie et al. |
| 2009/0062915 | A1 | 3/2009 | Kohm et al. |
| 2009/0062918 | A1 | 3/2009 | Wang et al. |
| 2009/0062920 | A1 | 3/2009 | Tauber |
| 2009/0076333 | A1 | 3/2009 | Bjork |
| 2009/0076516 | A1 | 3/2009 | Lowry et al. |
| 2009/0076615 | A1 | 3/2009 | Duggal et al. |
| 2009/0082808 | A1 | 3/2009 | Butler et al. |
| 2009/0082813 | A1 | 3/2009 | Long et al. |
| 2009/0093884 | A1 | 4/2009 | Bass |
| 2009/0099601 | A1 | 4/2009 | Aferzon et al. |
| 2009/0105547 | A1 | 4/2009 | Vayser et al. |
| 2009/0105761 | A1 | 4/2009 | Robie |
| 2009/0105768 | A1 | 4/2009 | Cragg et al. |
| 2009/0105773 | A1 | 4/2009 | Lange et al. |
| 2009/0105830 | A1 | 4/2009 | Jones et al. |
| 2009/0105831 | A1 | 4/2009 | Jones et al. |
| 2009/0118766 | A1 | 5/2009 | Park et al. |
| 2009/0118771 | A1 | 5/2009 | Gonzalez-Hernandez |
| 2009/0124861 | A1 | 5/2009 | Fetzer |
| 2009/0125062 | A1 | 5/2009 | Arnin |
| 2009/0125071 | A1 | 5/2009 | Skinlo et al. |
| 2009/0132054 | A1 | 5/2009 | Zeegers |
| 2009/0143859 | A1 | 6/2009 | McClellan, III et al. |
| 2009/0149956 | A1 | 6/2009 | Greenhalgh et al. |
| 2009/0149959 | A1 | 6/2009 | Conner et al. |
| 2009/0157186 | A1 | 6/2009 | Magerl |
| 2009/0157188 | A1 | 6/2009 | Zeegers |
| 2009/0163920 | A1 | 6/2009 | Hochschuler et al. |
| 2009/0163957 | A1 | 6/2009 | St et al. |
| 2009/0163961 | A1 | 6/2009 | Kirschman |
| 2009/0164020 | A1 | 6/2009 | Janowski et al. |
| 2009/0171394 | A1 | 7/2009 | Abdou |
| 2009/0177238 | A1 | 7/2009 | Abdou |
| 2009/0177262 | A1 | 7/2009 | Oberti et al. |
| 2009/0182429 | A1 | 7/2009 | Humphreys et al. |
| 2009/0182430 | A1 | 7/2009 | Tyber et al. |
| 2009/0186333 | A1 | 7/2009 | Mills et al. |
| 2009/0187249 | A1 | 7/2009 | Osman |
| 2009/0192613 | A1 | 7/2009 | Wing et al. |
| 2009/0192615 | A1 | 7/2009 | Tyber et al. |
| 2009/0198211 | A1 | 8/2009 | Thorne, Jr. et al. |
| 2009/0198277 | A1 | 8/2009 | Gordon et al. |
| 2009/0204151 | A1 | 8/2009 | Bracken |
| 2009/0204154 | A1 | 8/2009 | Kiester |
| 2009/0204218 | A1 | 8/2009 | Richelsoph |
| 2009/0204219 | A1 | 8/2009 | Beaurain et al. |
| 2009/0210007 | A1 | 8/2009 | Levy et al. |
| 2009/0210015 | A1 | 8/2009 | Cermak et al. |
| 2009/0210062 | A1 | 8/2009 | Thalgott et al. |
| 2009/0216234 | A1 | 8/2009 | Farr et al. |
| 2009/0216241 | A1 | 8/2009 | Dinville |
| 2009/0222046 | A1 | 9/2009 | Gorek |
| 2009/0222092 | A1 | 9/2009 | Davis et al. |
| 2009/0222100 | A1 | 9/2009 | Cipoletti et al. |
| 2009/0227845 | A1 | 9/2009 | Lo et al. |
| 2009/0228045 | A1 | 9/2009 | Hayes et al. |
| 2009/0228108 | A1 | 9/2009 | Keller |
| 2009/0228110 | A1 | 9/2009 | McClintock |
| 2009/0234364 | A1 | 9/2009 | Crook |
| 2009/0234455 | A1 | 9/2009 | Moskowitz et al. |
| 2009/0240334 | A1 | 9/2009 | Richelsoph |
| 2009/0240335 | A1 | 9/2009 | Arcenio et al. |
| 2009/0247819 | A1 | 10/2009 | Wilson et al. |
| 2009/0248078 | A1 | 10/2009 | Dant |
| 2009/0248089 | A1 | 10/2009 | Jacofsky et al. |
| 2009/0254125 | A1 | 10/2009 | Predick |
| 2009/0259257 | A1 | 10/2009 | Prevost |
| 2009/0259316 | A1 | 10/2009 | Ginn et al. |
| 2009/0265007 | A1 | 10/2009 | Colleran |
| 2009/0270918 | A1 | 10/2009 | Attia et al. |
| 2009/0270989 | A1 | 10/2009 | Conner et al. |
| 2009/0270990 | A1 | 10/2009 | Louis et al. |
| 2009/0276040 | A1 | 11/2009 | Rowe et al. |
| 2009/0276049 | A1 | 11/2009 | Weiland |
| 2009/0281628 | A1 | 11/2009 | Oglaza et al. |
| 2009/0290316 | A1 | 11/2009 | Kariya |
| 2009/0292361 | A1 | 11/2009 | Lopez |
| 2009/0299478 | A1 | 12/2009 | Carls et al. |
| 2009/0326538 | A1 | 12/2009 | Sennett et al. |
| 2009/0326581 | A1 | 12/2009 | Galley et al. |
| 2009/0326584 | A1 | 12/2009 | Slivka et al. |
| 2010/0004664 | A1 | 1/2010 | Boyajian et al. |
| 2010/0009929 | A1 | 1/2010 | Cheng et al. |
| 2010/0016897 | A1 | 1/2010 | Le et al. |
| 2010/0016906 | A1 | 1/2010 | Abdou |
| 2010/0023061 | A1 | 1/2010 | Randol et al. |
| 2010/0023064 | A1 | 1/2010 | Brunger et al. |
| 2010/0036423 | A1 | 2/2010 | Hayes et al. |
| 2010/0036495 | A1 | 2/2010 | Daum et al. |
| 2010/0042149 | A1 | 2/2010 | Chao et al. |
| 2010/0049324 | A1 | 2/2010 | Valdevit et al. |
| 2010/0069929 | A1 | 3/2010 | Abdou |
| 2010/0069962 | A1 | 3/2010 | Harms et al. |
| 2010/0069965 | A1 | 3/2010 | Abdou |
| 2010/0070041 | A1 | 3/2010 | Peterman et al. |
| 2010/0076448 | A1 | 3/2010 | Abdou |
| 2010/0082109 | A1 | 4/2010 | Greenhalgh et al. |
| 2010/0087858 | A1 | 4/2010 | Abdou |
| 2010/0087869 | A1 | 4/2010 | Abdou |
| 2010/0087878 | A1 | 4/2010 | Abdou |
| 2010/0087923 | A1 | 4/2010 | Abdou |

(56) References Cited

U.S. PATENT DOCUMENTS

| | | | |
|---|---|---|---|
| 2010/0094422 | A1 | 4/2010 | Hansell et al. |
| 2010/0100137 | A1 | 4/2010 | Justis et al. |
| 2010/0106250 | A1 | 4/2010 | Abdou |
| 2010/0121384 | A1 | 5/2010 | Abdou |
| 2010/0130827 | A1 | 5/2010 | Pimenta et al. |
| 2010/0152603 | A1 | 6/2010 | Miles et al. |
| 2010/0152778 | A1 | 6/2010 | Saint |
| 2010/0174315 | A1 | 7/2010 | Scodary et al. |
| 2010/0179657 | A1 | 7/2010 | Greenhalgh et al. |
| 2010/0185291 | A1 | 7/2010 | Jimenez et al. |
| 2010/0191336 | A1 | 7/2010 | Greenhalgh |
| 2010/0191337 | A1 | 7/2010 | Zamani et al. |
| 2010/0198140 | A1 | 8/2010 | Lawson |
| 2010/0204795 | A1 | 8/2010 | Greenhalgh |
| 2010/0211101 | A1 | 8/2010 | Blackwell et al. |
| 2010/0211176 | A1 | 8/2010 | Greenhalgh |
| 2010/0211177 | A1 | 8/2010 | Abdou |
| 2010/0217382 | A1 | 8/2010 | Chau et al. |
| 2010/0222644 | A1 | 9/2010 | Sebastian et al. |
| 2010/0222816 | A1 | 9/2010 | Gabelberger et al. |
| 2010/0222884 | A1 | 9/2010 | Greenhalgh et al. |
| 2010/0234889 | A1 | 9/2010 | Hess |
| 2010/0234952 | A1 | 9/2010 | Peterman |
| 2010/0234956 | A1 | 9/2010 | Attia et al. |
| 2010/0241168 | A1 | 9/2010 | Franck et al. |
| 2010/0249933 | A1 | 9/2010 | Trieu |
| 2010/0256759 | A1 | 10/2010 | Hansell et al. |
| 2010/0256760 | A1 | 10/2010 | Hansell |
| 2010/0262245 | A1 | 10/2010 | Alfaro et al. |
| 2010/0262248 | A1 | 10/2010 | Sournac et al. |
| 2010/0268281 | A1 | 10/2010 | Abdou |
| 2010/0280622 | A1 | 11/2010 | McKinley |
| 2010/0286483 | A1 | 11/2010 | Bettuchi et al. |
| 2010/0286779 | A1 | 11/2010 | Thibodeau |
| 2010/0286780 | A1 | 11/2010 | Dryer et al. |
| 2010/0292796 | A1 | 11/2010 | Greenhalgh et al. |
| 2010/0305705 | A1 | 12/2010 | Butler et al. |
| 2010/0312282 | A1 | 12/2010 | Abdou |
| 2010/0312347 | A1 | 12/2010 | Arramon et al. |
| 2010/0318128 | A1 | 12/2010 | Abdou |
| 2010/0331883 | A1 | 12/2010 | Schmitz et al. |
| 2010/0331887 | A1 | 12/2010 | Jackson et al. |
| 2010/0331889 | A1 | 12/2010 | Abdou |
| 2010/0331981 | A1 | 12/2010 | Mohammed |
| 2010/0331985 | A1 | 12/2010 | Gordon et al. |
| 2011/0004248 | A1 | 1/2011 | Abdou |
| 2011/0009969 | A1 | 1/2011 | Puno |
| 2011/0009970 | A1 | 1/2011 | Puno |
| 2011/0022090 | A1 | 1/2011 | Gordon et al. |
| 2011/0029083 | A1 | 2/2011 | Hynes et al. |
| 2011/0029085 | A1 | 2/2011 | Hynes et al. |
| 2011/0035011 | A1 | 2/2011 | Cain |
| 2011/0046679 | A1 | 2/2011 | Chow et al. |
| 2011/0046740 | A1 | 2/2011 | Chen et al. |
| 2011/0054531 | A1 | 3/2011 | Lamborne et al. |
| 2011/0060366 | A1 | 3/2011 | Heim et al. |
| 2011/0066186 | A1 | 3/2011 | Boyer, II et al. |
| 2011/0082551 | A1 | 4/2011 | Kraus |
| 2011/0082553 | A1 | 4/2011 | Abdou |
| 2011/0093074 | A1 | 4/2011 | Glerum et al. |
| 2011/0098749 | A1 | 4/2011 | Boomer et al. |
| 2011/0106163 | A1 | 5/2011 | Hochschuler et al. |
| 2011/0106259 | A1 | 5/2011 | Lindenmann et al. |
| 2011/0118552 | A1 | 5/2011 | Fischvogt |
| 2011/0125266 | A1 | 5/2011 | Rodgers et al. |
| 2011/0130793 | A1 | 6/2011 | Woolley et al. |
| 2011/0137353 | A1 | 6/2011 | Buttermann |
| 2011/0144692 | A1 | 6/2011 | Saladin et al. |
| 2011/0160772 | A1 | 6/2011 | Arcenio et al. |
| 2011/0166600 | A1 | 7/2011 | Lamborne et al. |
| 2011/0172720 | A1 | 7/2011 | Metcalf, Jr. et al. |
| 2011/0172772 | A1 | 7/2011 | Abdou |
| 2011/0184471 | A1 | 7/2011 | Foley et al. |
| 2011/0190825 | A1 | 8/2011 | Thalgott et al. |
| 2011/0196492 | A1 | 8/2011 | Lambrecht et al. |
| 2011/0213465 | A1 | 9/2011 | Landry et al. |
| 2011/0224496 | A1 | 9/2011 | Weiman |
| 2011/0224497 | A1 | 9/2011 | Weiman et al. |
| 2011/0238181 | A1 | 9/2011 | Trieu |
| 2011/0251693 | A1 | 10/2011 | Barreiro et al. |
| 2011/0264218 | A1 | 10/2011 | Asaad |
| 2011/0264228 | A1 | 10/2011 | Johnson et al. |
| 2011/0276099 | A1 | 11/2011 | Champagne et al. |
| 2011/0276142 | A1 | 11/2011 | Niemiec et al. |
| 2011/0282459 | A1 | 11/2011 | McClellan, III et al. |
| 2011/0288588 | A1 | 11/2011 | Chin et al. |
| 2011/0288594 | A1 | 11/2011 | Woolley et al. |
| 2011/0288644 | A1 | 11/2011 | Gray et al. |
| 2011/0288645 | A1 | 11/2011 | Braddock, Jr. et al. |
| 2011/0301710 | A1 | 12/2011 | Mather et al. |
| 2011/0301712 | A1 | 12/2011 | Palmatier et al. |
| 2011/0307011 | A1 | 12/2011 | Moskowitz et al. |
| 2011/0307012 | A1 | 12/2011 | Mir et al. |
| 2011/0319941 | A1 | 12/2011 | Bar et al. |
| 2011/0319995 | A1 | 12/2011 | Voellmicke et al. |
| 2012/0010472 | A1 | 1/2012 | Spann |
| 2012/0010658 | A1 | 1/2012 | Kirschman |
| 2012/0016481 | A1 | 1/2012 | Zwirkoski |
| 2012/0029565 | A1 | 2/2012 | Seifert et al. |
| 2012/0029639 | A1 | 2/2012 | Blackwell et al. |
| 2012/0035424 | A1 | 2/2012 | Schulte |
| 2012/0041272 | A1 | 2/2012 | Dietze, Jr. et al. |
| 2012/0071980 | A1 | 3/2012 | Purcell et al. |
| 2012/0078301 | A1 | 3/2012 | Hess |
| 2012/0089184 | A1 | 4/2012 | Yeh |
| 2012/0095512 | A1 | 4/2012 | Nihalani |
| 2012/0101528 | A1 | 4/2012 | Souza et al. |
| 2012/0109206 | A1 | 5/2012 | Abdou |
| 2012/0123546 | A1 | 5/2012 | Medina |
| 2012/0136442 | A1 | 5/2012 | Kleiner |
| 2012/0150229 | A1 | 6/2012 | Hess |
| 2012/0150302 | A1 | 6/2012 | Gray |
| 2012/0158060 | A1 | 6/2012 | Abrahams et al. |
| 2012/0158140 | A1 | 6/2012 | Miller et al. |
| 2012/0158150 | A1 | 6/2012 | Siegal |
| 2012/0179260 | A1 | 7/2012 | Nottingham |
| 2012/0185045 | A1 | 7/2012 | Morris et al. |
| 2012/0190933 | A1 | 7/2012 | Kleyman |
| 2012/0191135 | A1 | 7/2012 | Abdou |
| 2012/0197297 | A1 | 8/2012 | Bootwala et al. |
| 2012/0197401 | A1 | 8/2012 | Duncan et al. |
| 2012/0197402 | A1 | 8/2012 | Blackwell et al. |
| 2012/0203279 | A1 | 8/2012 | Walters et al. |
| 2012/0209271 | A1 | 8/2012 | Cohen et al. |
| 2012/0209383 | A1 | 8/2012 | Tsuang et al. |
| 2012/0215316 | A1 | 8/2012 | Mohr et al. |
| 2012/0221049 | A1 | 8/2012 | Blain et al. |
| 2012/0221060 | A1 | 8/2012 | Blain |
| 2012/0226313 | A1 | 9/2012 | Dace |
| 2012/0232592 | A1 | 9/2012 | Massoudi |
| 2012/0232658 | A1 | 9/2012 | Morgenstern et al. |
| 2012/0238825 | A1 | 9/2012 | Smith |
| 2012/0245425 | A1 | 9/2012 | Okoniewski |
| 2012/0245431 | A1 | 9/2012 | Baudouin et al. |
| 2012/0245432 | A1 | 9/2012 | Karpowicz et al. |
| 2012/0245704 | A1 | 9/2012 | Childs et al. |
| 2012/0253393 | A1 | 10/2012 | Fiorella |
| 2012/0253396 | A1 | 10/2012 | Stern et al. |
| 2012/0259416 | A1 | 10/2012 | Blackwell et al. |
| 2012/0265021 | A1 | 10/2012 | Nottmeier |
| 2012/0271119 | A1 | 10/2012 | White |
| 2012/0277864 | A1 | 11/2012 | Brodke et al. |
| 2012/0283521 | A1 | 11/2012 | Smith et al. |
| 2012/0290017 | A1 | 11/2012 | Haidukewych |
| 2012/0290096 | A1 | 11/2012 | Messerli |
| 2012/0296171 | A1 | 11/2012 | Lovell et al. |
| 2012/0296377 | A1 | 11/2012 | Ferree et al. |
| 2012/0310282 | A1 | 12/2012 | Abdou |
| 2013/0018467 | A1 | 1/2013 | Suh |
| 2013/0023933 | A1 | 1/2013 | Haas |
| 2013/0023937 | A1 | 1/2013 | Biedermann et al. |
| 2013/0030467 | A1 | 1/2013 | Karas et al. |
| 2013/0030469 | A1 | 1/2013 | Karas et al. |
| 2013/0030470 | A1 | 1/2013 | Karas et al. |

(56) References Cited

U.S. PATENT DOCUMENTS

| | | | |
|---|---|---|---|
| 2013/0041471 | A1 | 2/2013 | Siegal et al. |
| 2013/0053896 | A1 | 2/2013 | Voyadzis |
| 2013/0060284 | A1 | 3/2013 | Abdou |
| 2013/0066374 | A1 | 3/2013 | Galley et al. |
| 2013/0079883 | A1 | 3/2013 | Butler et al. |
| 2013/0090691 | A1 | 4/2013 | Zhang et al. |
| 2013/0103088 | A1 | 4/2013 | Karahalios et al. |
| 2013/0103089 | A1 | 4/2013 | Gordon et al. |
| 2013/0123849 | A1 | 5/2013 | Abdou |
| 2013/0123924 | A1 | 5/2013 | Butler et al. |
| 2013/0131738 | A1 | 5/2013 | Powell et al. |
| 2013/0144339 | A1 | 6/2013 | Choi et al. |
| 2013/0144340 | A1 | 6/2013 | Sheffer et al. |
| 2013/0144387 | A1 | 6/2013 | Walker et al. |
| 2013/0144391 | A1 | 6/2013 | Siegal et al. |
| 2013/0150886 | A1 | 6/2013 | Altarac et al. |
| 2013/0150970 | A1 | 6/2013 | Thaiyananthan |
| 2013/0158359 | A1 | 6/2013 | Predick et al. |
| 2013/0165982 | A1 | 6/2013 | Ek et al. |
| 2013/0172736 | A1 | 7/2013 | Abdou |
| 2013/0172932 | A1 | 7/2013 | Altarac et al. |
| 2013/0172933 | A1 | 7/2013 | Altarac et al. |
| 2013/0172934 | A1 | 7/2013 | Walker et al. |
| 2013/0178903 | A1 | 7/2013 | Abdou |
| 2013/0184752 | A1 | 7/2013 | Binder |
| 2013/0184758 | A1 | 7/2013 | Karim |
| 2013/0190573 | A1 | 7/2013 | Smith |
| 2013/0190575 | A1 | 7/2013 | Mast et al. |
| 2013/0197587 | A1 | 8/2013 | Abdou |
| 2013/0197588 | A1 | 8/2013 | Abdou |
| 2013/0197647 | A1 | 8/2013 | Wolters et al. |
| 2013/0204091 | A1 | 8/2013 | Menendez et al. |
| 2013/0218166 | A1 | 8/2013 | Elmore |
| 2013/0226240 | A1 | 8/2013 | Abdou |
| 2013/0245383 | A1 | 9/2013 | Friedrich et al. |
| 2013/0253585 | A1 | 9/2013 | Garcia et al. |
| 2013/0253586 | A1 | 9/2013 | Rathbun et al. |
| 2013/0261401 | A1 | 10/2013 | Hawkins et al. |
| 2013/0261666 | A1 | 10/2013 | Gundanna |
| 2013/0274883 | A1 | 10/2013 | McLuen et al. |
| 2013/0274884 | A1 | 10/2013 | Matsumoto et al. |
| 2013/0296939 | A1 | 11/2013 | Perkins |
| 2013/0296940 | A1 | 11/2013 | Northcutt et al. |
| 2013/0310942 | A1 | 11/2013 | Abdou |
| 2013/0325128 | A1 | 12/2013 | Perloff et al. |
| 2014/0005484 | A1 | 1/2014 | Charles |
| 2014/0031874 | A1 | 1/2014 | Kucharzyk et al. |
| 2014/0058512 | A1 | 2/2014 | Petersheim |
| 2014/0058513 | A1 | 2/2014 | Gahman et al. |
| 2014/0067070 | A1 | 3/2014 | Abdou |
| 2014/0081331 | A1 | 3/2014 | Zappacosta et al. |
| 2014/0094922 | A1 | 4/2014 | Abdou |
| 2014/0107783 | A1 | 4/2014 | Abdou |
| 2014/0114137 | A1 | 4/2014 | Reglos et al. |
| 2014/0114138 | A1 | 4/2014 | Fedorov et al. |
| 2014/0114139 | A1 | 4/2014 | Ziolo et al. |
| 2014/0114414 | A1 | 4/2014 | Abdou et al. |
| 2014/0121705 | A1 | 5/2014 | Abdou |
| 2014/0128917 | A1 | 5/2014 | Abdou |
| 2014/0135584 | A1 | 5/2014 | Lee et al. |
| 2014/0148652 | A1 | 5/2014 | Weiman |
| 2014/0148856 | A1 | 5/2014 | Ibarra et al. |
| 2014/0155939 | A1 | 6/2014 | Sugawara |
| 2014/0172002 | A1 | 6/2014 | Predick |
| 2014/0172105 | A1 | 6/2014 | Frasier et al. |
| 2014/0172107 | A1 | 6/2014 | Thirugnanasambanda et al. |
| 2014/0188223 | A1 | 7/2014 | Jensen et al. |
| 2014/0188233 | A1 | 7/2014 | Mutchler et al. |
| 2014/0249631 | A1 | 9/2014 | Weiman |
| 2014/0257466 | A1 | 9/2014 | Board et al. |
| 2014/0277143 | A1 | 9/2014 | Zappacosta |
| 2014/0277486 | A1 | 9/2014 | Abdou et al. |
| 2014/0277490 | A1 | 9/2014 | Perloff et al. |
| 2014/0277499 | A1 | 9/2014 | Ainsworth et al. |
| 2014/0277502 | A1 | 9/2014 | Schiffman et al. |
| 2014/0288480 | A1 | 9/2014 | Zimmerman et al. |
| 2014/0309741 | A1 | 10/2014 | Ganter et al. |
| 2014/0336471 | A1 | 11/2014 | Pfabe et al. |
| 2014/0343608 | A1 | 11/2014 | Whiton et al. |
| 2014/0343678 | A1 | 11/2014 | Suddaby et al. |
| 2014/0350347 | A1 | 11/2014 | Karpowicz et al. |
| 2014/0379032 | A1 | 12/2014 | Hennard |
| 2014/0379086 | A1 | 12/2014 | Elahinia et al. |
| 2015/0005882 | A1 | 1/2015 | Abdou |
| 2015/0018829 | A1 | 1/2015 | Woodburn, Sr. et al. |
| 2015/0057755 | A1 | 2/2015 | Suddaby et al. |
| 2015/0080973 | A1 | 3/2015 | Eastlack et al. |
| 2015/0081021 | A1 | 3/2015 | Ciupik |
| 2015/0094814 | A1 | 4/2015 | Emerick et al. |
| 2015/0190242 | A1 | 7/2015 | Blain et al. |
| 2015/0202053 | A1 | 7/2015 | Willis et al. |
| 2015/0257894 | A1 | 9/2015 | Levy et al. |
| 2015/0305785 | A1 | 10/2015 | Taber et al. |
| 2015/0313585 | A1 | 11/2015 | Abidin et al. |
| 2015/0313650 | A1 | 11/2015 | Taber et al. |
| 2015/0351738 | A1 | 12/2015 | Perrow |
| 2015/0351925 | A1 | 12/2015 | Emerick et al. |
| 2015/0359640 | A1 | 12/2015 | Taber et al. |
| 2016/0000419 | A1 | 1/2016 | Weisshaupt et al. |
| 2016/0030030 | A1 | 2/2016 | Bass |
| 2016/0045333 | A1 | 2/2016 | Baynham |
| 2016/0081681 | A1 | 3/2016 | Waugh et al. |
| 2016/0089247 | A1 | 3/2016 | Nichols et al. |
| 2016/0103689 | A1 | 4/2016 | Sanghi et al. |
| 2016/0143747 | A1 | 5/2016 | Agarwal et al. |
| 2016/0199195 | A1 | 7/2016 | Hauck et al. |
| 2016/0213443 | A1 | 7/2016 | Lueck et al. |
| 2016/0270772 | A1 | 9/2016 | Beale et al. |
| 2016/0287236 | A1 | 10/2016 | Garcia-Bengochea et al. |
| 2016/0310294 | A1 | 10/2016 | McConnell et al. |
| 2016/0317323 | A1 | 11/2016 | Cho et al. |
| 2016/0317324 | A1 | 11/2016 | Cho et al. |
| 2016/0354210 | A1 | 12/2016 | Tran |
| 2016/0361177 | A1 | 12/2016 | Biedermann et al. |
| 2017/0007226 | A1 | 1/2017 | Fehling |
| 2017/0014117 | A1 | 1/2017 | Capote |
| 2017/0042527 | A1 | 2/2017 | Farley et al. |
| 2017/0056194 | A1 | 3/2017 | Biedermann et al. |
| 2017/0065269 | A1 | 3/2017 | Thommen et al. |
| 2017/0112635 | A1 | 4/2017 | Ty et al. |
| 2017/0143325 | A1 | 5/2017 | Lynn et al. |
| 2017/0172759 | A1 | 6/2017 | Kukkar et al. |
| 2017/0172760 | A1 | 6/2017 | Loebl et al. |
| 2017/0231613 | A1 | 8/2017 | Casey et al. |
| 2017/0245997 | A1 | 8/2017 | Trischler et al. |
| 2017/0340451 | A1 | 11/2017 | McCormack et al. |
| 2018/0021149 | A1 | 1/2018 | Boehm et al. |
| 2018/0085105 | A1 | 3/2018 | Kim |
| 2018/0193165 | A1 | 7/2018 | Abdou |
| 2018/0206834 | A1 | 7/2018 | Villamil et al. |
| 2018/0235724 | A1 | 8/2018 | Nowatschin et al. |
| 2018/0249992 | A1 | 9/2018 | Truckey |
| 2018/0256363 | A1 | 9/2018 | Moon |
| 2018/0289506 | A1 | 10/2018 | Kim et al. |
| 2018/0303624 | A1 | 10/2018 | Shoshtaev |
| 2018/0310927 | A1 | 11/2018 | Garcia-Bengochea et al. |
| 2018/0333061 | A1 | 11/2018 | Pracyk et al. |
| 2018/0344481 | A1 | 12/2018 | Garcia-Bengochea |
| 2018/0360621 | A1 | 12/2018 | Moon |
| 2019/0021875 | A1 | 1/2019 | Abdou et al. |
| 2019/0091037 | A1 | 3/2019 | Abdou et al. |
| 2019/0192312 | A1 | 6/2019 | Ullrich, Jr. et al. |
| 2019/0209154 | A1 | 7/2019 | Richter et al. |
| 2019/0216450 | A1 | 7/2019 | Bjork et al. |
| 2019/0216453 | A1 | 7/2019 | Predick et al. |
| 2019/0307439 | A1 | 10/2019 | Chhit et al. |
| 2019/0321022 | A1 | 10/2019 | Karpowicz et al. |
| 2020/0000497 | A1 | 1/2020 | Abdou |
| 2020/0085530 | A1 | 3/2020 | Sauer, Md |
| 2020/0100914 | A1 | 4/2020 | Abdou et al. |
| 2020/0113713 | A1 | 4/2020 | LaMarca et al. |
| 2020/0229943 | A1 | 7/2020 | Abdou |
| 2020/0330244 | A1 | 10/2020 | Abdou |
| 2020/0337861 | A1 | 10/2020 | Abdou |

(56) References Cited

U.S. PATENT DOCUMENTS

| | | | |
|---|---|---|---|
| 2020/0360155 | A1 | 11/2020 | Abdou |
| 2021/0228379 | A1 | 7/2021 | Abdou |
| 2022/0071667 | A1 | 3/2022 | Abdou |
| 2022/0211517 | A1 | 7/2022 | Abdou et al. |

FOREIGN PATENT DOCUMENTS

| | | | |
|---|---|---|---|
| BR | PI0512056 | A | 2/2008 |
| CH | 1814474 | | 9/2011 |
| DE | 3114872 | A1 | 10/1982 |
| DE | 3741493 | A1 | 6/1989 |
| DE | 29911422 | U1 | 8/1999 |
| DE | 10035182 | A1 | 2/2002 |
| DE | 20320454 | U1 | 10/2004 |
| DE | 10323363 | A1 | 12/2004 |
| DE | 602005030074 | | 9/2011 |
| EP | 0077159 | A1 | 4/1983 |
| EP | 0274713 | A1 | 7/1988 |
| EP | 0301489 | A1 | 2/1989 |
| EP | 0317972 | A1 | 5/1989 |
| EP | 0333990 | A2 | 9/1989 |
| EP | 0356112 | A1 | 2/1990 |
| EP | 0418387 | A1 | 3/1991 |
| EP | 0512529 | A1 | 11/1992 |
| EP | 0560141 | A1 | 9/1993 |
| EP | 0566810 | A1 | 10/1993 |
| EP | 0611116 | A1 | 8/1994 |
| EP | 0614649 | A1 | 9/1994 |
| EP | 0637439 | A1 | 2/1995 |
| EP | 0697200 | A1 | 2/1996 |
| EP | 0611116 | B1 | 7/1996 |
| EP | 0566810 | B1 | 8/1996 |
| EP | 0747025 | A1 | 12/1996 |
| EP | 0951879 | A2 | 10/1999 |
| EP | 0955021 | A1 | 11/1999 |
| EP | 0965313 | A1 | 12/1999 |
| EP | 1180348 | A2 | 2/2002 |
| EP | 1192910 | A2 | 4/2002 |
| EP | 1222903 | A1 | 7/2002 |
| EP | 1254640 | A2 | 11/2002 |
| EP | 1287795 | A1 | 3/2003 |
| EP | 1442715 | A2 | 8/2004 |
| EP | 1504733 | A1 | 2/2005 |
| EP | 1374808 | B1 | 12/2005 |
| EP | 1758511 | A2 | 3/2007 |
| EP | 1848352 | A2 | 10/2007 |
| EP | 1872731 | A1 | 1/2008 |
| EP | 1942816 | A2 | 7/2008 |
| EP | 1942838 | A2 | 7/2008 |
| EP | 1968466 | A2 | 9/2008 |
| EP | 1980222 | A1 | 10/2008 |
| EP | 1988854 | A2 | 11/2008 |
| EP | 1389978 | B1 | 1/2009 |
| EP | 2032086 | A2 | 3/2009 |
| EP | 2101691 | A2 | 9/2009 |
| EP | 2113228 | A1 | 11/2009 |
| EP | 2327375 | A1 | 6/2011 |
| EP | 2340788 | A1 | 7/2011 |
| EP | 1814474 | B1 | 9/2011 |
| EP | 2363080 | A1 | 9/2011 |
| EP | 2131790 | B1 | 10/2012 |
| EP | 2729081 | A1 | 5/2014 |
| EP | 3111896 | A1 | 1/2017 |
| FR | 1037262 | A | 9/1953 |
| FR | 2124815 | A5 | 9/1972 |
| FR | 2632516 | A1 | 12/1989 |
| FR | 2659226 | A1 | 9/1991 |
| FR | 2703239 | A1 | 10/1994 |
| FR | 2703580 | A1 | 10/1994 |
| FR | 2723841 | A1 | 3/1996 |
| FR | 2724108 | A1 | 3/1996 |
| FR | 2730159 | A1 | 8/1996 |
| FR | 2733413 | A1 | 10/1996 |
| FR | 2747034 | A1 | 10/1997 |
| FR | 2781359 | A1 | 1/2000 |
| FR | 2787021 | A1 | 6/2000 |
| FR | 2788958 | A1 | 8/2000 |
| FR | 2806614 | A1 | 9/2001 |
| FR | 2808995 | A1 | 11/2001 |
| FR | 2813782 | A1 | 3/2002 |
| FR | 2824261 | A1 | 11/2002 |
| FR | 2827156 | A1 | 1/2003 |
| FR | 2831796 | A1 | 5/2003 |
| FR | 2846550 | A1 | 5/2004 |
| FR | 2856271 | A1 | 12/2004 |
| FR | 2861582 | A1 | 5/2005 |
| FR | 2865629 | A1 | 8/2005 |
| FR | 2879436 | A1 | 6/2006 |
| FR | 2880795 | A1 | 7/2006 |
| FR | 2887762 | A1 | 1/2007 |
| FR | 2891135 | A1 | 3/2007 |
| FR | 2893838 | A1 | 6/2007 |
| FR | 2897259 | A1 | 8/2007 |
| FR | 2902639 | A1 | 12/2007 |
| FR | 2916956 | A1 | 12/2008 |
| FR | 2930718 | A1 | 11/2009 |
| FR | 1814474 | | 11/2011 |
| GB | 780652 | A | 8/1957 |
| GB | 2178323 | A | 2/1987 |
| GB | 1814474 | | 9/2011 |
| JP | H02261446 | A | 10/1990 |
| JP | H0998983 | A | 4/1997 |
| KR | 100858306 | B1 | 9/2008 |
| WO | WO-9000037 | A1 | 1/1990 |
| WO | WO-9107931 | A1 | 6/1991 |
| WO | WO-9301771 | A1 | 2/1993 |
| WO | WO-9307823 | A1 | 4/1993 |
| WO | WO-9314721 | A1 | 8/1993 |
| WO | WO-9404100 | A1 | 3/1994 |
| WO | WO-9420048 | A1 | 9/1994 |
| WO | WO-9508306 | A1 | 3/1995 |
| WO | WO-9510240 | A1 | 4/1995 |
| WO | WO-9515133 | A1 | 6/1995 |
| WO | WO-9525474 | A1 | 9/1995 |
| WO | WO-9715248 | A1 | 5/1997 |
| WO | WO-9723174 | A1 | 7/1997 |
| WO | WO-9730666 | A2 | 8/1997 |
| WO | WO-9737620 | A1 | 10/1997 |
| WO | WO-9801091 | A1 | 1/1998 |
| WO | WO-9817209 | A2 | 4/1998 |
| WO | WO-9855052 | A1 | 12/1998 |
| WO | WO-9900065 | A1 | 1/1999 |
| WO | WO-9904718 | A1 | 2/1999 |
| WO | WO-9909914 | A1 | 3/1999 |
| WO | WO-9921500 | A1 | 5/1999 |
| WO | WO-9921502 | A1 | 5/1999 |
| WO | WO-9933405 | A1 | 7/1999 |
| WO | WO-9938463 | A2 | 8/1999 |
| WO | WO-9953871 | A1 | 10/1999 |
| WO | WO-9956653 | A1 | 11/1999 |
| WO | WO-9956675 | A1 | 11/1999 |
| WO | WO-9956676 | A1 | 11/1999 |
| WO | WO-9963914 | A1 | 12/1999 |
| WO | WO-9965412 | A1 | 12/1999 |
| WO | WO-9966864 | A1 | 12/1999 |
| WO | WO-0015125 | A1 | 3/2000 |
| WO | WO-0018312 | A1 | 4/2000 |
| WO | WO-0023015 | A1 | 4/2000 |
| WO | WO-0024325 | A1 | 5/2000 |
| WO | WO-0024327 | A2 | 5/2000 |
| WO | WO-0053127 | A1 | 9/2000 |
| WO | WO-0064362 | A1 | 11/2000 |
| WO | WO-0072770 | A1 | 12/2000 |
| WO | WO-0074606 | A1 | 12/2000 |
| WO | WO-0078238 | A1 | 12/2000 |
| WO | WO-0101874 | A1 | 1/2001 |
| WO | WO-0103592 | A1 | 1/2001 |
| WO | WO-0106940 | A1 | 2/2001 |
| WO | WO-0119295 | A1 | 3/2001 |
| WO | WO-0126566 | A1 | 4/2001 |
| WO | WO-0128465 | A2 | 4/2001 |
| WO | WO-0141680 | A1 | 6/2001 |
| WO | WO-0143620 | A2 | 6/2001 |
| WO | WO-0145577 | A2 | 6/2001 |

(56) References Cited

FOREIGN PATENT DOCUMENTS

| | | | |
|---|---|---|---|
| WO | WO-0160270 | A1 | 8/2001 |
| WO | WO-0162191 | A2 | 8/2001 |
| WO | WO-0170141 | A1 | 9/2001 |
| WO | WO-0187194 | A1 | 11/2001 |
| WO | WO-0211633 | A2 | 2/2002 |
| WO | WO-0213732 | A2 | 2/2002 |
| WO | WO-0228299 | A1 | 4/2002 |
| WO | WO-0230307 | A2 | 4/2002 |
| WO | WO-02051326 | A1 | 7/2002 |
| WO | WO-02058599 | A2 | 8/2002 |
| WO | WO-02058600 | A2 | 8/2002 |
| WO | WO-02071960 | A1 | 9/2002 |
| WO | WO-02076315 | A1 | 10/2002 |
| WO | WO-02080788 | A1 | 10/2002 |
| WO | WO-02089701 | A2 | 11/2002 |
| WO | WO-03005939 | A2 | 1/2003 |
| WO | WO-03007829 | A1 | 1/2003 |
| WO | WO-03015646 | A2 | 2/2003 |
| WO | WO-03024298 | A2 | 3/2003 |
| WO | WO-03026522 | A2 | 4/2003 |
| WO | WO-03032850 | A1 | 4/2003 |
| WO | WO-03032851 | A1 | 4/2003 |
| WO | WO-03037200 | A2 | 5/2003 |
| WO | WO-03039400 | A2 | 5/2003 |
| WO | WO-03045262 | A2 | 6/2003 |
| WO | WO-03049629 | A1 | 6/2003 |
| WO | WO-03051212 | A2 | 6/2003 |
| WO | WO-03059212 | A1 | 7/2003 |
| WO | WO-03075803 | A1 | 9/2003 |
| WO | WO-03075804 | A1 | 9/2003 |
| WO | WO-2004016217 | A2 | 2/2004 |
| WO | WO-2004032726 | A2 | 4/2004 |
| WO | WO-2004034935 | A1 | 4/2004 |
| WO | WO-2004039283 | A2 | 5/2004 |
| WO | WO-2004039291 | A1 | 5/2004 |
| WO | WO-2004041129 | A1 | 5/2004 |
| WO | WO-2004049915 | A2 | 6/2004 |
| WO | WO-2004062482 | A2 | 7/2004 |
| WO | WO-2004084774 | A1 | 10/2004 |
| WO | WO-2004093702 | A2 | 11/2004 |
| WO | WO-2004105577 | A2 | 12/2004 |
| WO | WO-2005007040 | A1 | 1/2005 |
| WO | WO-2005009262 | A1 | 2/2005 |
| WO | WO-2005011522 | A2 | 2/2005 |
| WO | WO-2005020829 | A1 | 3/2005 |
| WO | WO-2005044119 | A2 | 5/2005 |
| WO | WO-2005046534 | A1 | 5/2005 |
| WO | WO-2005051243 | A2 | 6/2005 |
| WO | WO-2005074839 | A1 | 8/2005 |
| WO | WO-2005077288 | A1 | 8/2005 |
| WO | WO-2005104996 | A1 | 11/2005 |
| WO | WO-2005117728 | A1 | 12/2005 |
| WO | WO-2005122922 | A2 | 12/2005 |
| WO | WO-2006016384 | A1 | 2/2006 |
| WO | WO-2006041963 | A2 | 4/2006 |
| WO | WO-2006042335 | A1 | 4/2006 |
| WO | WO-2006045089 | A2 | 4/2006 |
| WO | WO-2006047587 | A2 | 5/2006 |
| WO | WO-2006058221 | A2 | 6/2006 |
| WO | WO-2006062960 | A2 | 6/2006 |
| WO | WO-2006086241 | A2 | 8/2006 |
| WO | WO-2006089292 | A2 | 8/2006 |
| WO | WO-2006096756 | A2 | 9/2006 |
| WO | WO-2006106268 | A2 | 10/2006 |
| WO | WO-2006110578 | A2 | 10/2006 |
| WO | WO-2006120505 | A1 | 11/2006 |
| WO | WO-2006130460 | A2 | 12/2006 |
| WO | WO-2006136760 | A2 | 12/2006 |
| WO | WO-2007000634 | A1 | 1/2007 |
| WO | WO-2007000654 | A2 | 1/2007 |
| WO | WO-2007034310 | A1 | 3/2007 |
| WO | WO-2007038475 | A2 | 4/2007 |
| WO | WO-2007041648 | A2 | 4/2007 |
| WO | WO-2007044705 | A2 | 4/2007 |
| WO | WO-2007044836 | A2 | 4/2007 |
| WO | WO-2007056516 | A2 | 5/2007 |
| WO | WO-2007059207 | A2 | 5/2007 |
| WO | WO-2007063398 | A2 | 6/2007 |
| WO | WO-2007064695 | A2 | 6/2007 |
| WO | WO-2007075843 | A2 | 7/2007 |
| WO | WO-2007078978 | A2 | 7/2007 |
| WO | WO-2007087535 | A2 | 8/2007 |
| WO | WO-2007089975 | A1 | 8/2007 |
| WO | WO-2007093900 | A2 | 8/2007 |
| WO | WO-2007095333 | A2 | 8/2007 |
| WO | WO-2007106573 | A2 | 9/2007 |
| WO | WO-2007075843 | A3 | 12/2007 |
| WO | WO-2007140382 | A2 | 12/2007 |
| WO | WO-2008013960 | A2 | 1/2008 |
| WO | WO-2008021319 | A2 | 2/2008 |
| WO | WO-2008024373 | A2 | 2/2008 |
| WO | WO-2008067452 | A1 | 6/2008 |
| WO | WO-2008073447 | A2 | 6/2008 |
| WO | WO-2008082836 | A1 | 7/2008 |
| WO | WO-2008085521 | A1 | 7/2008 |
| WO | WO-2008099277 | A2 | 8/2008 |
| WO | WO-2008106140 | A2 | 9/2008 |
| WO | WO-2008131084 | A2 | 10/2008 |
| WO | WO-2008149223 | A2 | 12/2008 |
| WO | WO-2009033100 | A1 | 3/2009 |
| WO | WO-2009064787 | A2 | 5/2009 |
| WO | WO-2009135208 | A1 | 11/2009 |
| WO | WO-2009152126 | A1 | 12/2009 |
| WO | WO-2010057980 | A1 | 5/2010 |
| WO | WO-2013006830 | A1 | 1/2013 |
| WO | WO-2020072600 | A1 | 4/2020 |
| WO | WO-2021158571 | A1 | 8/2021 |

OTHER PUBLICATIONS

Abstract for French Patent Publication FR2856271, Published Dec. 24, 2004, Osteo-Synthesis Vertebral col. Plate, has Connection Head Integrated with Plate and Movable in Three Directions of Space So as to Adapt itself to Connection Rod, and Including Opening to Facilitate Introduction of Rod. Accession No. 14694557, (Derwent Information Ltd.).

Abstract for German Patent No. DE10035182. (Derwent Information Ltd.), publication date Feb. 7, 2002.

Andersen T., et al., "Pain 5 years After Instrumented and Non-Instrumented Posterolateral Lumbar Spinal Fusion," European Spine Journal, 2003, vol. 12 (4), pp. 393-399.

Asazuma T., et al., "Intersegmental Spinal Flexibility With Lumbosacral Instrumentation. An In Vitro Biomechanical Investigation," Spine (Phila Pa 1976), 1990, vol. 15 (11), pp. 1153-1158.

Balderston R.A., et al., "Technique for Achievement and Maintenance of Reduction for Severe Spondylolisthesis Using Spinous Process Traction Wiring and External Fixation of the Pelvis," Spine (Phila Pa 1976), 1985, vol. 10 (4), pp. 376-382.

Barbre C.J.,, "Devices for Targeting the Needle, " Neurosurgery Clinics of North America, 2009, vol. 20 (2), pp. 187-191.

Bendo J.A., et al., "Instrumented Posterior Arthrodesis of the Lumbar Spine in Patients with Diabetes Mellitus," American Journal of Orthopedics (Belle Mead, NJ), 2000, vol. 29 (8), pp. 617-620.

Benz R.J., et al., "Current Techniques of Decompression of the Lumbar Spine," Clinical Orthopaedics and Related Research, 2001, No. (384), pp. 75-81.

Bostman O., et al., "Posterior Spinal Fusion Using Internal Fixation with the Daab Plate," Acta Orthopaedica Scandinavica, 1984, vol. 55 (3), pp. 310-314.

Branch C.L., et al., "Posterior Lumbar Interbody Fusion with the Keystone Graft: Technique and Results," Surgical Neurology, 1987, vol. 27 (5), pp. 449-454.

Bridwell K. H., et al., "Decision Making Regarding Smith-Petersen vs. Pedicle Subtraction Osteotomy vs. Vertebral Column Resection for Spinal Deformity," Spine, 2006, vol. 31(19S), pp. S171-S178.

Chen W.J., et al., "Surgical Treatment of Adjacent Instability After Lumbar Spine Fusion," Spine (Phila Pa 1976), 2001, vol. 26 (22), pp. E519-E524.

(56) References Cited

OTHER PUBLICATIONS

Chiba M., et al., "Short-Segment Pedicle Instrumentation. Biomechanical Analysis of Supplemental Hook Fixation," Spine (Phila Pa 1976), 1996, vol. 21 (3), pp. 288-294.
Cobo S.J., et al., "Predictors of Outcome After Decompressive Lumbar Surgery and Instrumented Posterolateral Fusion," European Spine Journal, 2010, vol. 19 (11), pp. 1841-1848.
Collins P., Carbon Multiwall Nanotubes: A High-Performance Conductive Additive for Demanding Plastics Applications, Materials Integrity Management Symposium, Jun. 2004, Retrieved from the Internet URL : (http://hyperioncatalysis.com/PDFs/CMWNT.pdf).
"Curve, The Ultimate Control and Information Center" from https://www.brainlab.com/surgery-products/overview-platform-products/curve-image-guided-surgery/, 8 pages, downloaded from the Internet Mar. 27, 2014.
Dar G., et al., "The Epiphyses Ring: A Long Forgotten Anatomical Structure with Significant Physiological Function", Spine Anatomy, (PA 1976). May 15, 2011, vol. 36 (11), pp. 850-856.
Dawson E.G., et al., "Intertransverse Process Lumbararthodesis with Autogenous Bone Graft," Clinical Orthopaedics and Related Research, 1981, No. (154), pp. 90-96.
Deguchi M., et al., "Biomechanical Comparison of Spondylolysis Fixation Techniques," Spine (Phila Pa 1976), 1999, vol. 24 (4), pp. 328-333.
Denis, F., "The Three col. Spine and its Significance in the Classification of Acute Thoracolumbar Spinal Injuries," Spine (Phila Pa 1976), 1983, vol. 8 (8), pp. 817-831.
Dove J., "Internal Fixation of the Lumbar Spine. The Hartshill Rectangle," Clinical Orthopaedics and Related Research, 1986, No. (203), pp. 135-140.
Fischgrund J.S., et al., "1997 Volvo Award Winner in Clinical Studies. Degenerative Lumbar Spondylolisthesis with Spinal Stenosis: A Prospective, Randomized Study Comparing Decompressive Laminectomy and Arthrodesis with and without Spinal Instrumentation," Spine (Phila Pa 1976), 1997, vol. 22 (24), pp. 2807-2812.
"Flexural Pivot Bearings for Frictionless Applications" printout of web page as displayed from Feb. 10, 2010 accessed Sep. 16, 2019 via the Internet Wayback Machine. https://web.archive.org/web/20100210030115/http://www.flexpivots.com/.
Freeman B.J., et al., "Posterior Lumbar Interbody Fusion Combined with Instrumented Postero-Lateral Fusion: 5-year Results in 60 Patients," European Spine Journal, 2000, vol. 9 (1), pp. 42-46.
Frogley M.D., et al., "Mechanical Properties of Carbon Nanoparticle-Reinforced Elastomers," Composites Science and Technology, 2003, vol. 63 (11), pp. 1647-1654.
Gibson J.N., et al., "Surgery for Degenerative Lumbar Spondylosis," Cochrane Database of Systematic Reviews, 2005, No. (4), pp. CD001352.
Gill G.G., "Long-Term Follow-Up Evaluation of a Few Patients with Spondylolisthesis Treated by Excision of the Loose Lamina with Decompression of the Nerve Roots without Spinal Fusion," Clinical Orthopaedics and Related Research, 1984, No. (182), pp. 215-219.
Greenough C.G., et al., "Instrumented Posterolateral Lumbar Fusion. Results and Comparison with Anterior Interbody Fusion," Spine (Phila Pa 1976), 1998, vol. 23 (4), pp. 479-486.
Gunzburg R., et al., "The Conservative Surgical Treatment of Lumbar Spinal Stenosis in the Elderly," European Spine Journal, 2003, vol. 12 (Suppl. 2), pp. S176-S180.
Hajek P.D., et al., "Biomechanical Study of C1-C2 Posterior Arthrodesis Techniques," Spine (Phila Pa 1976), 1993, vol. 18 (2), pp. 173-177.
Heggeness M.H., et al., "Translaminar Facet Joint Screw Fixation for Lumbar and Lumbosacral Fusion. A Clinical and Biomechanical Study," Spine (Phila Pa 1976), 1991, vol. 16 (6 Suppl), pp. S266-S269.
Holland N.R., et al., "Intraoperative Electromyography During Thoracolumbar Spinal Surgery," Spine (Phila Pa 1976), 1998, vol. 23 (17), pp. 1915-1922.
Hoshide R., et al., "Cadaveric Analysis of the Kambin's Triangle" Cureus, Feb. 2, 2016, vol. 8 (2), pp. e475.
Katz J.N., et al., "Lumbar Laminectomy Alone or with Instrumented or Noninstrumented Arthrodesis in Degenerative Lumbar Spinal Stenosis. Patient Selection, Costs, and Surgical Outcomes," Spine (Phila Pa 1976), 1997, vol. 22 (10), pp. 1123-1131.
Kis A., et al., "Reinforcement of Single-Walled Carbon Nanotube Bundles by Intertube Bridging," Nature Materials, 2004, vol. 3 (3), pp. 153-157.
Korkala O., et al., "Reduction and Fixation of Late Diagnosed Lower Ccervical Spine Dislocations Using the Daab Plate. A Report of Two Cases," Archives of Orthopaedic and Trauma Surgery, 1984, vol. 103 (5), pp. 353-355.
Krag M.H., et al., "An Internal Fixator for Posterior Application to Short Segments of the Thoracic, Lumbar, or Lumbosacral Spine. Design and Testing," Clinical Orthopaedics and Related Research, 1986, No. (203), pp. 75-98.
Lin P.M., et al., "Internal Decompression for Multiple Levels of Lumbar Spinal Stenosis: A Technical Note," Neurosurgery, 1982, vol. 11 (4), pp. 546-549.
Liquidmetal Technologies product page from http://liquidmetal.com/our-products/product-parts/, What we Sell, 5 pages, downloaded from the internet Mar. 27, 2014.
Lorenz M., et al., "A Comparison of Single-Level Fusions with and without Hardware," Spine (Phila Pa 1976), 1991, vol. 16 (8 Suppl), pp. S455-S458.
Lowery G.L., "Orion Anterior Cervical Plate System" in: Spinal Instrumentation—Surgical Techniques, Kim D.H., et al., eds., Thieme Medical Publications (New York), 2005, pp. 116-122.
Luque E.R., "Segmental Spinal Instrumentation of the Lumbar Spine," Clinical Orthopaedics and Related Research, 1986, No. (203), pp. 126-134.
Madan S., et al., "Outcome of Posterior Lumbar Interbody Fusion Versus Posterolateral Fusion for Spondylolytic Spondylolisthesis," Spine (Phila Pa 1976), 2002, vol. 27 (14), pp. 1536-1542.
Madan S.S., et al., "Circumferential and Posterolateral Fusion for Lumbar Disc Disease," Clinical Orthopaedics and Related Research, 2003, No. (409), pp. 114-123.
Marotta N., et al., "A Novel Minimally Invasive Presacral Approach and Instrumentation Technique for Anterior L5-S1 Intervertebral Discectomy and Fusion: Technical Description and Case Presentations," Neurosurgical Focus, 2006, vol. 20 (1), pp. E9.
McInerney J., et al., "Frameless Stereotaxy of the Brain," The Mount Sinai Journal of Medicine, 2000, vol. 67 (4), pp. 300-310.
Moskowitz A., "Transforaminal Lumbar Interbody Fusion," Orthopedic Clinics of North America, 2002, vol. 33 (2), pp. 359-366.
Nardi P., et al., "Aperius PercLID Stand Alone Interspinous System for the Treatment of Degenerative Lumbar Stenosis: Experience on 152 Cases," Journal of Spinal Disorders & Techniques, 2010, vol. 23 (3), pp. 203-207.
Neo M., et al., "Spinous Process Plate Fixation As a Salvage Operation for Failed Anterior Cervical Fusion. Technical Note," Journal of Neurosurgery: Spine, 2006, vol. 4 (1), pp. 78-81.
Netter F., Atlas of Human Anatomy, 3rd Edition, Icon Learning Systems, Tegerboro, New Jersey (2004).
O'Leary P.F., et al., "Distraction Laminoplasty for Decompression of Lumbar Spinal Stenosis," Clinical Orthopaedics and Related Research, 2001, No. (384), pp. 26-34.
Ozgur B.M., et al., "Extreme Lateral Interbody Fusion (XLIF): A Novel Surgical Technique for Anterior Lumbar Interbody Fusion," Spine Journal, 2006, vol. 6 (4), pp. 435-443.
Polly D.W., et al., "Surgical Treatment for the Painful Motion Segment: Matching Technology with the Indications: Posterior Lumbar Fusion," Spine (Phila Pa 1976), 2005, vol. 30 (16 Suppl), pp. S44-S51.
Qian D., et al., "Mechanics of Carbon Nanotubes," Applied Mechanics Reviews, 2002, vol. 55 (2), pp. 495-533.
Rapoff A. J., et al., "Biomechanical Comparison of Posterior Lumbar Interbody Fusion Cages," Spine, 1997, vol. 22 (20), pp. 2375-2379.
Rompe J. D., et al., "Degenerative Lumbar Spinal Stenosis. Long-Term Results After Undercutting Decompression Compared with Decompressive Laminectomy Alone or with Instrumented Fusion," Neurosurgical Review, 1999, vol. 22 (2-3), pp. 102-106.

(56) References Cited

OTHER PUBLICATIONS

Rousseau M. A., et al., "Predictors of Outcomes After Posterior Decompression and Fusion in Degenerative Spondylolisthesis," European Spine Journal, 2005, vol. 14 (1), pp. 55-60.
Santoni B. G., et al., "Cortical Bone Trajectory for Lumbar Pedicle Screws," The Spine Journal, 2009, vol. 9(5), pp. 366-373.
Sasso R. C., et al., "Translaminar Facet Screw Fixation," World Spine Journal, 2006, vol. 1(1), pp. 34-39.
Sidhu K.S., et al., "Spinal Instrumentation in the Management of Degenerative Disorders of the Lumbar Spine," Clinical Orthopaedics and Related Research, 1997, No. (335), pp. 39-53.
Smith M. D., et al., "A Biomechanical Analysis of Atlantoaxial Stabilization Methods Using a Bovine Model. C1/C2 Fixation Analysis," Clinical Orthopaedics and Related Research, 1993, No. 290, pp. 285-295.
Stambough J. L., et al., "Instrumented One and Two-Level Posterolateral Fusions with Recombinant Human Bone Morphogenetic Protein-2 and Allograft: A Computed Tomography Study," Spine (Phila Pa 1976), 2010, vol. 35(1), pp. 124-129.
Stambough J. L., "Lumbosacral Instrumented Fusion: Analysis of 124 Consecutive Cases," Journal of Spinal Disorders, 1999, vol. 12 (1), pp. 1-9.
Suzuki Y., "Shape Memory and Super-Elasticity Effects in NiTi Alloys," Titanium-Zirconium, 1982, vol. 30 (4), pp. 185-192.
Swanson K.E., et al., "The Effects of an Interspinous Implant on Intervertebral Disc Pressures," Spine (Phila Pa 1976), 2003, vol. 28 (1), pp. 26-32.
Thomsen K., et al., "1997 Volvo Award Winner in Clinical Studies. The Effect of Pedicle Screw Instrumentation on Functional Outcome and Fusion Rates in Posterolateral Lumbar Spinal Fusion: A Prospective, Randomized Clinical Study," Spine (Phila Pa 1976), 1997, vol. 22 (24), pp. 2813-2822.
Tseng Y. C., et al., "Monolithic Integration of Carbon Nanotube Devices with Silicon MOS Technology," Nano Letters, 2004, vol. 4(1), pp. 123-127.
Vaccaro, et al., Principles of Practice of Spine Surgery; Mosby Press, Philadelphia, PA; 2003.
Vamvanij V., et al., "Surgical Treatment of Internal Disc Disruption: An Outcome Study of Four Fusion Techniques," Journal of Spinal Disorders, 1998, vol. 11 (5), pp. 375-382.
Voor M. J., et al., "Biomechanical Evaluation of Posterior and Anterior Lumbar Interbody Fusion Techniques," Journal of Spinal Disorders, 1998, vol. 11 (4), pp. 328-334.
Wang J. C., et al., "Comparison of CD HORIZON SPIRE Spinous Process Plate Stabilization and Pedicle Screw Fixation after Anterior Lumbar Interbody Fusion. Invited Submission from the Joint Section Meeting On Disorders of the Spine and Peripheral Nerves, Mar. 2005," Journal of Neurosurgery: Spine, 2006, vol. 4(2), pp. 132-136.
Wang J. C., et al., "SPIRE Spinous Process Stabilization Plate: Biomechanical Evaluation of a Novel Technology. Invited Submission from the Joint Section Meeting on Disorders of the Spine and Peripheral Nerves, Mar. 2005," Journal of Neurosurgery: Spine, 2006, vol. 4(2), pp. 160-164.
Webster T. J., et al., "Increased Osteoblast Adhesion on Nanophase Metals: Ti, Ti6Al4V, and CoCrMo," Biomaterials, 2004, vol. 25 (19), pp. 4731-4739.
Willard, F. H., et al., "The Thoracolumbar Fascia: Anatomy, Function and Clinical Considerations." Journal of Anatomy, 2012, vol. 221(6), pp. 507-536.
Wohns R. N. W., et al., "Day Surgery for Anterior Cervical Microdiskectomy: Experience with 75 Cases," Jul. 11, 2002, pp. 1-3.
Wood M.J., et al., "Improving Accuracy and Reducing Radiation Exposure in Minimally Invasive Lumbar Interbody Fusion," Journal of Neurosurgery: Spine, 2010, vol. 12 (5), pp. 533-539.
Yang C.K., et al., "Binding energies and electronic Structures of Adsorbed Titanium Chains on Carbon Nanotubes," Physical Review 66, 2002, 041403-1.
Yerby S., et al., "The Effect of Cutting Flute Design on the Insertion and Pullout Properties of Self-tapping Bone Screws," Jul. 2, 2002, pp. 1-2.

* cited by examiner

DEVICES AND METHODS FOR SPINAL IMPLANTATION

PRIORITY

This application is a continuation of and claims the benefit of priority to co-owned and co-pending U.S. patent application Ser. No. 16/590,300 entitled "DEVICES AND METHODS FOR SPINAL IMPLANTATION" and filed Oct. 1, 2019, which claims the benefit of priority to each of co-owned U.S. Provisional Patent Application Ser. No. 62/766, 127 entitled "Spinal Implant with Placement Instrument Comprising a Non-detachable Distraction Member," filed Oct. 2, 2018, and U.S. Provisional Patent Application Ser. No. 62/766,123 entitled "Spinal Implant with Placement Instrument Comprising a Detachable Distraction Member," filed Oct. 2, 2018, each of which is incorporated herein by reference in its entirety.

RELATED APPLICATIONS

This application is related to co-owned and co-pending U.S. patent application Ser. No. 17/352, 0773 entitled "DEVICES AND METHODS FOR SPINAL IMPLANTATION" and filed concurrently herewith, which also is a continuation of and claims the benefit of priority to co-owned and co-pending U.S. patent application Ser. No. 16/590,300 entitled "DEVICES AND METHODS FOR SPINAL IMPLANTATION" and filed Oct. 1, 2019, each of which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Disclosure

This disclosure relates generally to medical devices, and in one exemplary aspect to bone implants and implantation apparatus and systems, components thereof, and methods of implant placement, which can be used to, inter alfa, adjust, align and maintain the spatial relationship(s) of adjacent bones or bony fragments during and/or after surgical reconstruction of skeletal segments.

2. Description of Related Technology

Whether from congenital malformation, degenerative disease, traumatic disruption, infection or neoplastic invasion, alteration in the anatomical alignment between the spinal vertebrae can cause significant pain, deformity, neurological decline and disability. Spinal disease is a major health problem in the industrialized world and the surgical treatment of spinal pathology is an evolving discipline. The traditional surgical treatment of abnormal vertebral motion and/or formation is the complete immobilization and bony fusion of the involved spinal segment and an extensive array of surgical techniques and implantable devices have been formulated to accomplish the treatment objective.

Vertebral fusion may be accomplished by using various approaches to a target spinal segment, such as e.g., anterior, antero-lateral, lateral, posterolateral, or posterior approaches (or variations and/or combinations thereof), each of which may have advantages and disadvantages. Frequently, circumferential fusion of the unstable or diseased portion of the spine with fixation of both the anterior and the posterior aspects thereof is desired. Such fusion typically requires that a patient undergoes a combination of the aforementioned approaches. For example, the anterior and/or the lateral approaches can be used to insert the bone graft into the disc space between the adjacent vertebrae, while the posterior approach is used to place bone screws or similar fasteners that are used to immobilize the vertebral bodies.

However, the combined surgical approaches utilized for circumferential fusion (as well as the multiple tools required for the procedures) can cause additional recovery time and/or discomfort for the patient, as well as increase the duration and/or complexity of a surgical procedure for the practitioner. Further, the foregoing conventional implantation systems and methods may be insufficient for treatment of patients with unusual or complex spinal curvatures and maladies, which may occur in conditions such as e.g., spondylolisthesis, coronal plane deformity (such as scoliosis), sagittal plane deformity (such as alternation in segmental kyphosis or lordosis), axial translation, rotational deformity, etc.

Hence there is a salient need for alternative methods and devices for the alteration and/or correction of spinal curvature, which, inter alia, enable minimally invasive procedures (including percutaneous operations) for treatment of the aforementioned spinal conditions. Further, it is desirable that such alternative methods and devices be usable in combination with conventional implantation systems and methods.

SUMMARY

Improved devices, systems, and methods to alter vertebral alignment and/or to otherwise treat a target spinal segment are described herein.

In one aspect, an implant delivery apparatus is disclosed. In one embodiment, the apparatus comprises a distraction member configured for distraction of a disc space and an implant track configured for slidable delivery of a substantially linear implant to the distracted disc space.

In one variant, the distraction member comprises a non-detachable distraction mechanism configured to be reversibly actuated to increase a height thereof so as to enable (i) vertebral alignment or correction of e.g., spondylolisthesis, (ii) delivery of the implant to the disc space, and (iii) removal of the distraction member from the disc space after delivery of the implant. Further, the non-detachable distraction mechanism comprises an upper plate and lower plate, and the upper and lower plates are configured to be reversibly movable between a closed (non-distracted) configuration and an open (distracted) configuration.

In one implementation, the upper and lower plates are configured to move along a vertical axis which is substantially perpendicular to a longitudinal axis of the implant track. Further, the upper and lower plates are configured to alter vertebral alignment in the coronal plane and reduce e.g., lateral spondylolisthesis.

In another implementation, the upper and lower plates are configured to move along a vertical axis which is substantially perpendicularly to a longitudinal axis of the implant track, as well as along a lateral axis which is substantially parallel to the longitudinal axis of the implant track. Further, the upper and lower plates are configured to increase a height of the vertebral disc space, as well as alter vertebral alignment in the sagittal plane and thereby reduce e.g., anterior or posterior spondylolisthesis.

In another variant, the distraction member comprises a detachable distraction mechanism configured to be actuated to increase a height thereof enable (i) vertebral alignment and/or correction of e.g., spondylolisthesis, (ii) delivery of the implant to the disc space, and (iii) co-implantation of the distraction member within the disc space along with the implant (after withdrawal of the implant delivery instrument).

In another embodiment, the device comprises a distraction member configured for distraction of a disc space and an implant track configured for slidable delivery of a substantially curved implant to the distracted disc space.

In another aspect, a method of inserting an implantable device within an intervertebral space is disclosed. In one embodiment, the method includes (i) inserting a distraction member of an implant delivery apparatus into an intervertebral disc space, (ii) actuating the distraction mechanism to move the distraction mechanism into an open (distracted) position and to alter a position of a superior vertebral bone relative to an inferior vertebral bone, (iii) loading an implant onto an implant track of the implant delivery apparatus, and (iv) releasing a pusher device to slidably advance the implant down the implant track and into the intervertebral disc space.

In one variant, the method further includes moving the distraction member into a closed (non-distracted) configuration and withdrawing the distraction member and the implant track from the intervertebral disc space.

In another variant, the method further includes maintaining the distraction member in the distracted configuration, detaching the distraction member from implant track, and withdrawing the implant track from the intervertebral disc space.

In another aspect, an implant is disclosed. In one embodiment, the implant comprises a superior member, an inferior member, and at least one side wall connecting the superior and inferior members. Further, superior and inferior members and the at least one side wall define an interior cavity of the implant, which is configured to (i) receive and engage with an implant track of an implant delivery apparatus during implant delivery, and (ii) receive a bone forming material after implantation thereof in the disc space.

In one variant, the implant has a generally curved cuboid shape.

In another variant, the implant has a generally rectangular cuboid shape.

In yet another variant, the superior and inferior members each comprise an inclined surface such that the implant has a greater height one one side of the implant relative to an opposing side of the implant, such that the implant has a generally tapered shape.

In another aspect, an implant delivery apparatus is disclosed. In one embodiment, the implant delivery apparatus includes an implant track that is continuous with a distraction member disposed at a distal end of the apparatus. The implant delivery apparatus enables distraction of the target intervertebral disc space and delivery of an implant using a single device.

In another aspect, a method for correction of spinal conditions is disclosed.

In a further aspect, a system for correction of spinal conditions is disclosed. In one embodiment, the system includes: (i) an implant delivery apparatus comprising a distraction member and an implant track, and (ii) an implant.

BRIEF DESCRIPTION OF THE DRAWINGS

FIGS. 13-14C show top plan views illustrating loading and movement of the implant of FIGS. 12A-12G when utilized with the the implant delivery instrument of FIGS. 7A-7C.

FIG. 22A-22C.

Figures 1A, 1B, 1C:
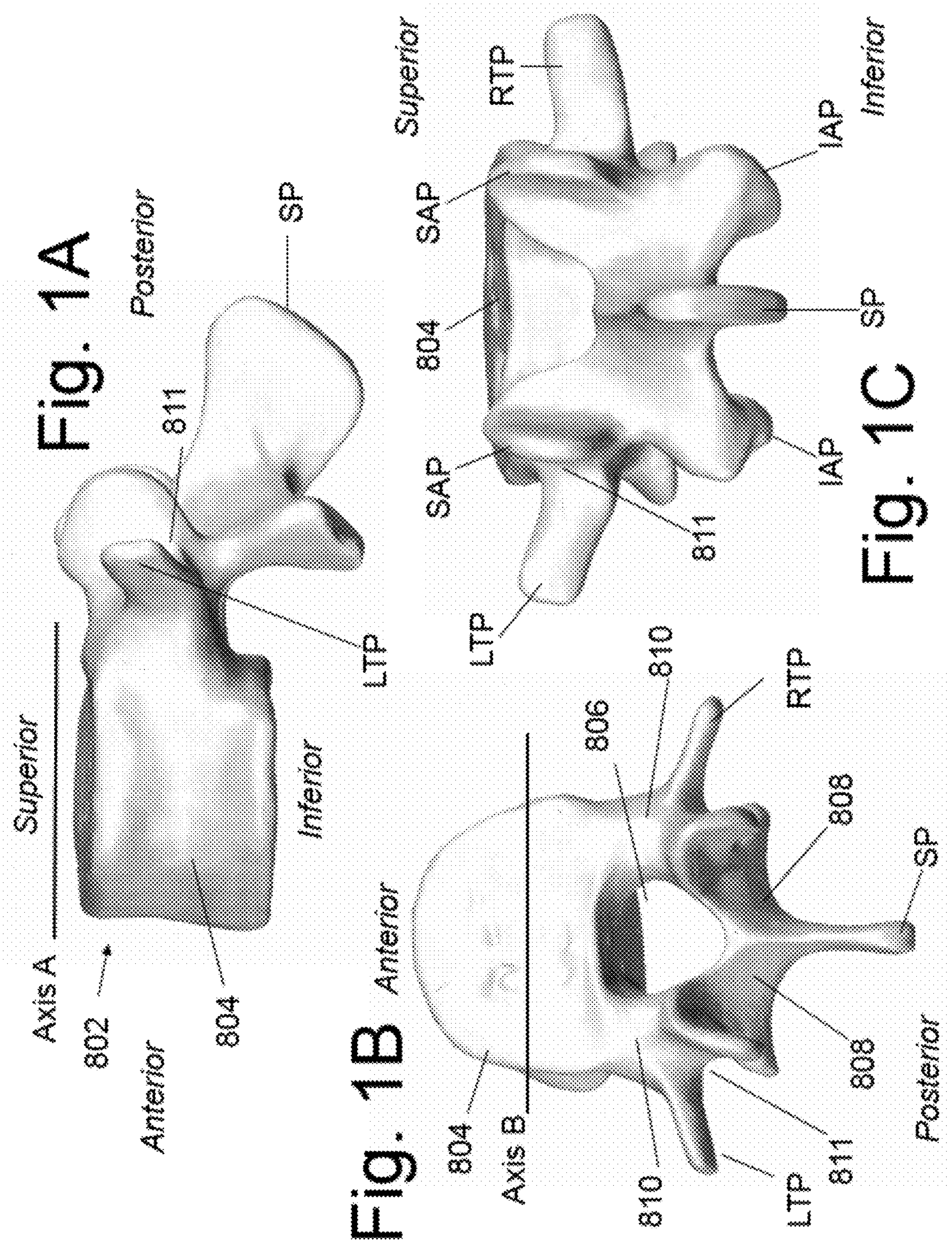
FIGS. 1A-1C show diagrammatic representations of a spinal vertebral bone in multiple views.

All Figures ©Copyright 2013-2017. Samy Abdou. All rights reserved.

DETAILED DESCRIPTION

In order to promote an understanding of the principals of the disclosure, reference is made to the drawings and the embodiments illustrated therein, and wherein like numerals refer to like parts throughout. Nevertheless, it will be understood that the drawings are illustrative and no limitation of the scope of the claims is thereby intended. Any such alterations and further modifications in the illustrated embodiments, and any such further applications of the principles of the disclosed devices as illustrated herein are contemplated as would normally occur to one of ordinary skill in the art.

Overview

In one aspect, improved devices, systems, and methods to alter vertebral alignment, or otherwise manipulate and fix a position of the vertebrae are described herein. Specifically, implantable devices and systems for implantation thereof (e.g., related components) and methods of use are disclosed herein.

It will be appreciated that in a variety of disorders, the vertebral bones of a human (or other vertebrate organism) may become mal-aligned and produce, among other conditions, translational, rotational and/or angulational deformities of the spinal column. The devices and methods disclosed herein can advantageously be used in the treatment of many spinal disorders, such as, inter alia, spondylolisthesis (anterior, posterior or lateral), coronal plane deformity (such as scoliosis), sagittal plane deformity (such as alternation in segmental kyphosis or lordosis), axial translation, rotational deformity, and the like.

In one example, spinal segment to be surgically treated using the methods and apparatus disclosed herein includes at least a superior vertebral bone, an immediately inferior vertebral bone, and the intervening intervertebral disc space. A spinal segment comprised of two immediately adjacent vertebral bones and the intervertebral disc space disposed therebetween defines a "functional spinal unit" (FSU)—as described further below. An FSU to be surgically treated will be referred to as a target FSU and its intervertebral disc space as a target intervertebral disc space.

In one embodiment, an implant delivery apparatus includes a body, a handle extending from the body, an implant track disposed on distal side of the body, a distraction mechanism disposed at a distal end of the implant track, an implant pusher device disposed on operatively connected to the body. The implant delivery apparatus is configured to enable distraction of the target intervertebral disc space and delivery of an implant to the distracted disc space. The distraction mechanism is configured to move the vertebral bones of the target FSU into a desired configuration and correct alignment thereof. The implant track is configured to have an implant loaded thereon and slidably delivered to the distracted disc space utilizing the implant pusher. The implant includes a superior plate (configured to abut the superior vertebral bone), an inferior plate (configured to abut the inferior vertebral bone), and a side wall connecting the superior plate and the inferior plate. The superior plate, the inferior plate, and the side wall define a cavity which is configured to receive an outer aspect of the implant track. Further, protrusions may be disposed on the interior surfaces of the plates, which are configured to engage with grooves on the implant track. Alternatively or additionally, protrusions/ridges may be disposed on the exterior surface of the implant track, which are configured to engage with grooves on the interior surfaces of the implant.

In one variant, the distraction member is non-detachable and is configured to be removed from the target disc space after implantation of the implant. In another variant, the distraction member is detachable and is configured to be released from the implant track and implanted in the disc space along with the implant (having been advanced down the implant track and into the target disc space).

In one embodiment, a method of treatment includes entering the target intervertebral disc space and removing at least a portion of the viscoelastic material that comprises the natural nucleus pulposus within (at least a portion of) the intervertebral disc space. The target intervertebral disc space may be accessed using various surgical approaches (such as e.g., a direct anterior approach, an anterolateral approach, and/or a direct lateral approach, posterolateral approach, posterior approach, etc.), thereby creating one or more operative corridors at desired vertebral level(s) of the spinal column.

After removal of the viscoelastic material (and optional decortication of the bony surfaces adjacent to the evacuated disc space segment(s)), the method further includes inserting the distraction member into the target intervertebral disc space, and actuating the distraction member to alter alignment of the superior and inferior vertebral bones. Next, an implant is loaded onto the implant track and advanced down the track via release of the implant pusher, and the implant is positioned within the target intervertebral disc space. In one variant, the distraction member is removed from the disc space as the implant delivery instrument is withdrawn. In another variant, the method further includes detaching the distraction member from the implant track such that the distraction member is implanted into the disc space along with the implant.

Detailed Description of the Exemplary Embodiments

Exemplary embodiments of the apparatus and methods of the present disclosure are now described in detail.

It will be appreciated that while the exemplary embodiments are described with respect to human beings, various of the methods, apparatus and systems disclosed herein may be applied to other species having a spinal structure (i.e., vertebrates).

FIGS. 1A-1C show diagrammatic representations of a spinal vertebral bone 802 in multiple views. For clarity of illustration, the vertebral bone of FIGS. 1A-1C and those of other illustrations disclosed herein are represented schematically and it should be appreciated that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. It will be appreciated that the disclosed devices and methods may be employed at any applicable spinal level.

Additionally, the term "sagittal plane", as used herein, refers without limitation to the plane that splits the body into left and right segments. The terms "mid-sagittal plane" or "median plane", as used herein, refer to the plane that specifically splits the body into equal left and right halves. The term "coronal plane", as used herein, refers without limitation to the plane that divides the body into anterior (front) and posterior (back) segments. It will be appreciated that the coronal and sagittal planes are substantially perpendicular to one another.

As can be seen in FIGS. 1A-1C, the vertebral bone 802 contains an anteriorly-disposed vertebral body 804, a centrally-disposed spinal canal 806 and a posteriorly-placed lamina 808. The pedicle segments 810 of the vertebral bone 802 form the lateral aspects of the spinal canal 806 and connect the laminas 808 to the vertebral body 804. The spinal canal 806 contains neural structures such as the spinal cord and/or nerves. A midline protrusion termed the spinous process (SP) extends posteriorly from the medial aspect of laminas 808. A protrusion extends laterally from each side of the posterior aspect of the vertebral bone 802 and is termed the transverse process (TP). A right transverse process (RTP) extends to the right from the lateral aspect of the right pedicle. A left transverse process (LTP) extends to the left from the lateral aspect of the left pedicle. A superior protrusion extends above the lamina 808 on each side of the vertebral midline, and is termed the superior articulating process (SAP). An inferior protrusion extends inferiorly below the lamina 808 on each side of the vertebral midline, and is termed the inferior articulating process (IAP).

As a brief aside, it is noted that the posterior aspect of the pedicle 810 can be accessed at an indentation 811 in the vertebral bone 802 between the lateral aspect of the SAP and the medial aspect of the TP. In surgery, it can be common practice to anchor a bone fastener into the pedicle portion 810 of a vertebral bone 802 by inserting the fastener through indentation 811 and into the underlying pedicle 810 in a posterior to anterior direction.

Figure 2B:
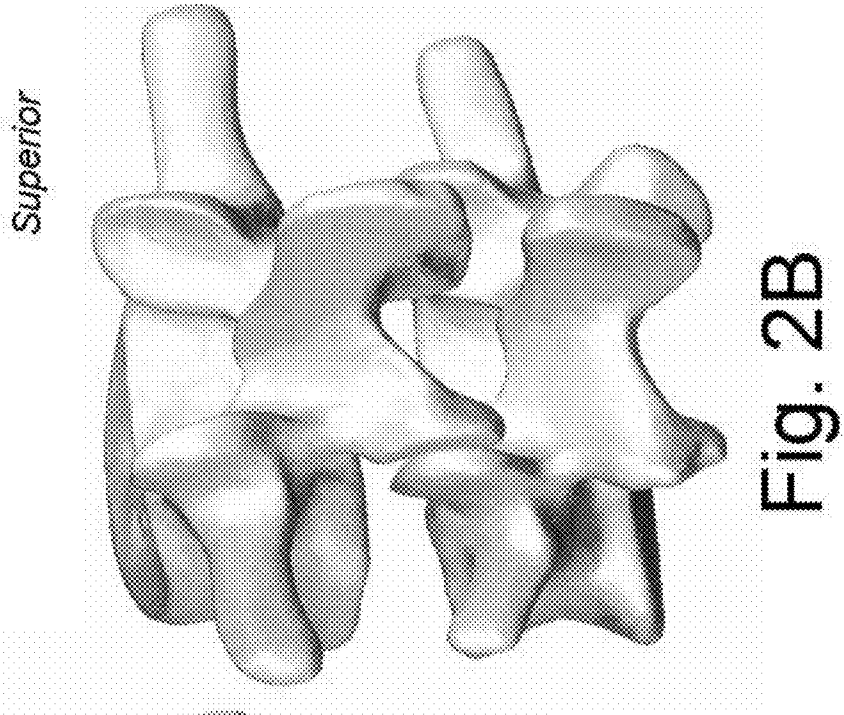
FIGS. 2A and 2B illustrate a functional spinal unit (FSU), which includes two adjacent vertebrae and the intervertebral disc between them in multiple views.
Figure 2A:
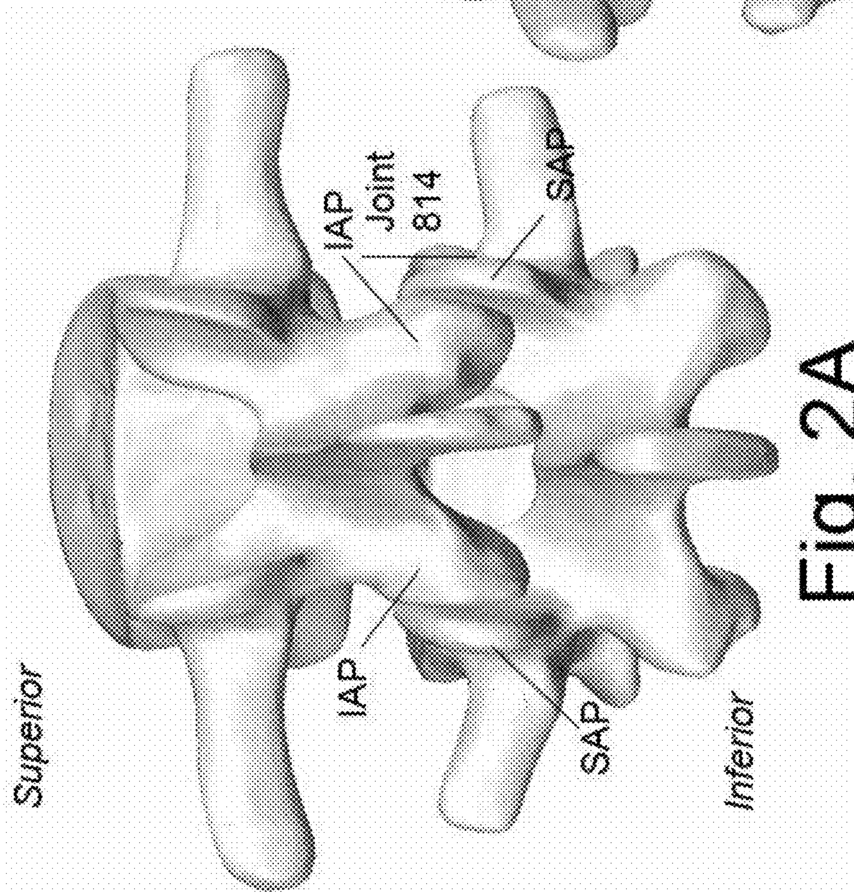

FIGS. 2A and 2B illustrate a functional spinal unit (FSU), which includes two adjacent vertebrae and the intervertebral disc disposed therebetween. The intervertebral disc resides between the inferior surface of the upper vertebral body and the superior surface of the lower vertebral body, although it is not specifically shown in the figures. FIG. 2A shows the posterior surface of the adjacent vertebrae and the articulations between them. FIG. 2B shows an oblique view. The FSU contains three joints between the two vertebral bones, with the intervertebral disc comprising the anterior joint. The posterior joints include a facet joint 814 on each side of the midline, wherein each facet joint 814 is comprised of the articulation between the IAP of the superior vertebral bone and the SAP of the inferior bone.

These illustrations and definitions of anatomical structures are known to those of ordinary skill in the art. They are described in more detail in *Atlas of Human Anatomy*, by Frank Netter, third edition, *Icon Learning Systems*, Teterboro, N.J., which is incorporated herein by reference in its entirety. It should be appreciated that the directional language and terms regarding orientation such as upper, lower, upward, downward etc., are used throughout merely for convenience of description and are not limiting.

Figure 3:
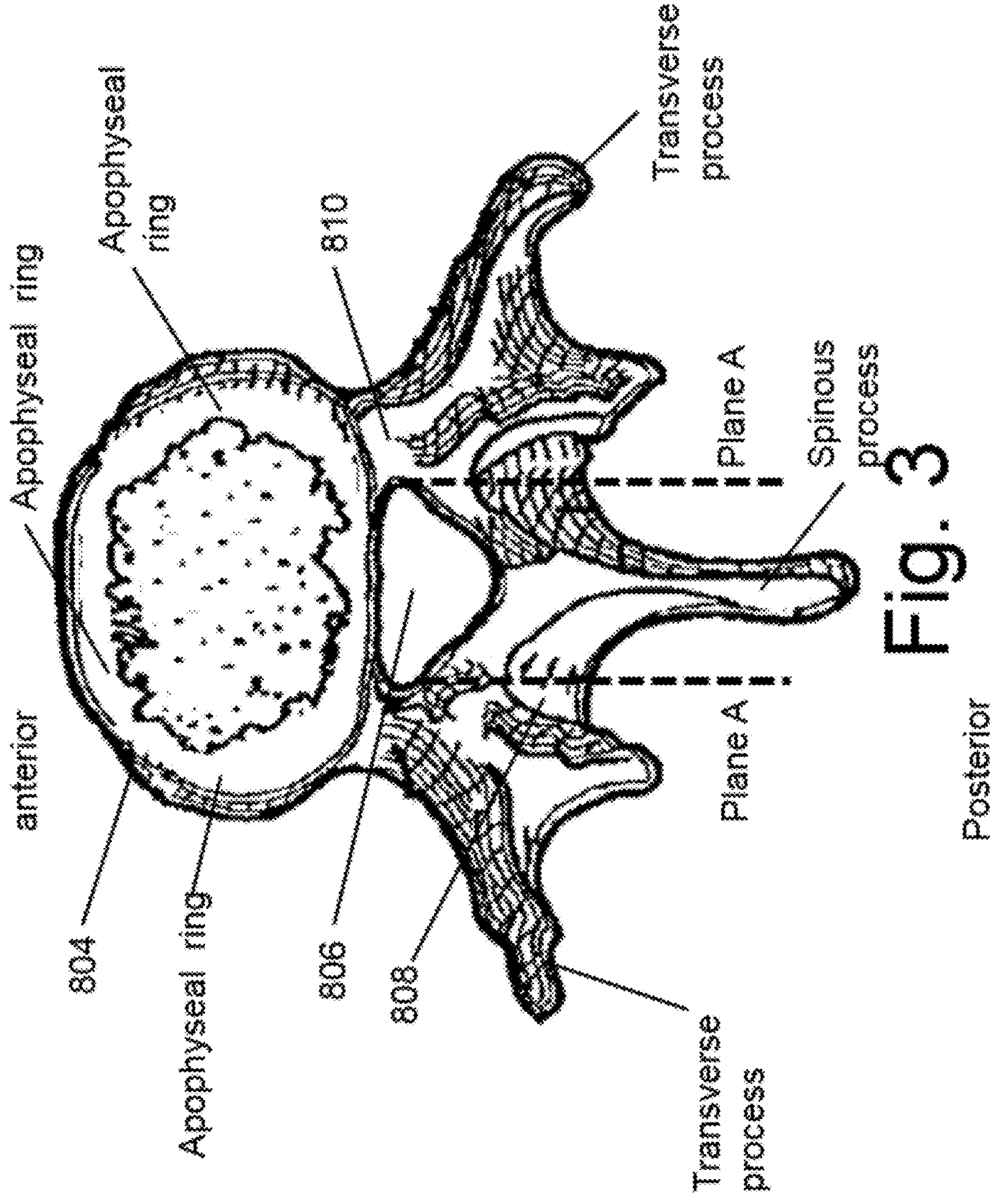
FIG. 3 illustrates a top view of a schematic illustration of a vertebral bone.

As shown in FIG. 3, the apophyseal ring is an outer rim segment of the vertebral body that is located on each of the superior and the inferior surfaces of a vertebral bone and comprise bony surfaces that abut the intervertebral discs. Further, the apophyseal ring to is circumferentially positioned and forms the most dense and strongest portion of the superior and inferior surfaces of said vertebral bone. The ring is comprised of dense bone that anchors the external fibers of the annulus fibrosis of the adjacent intervertebral disc. The apophyseal ring is discussed in greater detail in The epiphyseal ring: a long forgotten anatomical structure with significant physiological function. Dar G, et al. *Spine* (Phila Pa 1976). 2011 May 15;36(11):850-6, which is incorporated herein by reference in its entirety.

In a healthy spine within normal physiological parameters (such as that shown in FIG. 4A), the two facet joints of a functional spinal unit (FSU) collectively function to prevent, inter alia, aberrant movement in the horizontal (i.e., axial) plane of the superior vertebral bone relative to the inferior vertebral bone. As a brief aside, it is noted that the horizontal plane of a human spine refers to a plane of the erect spine that is substantially parallel to a level floor on which the subject is standing.

Figure 4B:
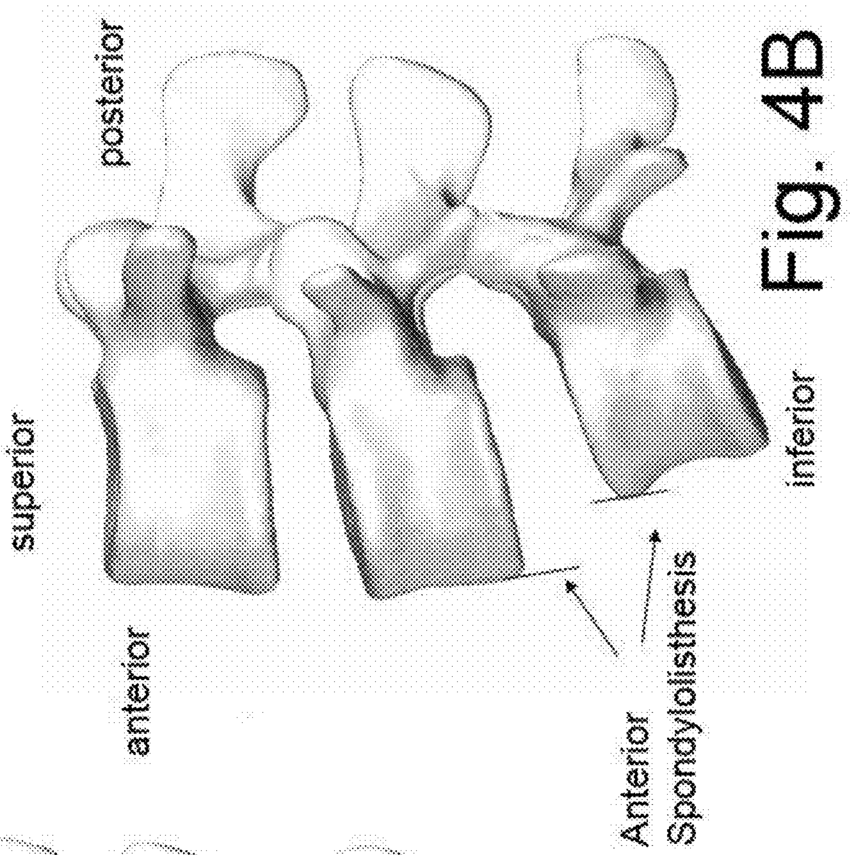
FIGS. 4A and 4B illustrate side views of a normally aligned spinal segment and a spinal segment having anterior spondylolisthesis, respectively.
Figure 4A:
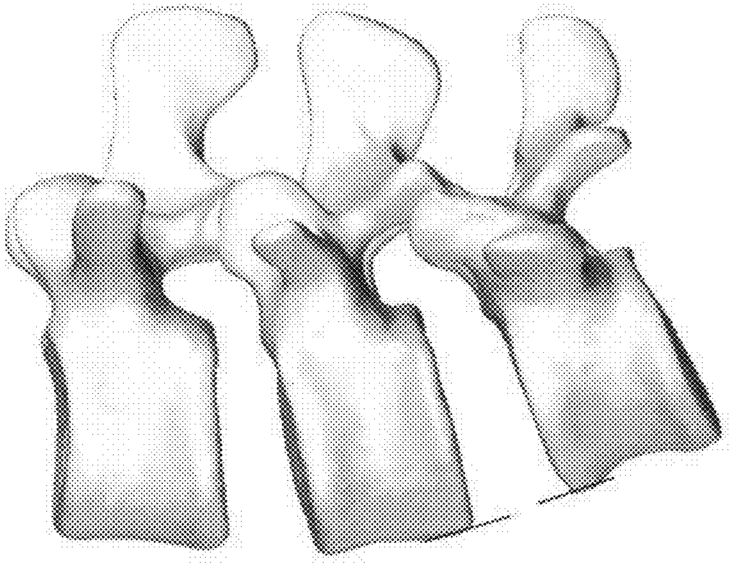

However, with aging and spinal degeneration, displacement of the vertebral bones in the horizontal plane may occur, which is a condition termed spondylolisthesis. FIG. 4A illustrates three vertebral bones with relatively normal alignment, whereas FIG. 4B shows the anterior displacement of the middle bone relative to the inferior-most bone. As illustrated therein, the vertebral column of FIG. 4B may be characterized as having an anterior spondylolisthesis of the middle vertebral bone relative to the inferior-most vertebral bone. A spondylolisthesis can be anterior, as shown in FIG. 4B, posterior (where a superior vertebral bone of an FSU is posteriorly displaced in the horizontal plane relative to the inferior vertebral bone) or lateral. In general, anterior sponylolisthesis is more clinically relevant than posterior spondylolisthesis, and any of the foregoing types of sponylolisthesis can be further classified based on the extent of vertebral displacement. Characterization of spondylolisthesis is discussed in greater detail in *Principles and Practice of Spine Surgery* by Vaccaro, Bets, Zeidman; Mosby press, Philadelphia, PA; 2003, which is incorporated herein by reference in its entirety.

With degeneration of the spine, constriction of the spinal canal and impingement of the nerve elements contained therein frequently occurs, and is termed spinal stenosis. Spondylolisthesis can exacerbate the extent of nerve compression within the spinal canal as misalignment of bone within the horizontal plane will often further reduce the size of the spinal canal. Relief of the compressed nerves can be achieved by the surgical removal of the bone and ligamentous structures that constrict the spinal canal. Decompression of the spinal canal can, however, further weaken the facet joints and increase the possibility of additional aberrant vertebral movement. Therefore, conventional spinal decompression procedures may actually worsen the extent of spondylolisthesis or produce spondylolisthesis in an otherwise normally aligned FSU elsewhere in subject's spine. Accordingly, after decompression, surgeons will commonly fuse and immobilize the adjacent spinal bones in order to prevent the development of post-operative vertebral misalignment and/or spondylolisthesis.

Figure 5:
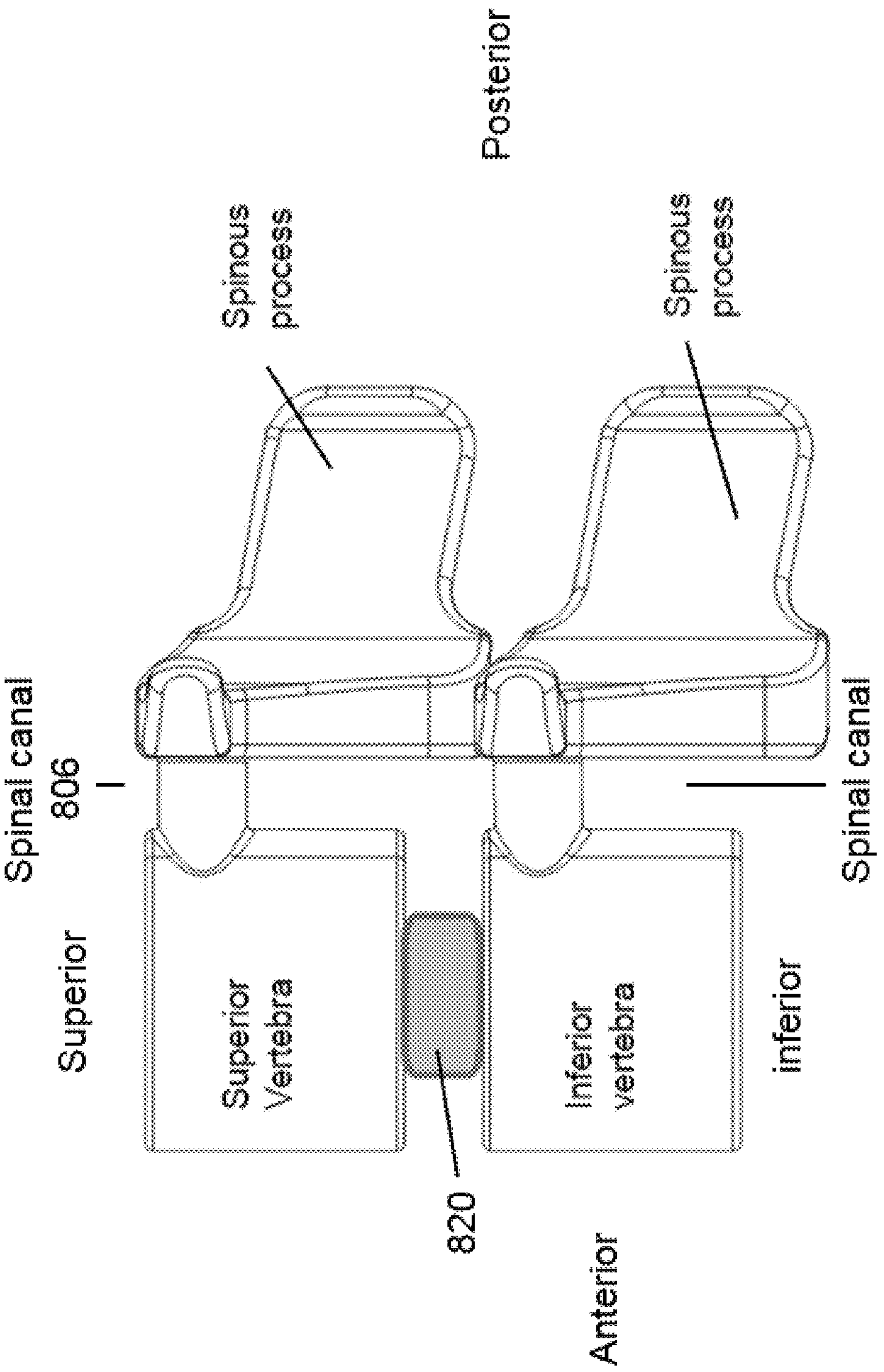
FIG. 5 illustrates schematic side view of a spinal segment having an exemplary implant inserted within a disc space thereof

Regardless of the clinical reasoning or indication for fusion of the vertebral bones, many surgeons position an implant within the disc space that rests between the two vertebral bones which are to be fused. An example of a generic interbody implant 820 positioned within a disc space between superior and inferior vertebral bodies of an immobilized FSU is depicted in FIG. 5, where a side view of a schematic FSU is shown. Many embodiments of interbody implants are known in the art, such as those shown and described in U.S. Pat. Nos. 4,636,217; 5,015,247; 5,192,327; 5,443514; 5,749,916, 6,251,140; 6,342,074; 6,706,070; 6,767,367; 6,770,096; 6,852,127; 7,037,339; 7,227,477; 7,641,690, each of which is incorporated herein by reference in its entirety.

In general, an interbody implant is usually comprised of an outer superstructure manufactured from a synthetic biocompatible material (such as e.g., metal alloy, plastic material, ceramics, or the like), and an internal cavity contained therein. The internal cavity is configured to receive and house a bone forming material that may be inserted by the surgeon into the interbody implant at the time of implantation. Openings in the superstructure permit communication and fusion between the vertebral bone(s) outside of the device and the bone forming material contained within the cavity. In general, the superstructure separates and supports the vertebral bones that abut the implanted disc space. In this way, the device can be used to maintain the disc space height. The internal cavity contains the bone formation material that will form a fusion mass which will (over time) extend from the superior vertebral bone to the inferior vertebral bone. When the superstructure is manufactured from metallic alloy, it can be advantageously made of limited thickness thereby providing a larger internal cavity for containment of a greater volume of bone forming material. However, the metallic superstructure is generally X-ray opaque, thereby limiting the ability to follow bone healing in the post-operative period via X-ray imaging. In contrast, manufacture of the superstructure from plastic materials (such as PEEK or the like) or ceramic permits X-ray visualization of the healing bone within, but significantly limits the size of the internal cavity and the volume of bone forming material contained therein as the foregoing materials have a lower mechanical strength (relative to metallic materials) and require thicker walls to provide the necessary resistance to load, strain and/or stress on the implanted device.

In alternate embodiments, interbody implants may be manufactured without a dedicated internal cavity. In these latter embodiments, the outer surface of the implant may be at least partially comprised of a material capable of promoting osseointegration (e.g., direct bony ingrowth into the implant from the adjacent bone).

Considerable clinical experience has been gained by the implantation of the aforedescribed interbody implants via a posterior surgical corridor, and practitioners have become aware of the limitations and disadvantages associated therewith. For example, in a first limitation, the implants are generally large, having a width of at least 9 mm, and therefore require substantial bony resection of the posterior spinal elements for implantation. Specifically, implantation of such devices through a posterior surgical approach often involves removal of substantial portions of the facet joint at the implanted level. Facet joint resection can add time and complexity to the surgical work, as well as increased pain and/or recovery time for the patient. Further, in another limitation, facet joint resection can also significantly destabilize the implanted FSU so that pedicle screw fixation is needed to re-stabilize the spine. In other words, implantation of the interbody device may require a high degree of bony resection so as to require extensive supplemental fixation, which (again) adds time and complexity to the surgical process and can also increase pain and/or recovery time for the patient. In yet another limitation, given the proximity to nerve elements to the posterior surgical corridor, implant placement with limited facet resection requires a greater degree of nerve retraction and increases the risk of nerve injury.

Prior attempts to reduce the width of the interbody implant and avoid the foregoing limitations have yielded implants with a height to width ratio that is greater than one, however, these implants have an increased risk of roll-over and/or dislodging within the disc space.

The interbody implants and associated implantation devices and methods disclosed herein address the above identified issues with conventional spinal implants and techniques. The devices and methods are particularly advantageous for use in minimally invasive procedures—including percutaneous operations. Although specific examples are shown and described herein, it will be appreciated that the spinal implantation devices and methods of implantation of the present disclosure may be employed in a myriad of applicable interbody fusion procedures using a variety of surgical corridor/approaches and at various spinal segments and/or structures.

It is a purpose of the present disclosure to describe implantation devices and methods for the safe and reproducible placement of an interbody device into an intervertebral disc space. In one embodiment, the interbody device may be employed without other bone fixation implants (i.e., as a "stand alone" device). In another embodiment, the interbody device may be employed in conjunction with a spinous process fixation implant. In yet another embodiment, the interbody device may be used with screw fixation of the vertebral bones, such as, for example, pedicle screw assemblies or the like. In one implementation, a pedicle screw assembly is placed into an ipsilateral pedicle of each of the superior and inferior vertebral bones that abut the implanted disc space. The screw assemblies are joined by an interconnecting member, such as a rod, and the screw assembly and joined interconnecting member are used to rigidly fixate the vertebral bones to one another. The interbody device or the pedicle screw/rod assembly may be used on one side (i.e., unilateral) of the vertebral midline alone or, alternatively, on both sides (i.e., bilateral) of the vertebral midline, where the vertebral midline is substantially defined by the mid-sagittal plane that bisects the implanted disc space/vertebral bones into a right half and a left half. In still other embodiments, the interbody device may be used with one or more additional bone fixation implants.

Figure 6B:
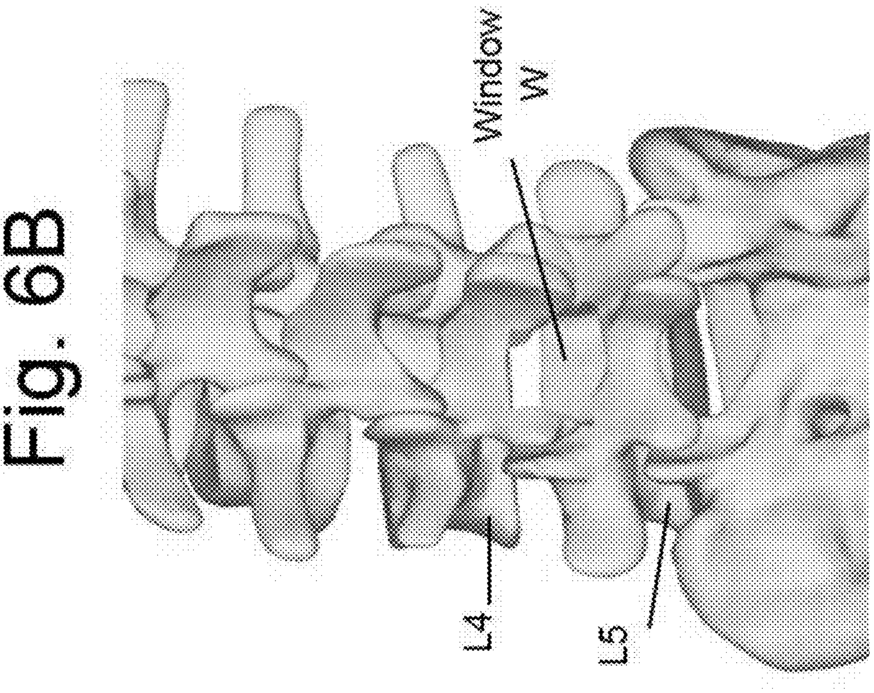
FIGS. 6A and 6B illustrate views of a spinal segment showing resection of a portion of the spine.
Figure 6A:
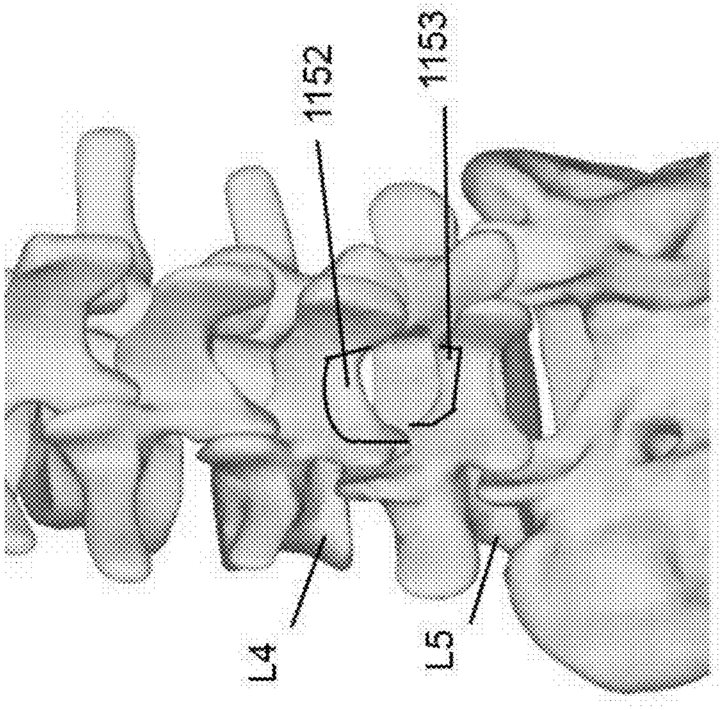

In one embodiment, the disc space that is targeted for inter-body device implantation is identified using radiographic imaging techniques (such as X-rays, CT, MRI and the like). A skin incision is made in the skin immediately posterior to the target disc space. The paraspinal muscles are retracted and a corridor is developed adjacent to the spinous process and the posterior aspect of the lamina. The lamina of each of the superior and inferior vertebrae that border the targeted disc space are identified—preferably by use of an imaging modality. Resection of the lamina posterior to the target disc space is performed, where at least a portion of the inferior aspect of the lamina of the superior vertebral bone (i.e., the vertebral bone that forms the superior border of the target disc space) is removed. FIG. 6A shows a schematic depiction of an exemplary resection of a segment 1152 of the inferior aspect of the lamina of the superior vertebral bone (when targeting the L4/5 disc space).

An additional resection of the lamina posterior to the target disc is then performed, where at least a portion of the superior aspect of the lamina of the inferior vertebral bone (i.e., the vertebral bone that forms the inferior border of the target disc space) is removed. The schematic depiction of FIG. 6A additionally shows an exemplary resection of a segment 1153 of the superior aspect of the lamina of the inferior vertebral bone. At least a portion of the ligament (i.e., the ligamentum flavum) that spans the region of lamina resection can also be removed such that the posterior aspect of the thecal sac is exposed through a window W of FIG. 6B. While shown as being formed on only one side of the midline in FIG. 6A, alternatively the window W may be formed bilaterally (i.e., the window W may be formed on both sides of the vertebral midline, where the vertebral midline is defined by a sagittal plane that substantially extends through the spinous process and divides a vertebral bone into left and right halves).

The posterior aspect of the target disc space can then be exposed through a corridor that is lateral to the thecal sac. The thecal sac may be retracted gently in the medial direction to enable identification of the posterior aspect of the target disc space. The disc space can then be entered and at least a segment of the disc material may be removed (i.e., discectomy). If necessary, a collapsed disc space having a small vertical height that is substantially below the normal value for that disc space level may be distracted to a desired (increased) height via sequential or iterative placement of shims or distractors within the disc space, where the disc space height is defined as the vertical distance from the superior disc space surface to the inferior disc space surface.

Additionally or alternatively, an implant placement instrument can be configured for distraction of the disc space. For example, the exemplary implant placement instruments disclosed herein have an intra-discal segment that is sized to be positioned within the disc space. The intra-discal segment includes opposing upper and lower plates or members, and the upper plate can be forcibly distracted away from the lower plate to enable the implant placement instrument to function as distraction device. Accordingly, the vertebral bone superior to the target disc space and its immediately inferior vertebral bone can be forcibly moved away from one another, thereby increasing the vertical height of the target disc space.

Implant and Implant Placement Apparatus

One exemplary embodiment of an implant placement instrument 100 is shown in FIGS. 7A-11B. As depicted therein, the implant placement instrument 100 includes a body 105 and a handle 104 extended outwardly therefrom. An implant track 120 extends outwardly from an anterior surface of the body 105, and a distraction member extends outwardly from a distal end of the implant track 120.

As shown in FIGS. 7C and 9A-9F, in one embodiment, a distraction member 124 includes an upper plate 1242 and a lower plate 1244. The plates 1242 and 1244 are configured to be distracted apart so as to apply a distraction force onto the vertebral bones when the distraction member 124 is positioned within the intervertebral disc space. A distal end of each of the plates 1242 and 1244 comprises a generally continuously curved surface, such that each distal end has a generally quarter circle cross-section. A proximal end of each of the plates 1242 and 1244 also comprises a curved surface, although the proximal ends are of an irregular curvature which differs from the continuous curvature of the distal ends. In alternate implementations, the curvature of the proximal and distal ends may be identical (e.g., the proximal ends may comprise a continuously curved surface), or the proximal ends may have a non-curved surface (e.g., a squared surface, an inclined surface, etc.).

Figure 9A:
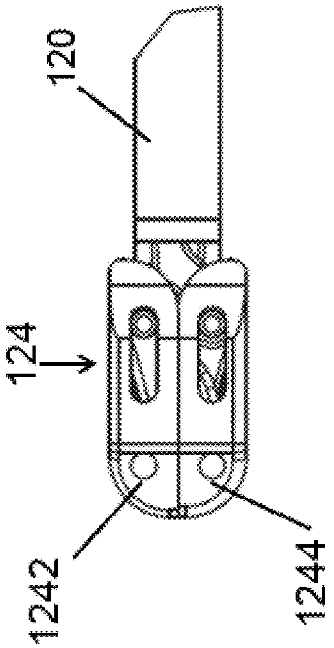
FIGS. 9A and 9B show side elevation views of a first embodiment of a distraction member for use with the implant delivery instrument of FIGS. 7A-7C.
Figure 9B:
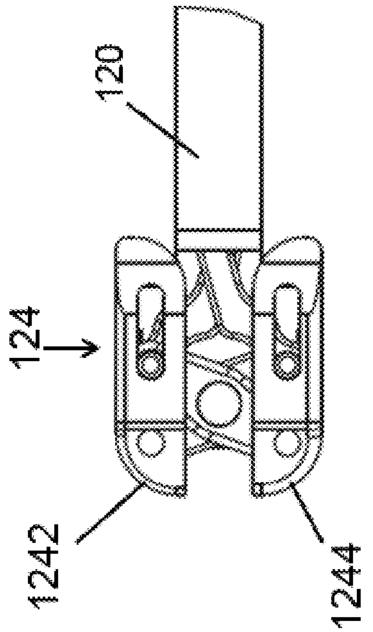
Figure 9C:
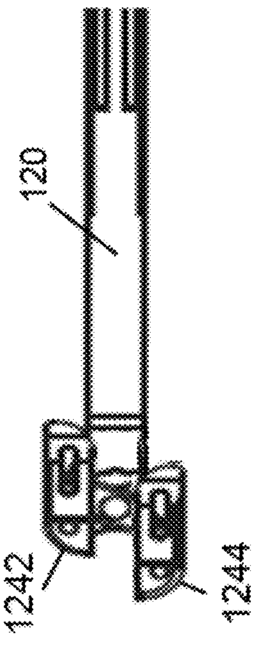
FIGS. 9C-9F show side elevation views of the first embodiment of a distraction member of FIGS. 9A and 9B, illustrating exemplary movements thereof.
Figure 9D:
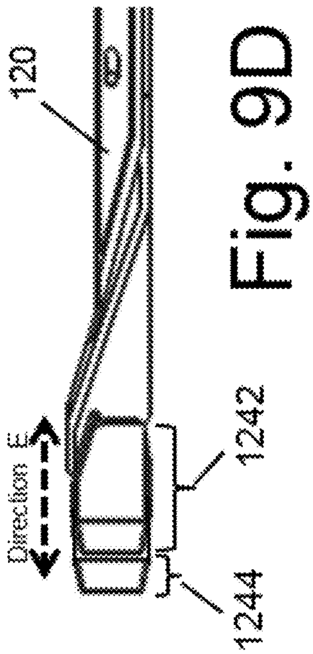

An exemplary closed (non-distracted) configuration of the distraction member 124 is shown in FIG. 9A, while an exemplary open (distracted) configuration is shown in FIG. 9B. As can be seen in FIG. 9A, in the closed configuration of the present embodiment, an interior surface of the upper plate 1242 is abutted to an interior surface of the lower plate 1244, and the continuously curved distal ends of the upper and lower plates 1242 and 1244 cooperatively form a generally half circle cross-section. Further, a height of the plates in the closed configuration is greater than a height of the implant track 120 (i.e., the exterior surfaces of the plates 1242 and 1244 respectively extend above and below a boundary of the implant track 120). The half circle cross-section of the distraction member in the closed configuration (forming curved, non-blunt end of the distraction member) may assist in enabling the distraction member to be pushed through tissues and/or a tissue corridor within the subject during insertion of the distraction member into the intervertebral disc space. As can be seen in FIG. 9B, in the open configuration, a space is disposed between the interior surface of the upper plate 1242 and the interior surface of the lower plate 1244, such that an overall height of the distraction member 124 is increased in the open configuration relative to the closed configuration. It is noted that while the plates 1242 and 1244 are movable relative to one another in the present embodiment, the upper and lower surfaces of the implant track 120 are not movable relative to each other (i.e., the upper and lower surfaces of the implant track are non-distractable) and remain stationary during distraction of the distraction member and delivery of the implant to the target disc space.

In the present embodiment, the distraction member 124 is non-detachable from the implant placement instrument 100. Accordingly, the distraction member is removed the target disc space at the conclusion of the procedure, and does not remain implanted therein. As shown in the illustrated embodiment, the plates 1242 and 1244 are joined and operable via crossed linkages (e.g., a scissor jack-like distraction mechanism), which are coupled to a distal end of implant track 120 and configured for reversible distraction of the distraction member 124. It is contemplated, however, that alternative or additional mechanisms for distraction may be incorporated into the distraction member 124. These alternative/additional distraction mechanisms may include, for example, wedges/inclines, pulleys, balloons, magnets, hydraulic drives, pistons or the like.

For example, in one alternate embodiment, the distraction member may comprise a worm screw drive or gear mechanism and an associated ridged track, which is configured to be turned (wound) via an attachable and/or insertable adjustment tool or the tool may be integrated into the implant placement instrument (see e.g., the distraction mechanism discussed below with reference to FIGS. 11A and 11B). The tool may be operated in a first rotational direction to increase a height of the distraction member, thereby increasing a distance between the superior and inferior members. Further, in some examples, the tool may be operated in a second rotational direction to decrease the height of the distraction member, and thereby decrease the distance between the upper and lower plates. Various exemplary mechanical (non-fluidic) mechanisms that can be adapted into the distraction member are shown and described in U.S. Pat. No. 7,909,870 and U.S. Patent Publication No. 2003/0163199, each of which is incorporated herein by reference in its entirety.

In another embodiment, the distraction member may include a balloon distraction mechanism made of either non-compliant or compliant material, which may be porous or non-porous, or may include a mesh material which may be coated or lined with a porous or non-porous material. The balloon may further include a port for coupling to a source of an inflation and/or expansion medium (e.g., a gas, a liquid, a semi-solid, a gel, a liquid that hardens into a solid material, etc.) for inflating and/or expanding the distraction mechanism. The devices can further include one or more anchoring or attachment features for fixing the balloon to one or both of the superior and inferior members. Actuation of such an embodiment of the distraction mechanism involves inflation of the balloon with the expansion medium, where the act of balloon inflation provides at least part of the force needed to produce the change in configuration of the distraction member (such as an increase in the height of the distraction member). An exemplary balloon driven distraction mechanism that can be adapted into the distraction member is shown and described in U.S. Pat. No. 8,123,807, which is incorporated herein by reference in its entirety.

In yet another embodiment, the distraction member can include a piston-based distraction mechanism. Specifically, a piston can be disposed within a cavity of one or both of the upper or lower plates. Note that in one implementation, the distraction member can include one or more apertures that allow filling and/or bleeding of the working fluid from the piston chamber. See also, e.g., U.S. Patent Application Publication No. 2007/0093901, which is incorporated herein by reference in its entirety, and describes the exemplary use of pistons in the manufacture of an expandable interbody implant, which may be integrated into the distraction member described above.

Turning now to FIGS. 9C-9F, exemplary movements and orientations of the plates 1242 and 1244 relative to each other during distraction of the distraction member 124 are illustrated. In one implementation, shown in FIGS. 9C and 9D, the plates 1242 and 1244 are configured to move both (i) vertically away from one another so as to cause vertebral distraction of the disc space generally along a longitudinal axis of the spine when in erect orientation, and (ii) along a direction E, which is substantially parallel to the longitudinal axis of the implant track 120. In the closed configuration (FIG. 9D) the plates 1242 and 1244 have a side-by-side arrangement where a longitudinal axis of each of the plates is substantially aligned with the longitudinal axis of the implant track 120. In the open configuration, the plates are separated by a space, and the lower plate 1244 is positioned forward of (or distal relative to) the upper plate 1242. The present implementation (illustrated in FIGS. 9C and 9D) enables the distraction member 124 to e.g., increase a height of the vertebral disc space, as well as alter vertebral alignment in the sagittal plane and thereby reduce anterior or posterior spondylolisthesis of the target FSU. It will be appreciated that the plates can be moved in one or both of the foregoing directions to varying degrees as necessary for adjustment of the target FSU.

Figure 9E:
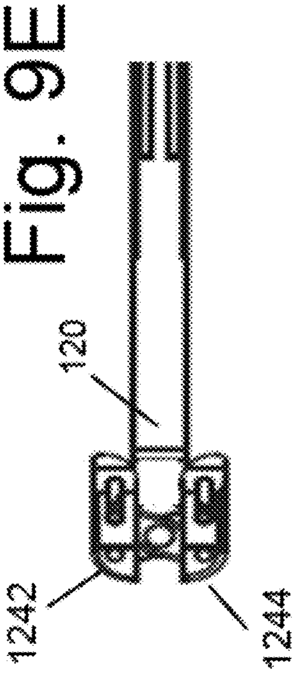
Figure 9F:
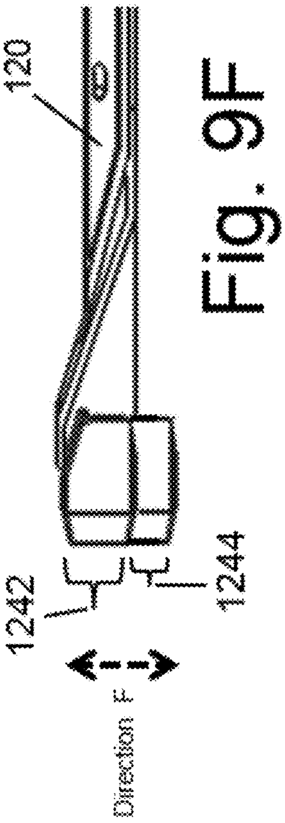

In another implementation, FIGS. 9E and 9F illustrate that the plates 1242 and 1244 are configured for movement along direction F, which is substantially perpendicular to the longitudinal axis of the track 120. In the closed configuration (FIG. 9F), the plates are in a stacked arrangement, and an interior surface of the upper plate 1242 is abutted to an interior surface of the lower plate 1244. Further, the longitudinal axis of the upper plate 1242 is generally aligned with the longitudinal axis of the implant track 120, whereas the longitudinal axis of lower plate 1244 is parallel to and offset from the longitudinal axis of the implant track 120. In the open configuration (FIG. 9E), the plates have a space disposed therebetween, yet remain in a generally stacked arrangement. In this latter implementation, the distraction member 124 is configured to, e.g., alter vertebral alignment in the coronal plane and reduce lateral spondylolisthesis.

While the plates 1242 and 1244 of the distraction member 124 are shown as moving into a substantially parallel configuration relative to one another (i.e., in each of the foregoing implementations shown in FIGS. 9C-9F the longitudinal axis of the upper plate 1242 remains substantially parallel to the longitudinal axis of the lower plate 1244 in both the non-distracted and the distracted configurations), in alternate or additional implementations, the plates may be configured to move into non-parallel configuration in order to impart a desired anatomical relationship to the target FSU. For example, the distraction member can be configured such that a distance between the distal ends of the plates is greater than a distance between the proximal ends of the plates when the distraction member is in the open/distracted configuration. In this implementation, the distraction member can be used to not only re-align the vertebral bones in the various planes described but to also confer a greater lordosis (and/or kyphosis) to the disc space of the target FSU.

Figure 10:
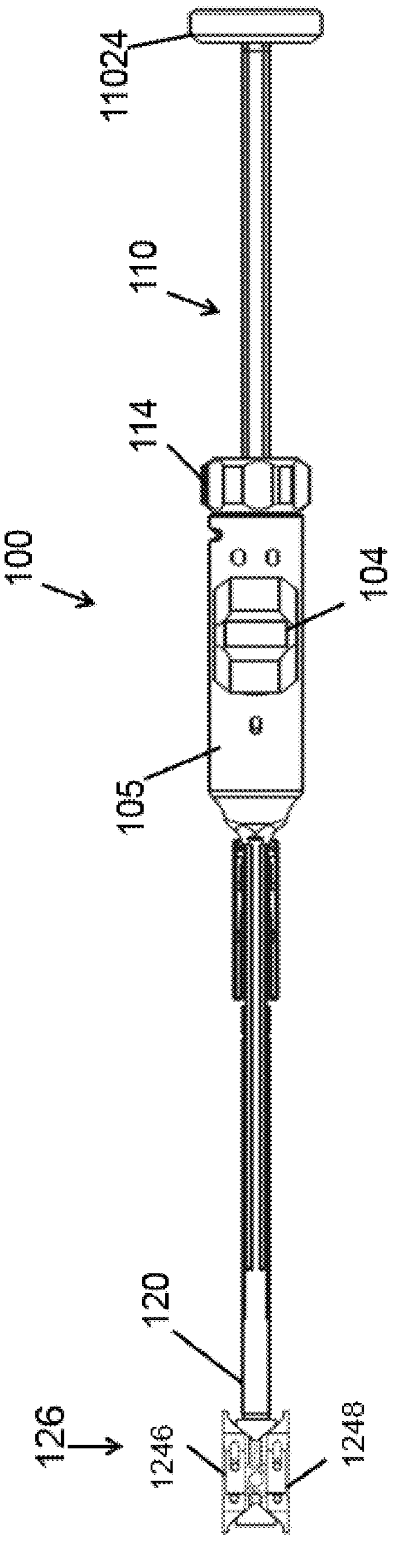
FIG. 10 shows a side elevation view of a second embodiment of a distraction member for use with the implant delivery instrument of FIGS. 7A-7C.
Figure 11A:
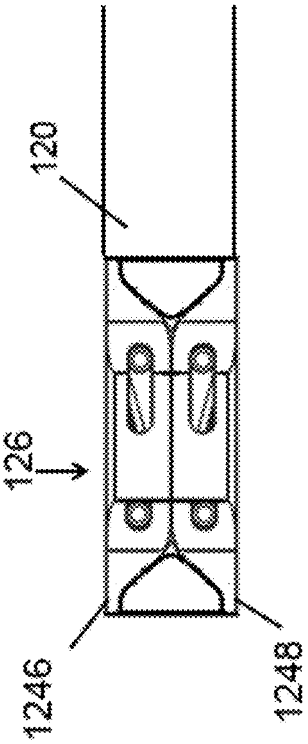
FIGS. 11A and 11B show side elevation views of the second embodiment of a distraction member of FIG. 10, illustrating exemplary movements thereof.
Figure 11B:
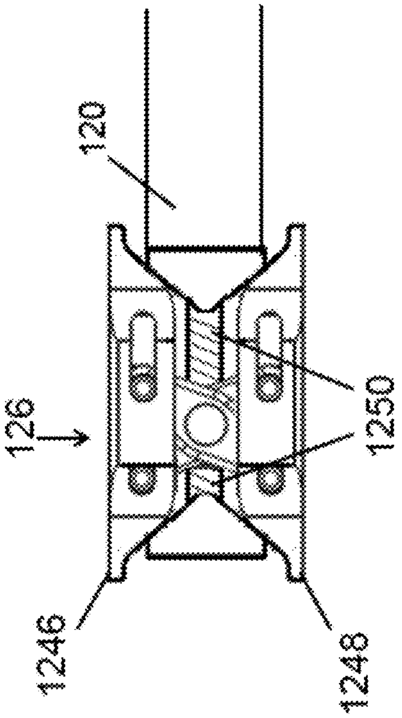

Turning now to FIGS. 10-11B, in an alternate embodiment, a detachable distraction member 126 includes an upper plate 1246 and a lower plate 1248. Similar to the plates 1242 and 1244 of the distraction member 124, the plates 1246 and 1248 are configured to be distracted apart so as to apply a distraction force onto the vertebral bones when the distraction member 126 is positioned within the intervertebral disc space. Different from the plates 1242 and 1244, each of the distal and proximal ends of the plates 1246 and 1248 comprises a generally inclined surface and have an overhang at a distal tip thereof. In alternate implementations, the proximal and distal ends comprise non-inclined surfaces (e.g., each having a squared surface, a continuously curved surface, an irregularly curved surface, etc.), or the proximal and distal ends may have different configurations (e.g., the proximal ends may comprise a continuously or irregularly curved surface, while the distal ends comprise the inclined surface).

An exemplary closed (non-distracted) configuration of the distraction member 126 is shown in FIG. 11A, while an exemplary open (distracted) configuration is shown in FIG. 11B. As can be seen in FIG. 11A, in the closed configuration, an interior surface of the upper plate 1246 is abutted to an interior surface of the lower plate 1248, and the plates have a generally stacked arrangement. Further, the inclined distal and proximal ends of the upper and lower plates cooperatively form a generally "V" shaped space therebetween, which overlaps with (aligns with) the implant track 120. The relatively small height the detachable distraction member in the closed configuration may assist in enabling the distraction member to be pushed through tissues and/or a tissue corridor within the subject during insertion thereof into the intervertebral disc space.

As depicted in FIG. 11B, in the open configuration, the upper and lower plates 1246 and 1248 have a space disposed therebetween, and remain in a generally stacked arrangement. Further, the upper and lower plates 1246 and 1248 form an "X"-like configuration.

The distraction member 126 is configured to be a separate, detachable member that may be uncoupled from the implant track 120 of the implant placement instrument 100 so as to enable implantation of the distraction member within the disc space in addition to an implant that is delivered by advancement along the implant track 120. After detachment from the implant placement instrument 100, the distraction member 126 is configured to be retained (or otherwise locked) in the distracted configuration. In the present embodiment, the plates 1246 and 1248 of the distraction member 126 are illustrated as being joined by linkages and driven by a screw 1250 (similar to a scissor jack-like distraction device with a worm screw drive). Specifically, the distraction member 126 comprises a worm screw drive or gear mechanism and an associated ridged track, which is configured to be turned (wound) via an adjustment tool integrated into the implant placement instrument. The tool may be operated in a first rotational direction to increase a height of the distraction member, thereby increasing a distance between the upper and lower plates. Further, the tool may be operated in a second rotational direction to decrease the height of the distraction member, and thereby decrease the distance between the upper and lower plates. While plates 1246 and 1248 are illustrated as being joined by linkages and driven by the screw 1250, it is contemplated that alterative distraction mechanisms may incorporated into the distraction member 126 (such as, e.g., wedges/inclines, pulleys, balloons, magnets, hydraulic drives, pistons or the like, specific examples of which are discussed above).

Further, while the plates 1246 and 1248 of distraction member 126 are shown as moving into a substantially parallel configuration relative to one another (i.e., in the foregoing implementation shown in FIGS. 11A-11B the longitudinal axis of the upper plate 1246 is substantially parallel to the longitudinal axis of the lower plate 1248 in both the non-distracted and the distracted configurations), in alternate or additional implementations, the plates may be configured to move into non-parallel configuration in order to impart a desired anatomical relationship to the target FSU. For example, the distraction member can be configured such that a distance between the distal ends of the plates is greater than a distance between the proximal ends of the plates when the distraction member is in the open/distracted configuration.

During use of the implant placement instrument 100, the operator may hold and manipulate the instrument using handle 104 for advancement of the distraction member 124 or 126 into the intervertebral disc space. If needed, a mallet, or the like, may be used to hammer against a proximal end 11024 of a proximal member 1102 in order to advance the distraction member 124 or 126 into the intervertebral disc space.

Figure 15:
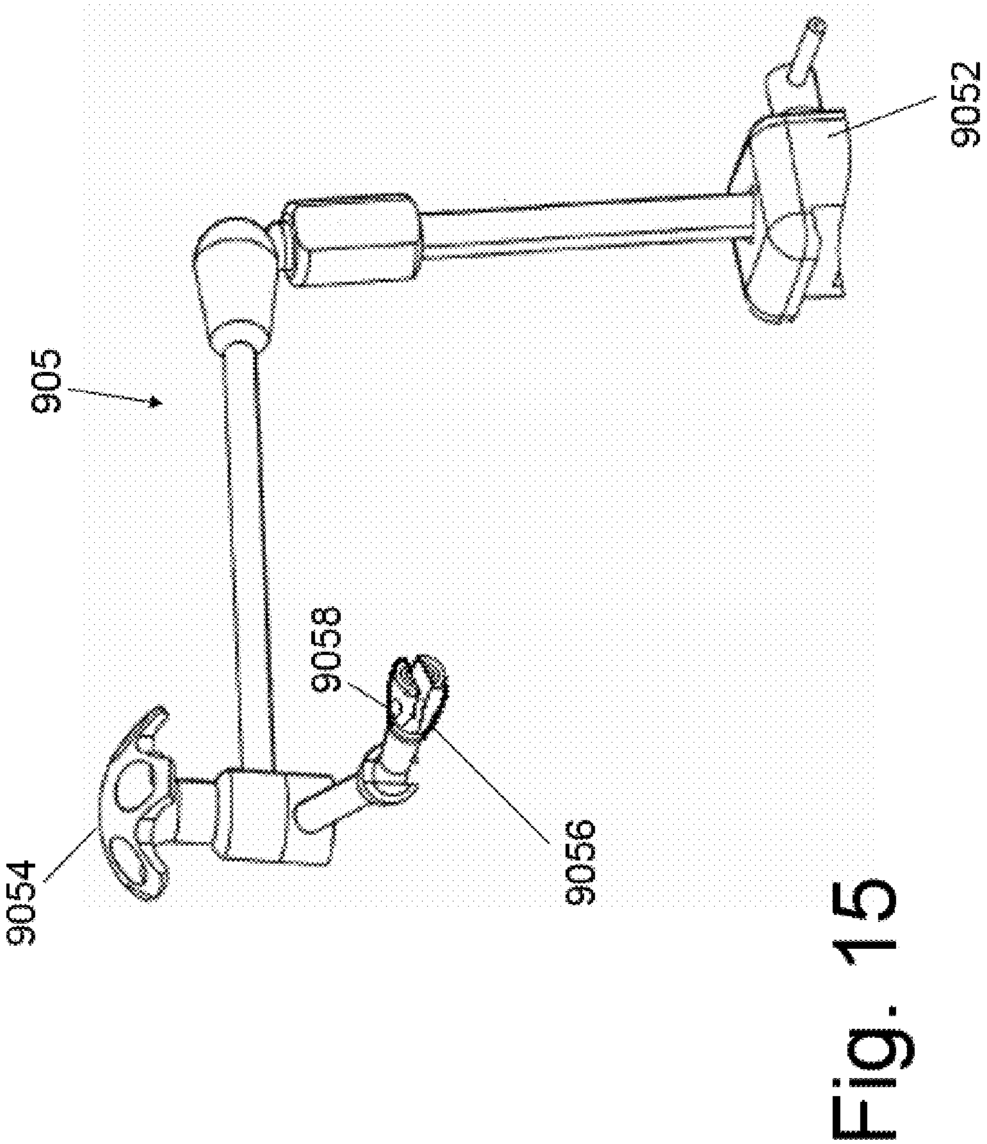
FIG. 15 illustrates a perspective view of an exemplary articulated frame configured for use with the implant delivery instruments disclosed herein.

Optionally, the implant placement instrument 100 may be stabilized via attachment to a fixation assembly that is anchored to a segment of the patient, such as, for example, a bony segment of the vertebral bone or another skeletal bone via a bone screw or the like. Additionally or alternatively, the implant placement instrument 100 may be stabilized via attachment to a fixation assembly that is anchored to the operating table on which the patient is positioned for surgery. An exemplary fixation assembly 905 is shown in FIG. 15 and is discussed elsewhere herein. The implant placement instrument 100 may also comprise a coupling region (for example, a coupling region 1046 of handle 104 shown in FIG. 7A) for attachment onto one or more of the fixation assemblies.

Once the distraction member 124 or 126 is positioned, a knob 114 is actuated so as to distract the intervertebral disc space and position the superior vertebral bone (i.e., the bone immediately above the target disc space) at a desired distance from and position relative to the inferior vertebral bone (i.e., the bone immediately below the target disc space). Specifically, in the embodiment shown in FIGS. 7A and 8B, the knob member 114 is disposed at a posterior surface of the body 105 of the implant placement instrument 100, and is configured to actuate the distraction member 124 or 126. For example, rotation of the knob member 114 in a first direction produces movement of the upper and lower plates away from one another towards the open (distracted) configuration (such as e.g., one of the configurations shown in FIGS. 9B, 9C, 9E or 11B), whereas rotation in an opposite direction causes movement of the upper and lower plates towards one another and into the closed (non-distracted) configuration (such as e.g., one of the configurations shown in FIGS. 9A, 9D, 9F or 11A). Alternatively, one of the plates may be movable and can be actuated via the knob, while the opposing plate is stationary. The knob 114 can be manually rotated by grasping the outer surface of the knob, or can be rotated by an instrument, such as, for example, a screw driver, a wrench, or the like that couples to a hex recess 1142 of the knob 114. In one exemplary implementation, a member 1102 attached at a posterior portion of the body 105 includes an aperture 11022 at a distal end portion 11024 which allows a screw driver to be advanced therethrough and into the recess 1142 of the knob 114 along trajectory D (see FIG. 7A).

After actuation of the knob 114 and distraction of the distraction member 124 or 126, an aperture 118 of the body 105 allows the operator to read a distance between a top surface of the upper plate 1242 and a bottom surface of the lower plate 1244. The reading can be used to select an appropriately sized implant to be advanced along the implant track 120 and into the distracted disc space, as will be discussed further below. The reading may be provided in a standard unit of measurement (such as millimeters, inches, etc.) or in selected letters and/or symbols that correspond to specific implant shapes and/or sizes. In the latter example, the implants usable with the implant placement instrument may be labeled with the corresponding letters and/or symbols.

One exemplary embodiment of an implant 205 configured for use with the implant placement instrument 100 is shown in FIGS. 12A-12G. As illustrated therein, the implant 205 includes a superior member 2051 and an inferior member 2052. An outer surface of the superior member 2051 is configured to abut an inferior surface of the vertebral bone immediately superior to the target disc space in which the implant 205 is positioned, while an outer surface of the inferior member 2052 is configured to abut a superior surface of the vertebral bone immediately inferior to the target disc space. The superior and inferior members 2051 and 2052 are connected by a side member (or side wall) 2053. The superior, inferior, and side members define an internal cavity 2055, which is disposed within the implant 205 and sized to receive at least a segment of the implant track 120 therein.

Although the implant 205 is depicted as having only one side member, it will be appreciated that in alternate embodiments, the implant may include one or more additional side members or partial side members. For example, the implant 205 can optionally include a movable side wall 20531, as depicted in FIGS. 12H and 12I. Specifically, the moveable side wall 20531 is moveable between a collapsed configuration (FIG. 12H) where the movable side wall 20531 is substantially flush with the side wall 2053, and an extended configuration (FIG. 12I) where the moveable side wall is disposed on an opposing lateral side of the implant 205 relative to the side wall 2053. The movable side wall 20531 may be comprised of a substantially elastic material. In one exemplary method of use, when loaded onto the implant track 120 the implant placement instrument 100, the movable side wall 20531 is compressed against the side member 2053 (in the collapsed configuration). When the insertion instrument 100 is removed from the disc space (after advancement of the implant into the disc space), the side wall is biased to the extended position. Stops (projections) on the top and bottom of the movable side wall may prevent the side wall from moving beyond the boundary of the implant (i.e., the projections are retained in the apertures in the superior and inferior members). It will be appreciated that the foregoing moveable side wall may enable (i) receipt of the exterior aspect of the implant track within the cavity and movement of the implant along with implant track in the collapsed configuration, (ii) added stability to the implant in the released configuration, and/or (iii) additional containment of bone graft material within the cavity.

Figure 12B:
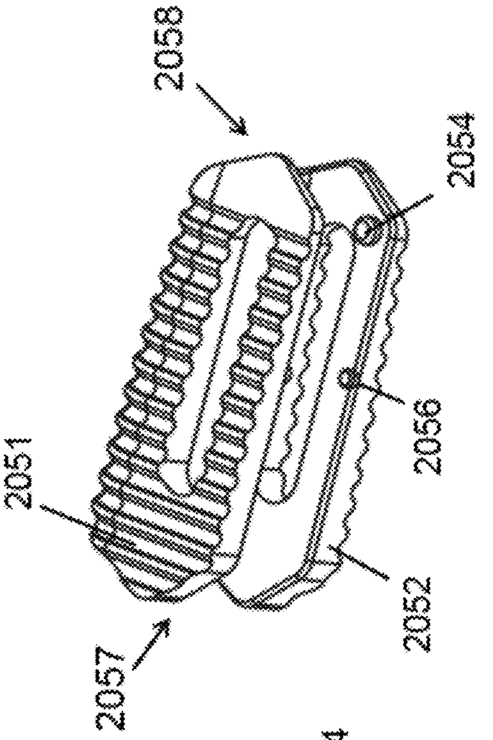
FIGS. 12A-12G respectively show front and side perspective views, as well as side elevation, front elevation, top plan, and rear elevation views of a first embodiment of an implant for use with the implant delivery instrument of FIGS. 7A-7C.
Figure 12C:
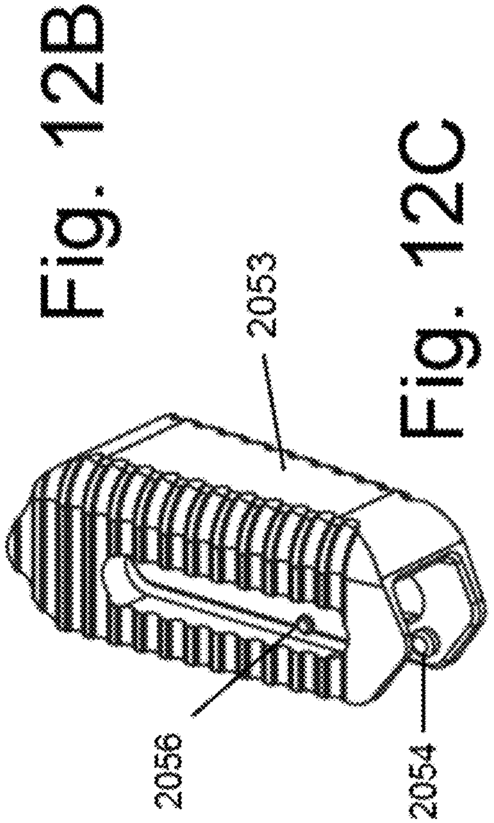
Figure 12A:
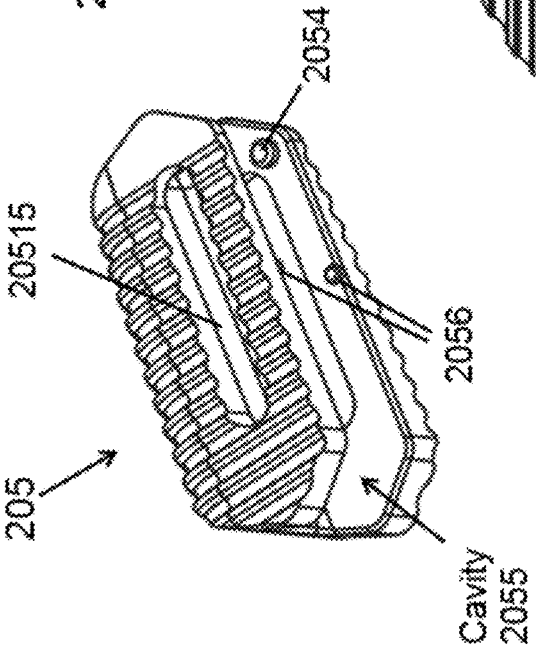
Figure 12E:
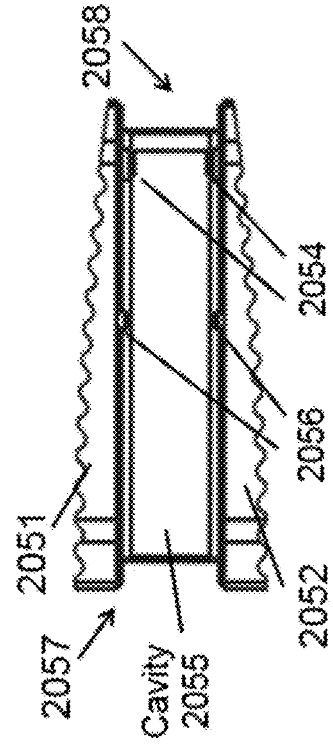
Figure 12G:
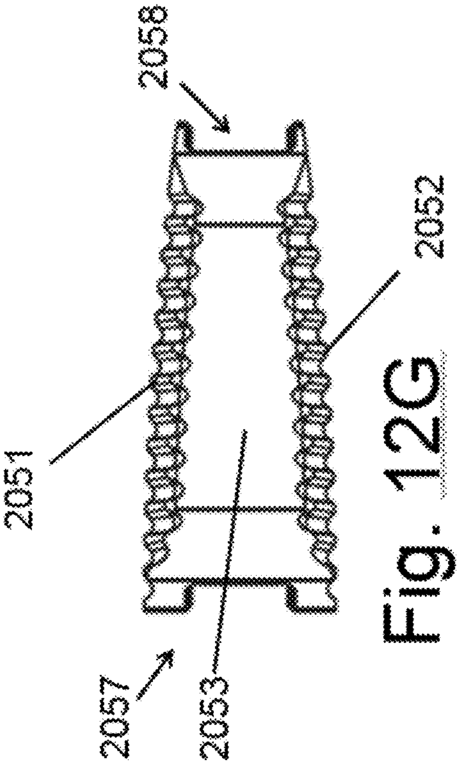
Figure 12D:
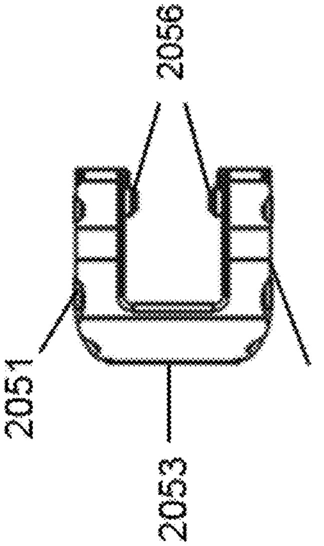
Figure 12F:
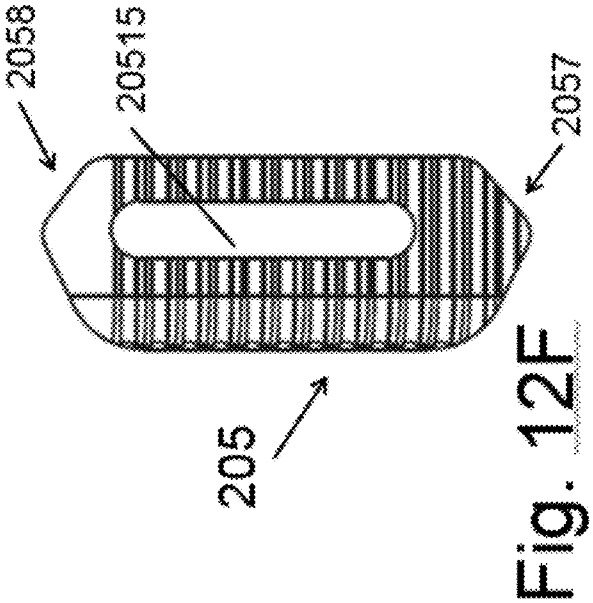
Figure 12H:
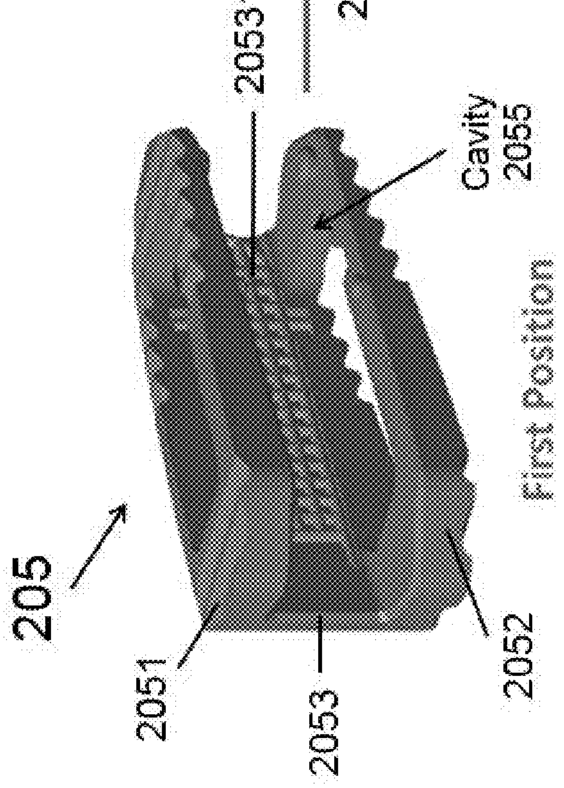
FIGS. 12H and 12I show front perspective views of the implant of FIGS. 12A-12G further including a movable member.
Figure 12I:
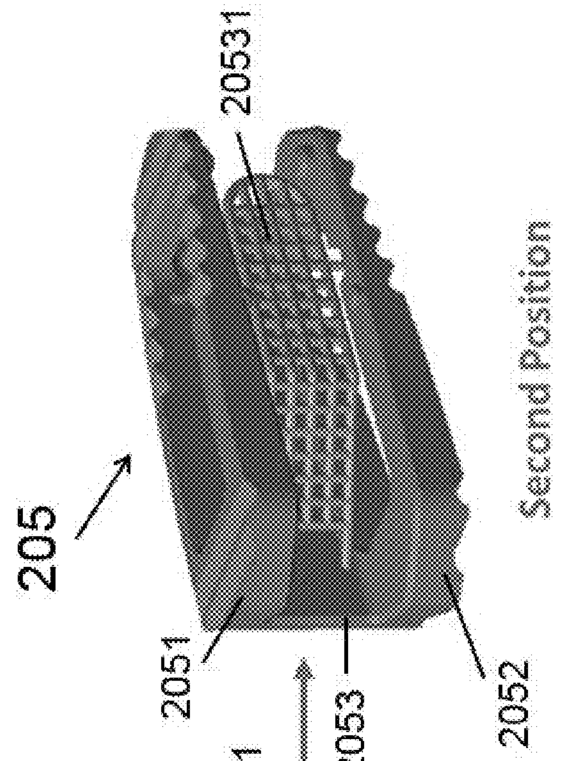

As best illustrated in FIGS. 12D and 12F, each of the superior and inferior members 2051 and 2052 includes substantially linear lateral edges and a substantially pointed or angled edge at each of a distal end 2057 and a proximal end 2058 of the implant 205. In alternate embodiments, the superior and inferior members can include one or more curved surfaces (see e.g., implants 505 and 705 depicted in FIGS. 23A-23D and 25A-25D, respectively), and/or one or more of the distal and proximal ends can have a different configuration (e.g., curved, blunted, etc.).

Turning again to FIG. 12E, each of the superior and inferior members 2051 and 2052 has an inclined exterior surface. Specifically, at the distal end 2057, each of the superior and inferior members 2051 and 2052 has a greater height than at the proximal end 2058 thereof. The foregoing features give the implant 205 a generally rectangular cuboid and tapered shape. In alternate embodiments, the superior and inferior members can have an equal height at each of the distal and proximal ends (giving the implant a non-tapered shape), or one or more of the superior or inferior members can be inclined to a greater degree than the exemplary embodiment shown in FIG. 12E.

As discussed elsewhere herein, it is contemplated a variety of implants of different shapes and/or sizes may be manufactured or provided to be usable with the implant placement instrument, and the appropriately shaped/sized implant can be selected from a pre-fabricated set of implants (or manufactured) to be specific to the condition of the target FSU in order to correct curvature or otherwise stabilize the FSU. In one embodiment, the implant 205 may be manufactured in various sizes and provided with the implant placement instrument as a kit. For example, the kit can include two lordotic options, 0° (parallel) and 8° (lordotic), with heights ranging from 8 mm to 16 mm and from 10 mm to 16 mm, respectively. Each of the implants has a width of approximately 10 mm, and can have a length of 25 mm to 30 mm.

As an alternative, the method of implant placement may include, prior to the surgical procedure, selecting a height to which the disc space will be distracted at the time of surgery (i.e., selecting the height as part of a pre-operative planning procedure performed at a date earlier than that of the surgery date). After selecting the height, the implant can be manufactured, such as e.g., via additive or subtractive 3-D printing, to the selected height, as well as dimensioned and contoured to conform to the patient-specific anatomy of the subject into which the implant will be subsequently implanted at surgery. The method may also include the use of computer-assisted navigation and/or robotics in the placement of the implant during the surgical procedure. Further, more than one target FSU may be treated/implanted at surgery and each treated FSU may be implanted with more than one implant.

Returning to FIGS. 12A-12G, each of the superior and inferior members 2051 and 2052 includes surface features (e.g., indentations and protrusions, endplate engaging surfaces, and/or anti-migration teeth) which increase implant fixation and anchor the implant onto adjacent bone. Although not shown, the side member 2053 can additionally include similar surface fixation features. Further, the surfaces of the members 2051, 2052 and/or 2053 may be coated or manufactured with an osteo-conductive bioactive material (such as, e.g., demineralized bone matrix, hydroxyapatite, and the like) and/or an osteo-inductive bioactive material (such as, e.g., Transforming Growth Factor “TGF-B,” Platelet-Derived Growth Factor “PDGF,” Bone-Morphogenic Protein “BMP,” and the like), which each promote bone formation. Furthermore, the surfaces of the implant 205 may be coated and/or manufactured with a textured or a porous ingrowth surface (such as, e.g., titanium wire mesh, plasma-sprayed titanium, tantalum, porous CoCr, and the like), provided with a bioactive coating (such as, e.g., a coating comprising tantalum, and/or helical rosette carbon nanotubes or other carbon nanotube-based coating) in order to promote bone in-growth and establish a mineralized connection between the bone and the implant.

Moreover, after implantation, the cavity 2055 may be filled with a bone forming material so as to enable a bony fusion that extends from the immediately superior vertebral bone, across the implant (via cavity 2055) and onto the immediately inferior vertebral bone. Each of surfaces 2051, 2052 and 2053 can include one or more apertures (such as, for example, an aperture 20515 within the superior surface 2051 shown in FIG. 12F) that allow direct communication between the cavity and the exterior of the implant. In this way, bone forming material placed into the cavity can form a bone bridge (i.e., fusion mass) across one or more of the the apertures and fuse the superior and inferior vertebral bones to one another. Each of the aforedescribed features can reduce the likelihood of implant dislodgement from the implantation site within the disc space.

Figure 13:
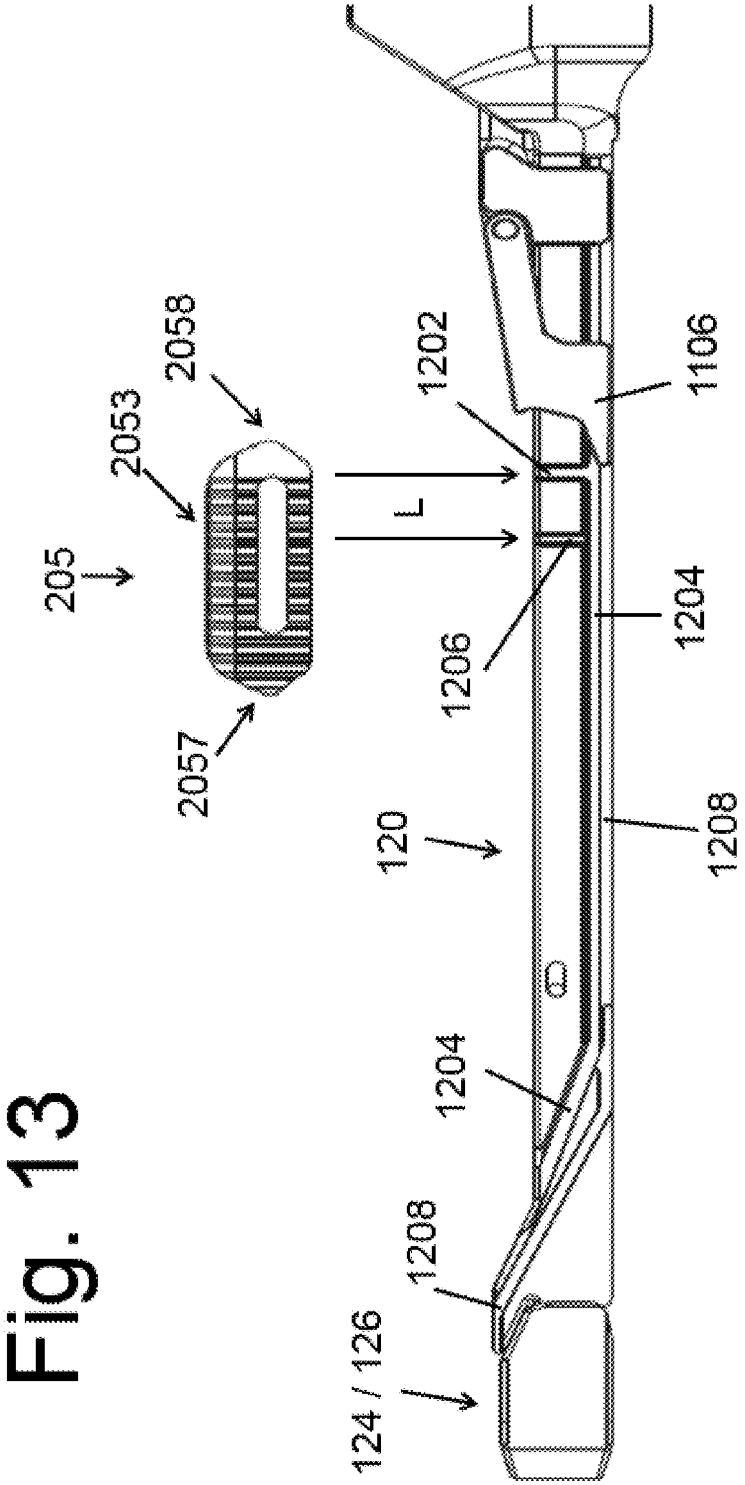

As can be seen in FIG. 13, once the distraction and/or positioning of the vertebral bones is performed and an appropriately sized/shaped implant has been selected, the implant 205 can be mounted onto an outer aspect of the implant track 120 for slidable delivery of the implant to the distracted disc space. Specifically, the implant 205 is mounted onto the implant track 120 along a direction L such that a pair of recesses 1202 and 1206 are aligned with and respectively receive complimentary protrusions of the implant. Accordingly, an upper surface of the implant track 120 engages with an interior surface of the superior member 2051, while a lower surface of the implant track 120 engages with an interior surface of the inferior member 2052.

As illustrated in 12A-12E and 12G, in one embodiment, a first pair of protrusions 2054 are disposed on an interior surface of each of the superior and inferior members 2051 and 2052 proximate to the proximal end 2058 of the implant 205, and are configured (sized and/or shaped) to be received within recesses 1202 and grooves 1204 (on opposing sides of the implant track 120) of the implant placement instrument 100. A second pair of protrusions 2056 are disposed on the interior surface of each of the superior and inferior members 2051 and 2052 at a central region of the implant 205, and are configured (sized and/or shaped) to be received within recesses 1206 and grooves 1208 (on opposing sides of the implant track 120) of the implant placement instrument 100. In one implementation, the protrusions have a head region that is greater in width/diameter than a stem region thereof (which may increase retainment of the implant to the implant track), or, in another implementation, the protrusions may be substantially cylindrical (which may increase ease of advancement of the implant along the implant track).

The protrusions are each (generally) disposed on the interior surfaces of the superior and inferior members on an opposing side of the implant 205 relative to the side member 2053. Accordingly, when the implant 205 is mounted onto the implant track 120, the side member 2053 is oriented away from the track. It is noted that, in the present embodiment, the protrusions 2054 are of different diameter, length/shape, and position within the cavity 2055 relative to the protrusions 2056, which thereby enables the first and second sets of protrusions to interact with and be slid within different (i.e., complimentarily configured) recesses and grooves when mounted onto and advanced down the implant track 120.

In alternate embodiments, the implant and the implant placement instrument can be configured with additional or fewer complimentary protrusions and grooves (such as e.g., having protrusions on an interior surface of only one of the superior and inferior members), and/or the protrusions can be of an identical or similar configuration (such as e.g., having two sets of protrusions of an equal diameter on each of the superior and inferior members). Further, in additional alternate embodiments, the interior surface of the side wall and an outer aspect of the implant track can be configured to have complimentary protrusions and grooves. Yet further, in additional alternate embodiments, the interior surfaces of the implant can include one or more grooves therein, which are configured to receive a rail or elongate projection on an exterior surface of the implant track. It will be appreciated that various combinations of the foregoing embodiments for engagement of the implant and the implant track are contemplated herein.

Figure 7A:
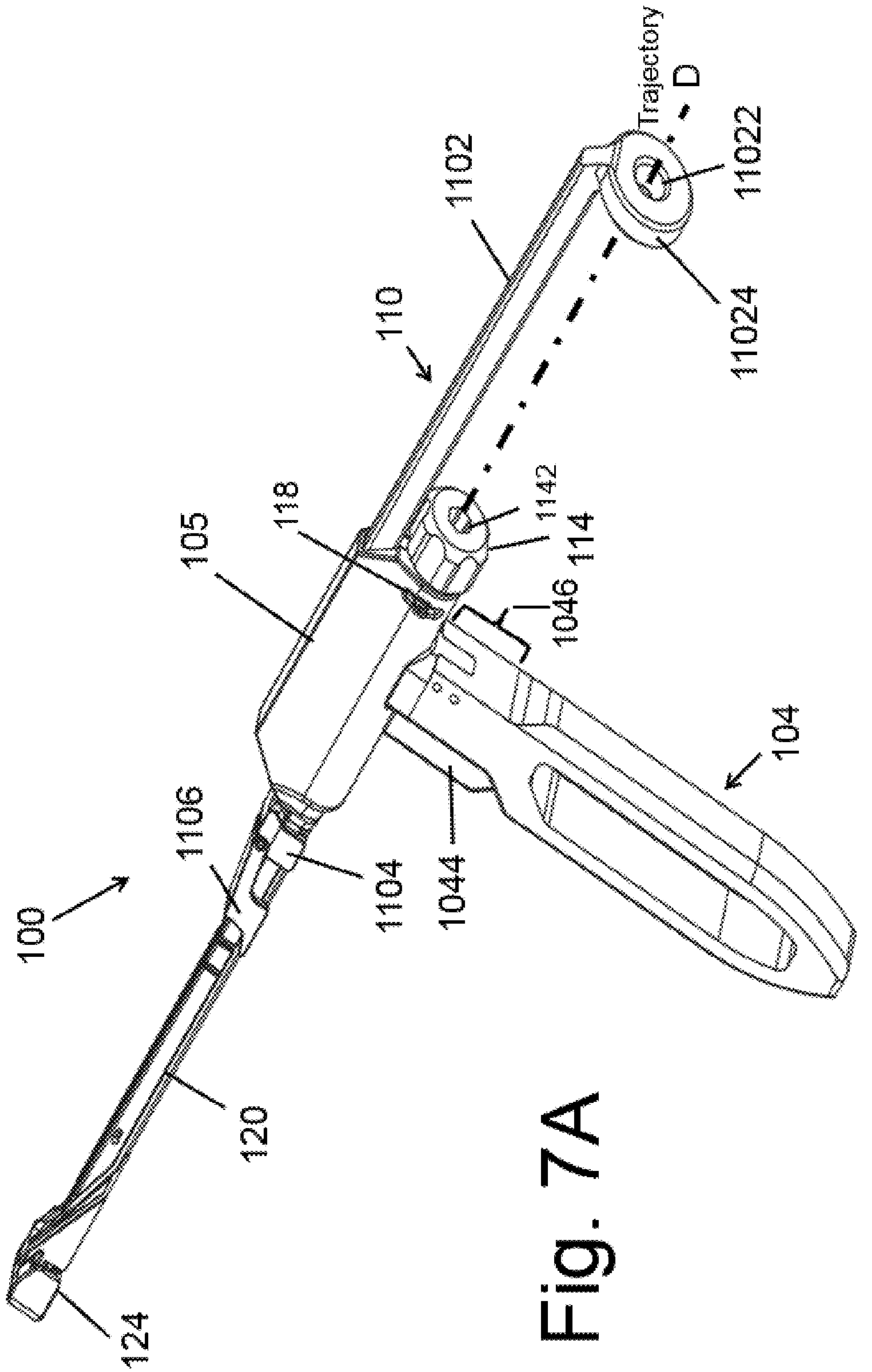
FIG. 7A-7C respectively show top perspective, top plan and side elevation views of an exemplary implant delivery instrument according to one embodiment of the present disclosure.
Figure 7B:
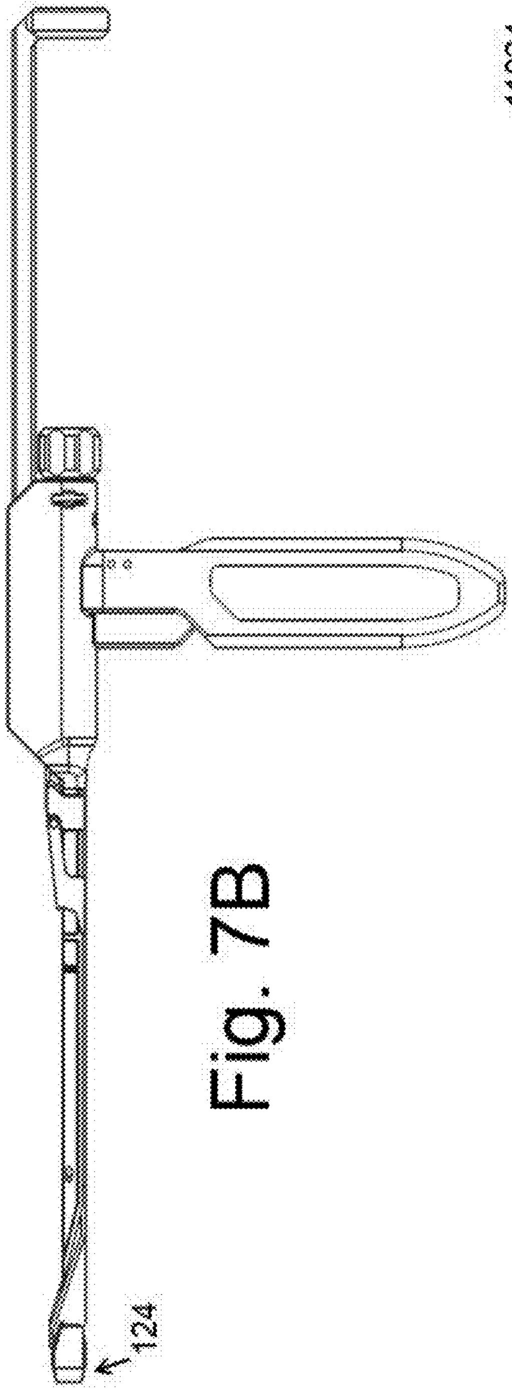
Figure 7C:
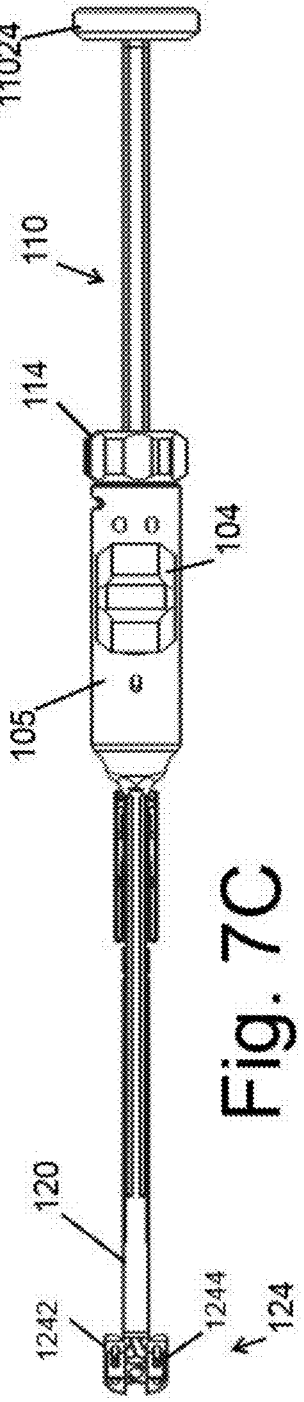
Figure 8A:
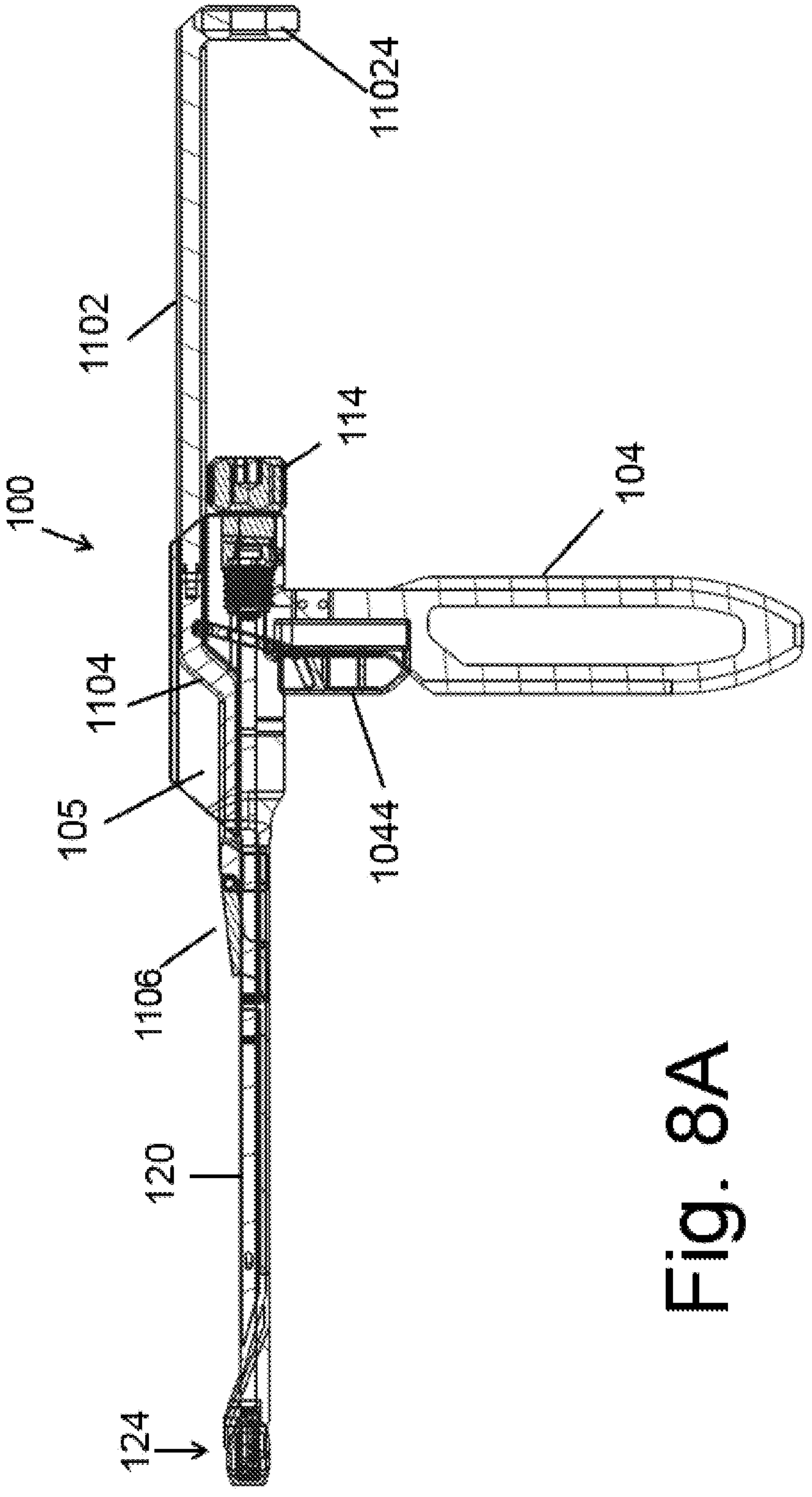
FIGS. 8A and 8B show cross-sectional views of the exemplary implant delivery instrument of FIGS. 7A-7C.
Figure 8B:
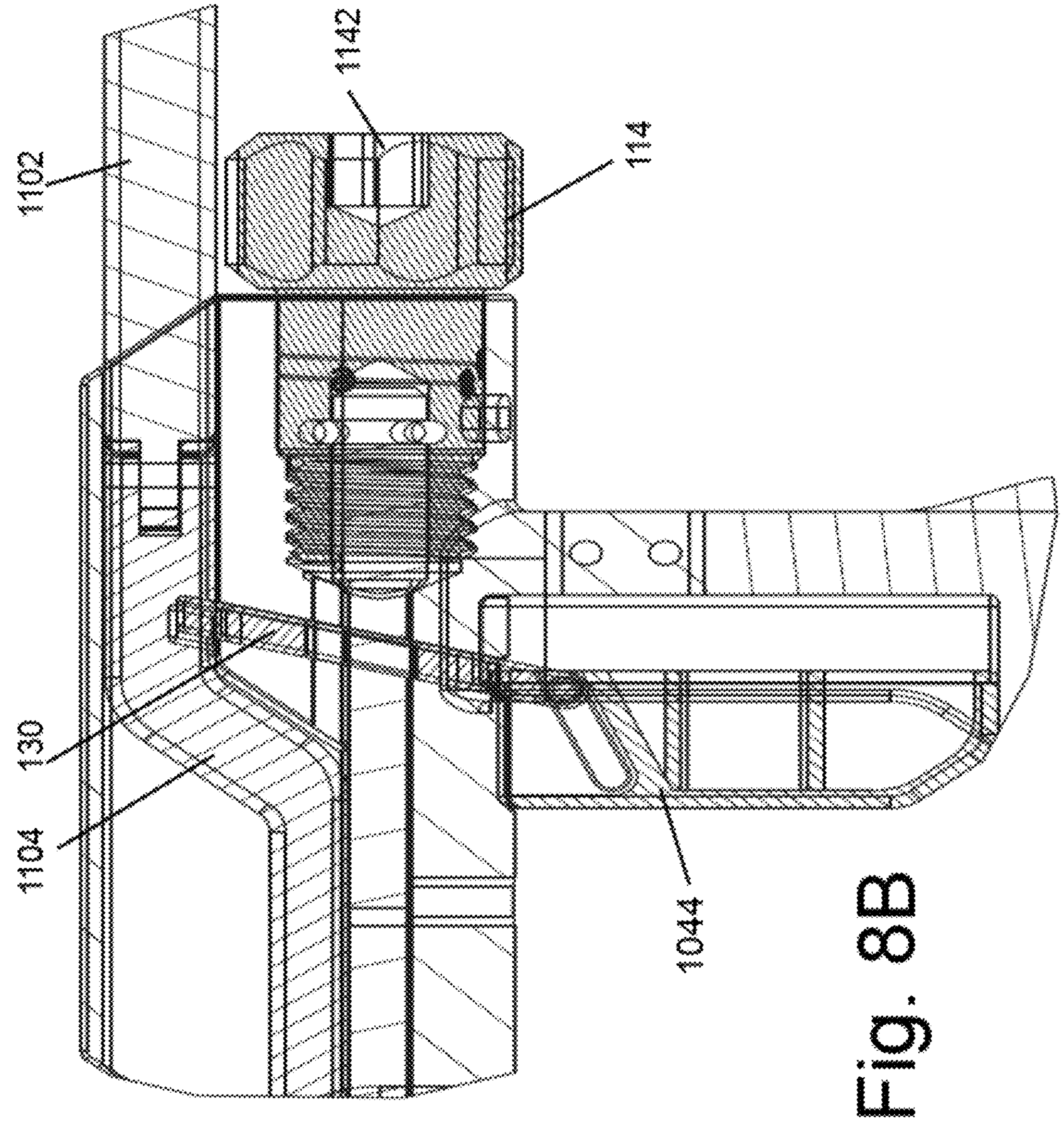

In order to enable the aforementioned mounting and sliding of the implant down the implant track, it is noted that the recesses 1202 are continuous with the grooves 1204, and the recesses 1206 are continuous with the grooves 1208 (on each side of the implant track 120). Thus, after the implant is mounted onto the implant track, a release member 1044 (FIG. 7A) on the handle 104 of the implant placement instrument 100 can be depressed to release an implant pusher 110. As shown in FIG. 7A, the implant pusher 110 includes the proximal member 1102, an intermediate member 1104, and a distal, rotatable member 1106. As can be seen in FIG. 8B, a bar 130 is coupled to the release member 1044 and is configured to enable actuation of the implant pusher 110 via the release member 1044. Specifically, when the release member 1044 is fully extended (i.e., when member 1044 is not depressed), one end of the bar 130 is positioned within a recess of the intermediate member 1104 so that the pusher 110 is immobilized relative to the body 105 and cannot be moved along the track 120. When the release member 1044 is depressed, the bar 130 is withdrawn from the recess within the intermediate member 1104 so that a force (such as, for example, a force exerted by a mallet, a manual force, a machine guided force, or a force from a spring loaded device) is applied to the proximal end 11024 to permit the (now-unconstrained) pusher 110 to advance along the implant track 120 and push the implant 205 towards the distraction member 124 or 126. Specifically, the implant 205 is engaged by the distal, rotatable member 1106 of the pusher 110 as it is advanced along the implant track 120. The implant 205 is retained onto the implant track 120 by the interaction of the protrusions 2054 and 2056 with the grooves 1204 and 1208 respectively. It is noted that the distal end 2057 is a leading edge or side of the implant, while the proximal end is a lagging edge or side of the implant when the implant 205 is advanced along the implant track 120.

Figures 14A, 14B, 14C:
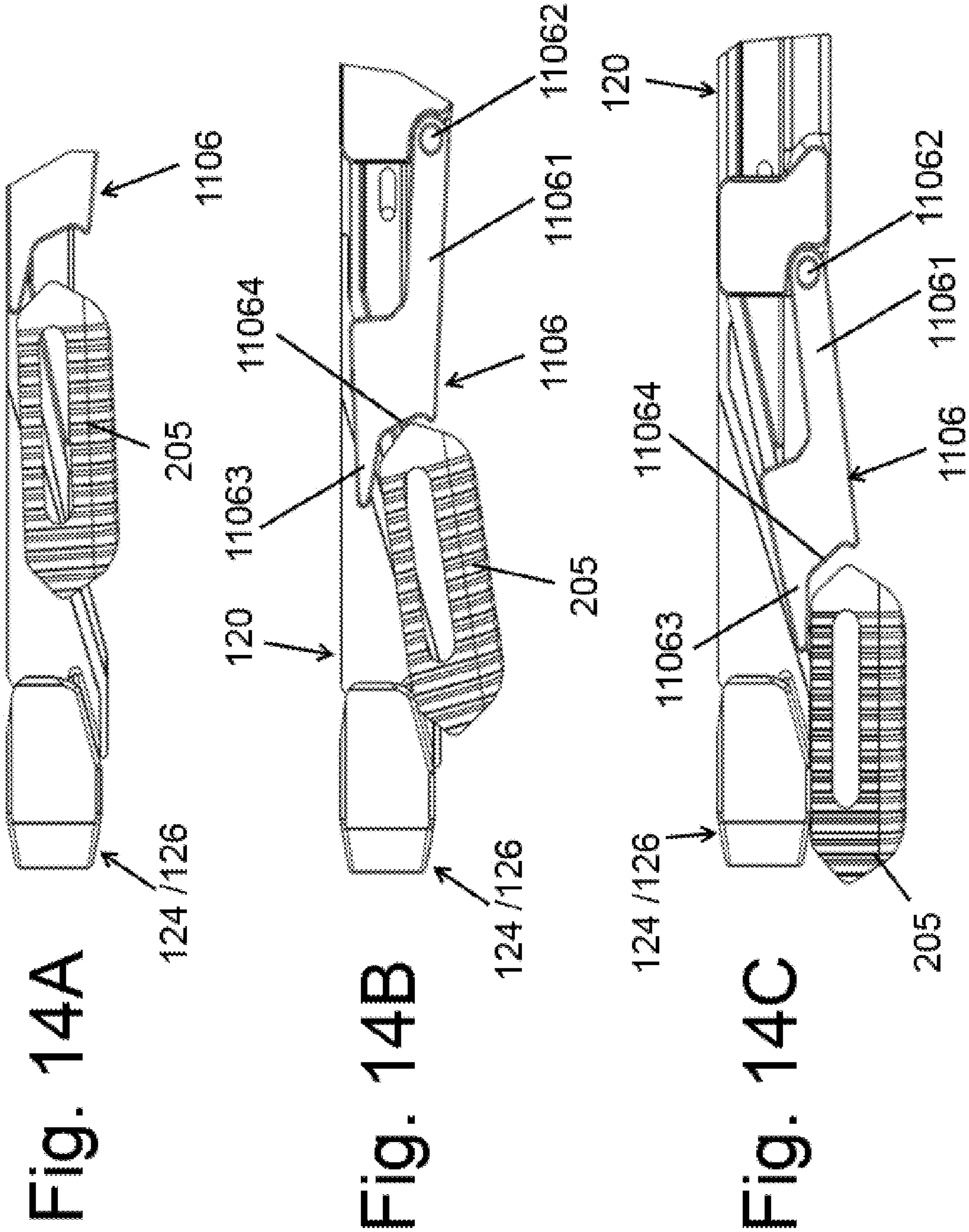
Figure 16A:
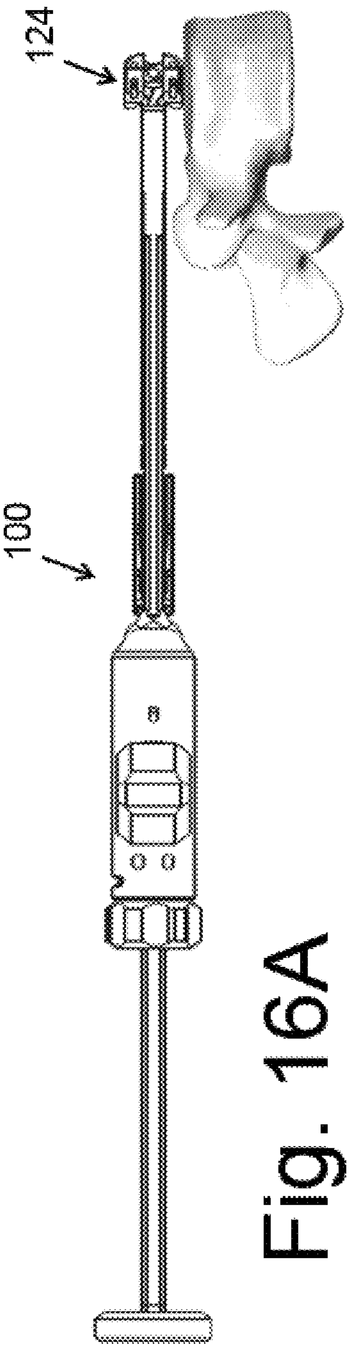
FIGS. 16A-16F show side and top views of a method of use of the implant delivery instrument of FIGS. 7A-7C having the first embodiment of a distraction member of FIGS. 9A and 9B for delivery of the implant of FIGS. 12A-12G.
Figure 16B:
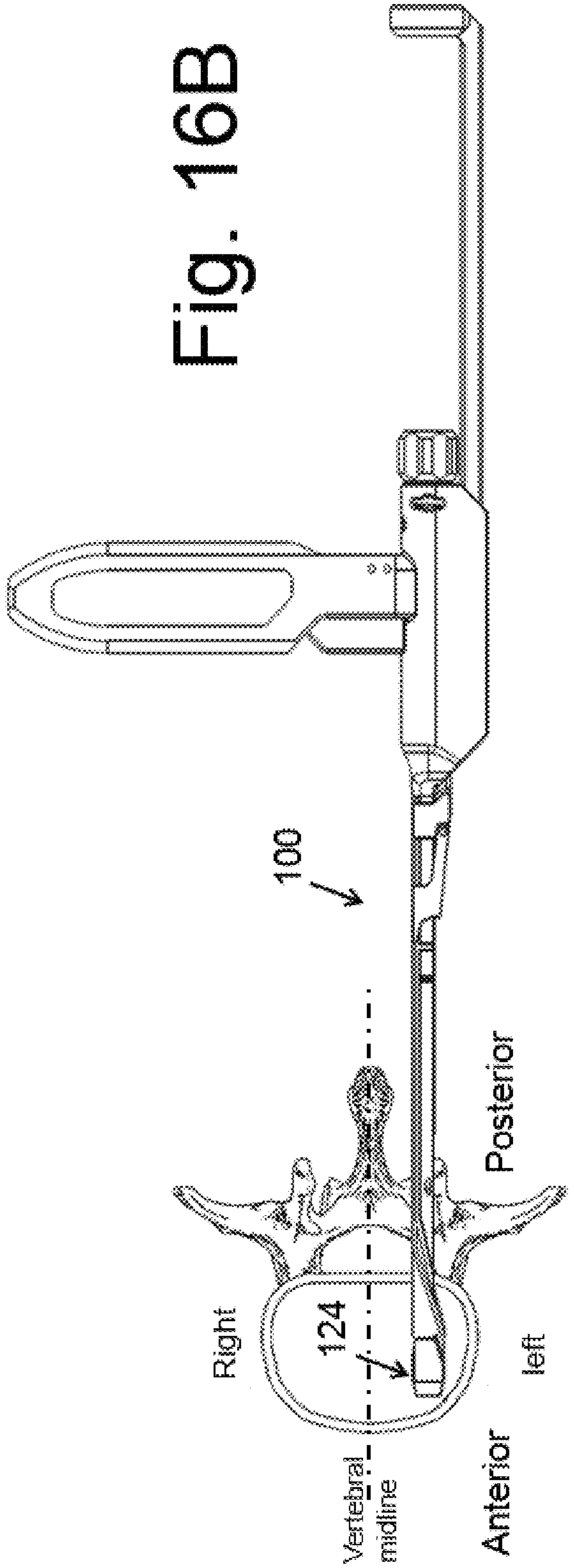
Figure 16C:
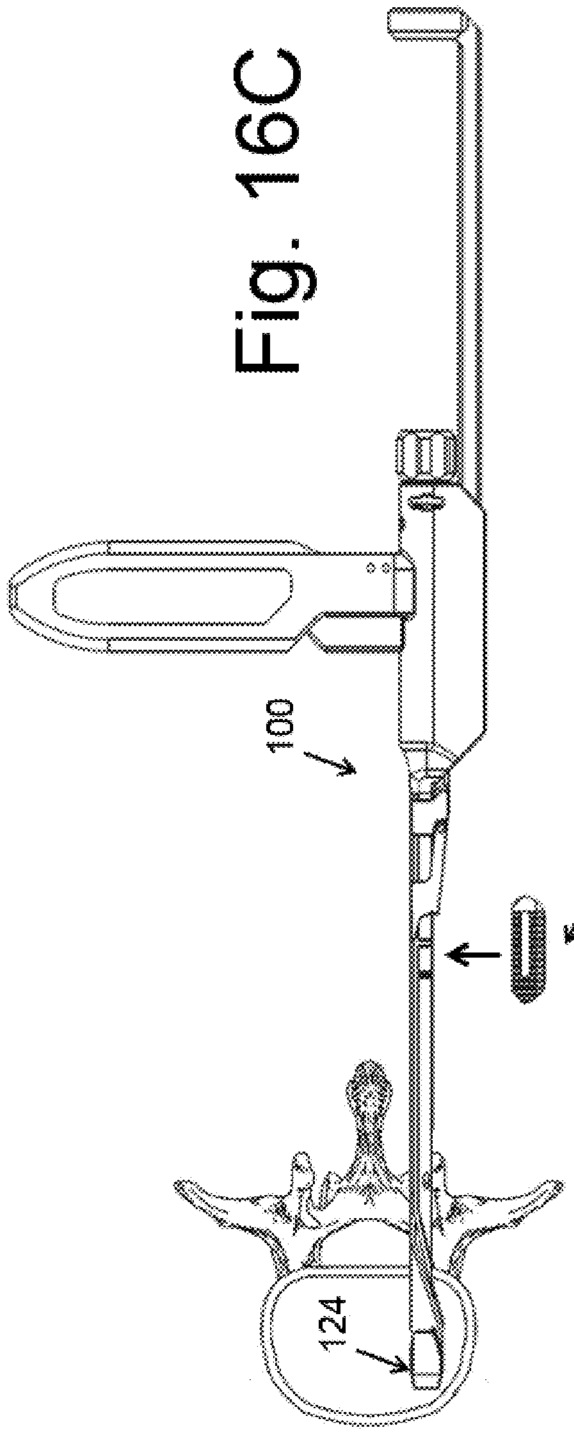
Figure 16D:
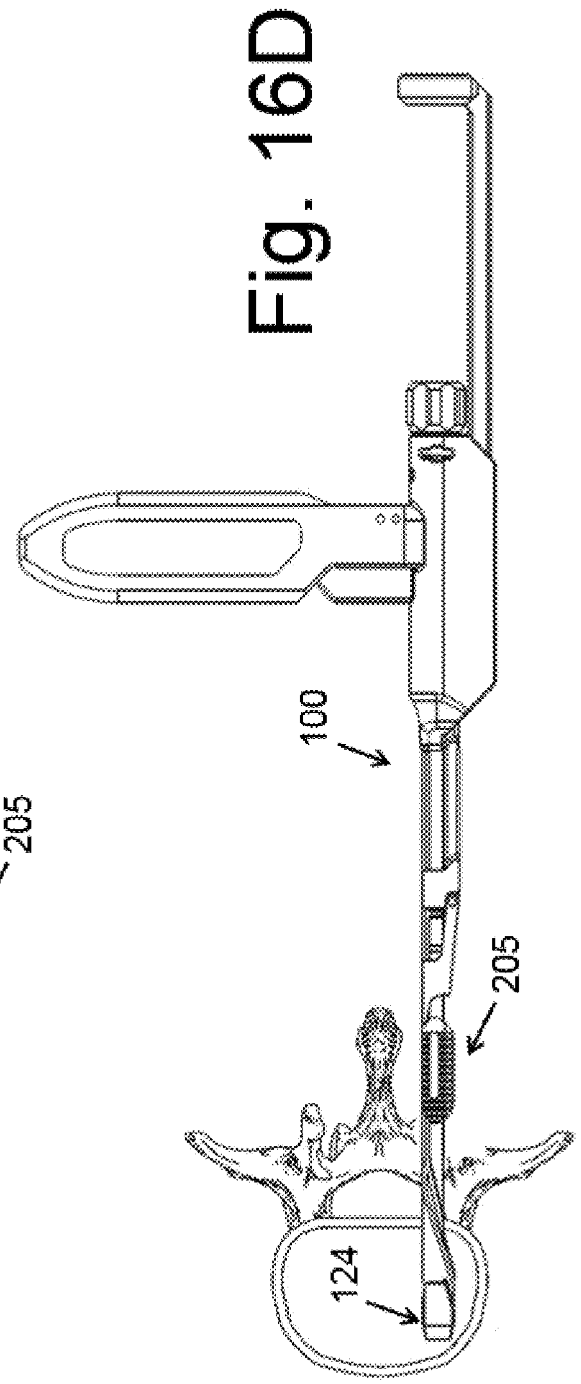
Figure 16E:
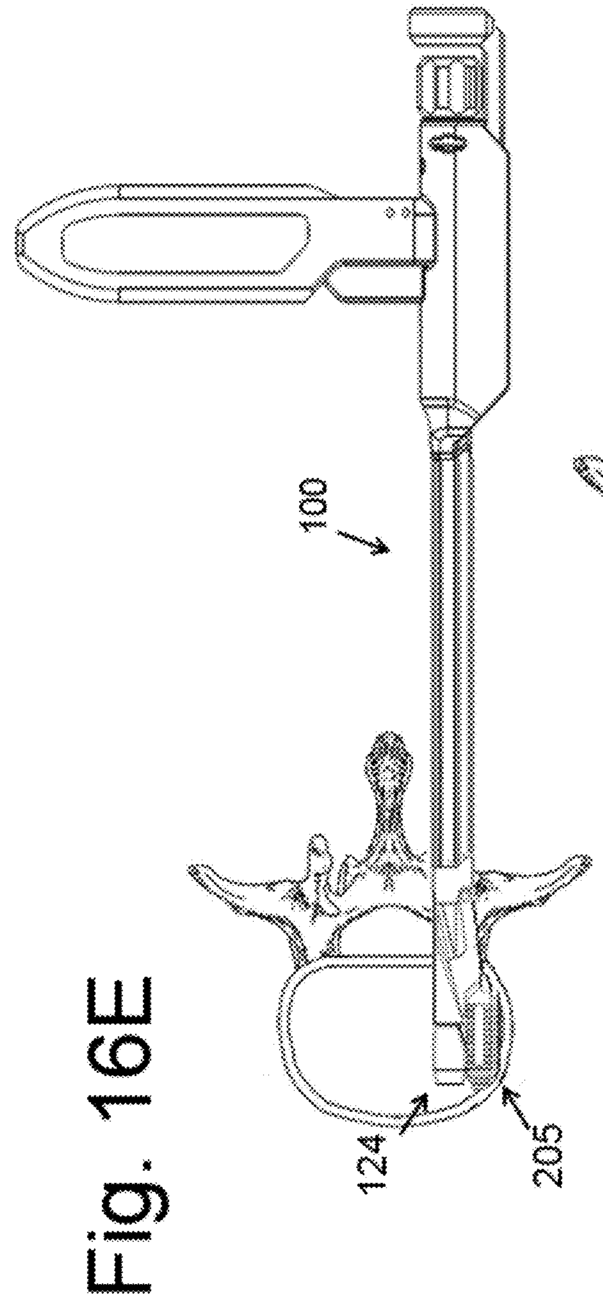

In the present embodiment, the implant is first advanced through a proximal region of the grooves along a linear pathway, and at the distal segment of the implant track the grooves include turns (curvatures or bends) so that the implant is ultimately positioned within the disc space at a lateral side of (and/or anterior to) the distraction member (as depicted in FIG. 16E and discussed below). FIGS. 14A-14C show step-wise movement of the implant 205 along the distal segment of the implant track 120. Specifically, the distal segment of the each of the grooves each 1204 and 1208 includes a bend, such that the terminal portion of each of the grooves is oblique or transverse relative to a longitudinal axis of the implant track 120. As the implant 205 is moved along terminal portion of the grooves 1204 and 1208 (via engagement with the distal, rotatable member 1106 of the implant pusher 110), the implant 205 moves laterally relative to the implant track 120 (i.e., onto a left side or a right side of the implant track), as well as forward toward the distal end of the implant track.

As can be seen in FIGS. 14A-14C, the distal, rotatable member 1106 of the implant pusher 110 includes (at a proximal end thereof) an arm 11061 rotatably connected to the intermediate member 1104 via a pin 11062, and (at a distal end thereof) an implant engagement portion comprising a protrusion 11063 and a shelf 11064. The protrusion 11063 is configured to engage the proximal end of the implant 205 at a side surface thereof in order to guide the implant through the bend at the terminal portion of the grooves 1204 and 1208 (FIG. 14A). Subsequently, the shelf 11064 is configured to engage an extended portion of the proximal end of the implant 205, and catch the extended portion on a raised lip of the shelf 11064. Such engagement enables further lateral (and forward) advancement of the implant 205, as well as rotation of the arm 11061 about an axis of the pin 11062 (FIGS. 14B and 14C), until the implant 205 is guided through an end of the grooves 1204 and 1208 (where the protrusions 2054 and 2056 disengage from the grooves 1204 and 1208, respectively) and is positioned adjacent to the distraction member 124 or 126.

While the longitudinal axis of implant track is aligned with the longitudinal axis of the distraction member in the present embodiments (as shown in e.g., FIG. 13), the latter may be alternatively offset from the longitudinal axis of the implant track. When the longitudinal axes of distraction member the implant track are offset relative to one another, the implant placement instrument may be configured, for example, so as advance the implant in a substantially linear trajectory along the implant track and into the target disc space (rather than including a curved trajectory at the distal end of the implant track).

Methods of Use

FIGS. 16A-17F illustrate exemplary methods for positioning a portion of the implant placement instrument within a target intervertebral disc space, mounting of the implant onto the implant track, advancement of the implant down the implant track and into the disc space, and removal of the implant placement instrument from the disc space.

Specifically, the disc space may be approached using any applicable corridor to the spine—such as, for example, via one or more of anterior, antero-lateral, lateral, postero-lateral and posterior tissue corridors. In one embodiment utilizing the postero-lateral and/or posterior approaches, for example, the paraspinal muscles are retracted after placement of a skin incision. A corridor is then developed to the postero-lateral and/or posterior aspect of the spinal column and at least a segment of the lamina and/or facet joint(s) can be removed. If necessary, a posterior aspect of the thecal sac can be exposed. The posterior aspect of the target disc space is then exposed through a corridor that is lateral to the thecal sac. The thecal sac is retracted gently in the medial direction, and the posterior aspect of the target disc space can be identified. The annulus fibrosis is incised and at least a segment of the native disc space is removed. After the preparation of the bony end plate, the target disc space is ready for advancement of an implant therein.

As discussed elsewhere herein, the implant placement instrument 100 may be hand held (using handle 104) during the procedure and/or the placement instrument may be anchored to a bony surface of the vertebral column. The placement instrument 100 may be additionally or alternatively attached to a coupler or segment of an articulating retention arm, which is anchored to the operating room table upon which the patient is positioned. Frame devices that anchor surgical instruments to the operating table are known in the art, and an exemplary articulating retention arm is show in FIG. 15. In the illustrated example, an articulated frame 905 has a member 9052 that reversibly attaches to the operating table onto which the patient is positioned. A member 9056 is adapted to reversibly and rigidly clamp onto (or otherwise couple with) a segment of the implant placement instrument 100 (such as, for example, a segment 1046 shown in FIG. 7A). A member 9054 is adapted to reversibly transition the frame 905 from a first state (i.e., a movable state where articulation of the frame segments is enabled) to a second state (i.e., a locked state where the frame segments are rigidly locked to one another). While the exemplary articulated frame 905 is illustrated, it is understood that other positioning or retaining devices may be alternatively (or additionally) used. Other exemplary positioning or retaining devices that can be used with the implant placement instruments described herein are disclosed in U.S. Pat. Nos. 4,254,763; 5,908,382; 6,302,843; 6,709,389; and 7,156,806, each of which is incorporated by reference herein in its entirety.

FIGS. 16A-16F illustrate a first exemplary embodiment of a method of use of the implant placement instrument 100. As depicted therein, the implant placement instrument 100 inserted into the target disc space via a posterior approach. As depicted in FIG. 16A (and discussed above with reference to FIGS. 7A-9F), after the distal end of the implant placement instrument is advanced into the target disc space, the knob 114 is actuated and the distraction member 124 is moved from the closed (non-distracted) configuration to the open (distracted) configuration in order to distract the disc space to a desired height and/or otherwise reposition the superior or inferior vertebral bones (such as, e.g., to correct anterior spondylolisthesis as shown in the exemplary distracted configuration of FIG. 9C, or to correct lateral spondylolisthesis as shown in the exemplary distracted configuration of FIG. 9E).

After the desired height of the disc space and position of the the superior or inferior vertebral bones is achieved, the implant size and/or shape may be selected based on the reading shown in the aperture 118. In alternate embodiments, the implant size and/or shape can be selected based on other criteria, such as, e.g., imaging of the target spinal segment.

Once the appropriate implant is selected (such as, e.g., implant 205 shown in FIGS. 12A-12G), it is mounted onto the implant track 120 as shown in FIG. 16C. The release member 1044 is then depressed and the implant pusher 110 is pushed forward (via, e.g., hammering with a mallet, manual movement, or machine guided movement, and/or a spring loaded device) such that the distal, rotatable member 1106 engages with the implant 205. The rotatable member 1106 advances the implant 205 along tract 120, as shown in FIG. 16D.

FIG. 16E illustrates delivery of the implant 205 into the disc space at a lateral position relative to the distraction member 124. In one embodiment of the method of implantation, the implant 205 is positioned to abut at least a portion of the inferior apophyseal ring of the superior vertebral bone and/or the superior apophyseal of the inferior vertebral bone. In an alternate embodiments, an implant can be positioned anterior to the distraction member or medial relative to the distraction member.

Figure 16F:
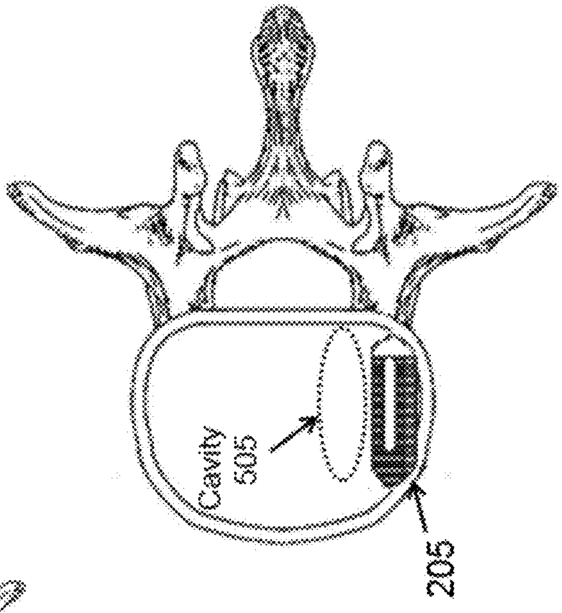
Figure 17A:
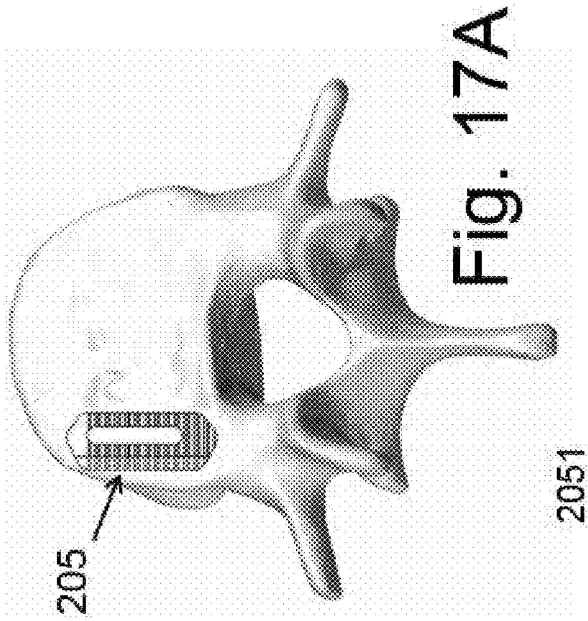
FIGS. 17A-17D illustrate top, rear, first side and second side views of a target disc space having the implant of FIGS. 12A-12G implanted therein.
Figure 17B:
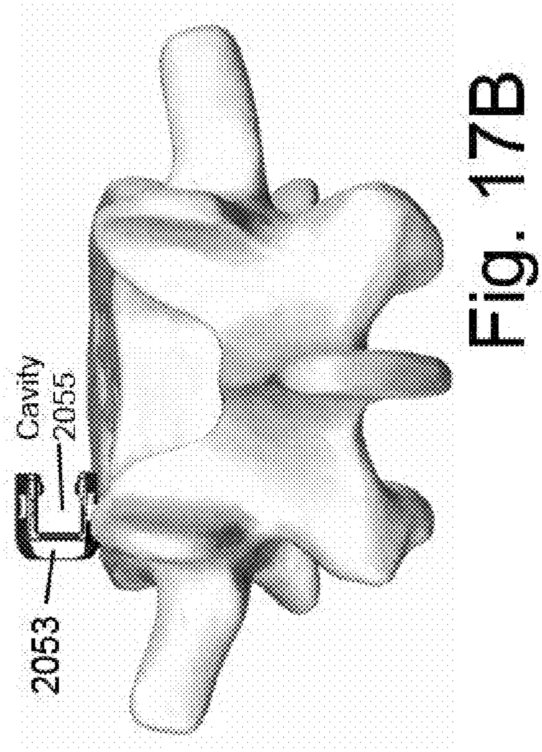
Figure 17C:
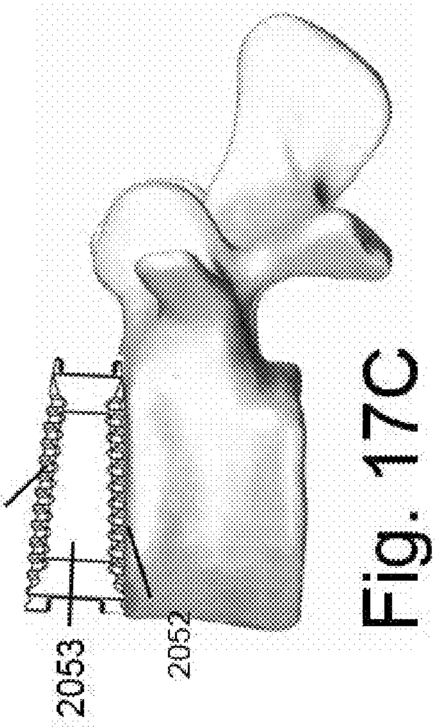
Figure 17D:
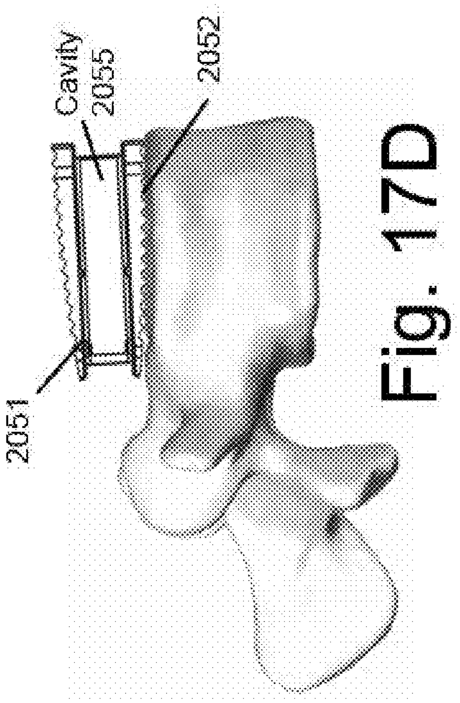

After the implant 205 is positioned within the target disc space, the knob 114 is actuated (e.g., actuated in a reverse direction) and the distraction member 124 is decreased in height to move the distraction member into the closed (non-distracted) configuration. The implant placement instrument 100 is then withdrawn from the disc space leaving the implant 205 positioned as shown in FIG. 16F.

FIGS. 17A-17D illustrate the implant 205 positioned within the disc space after the removal of the implant placement instrument 100 (the superior vertebral bone is not shown for diagrammatic simplicity).

In the embodiment of FIGS. 16A-16F, the distraction member 124 is a non-separable segment of the implant placement instrument 100 and is non-detachable therefrom. In other words, both of the distal end of the implant track and the distraction member are removed from the disc space prior to completion of the implantation procedure. Accordingly, after withdrawal of the placement instrument, a cavity 505 remains in the disc space at a location where the distraction member 124 had been positioned. Bone graft material may be packed into the cavity 2055 of the implant 205 and/or the cavity 505 (which is adjacent and medially disposed relative to the implant 205) so as to produce a bony fusion between the inferior surface of the superior vertebral bone and the superior vertebral surface of the inferior vertebral bone. It is noted that the bone graft material placed within the cavity 2055 may be in continuity with the bone graft placed within the cavity 505.

Figure 18A:
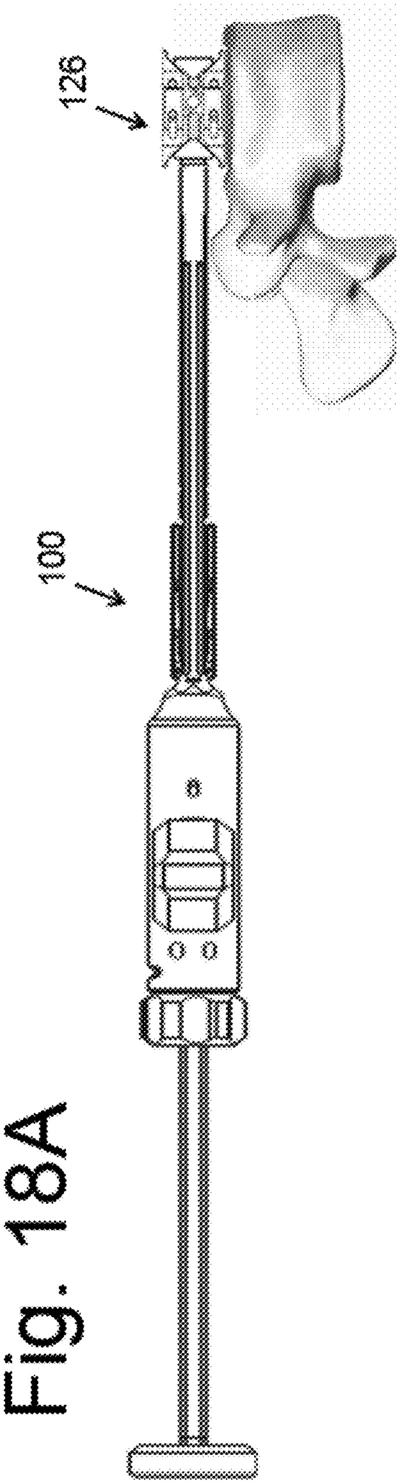
FIGS. 18A-18F show side and top views of a method of use of the the implant delivery instrument of FIGS. 7A-7C having the second embodiment of a distraction member of FIGS. 10-11B for delivery of the implant of FIGS. 12A-12G.
Figure 18B:
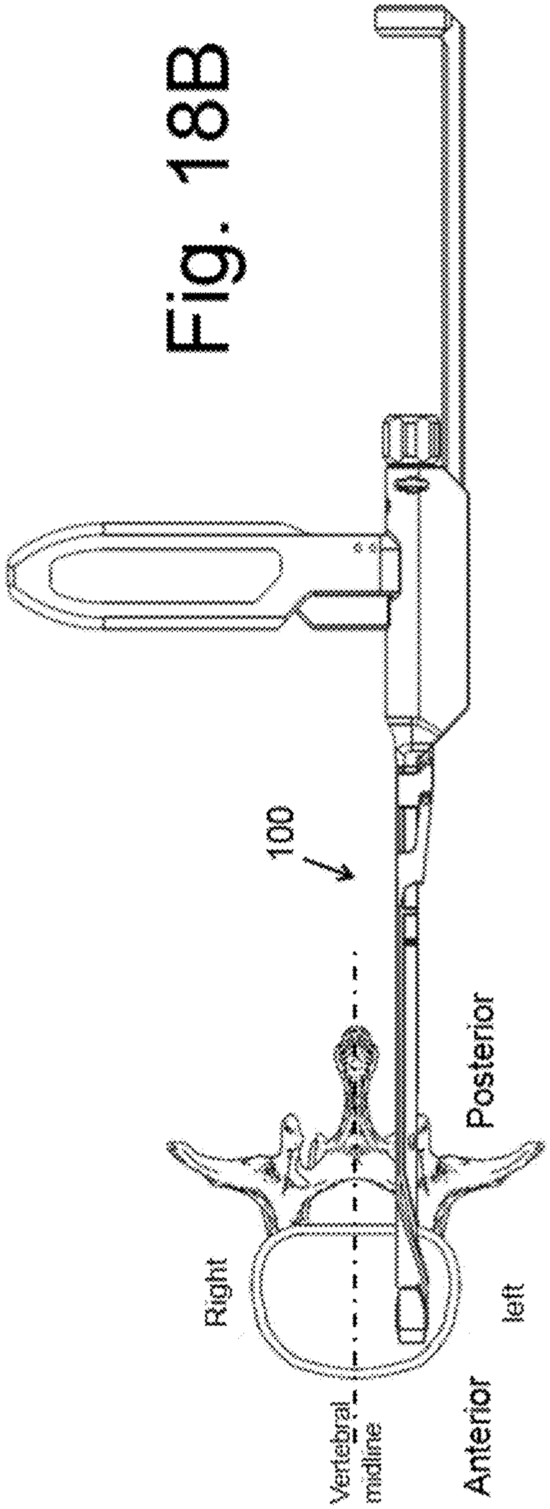
Figure 18C:
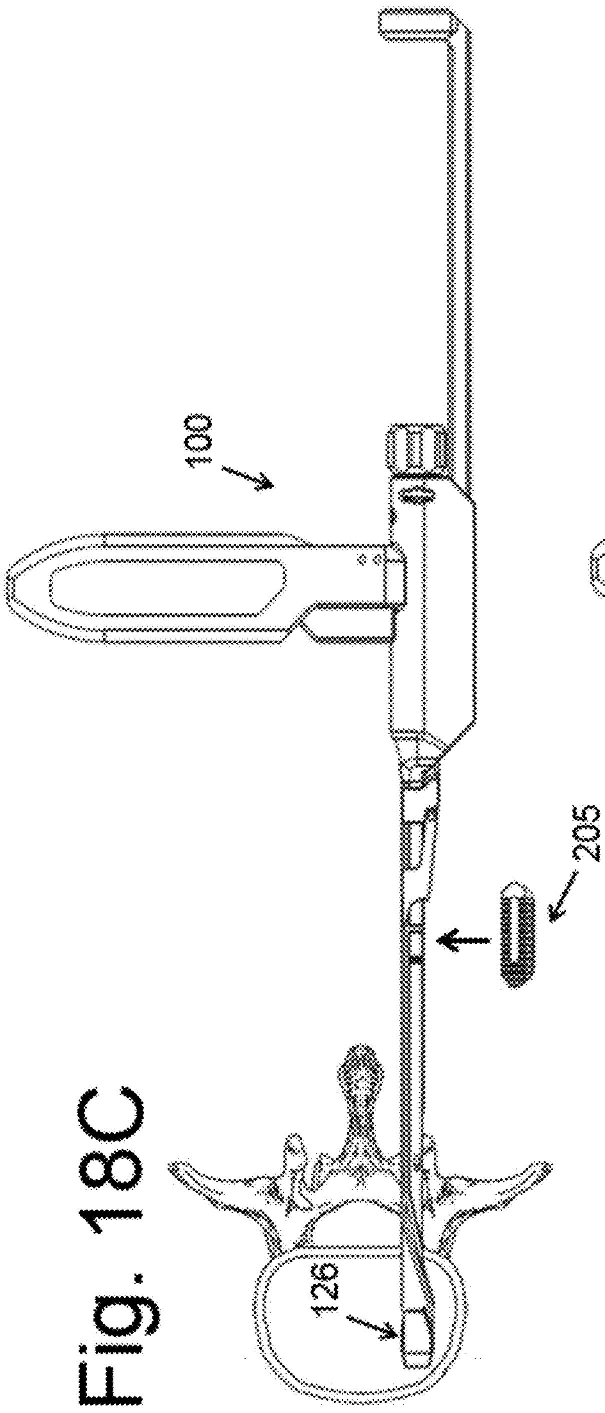
Figure 18D:
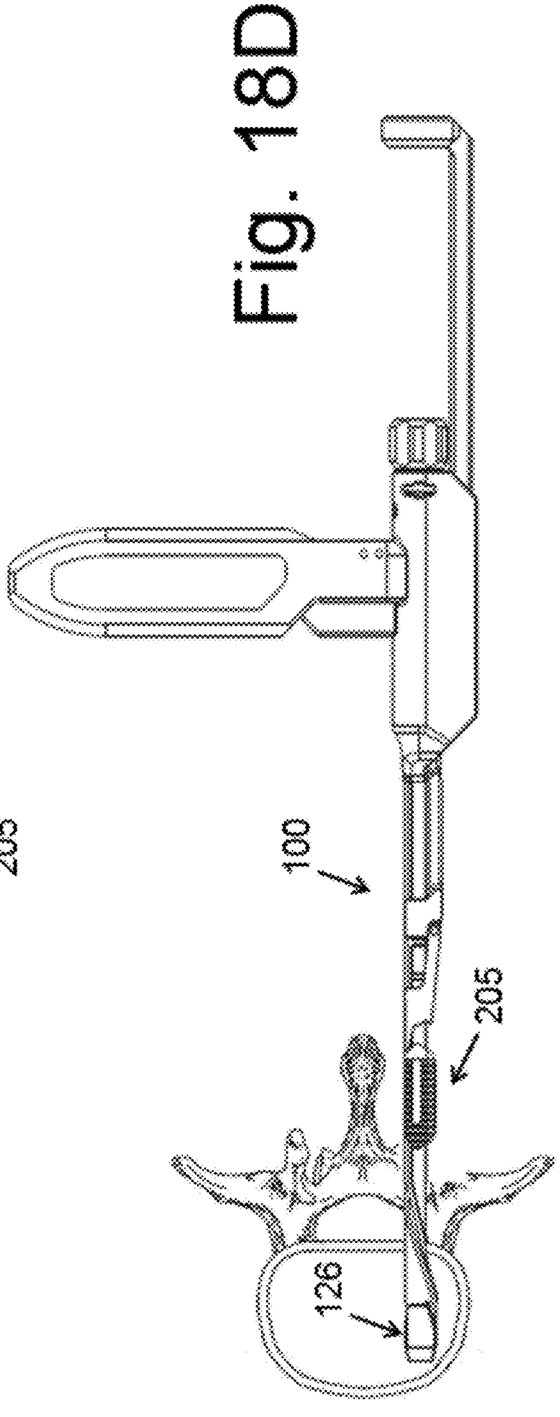
Figure 18E:
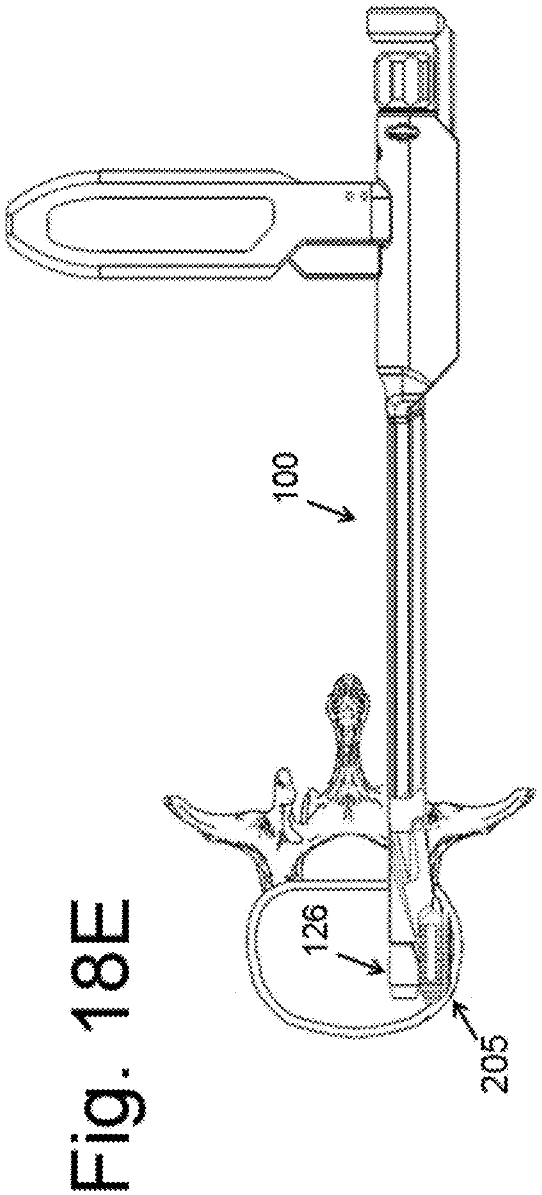

Turning now to FIGS. 18A-18F, another embodiment of a method of use of the devices disclosed herein is illustrated. First, the implant placement instrument 100 is inserted into the target disc space via a posterior approach. As depicted in FIG. 18A, after the distal end of the implant placement instrument is advanced into the target disc space, the knob 114 is actuated and the distraction member 126 is moved from the closed (non-distracted) configuration to the open (distracted) configuration in order to distract the disc space to a desired height and/or otherwise reposition the superior or inferior vertebral bones (such as, e.g., to correct lateral spondylolisthesis as shown in the exemplary distracted configuration of FIG. 11B). Similar to the method of use shown in FIGS. 16A-16F, after positioning of the implant placement instrument and distraction of the disc space (FIGS. 18A and 18B), the implant is selected (based on a size and/or configuration thereof) and mounted onto the implant track (FIG. 18C) and advanced along the track (FIG. 18D) and into the target disc space (FIG. 18E).

Different from the embodiment of FIGS. 16A-16F, in the present method, the distraction member 126 is a separate, detachable member that can be uncoupled from (reversibly attached to) the implant placement instrument 100 such that it remains in the disc space as an implant after the withdrawal of the implant placement instrument from the disc space. In other words, after the distraction member 126 is moved into the open (distracted) configuration and the implant 205 is positioned within the target disc space, the distraction member 126 is detached from the implant placement instrument 100 (via e.g., depression or actuation of a release member operatively coupled to the handle of the implant placement instrument 100) and the distraction member 126 retains its distracted height after the detachment. Specifically, once the desired distracted configuration is achieved, the distraction mechanism can be locked so as to make the configuration effectively permanent. Adhesives or yet other means for maintaining the desired position can be utilized as well.

Figure 18F:
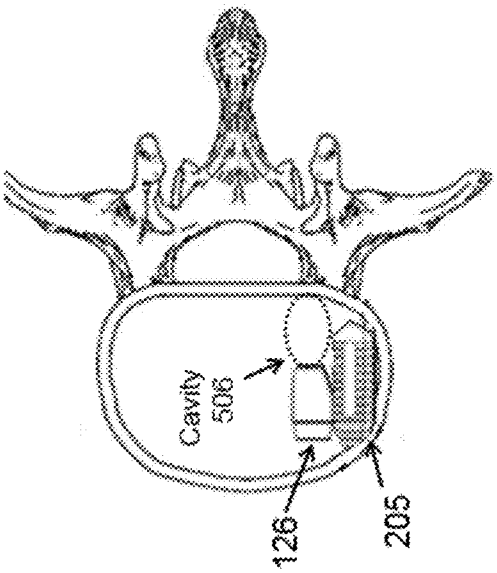

The implant placement instrument 100 is then removed from the disc space leaving the implant 205 and the detached distraction member 126—as shown in FIG. 18F. Bone graft material may be packed into the cavity 2055 of the implant 205 and/or the cavity 505 (which is adjacent and medially disposed relative to the implant 205, and adjacent to and posterior of the detached distraction member 126) so as to produce a bony fusion between the inferior surface of the superior vertebral bone and the superior surface of the inferior vertebral bone.

While implantation of only one implant (i.e., the implant 205) is shown in FIGS. 16E-17D, and implantation of only one implant (i.e., the implant 205) and one detached distraction member (i.e., the distraction member 126) is shown in FIGS. 18E-18F, it is contemplated that additional implants (having the same or a different configuration as the implant 205) and/or additional detached distraction members (having the same or a different configuration from the distraction member 126) can be implanted into a single target disc space in order to disperse the load and/or alter the alignment across the FSU.

Figure 19A:
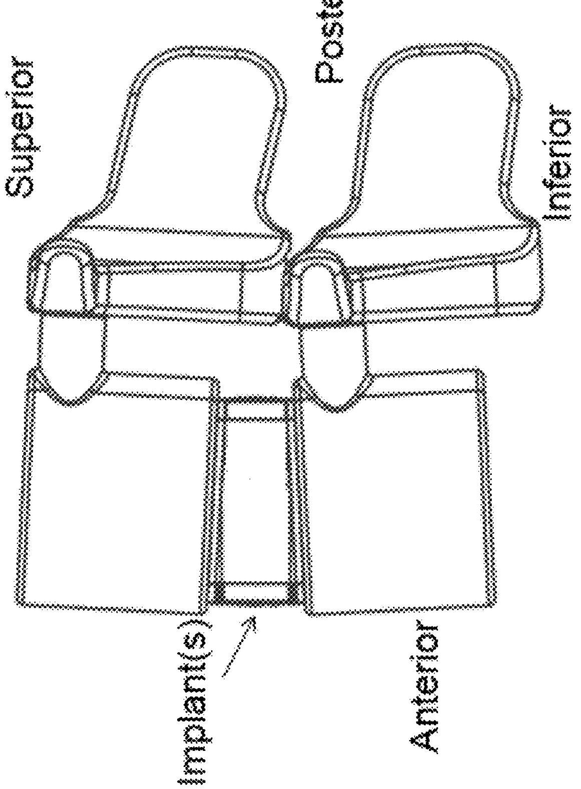
FIGS. 19A and 19B show schematic side and front views of a target disc space having two implants implanted therein.
Figure 19B:
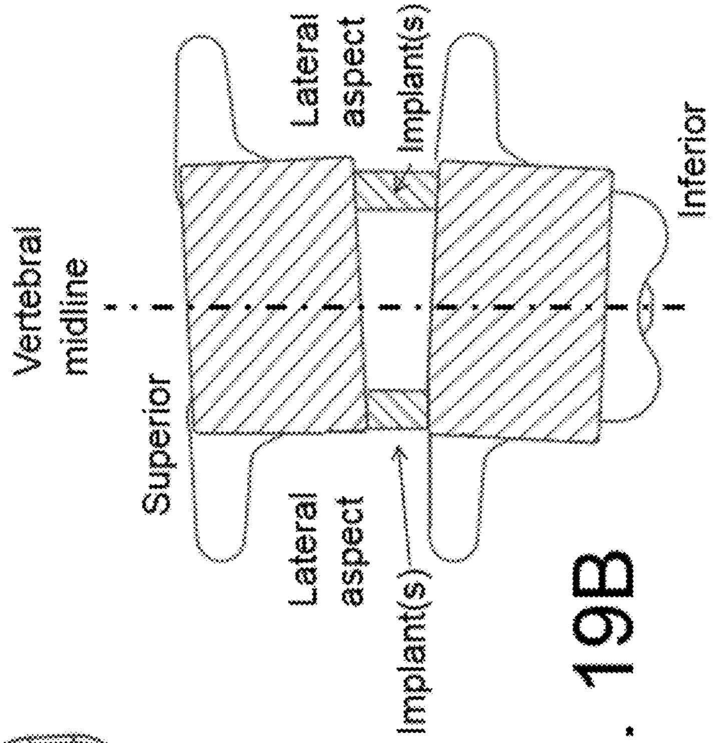

For example, FIGS. 19A and 19B illustrate how use of multiple implants (and/or detached distraction mechanisms of different shapes and/or sizes) can be used to alter the vertebral alignment within the vertebral column. Specifically, an implant (or detached distraction mechanism) may comprise a greater height at its anterior edge than at its posterior edge, as shown in FIG. 19A, so that a lordosis curve between the superior and inferior vertebral bones that abut the target disc space is altered (i.e., use of the implants or detached distraction mechanisms to a greater or lesser lordosis—or even leave the lordosis unchanged). Further, the implants (or detached distraction mechanisms) can be placed at opposing lateral sides of the target disc space so as to further alter the alignment of the implanted FSU. FIG. 19B illustrates that a first implant (or detached distraction mechanism) of a given height may be positioned at a first lateral side segment of the target disc space, and a second implant (or detached distraction mechanism) of a different height may be positioned at an opposing second lateral side segment of the target space, thereby altering the vertebral alignment in the coronal plane of the spinal column. In this way, this implant arrangement may be used in the treatment of spinal misalignment conditions such as, for example, scoliosis.

Additional Spinal Stabilization Devices and Techniques

One or more supplemental fixation devices and/or methods may be utilized with the foregoing apparatus and methods in order to rigidly immobilize the superior and inferior vertebral bones of the target FSU (having the implant 204 and/or the distraction member 206 implanted therein). In one example, pedicle screw immobilization can be employed by the placement of one or more bone screw assemblies into the posterior aspect of the ipsilateral pedicle of each of the superior and inferior vertebral bones (e.g., a screw my enter each of the bones in proximity to position 811 shown in FIGS. 1A-1C).

Figure 20A:
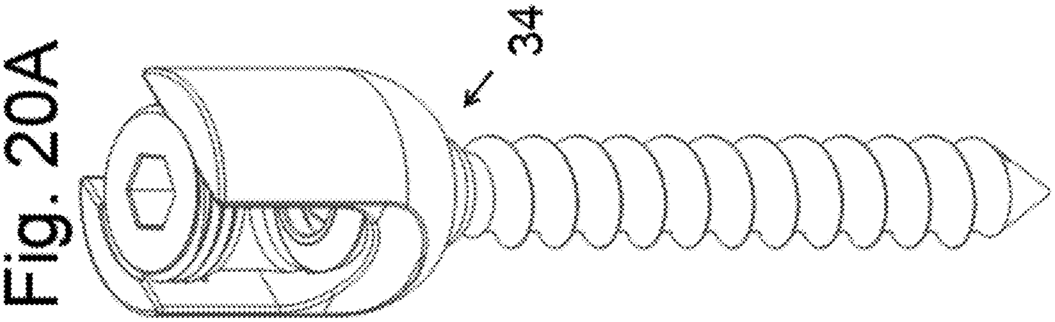
FIGS. 20A and 20B are respectively perspective and cross-sectional views of an exemplary pedicle screw assembly configured for use with the implants and implantation delivery devices disclosed herein.
Figure 20B:
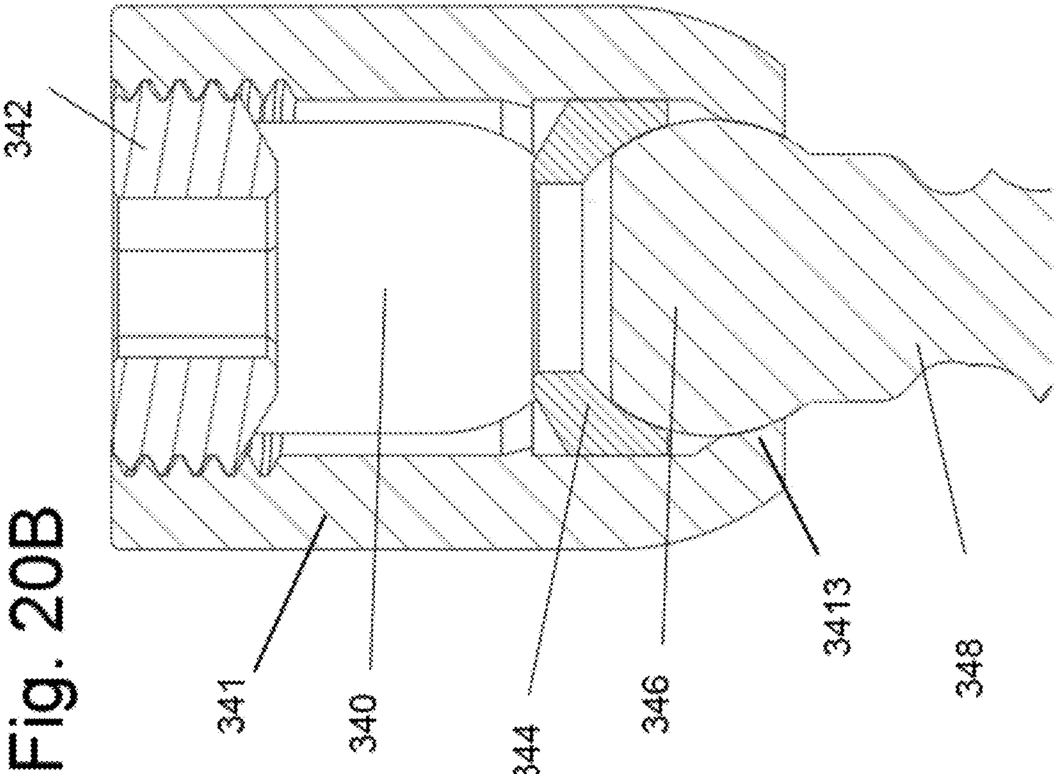

An exemplary pedicle screw assembly 34 is shown in FIGS. 20A and 20B. As depicted therein, the pedicle screw assembly 34 includes: a housing body 341 having a cavity 340 configured to receive an inter-connecting member (such as a rod), a set screw 342 that threadedly couples within a top portion of the cavity 340, a thrust washer 344 seated within a bottom portion of the cavity 340 (proximate to an anchor member-receiving portion 3413 of the housing body 341), and a bone anchor member including a head 346 and a threaded 348 configured for insertion into bone. In the assembly 34, the head 346 of the bone anchor member is seated within the anchor member-receiving portion 3413 and the threaded shank 348 of the bone anchor member extends out of an aperture that is positioned within the bottom of the anchor member-receiving portion 3413. It will be appreciated that the terms "above" and below" are relative and depend on the orientation of the assembly 34. As used herein, the assembly 34 is oriented with the set screw 342 at the superior aspect of the assembly and the threaded shank 348 at the inferior aspect of the assembly. Thus, the set screw is located "above" the bone anchor member and the cavity which receives the inter-connecting member receiving is disposed therebetween.

Figure 20D:
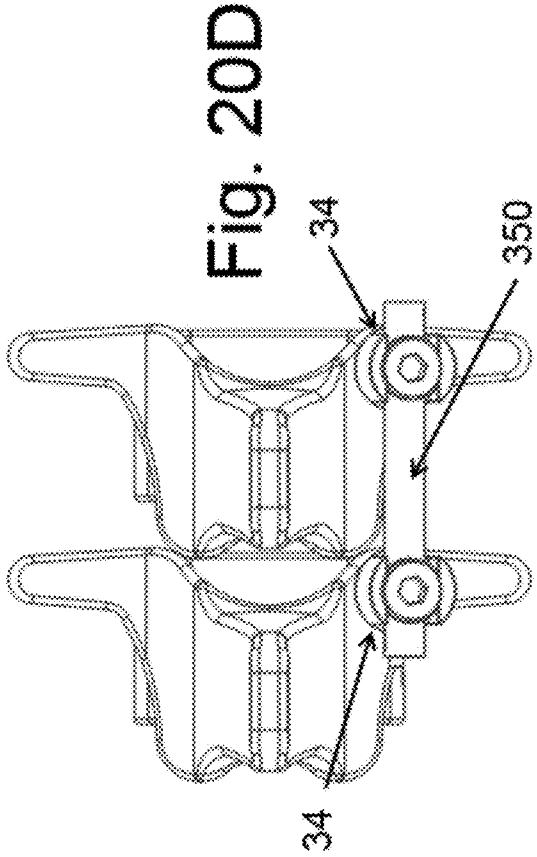
FIGS. 20C-20E respectively show schematic top, rear and side views of a spinal segment having the pedicle screw assembly of FIGS. 20A and 20B and the implant of FIGS. 12A-12G implanted therein.
Figure 20E:
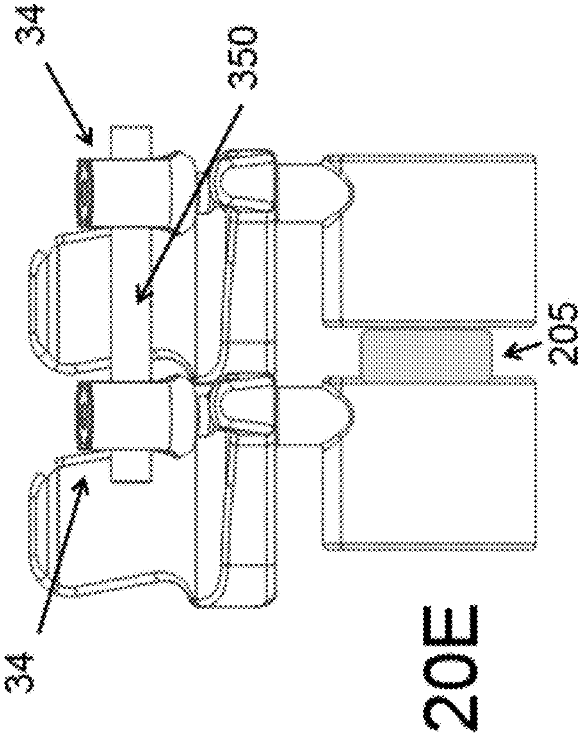
Figure 20C:
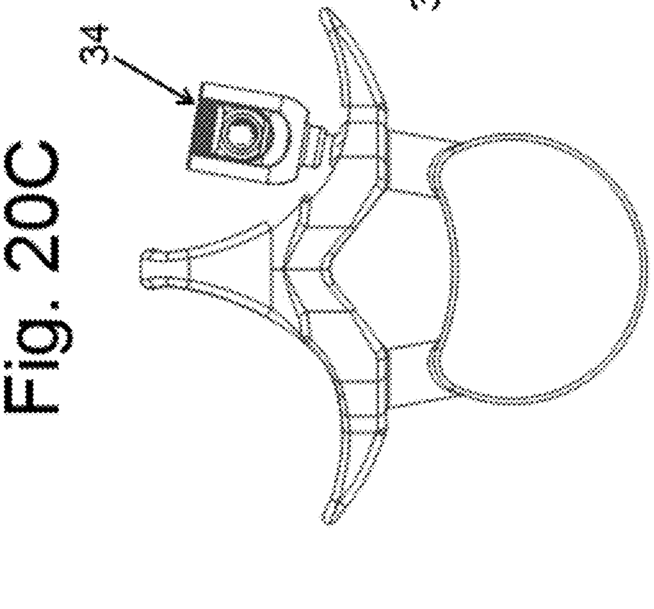

During use thereof (as shown in FIGS. 20C-20E), a connecting member 350 (such as a rod) is used to connect two or more of the assemblies 34, such as, e.g., connecting a first assembly 34 anchored into a superior vertebral bone and a second assembly 34 anchored into an inferior vertebral bone, the superior and inferior vertebral bones having one or more of the implants 205 (depicted in FIG. 20E) and/or the detached distraction members 126 implanted (not specifically depicted) therebetween. Each of the opposing ends of the connecting member 350 is received within the cavity 340 of one of the assemblies 34. Threaded engagement of the set screw 342 with the top portion of the cavity 340, the connecting member is movable within the cavity 340 relative to the housing body 341 and the head portion 346. Further, the head portion 346 can rotate within the anchor member-receiving portion 3413 such that a longitudinal axis of threaded shank 348 can assume different orientations and angles relative to a longitudinal axis of the housing body 341. With advancement of set screw 342, a compressive force is produced between the inter-connecting member 350 (contained within the inter-connecting member receiving portion 340) and the anchor member-receiving portion 3413 such that the interconnecting member 350, the head portion 346 and the housing 341 are immobilized relative to one another. In this way, the two assemblies are rigidly interconnected by the interconnecting member, and the procedure may optionally be repeated on the contra-lateral (opposing) side. Exemplary embodiments of pedicle screw fixation of adjacent vertebral bones (for use the the methods and apparatus described herein) are disclosed in U.S. Pat. No. RE37,665 and U.S. Patent Publication No. 2006/0084981, each of which is incorporated herein by reference in its entirety.

Figures 21A, 21B, 21C, 21D:
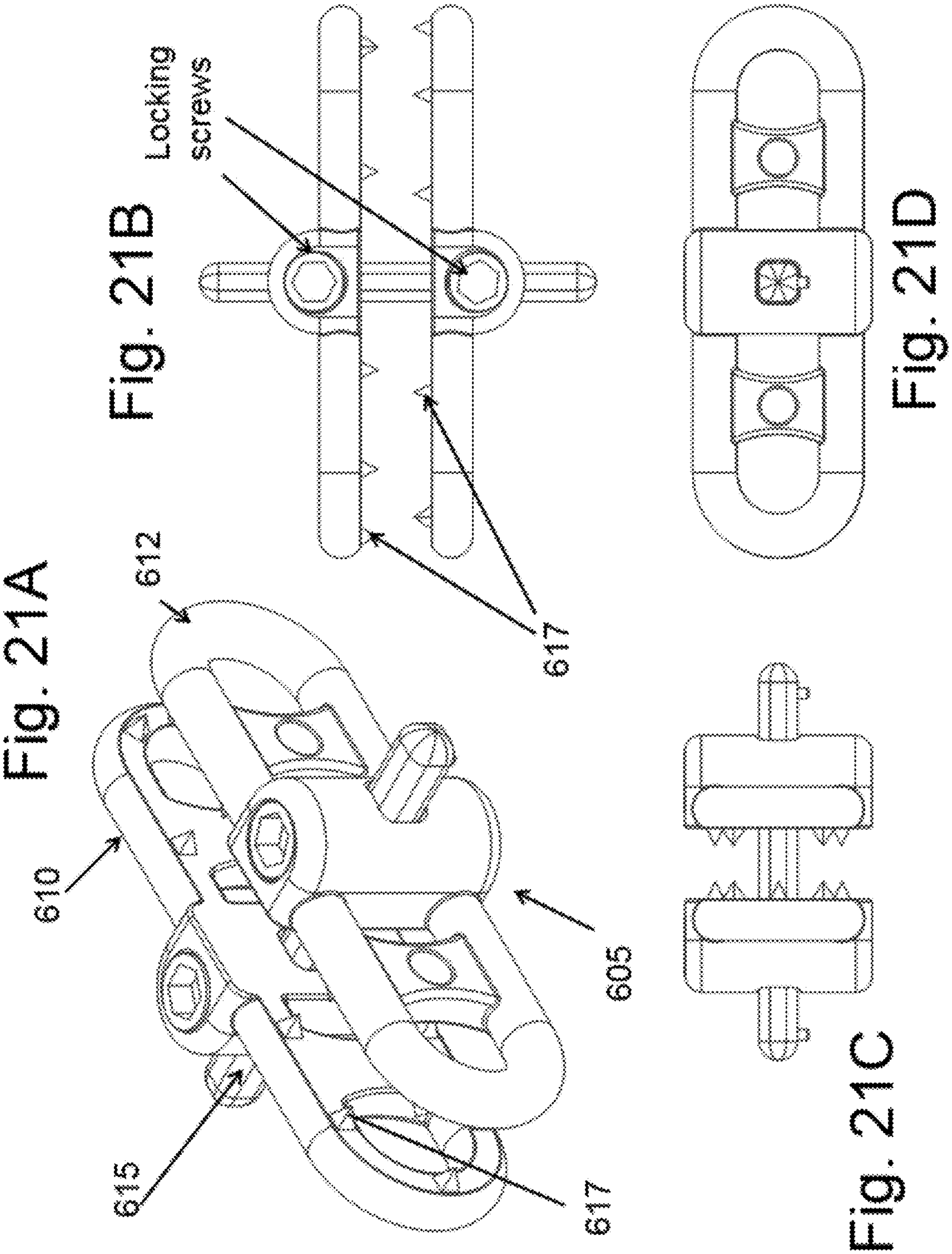
FIGS. 21A-21D respectively show front perspective, front elevation, top plan and side elevation views of an exemplary spinous process fixation device configured for use with the implants and implantation delivery devices disclosed herein.
Figure 21F:
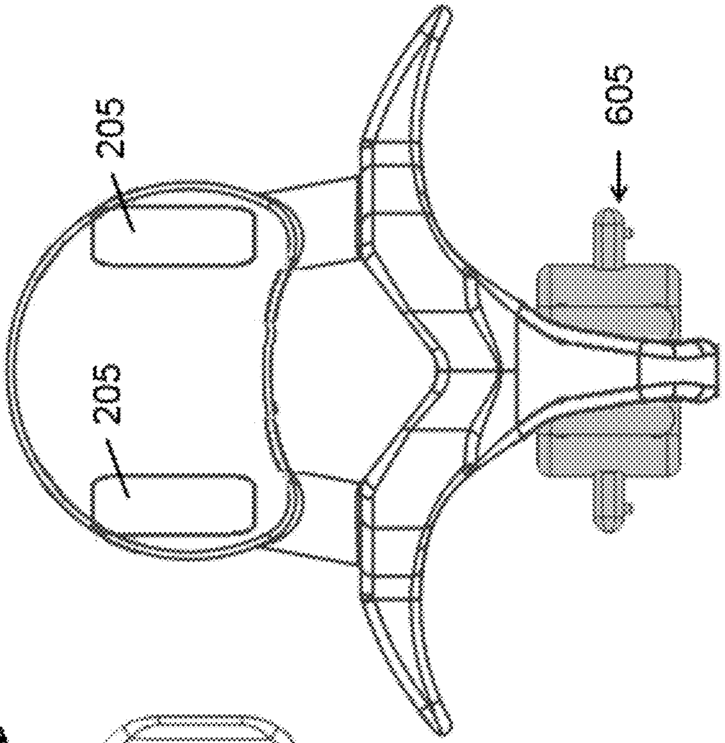
FIGS. 21E and 21F respectively show schematic side and top views of a spinal segment having the spinous process fixation device of FIGS. 21A-21D and the implant of FIGS. 12A-12G implanted therein.
Figure 21E:
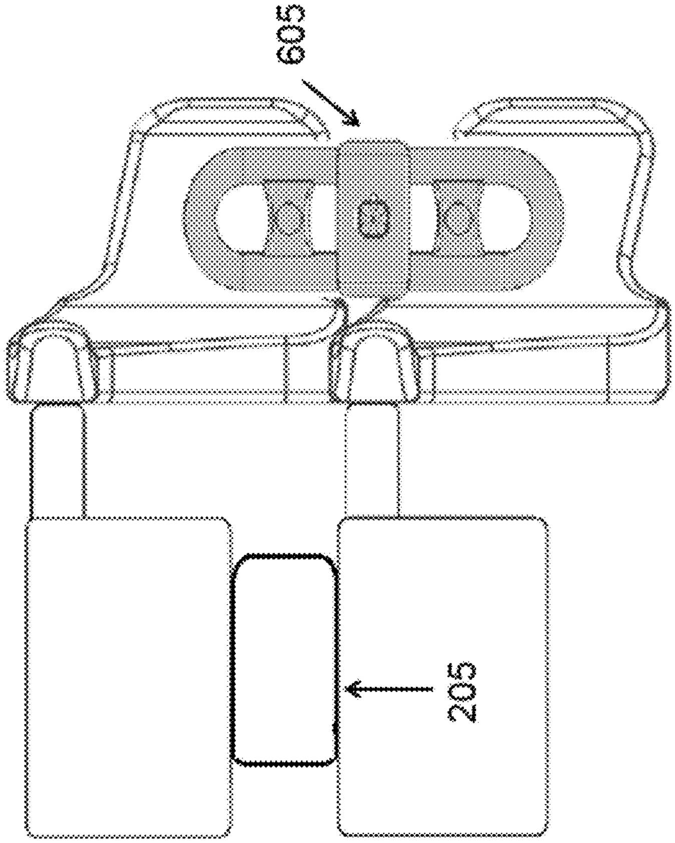

As an alternative (or in addition) to pedicle screw fixation, a spinous process fixation implant may be used for supplemental FSU stabilization. An exemplary spinous process fixation device 605 is illustrated in FIGS. 21A-21F. Specifically, the fixation device 605 includes a first member 610 and an opposing second member 612, which are configured to be adjoined via an interconnecting member 615 and attached onto opposing (contra-lateral) spinous processes of two adjacent vertebral bones. As depicted in FIGS. 21E and 21F, the spinous processes are forcibly captured between the first and second members 610 and 612. The interconnecting member 615 is then tightened or otherwise locked relative to the members 610 and 612, and prevents the members 610 and 612 from moving away from one another. A plurality of projections 617 on an interior surface of each of the members 610 and 612 penetrate the spinous processes and increase bone fixation onto the bone for the fixation device 605. In the present embodiment, two implants 205 interbody are implanted bilaterally within the target disc space. In the axial plane (FIG. 21F), the implants 205 provide two anterior column supports while the spinous process fixation device 605 provides posterior midline support. In the lateral view (FIG. 21E), the implants 205 form an anterior abutment surface, and the spinous process fixation device 605 forms posterior abutment surface. Thus, the combined use of the implants and the spinous process fixation device forms a balanced three-point support of the vertebral bones. Additionally, bone graft material may be placed between the spinous process and/or lamina of the superior and inferior vertebral bones after appropriate decortication of the bone at the intended graft recipient site, and/or one or more detached distraction members may be implanted within the disc space.

Alternate Configurations

It is further contemplated that, in alternate embodiments, the distraction member and/or the implant track could be configured to include a curvilinear segment. In such embodiments, an implant may follow a trajectory down the implant track that is at least partially curvilinear (and may have a segment of defined a specified curvature), or the implant trajectory may also (or instead) comprise a segment that at least partially follows a non-linear path around the distraction member.

Other alternate embodiments are shown in FIGS. 22A-26D. As depicted therein, an implant placement instrument 400 includes a body 405 and a handle 404 extended outwardly therefrom. An implant track 420 extends outwardly from an anterior surface of the body 405, and a distraction member 424 extends outwardly from a distal end of the implant track 420.

Although not specifically shown, it will be appreciated that the distraction member 424 may have a similar configuration and method of operation/use to those discussed above with reference to distraction members 124 and 126. For example, the distraction member 424 can include upper and lower plates that are (reversibly) moveable from a (closed) non-distracted configuration to an open (distracted) configuration via actuation of a knob 414, which can be manually rotated by grasping the outer surface of the knob, or can be rotated by an instrument, such as, for example, a screw driver, a wrench, or the like that couples to a hex recess 4142 of the knob 414. In one exemplary implementation, a member 4102 attached at a posterior portion of the body 405 includes an aperture 41022 at a distal end portion 41024 configured to enable a screw driver to be advanced therethrough and into the recess 4142 of the knob 414. After movement into the distracted configuration, an aperture 418 of the body 405 allows the operator to read a distance between the upper and lower plates for selection of an appropriately sized implant to be advanced along the implant track 420 and into the distracted disc space. In one implementation, the distraction member 424 is non-detachable and is configured for removal from the disc space after delivery of the implant thereto. In another implementation, the distraction member 424 is detachable and is configured to be implanted within the disc space after delivery of the implant thereto.

Figure 23A:
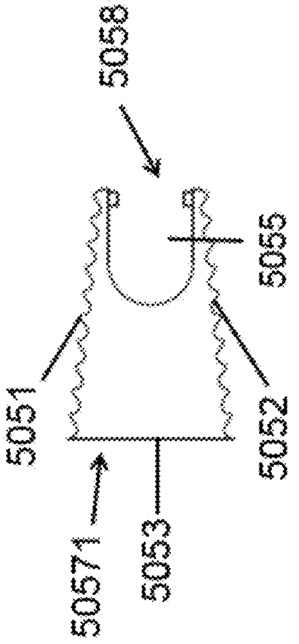
FIGS. 23A-23D respectively show front elevation, side elevation, top plan and top perspective views of a first embodiment of an implant for use with the implant delivery instrument of FIGS. 22A-22C.
Figure 23B:
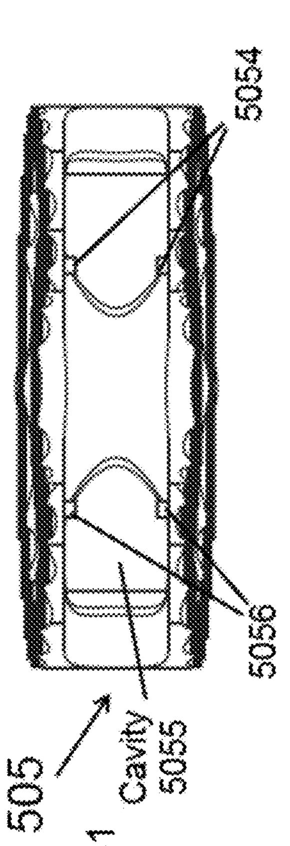
Figure 23C:
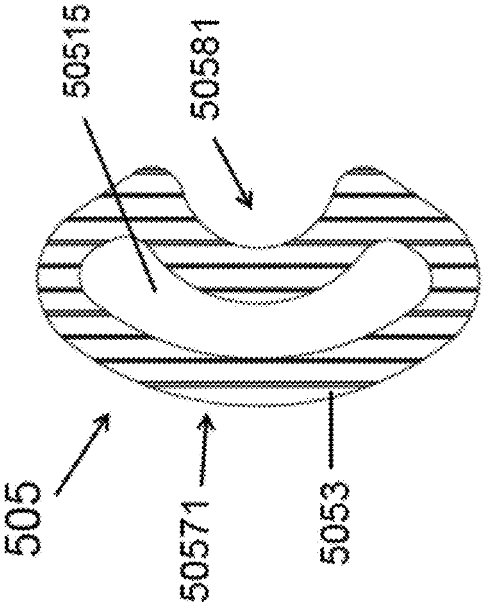

A first exemplary embodiment of an implant 505 configured for use with the implant placement instrument 400 is shown in FIGS. 23A-23D. As illustrated therein, the implant 505 includes a superior member 5051 and an inferior member 5052. An outer surface of the superior member 5051 is configured to abut an inferior surface of the vertebral bone immediately superior to the target disc space in which the implant 505 is positioned, while an outer surface of the inferior member 5052 is configured to abut a superior surface of the vertebral bone immediately inferior to the target disc space. The superior and inferior members 5051 and 5052 are connected by a side member (or side wall) 5053. In alternate embodiments, one more additional or partial side walls may additionally be included in the implant (such as e.g., a flexible/movable side wall). As best illustrated in FIGS. 23A and 23B, the superior, inferior, and side members define an internal cavity 5055, which is disposed within the implant 505 and sized to receive at least a segment of the implant track 520 therein.

Different from the implant 205 show in FIGS. 12A-12G, each of the superior and inferior members 5051 and 5052 includes substantially continuously curved lateral edges and a substantially linear edge at each of a distal end 5057 and a proximal end 5058 of the implant 505. More specifically, a first lateral side 50571 of the implant 505 (at a closed side of the cavity 5055) has a convex curvature, while a second lateral side 50581 thereof (at an open side of the cavity 5055) has a concave curvature. As can be seen in FIG. 23A, each of the superior and inferior members 5051 and 5052 has an inclined exterior surface. Specifically, at the first lateral side 50571, each of the superior and inferior members 5051 and 5052 has a greater height than at the second lateral side 50581 thereof. The foregoing features give the implant 505 a generally curved cuboid shape with tapered exterior surfaces inclined from the concave side to the convex side thereof.

In alternate embodiments, the superior and inferior members can have an equal height at each of the distal and proximal ends (giving the implant a non-tapered shape), or one or more of the superior or inferior surfaces can be inclined to a greater degree than the exemplary embodiment shown in FIG. 23A. Further, in other alternate embodiments the superior and inferior members can curved to a greater or lesser degree. One such alternate embodiment, a second exemplary embodiment of an implant 705 configured for use with the implant placement instrument 400, is illustrated in FIGS. 25A-25D. As can be seen therein, the implant 705 has a similar shape to implant 505, however, each of the superior and inferior members 7051 and 7052 includes a convex curvature a first lateral side 70571 of the implant 705 (at a closed side of a cavity 7055 which is closed by a side wall 7053) and a concave curvature a second lateral side 70581 thereof (at an open side of the cavity 5055), which each have a lesser degree of curvature as compared to the corresponding structures of the implant 505. Further, at each of a distal end 7057 and a proximal end 7058 of the implant 705, the implant includes curved edge (rather than a linear edge as in the implant 505).

As discussed elsewhere herein, it is contemplated a variety of implants of different shapes and/or sizes may be manufactured or provided to be usable with the implant placement instrument, and the appropriately shaped/sized implant can be selected from a pre-fabricated set of implants to be specific to the condition of the target FSU in order to correct curvature or otherwise stabilize the FSU. Alternatively, a pre-operative planning procedure may be carried out to select dimensions and/or configurations for one or more implants specific to the anatomy of the patient, and the one or more implants can be manufactured (such as e.g., via subtractive or additive 3-D printing) for later implantation thereof.

In the present embodiment, each of the superior and inferior members 5051 and 5052 of the implant 505 and the superior and inferior members 7051 and 7052 of the implant 705 includes surface features (indentations and protrusions) which increase implant fixation and anchor the implant onto adjacent bone. Although not shown, the side members 5053 and 7053 can additionally include similar surface fixation features. Further, the surfaces of the superior, inferior, and/or side members may be coated or manufactured with an osteo-conductive bioactive material (such as, e.g., demineralized bone matrix, hydroxyapatite, and the like) and/or an osteo-inductive bioactive material (such as, e.g., Transforming Growth Factor "TGF-B," Platelet-Derived Growth Factor "PDGF," Bone-Morphogenic Protein "BMP," and the like), which each promote bone formation. Still further, the surfaces of the implants may be coated and/or manufactured with a textured or a porous ingrowth surface (such as, e.g., titanium wire mesh, plasma-sprayed titanium, tantalum, porous CoCr, and the like), provided with a bioactive coating (such as, e.g., a coating comprising tantalum, and/or helical rosette carbon nanotubes or other carbon nanotube-based coating) in order to promote bone in-growth and establish a mineralized connection between the bone and the implant.

Moreover, after implantation, the cavity 5055 and 7055 may be filled with a bone forming material so as to enable a bony fusion that extends from the immediately superior vertebral bone, across the implant (via cavity 2055) and onto the immediately inferior vertebral bone. Each of the superior, inferior and/or side members can include one or more apertures (such as, for example, an aperture 50515 of the implant 505 and apertures 70515 of the implant 705 shown in e.g., FIGS. 23C and 25D, respectively) that allow direct communication between the cavity and the exterior of the implant. In this way, bone forming material placed into the cavity can form a bone bridge (i.e., fusion mass) across one or more of the the apertures and fuse the superior and inferior vertebral bones to one another. Each of the afore-described features can reduce the likelihood of implant dislodgement from the implantation site within the disc space.

Figure 23D:
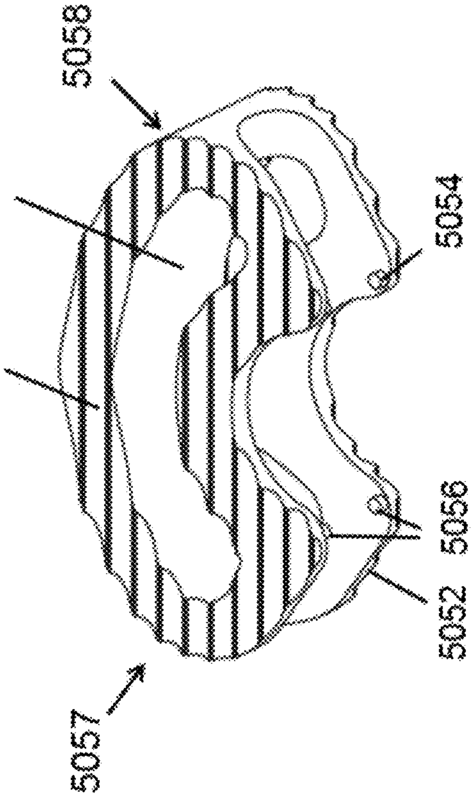
Figure 24A:
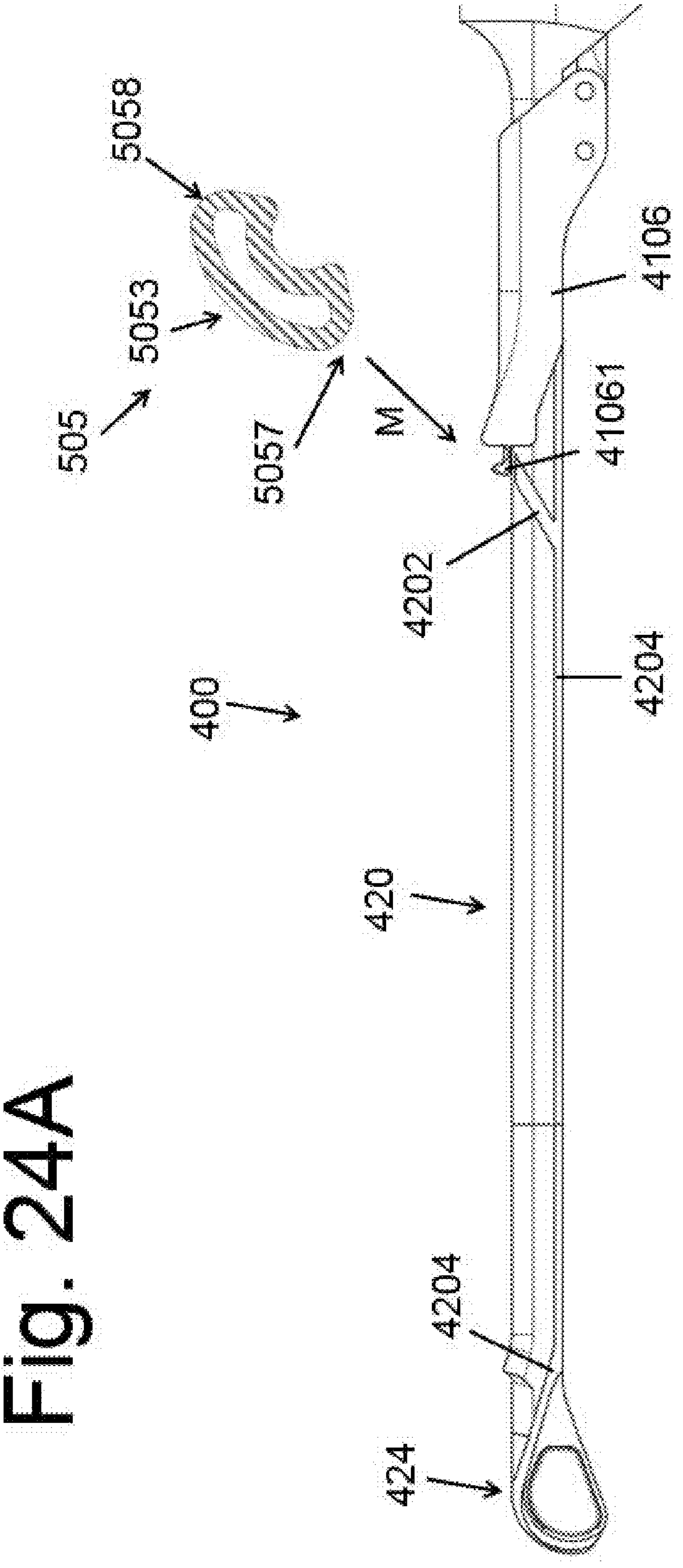
FIGS. 24A-24D show top plan views illustrating loading and movement of the implant of FIGS. 22A-22C when utilized with the implant delivery instrument of FIGS. 23A-23D.

Turning to FIG. 24A, once the distraction and/or positioning of the vertebral bones is performed and an appropriately sized/shaped implant has been selected, the implant 505 can be mounted onto an outer aspect of the implant track 420 for slidable delivery to the distracted disc space. Specifically, the implant 505 can be mounted onto the implant track 420 along a direction M such that a recess 4202 is aligned with receives complimentary protrusions on the interior surfaces of the implant. Specifically, as illustrated in FIGS. 23A, 23B and 23D, a first pair of protrusions 5054 are disposed on an interior surface of each of the superior and inferior members 2051 and 2052 proximate to the proximal end 2058 of the implant 505, and a second pair of protrusions 5056 are disposed on an interior surface of each of the superior and inferior members 5051 and 5052 proximate to the proximal end 5058 of the implant 505. The protrusions 5054 and 5056 are configured (sized and/or shaped) to be received within recesses 4202 (and grooves 4204 (on opposing sides of the implant track 120).

Each of the protrusions 5054 and 5056 is disposed on an opposing lateral side of the implant relative to the side wall 5053 (i.e., at the second lateral side 50581). Accordingly, when the implant 505 is mounted onto the implant track 420, the side member 5053 is oriented away from the track. It is noted that, in the present embodiment, the protrusions 5054 are of a similar diameter and length/shape to the protrusions 5056. In alternate embodiments, the implant and the implant placement instrument can be configured with additional or fewer complimentary protrusions and grooves, and/or the protrusions can be of different sizes, lengths, shapes or other configurations. Further, the implant placement instrument can include an offset, additional grooves configured to receive one of the pairs of protrusions (similar to the configuration shown in the implant placement instrument 100).

Figure 22A:
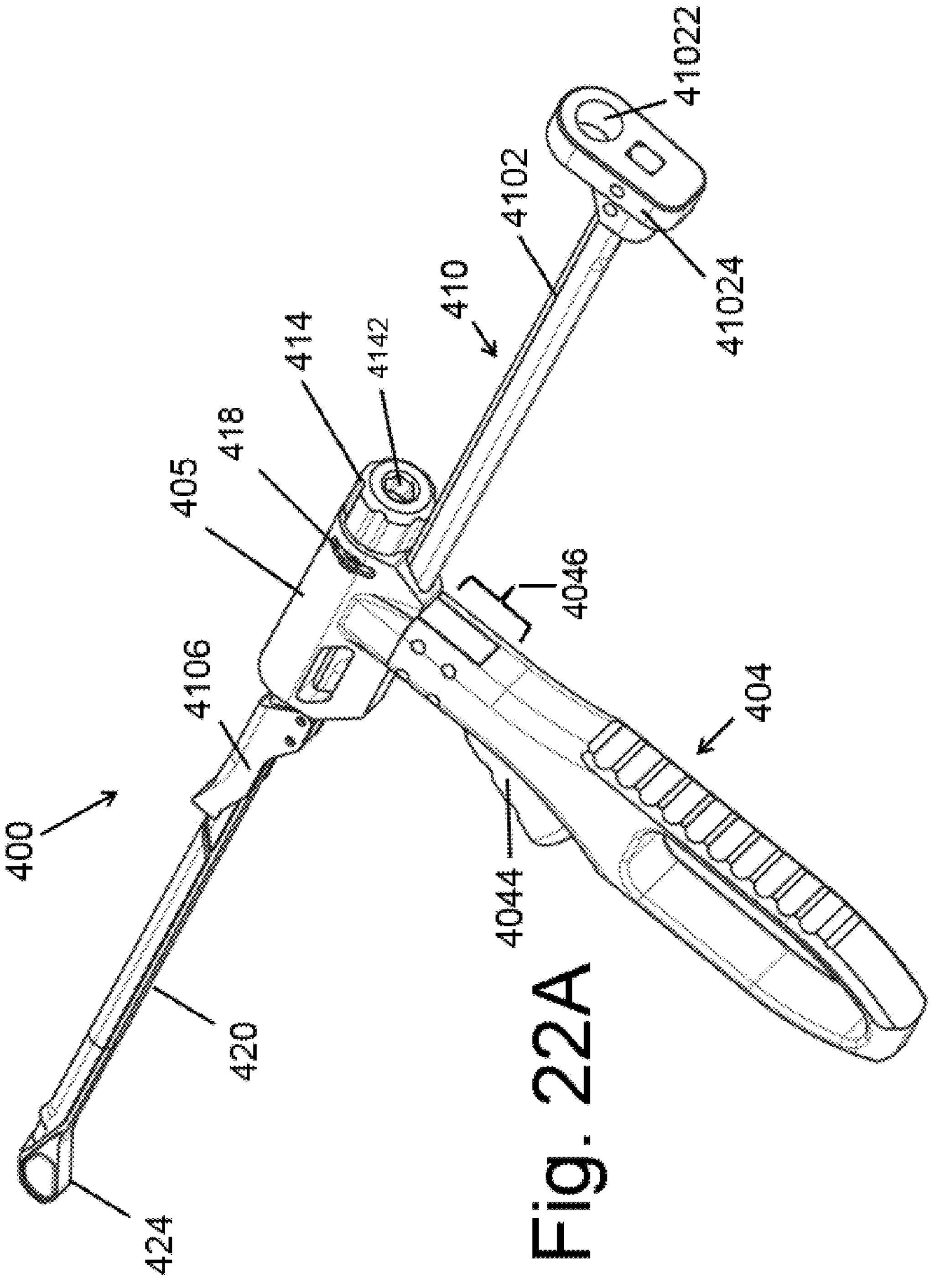
FIGS. 22A-22C respectively show top perspective, top plan and side elevation views of an exemplary implant delivery instrument according to another embodiment of the present disclosure.
Figure 22B:
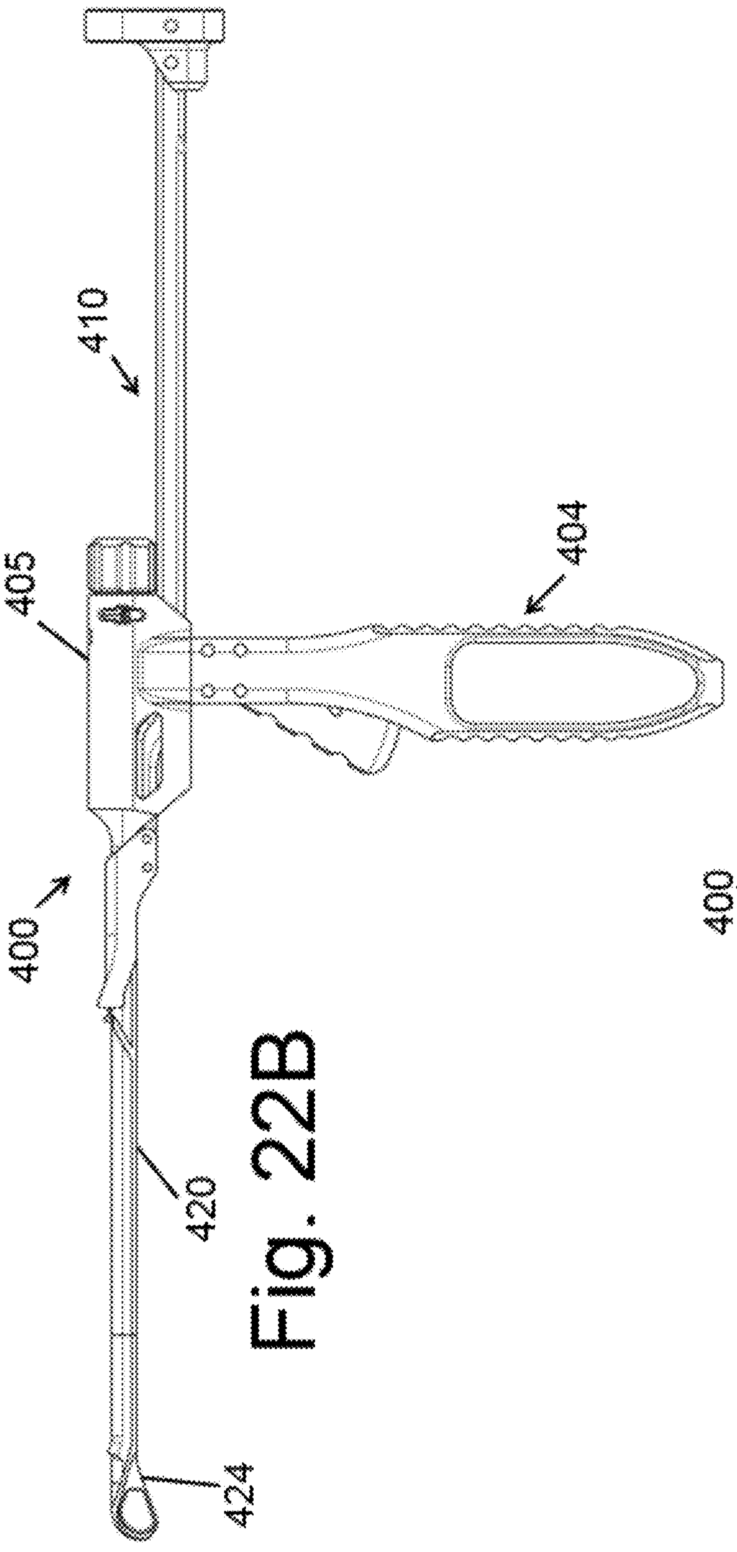
Figure 22C:
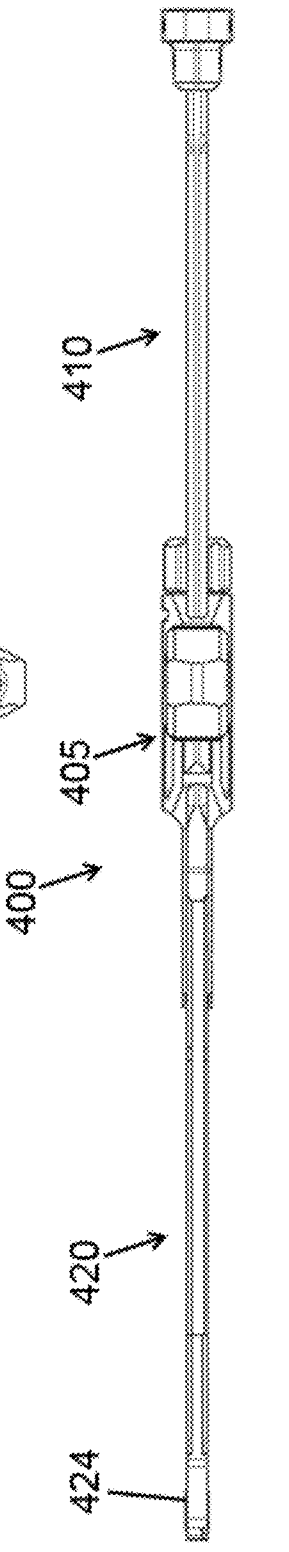
Figure 22D:
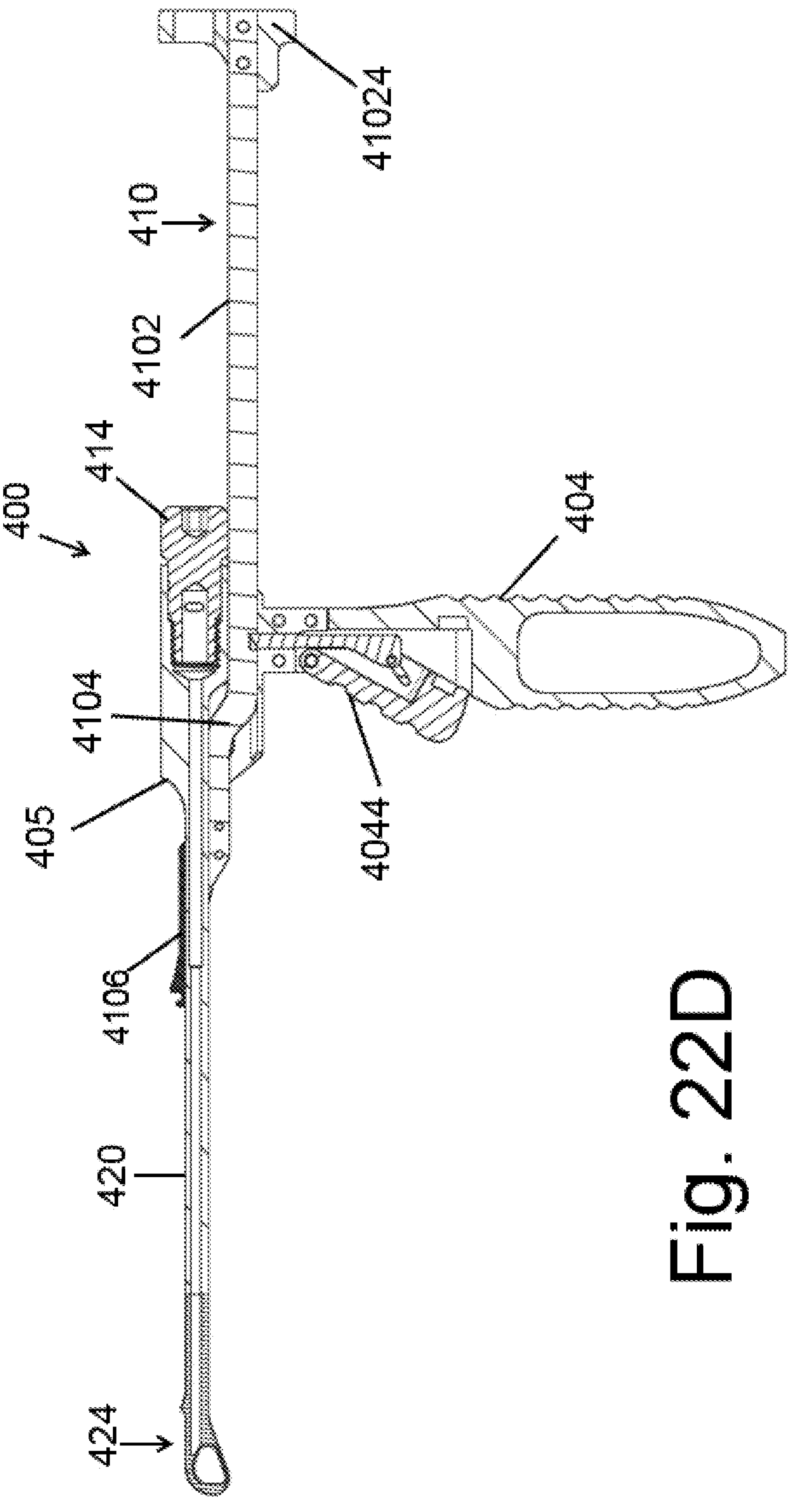
FIGS. 22D and 22E show cross-sectional views of the exemplary implant delivery instrument of FIGS.
Figure 22E:
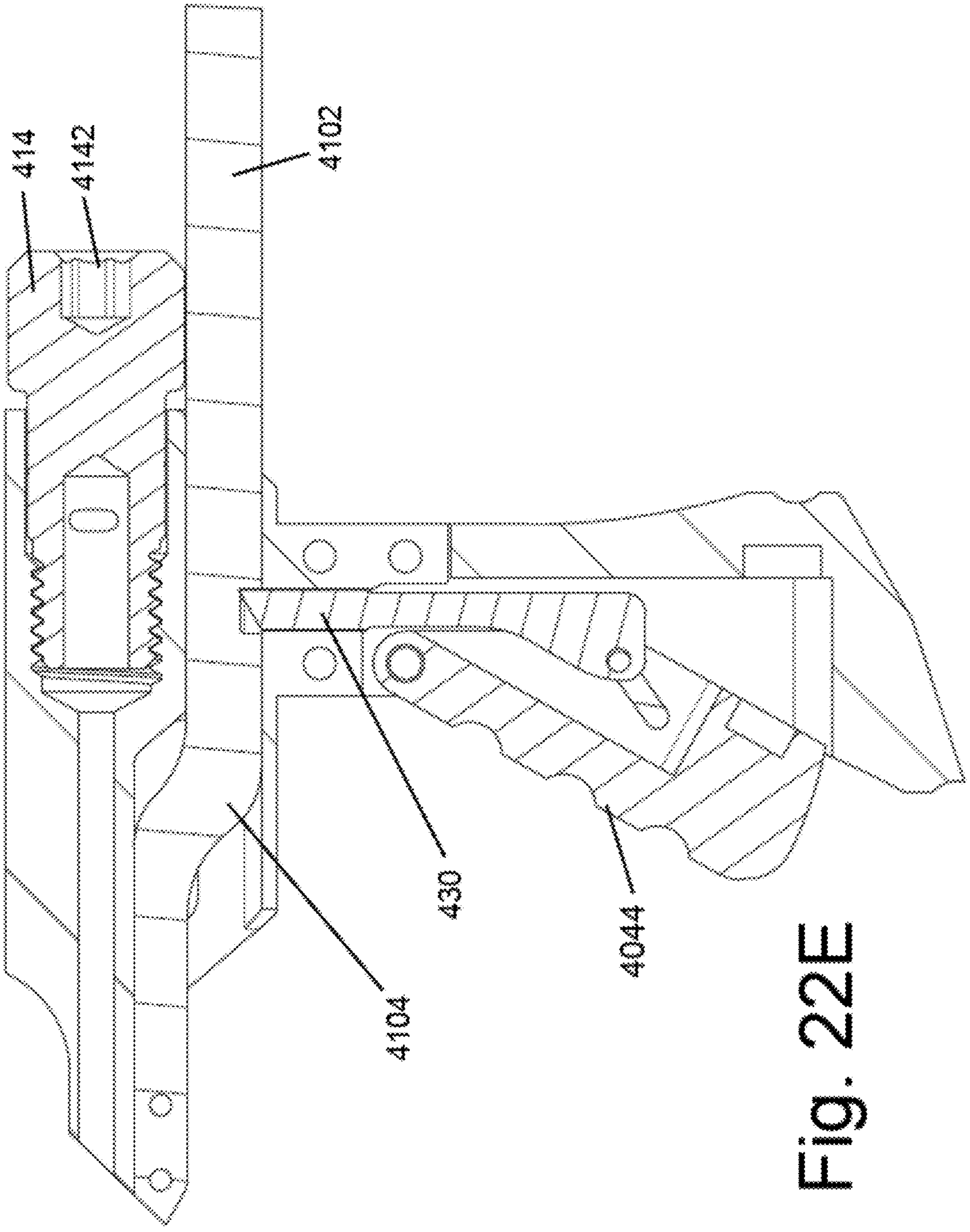

In order to enable the aforementioned mounting and sliding of the implant down the implant track, it is noted that the recesses 4202 are continuous with the grooves 4204 (on each side of the implant track 420). Thus, after the implant is mounted onto the implant track, a release member 4044 (FIG. 22A) on the handle 404 of the implant placement instrument 400 can be depressed to release an implant pusher 410. As shown in FIGS. 22A and 22D, the implant pusher 410 includes the proximal member 4102, an intermediate member 4104, and a distal member 4106. As can be seen in FIGS. 22D and 22E, a bar 430 is coupled to the release member 4044 and is configured to enable actuation of the implant pusher 410 via the release member 4044. Specifically, when the release member 4044 is fully extended (i.e., when member 1044 is not depressed), one end of the bar 430 is positioned within a recess of the intermediate member 4104 so that the pusher 410 is immobilized relative to the body 405 and cannot be moved along the implant track 420. When the release member 4044 is depressed, the bar 430 is withdrawn from the recess within the intermediate member 4104 so that a force (such as, for example, a force exerted by a mallet, a manual force, a machine guided force, or a force from a spring loaded device) is applied to the proximal end 41024 will permit the (now-unconstrained) pusher 410 to advance along the implant track 420 and push the implant 505 towards the distraction member 424. Specifically, the implant 505 is engaged by the distal member 4106 of the pusher 410 as it is advanced along the implant track 420. The implant 505 is retained onto the implant track 420 by the interaction of the protrusions 5054 and 5056 with the grooves 4204.

Figure 24B:
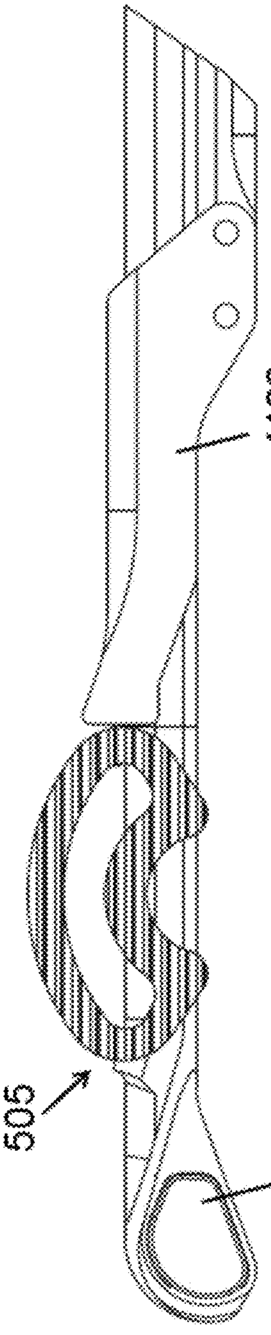
Figure 24C:
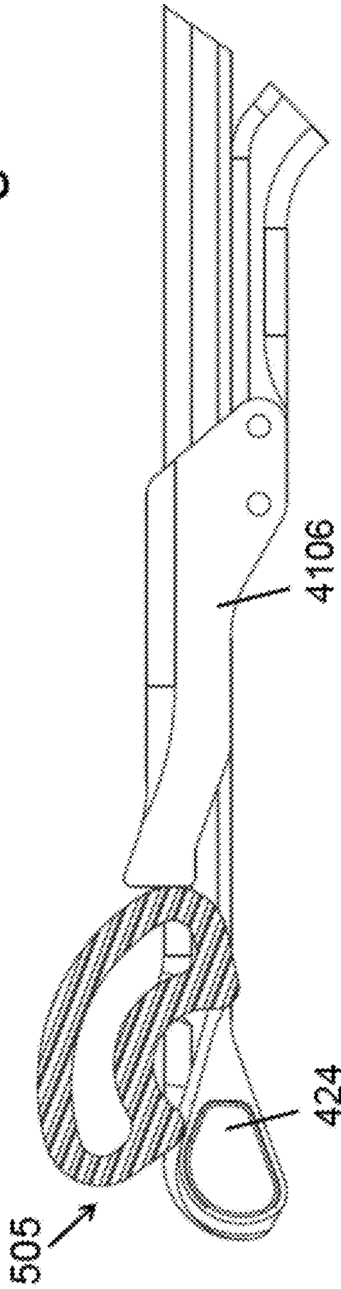
Figure 24D:
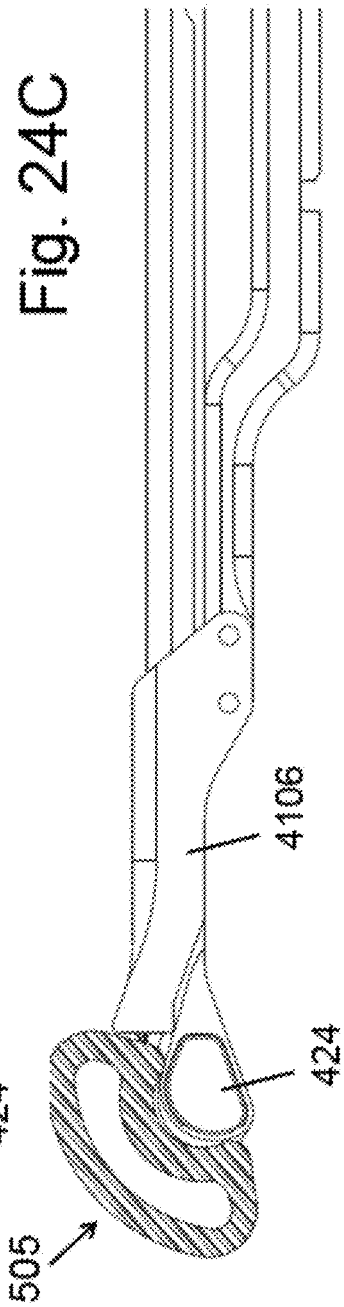

In the present embodiment, the implant is first advanced through a proximal region of the grooves along a substantially linear pathway (which can be coincident with or parallel to a longitudinal axis of the implant track), and at the distal segment of the implant track the grooves include turns (curvatures or bends) so that the implant is ultimately positioned within the disc space with the distal end 5057 (i.e., a leading edge of the implant) anterior of the distraction member 424. FIGS. 24B-24C show step-wise movement of the implant 505 along the distal segment of the implant track 420. Specifically, the distal segment of the each of the grooves each 1204 and 1208 includes a bend, such that the terminal portion of each of the grooves is oblique relative to a longitudinal axis of the implant track 420. As the implant 505 is moved along terminal portion of the grooves 4204 (via engagement with the distal member 4106 of the implant pusher 410), the implant 505 moves laterally relative to the implant track 420 (as well as forward toward the distal end of the implant track).

As can be seen in FIGS. 24A-24D, the distal member 4106 of the implant pusher 410 includes (at a proximal end thereof) includes a blunted end that engages with the proximal end 5058 of the implant 505. The distal member 4106 further comprises a hooked protrusion 41061 (FIG. 24A) that is configured to reversibly latch or otherwise reversibly couple with the proximal end 5058 of the implant 505. The engagement between the hooked protrusion and the implant enables an operator or surgeon performing the procedure to optionally back the implant out (reverse movement along the implant track) if necessary. (Although not specifically shown, a similar hooked protrusion can be incorporated into the implant placement instrument 100 to enable reverse movement of the implant.)

During forward movement of the implant 505 along the distal segment of the implant track 420, the engagement of the blunted end of the distal member 4106 with the implant 505 enables concurrent forward and lateral advancement of the implant 505. Specifically, the concave curvature of the second lateral side 50581 is guided around a curved exterior surface of the distraction member 424, until the implant 505 is pushed through an end of the grooves 4204 (where the grooves 4204 disengage from the protrusions 5054) and the implant is positioned adjacent anterior to and lateral of the distraction member 424. It will be appreciated that the foregoing description can be similarly applied to use of the implant 705 with the implant placement instrument 400.

Figure 24E:
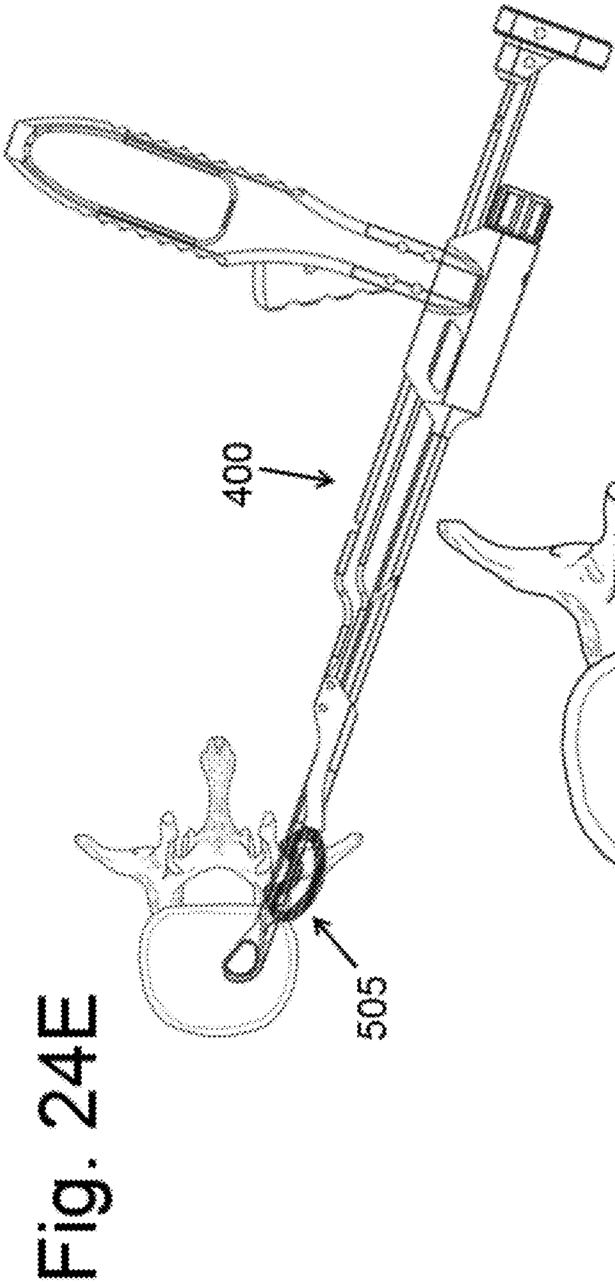
FIGS. 24E and 24F show top views of a method of use of the implant delivery instrument of FIGS. 22A-22C for delivery of the implant of FIGS. 23A-23D.
Figure 24F:
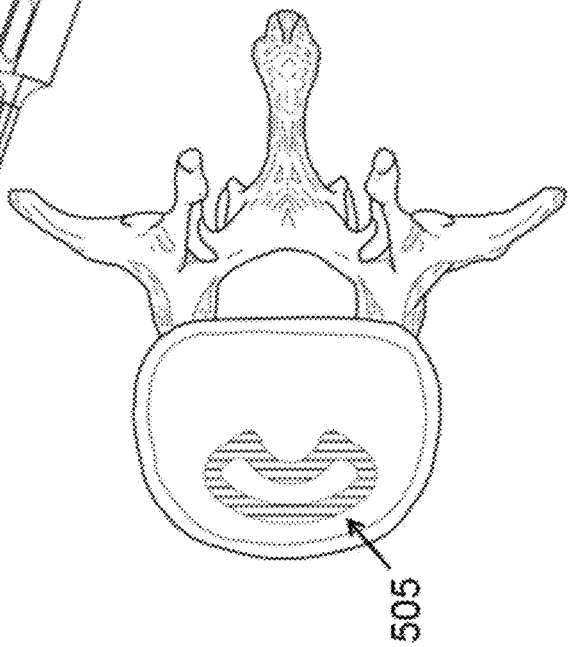
Figure 25A:
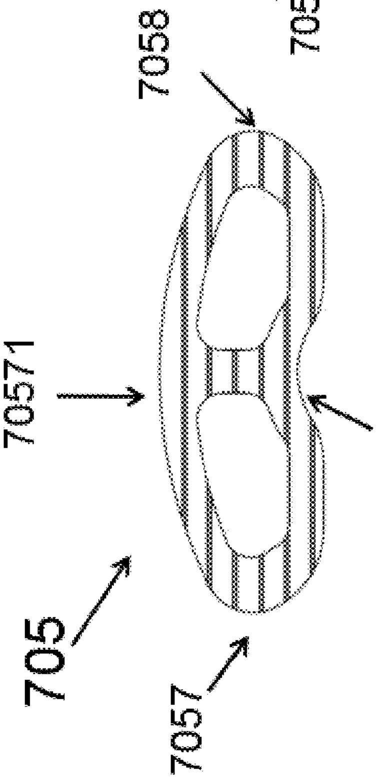
FIGS. 25A-25D respectively show top plan, front elevation, side elevation and top perspective views of a second embodiment of an implant for use with the implant delivery instrument of FIGS. 22A-22C.
Figure 25B:
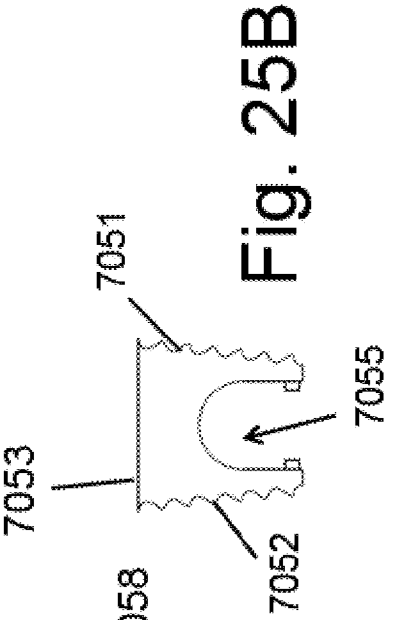
Figure 25C:
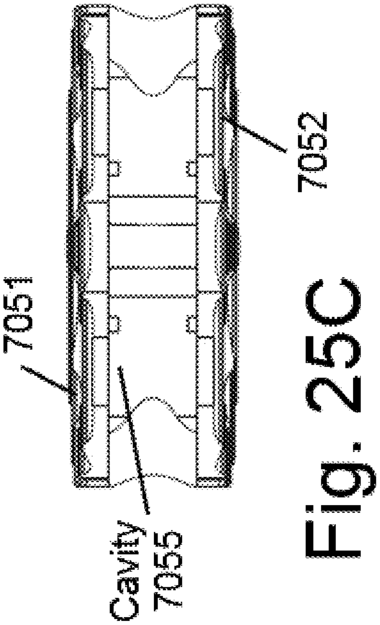
Figure 25D:
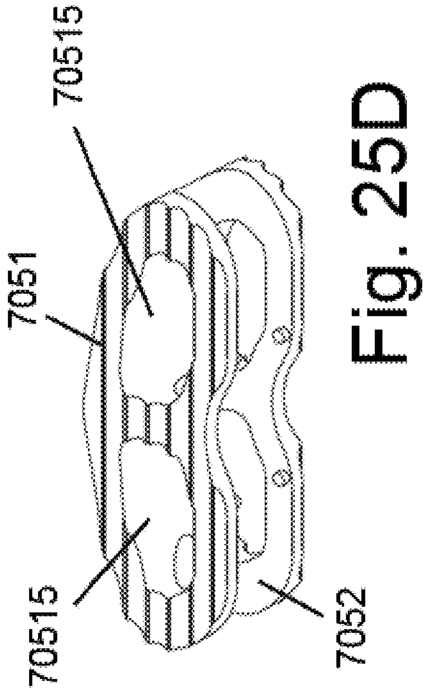
Figure 26A:
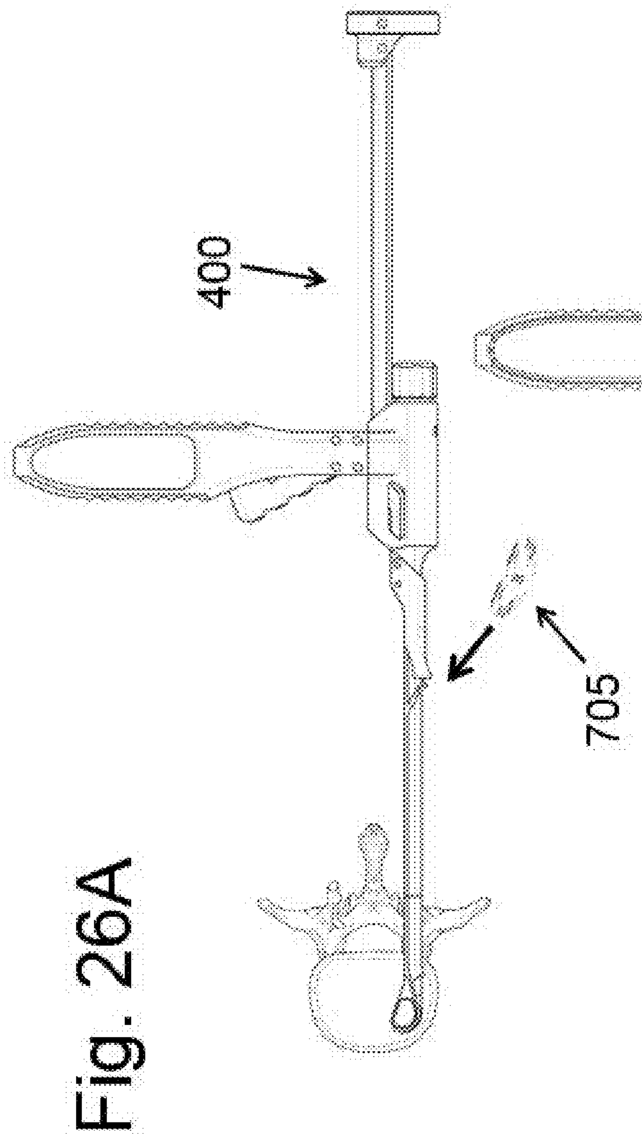
FIGS. 26A-26D show top views of a method of use of the implant delivery instrument of FIGS. 22A-22C for delivery of the implant of FIGS. 25A-25D.
Figure 26B:
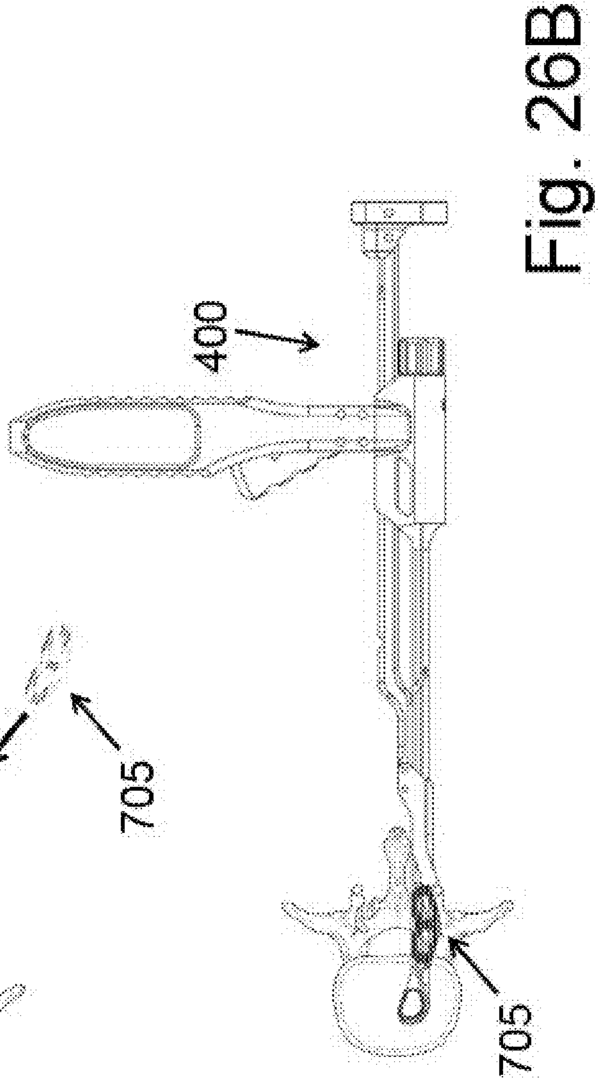
Figure 26C:
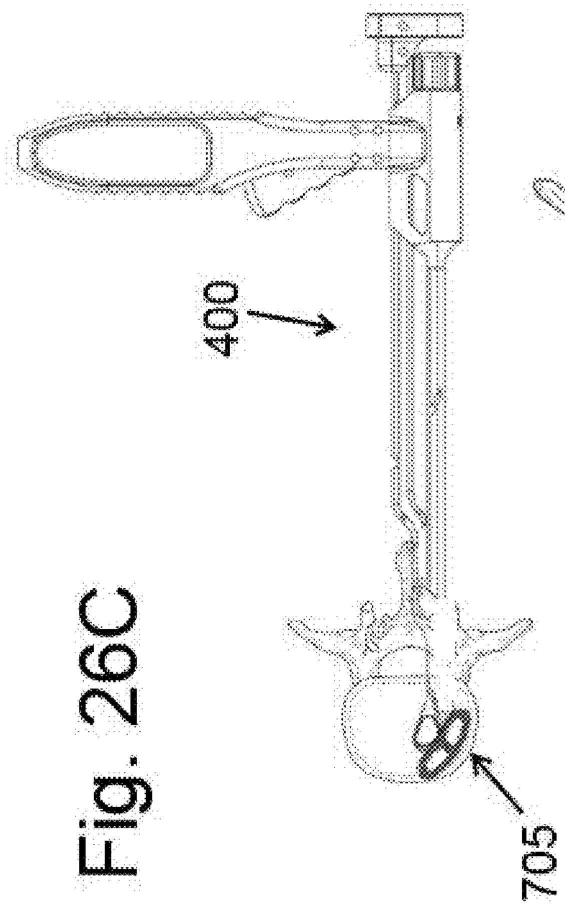
Figure 26D:
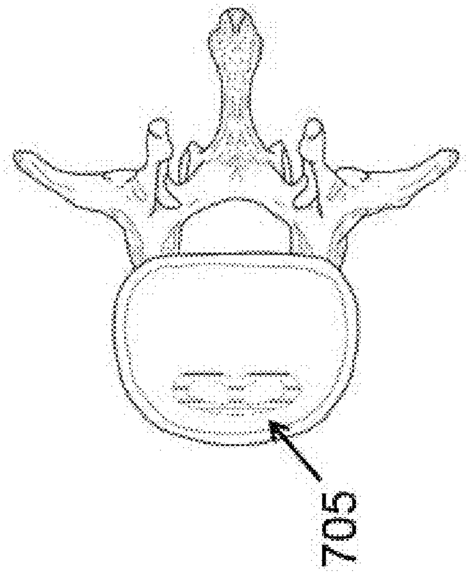

FIGS. 24E-24F and 26A-26D illustrate additional exemplary embodiments of methods of use of the devices disclosed herein. Specifically, FIGS. 24E and 24F depict the implant placement instrument 400 inserted into the target disc space via a postero-lateral approach for delivery of the implant 505 (having a greater degree of curvature than the implant 705). The postero-lateral approach enables sufficient space within the target FSU for the insertion of the implant 505 into the disc space and guidance around the curved exterior surface of the distraction member. After release from the implant placement instrument, the implant 505 is positioned proximate to the anterior portion of the disc space.

As depicted in FIGS. 26A-26D, the implant placement instrument 400 is inserted into the target disc space via a posterior approach for delivery of the implant 705 (having a lesser degree of curvature than the implant 505). The posterior approach enables sufficient space within the target FSU for the insertion of the implant 705 into the disc space and guidance around the curved exterior surface of the distraction member. After release from the implant placement instrument, the implant 705 is positioned proximate to the anterior portion of the disc space. In alternate embodiments, the implant placement instrument may be inserted along a posetero-lateral approach for delivery of the implant 705 to the disc space, and/or the implant can be positioned laterally, medially, or at another desired position within the disc space.

It will be appreciated that the methods of use discussed in detail above with reference to FIGS. 16A-18F are applicable to methods of using the implant placement instrument 400 with either of the implants 505 or 705.

It will be further appreciated that the disclosed device embodiments or any of their components can be made of any biologically adaptable or compatible materials. Materials considered acceptable for biological implantation are well known and include, but are not limited to, stainless steel, titanium, tantalum, combination metallic alloys, various plastics (such as PEEK and the like), resins, ceramics, biologically absorbable materials and the like. The system or any of its components can alternatively or additionally be entirely or partially made of a shape memory material or other deformable material. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation.

Further, any surface may be made with a porous ingrowth surface (such as, for example, porous titanium, titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. The system or any of its components may be made by additive or subtractive manufacturing, such as, for example, 3D-printing.

While this specification contains certain specific features and attributes, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

It will also be recognized that while certain aspects of the disclosure are described in terms of a specific sequence of steps of a method, these descriptions are only illustrative of the broader methods of the disclosure, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure disclosed and claimed herein.

What is claimed is:

1. A surgical implant assembly for use in an implantation procedure performed on a functional spinal unit of a subject, the functional spinal unit comprising a superior vertebral bone, an inferior vertebral bone, and an intervertebral disc space disposed between the superior vertebral bone and the inferior vertebral bone, the surgical implant assembly comprising:

an implant sized and configured to be at least partially received in the functional spinal unit and a non-implantable insertion instrument configured to advance the implant to the functional spinal unit, the implant comprising:

a superior member, an exterior surface of the superior member configured to abut an inferior surface of the superior vertebral bone;

an inferior member, an exterior of the inferior member configured to abut a superior surface of the inferior vertebral bone;

a first side wall connecting the superior member and the inferior member; and an internal cavity, at least a portion the internal cavity bordered by the superior member, the inferior member, and the first side wall; and the non-implantable insertion instrument comprising:

a handle assembly comprising a body, the body extending from a front portion to an opposing back portion;

an implant delivery track coupled to the front portion of the handle assembly and comprising an upper surface, a lower surface, a distal portion, and a proximal portion, the implant delivery track extending from the proximal portion to the distal portion along a first longitudinal axis;

a distraction assembly disposed at the distal portion of the implant delivery track and extended outwardly therefrom, the distraction assembly comprising a first plate and a second plate, the first plate movable relative to the second plate along at least one direction that is non-parallel to first longitudinal axis of the implant delivery track, the distraction assembly configured to transition the first plate from a non-distracted configuration to a distracted configuration relative to the second plate; and an implant pusher member movably coupled to the implant delivery track, the implant pusher member configured to advance the implant along at least a portion the implant delivery track and onto an implantation site of the subject;

wherein at least a portion of an interior surface the superior member of the implant is configured to engage with at least a portion of the upper surface of the implant delivery track, and at least a portion of an interior surface of the inferior member of the implant is configured to engage with at least a portion of the lower surface of the implant delivery track; and wherein the implant is configured such that at least a portion of the implant delivery track can be seated within the internal cavity of the implant when the at least portion of the upper surface is engaged with the at least portion of the interior surface of the superior member and the at least portion of the lower surface is engaged with the at least portion of the interior surface of the inferior member.

2. The surgical implant assembly of claim 1 wherein the non-implantable insertion instrument further comprises an actuator that is coupled to the distraction assembly, the actuator configured to vary a first distance between the first and second plate along a second axis, the second axis being orthogonal to the first longitudinal axis.

3. The surgical implant assembly of claim 2 wherein the non-implantable insertion instrument further comprises a display that provides a reading corresponding to a value of the first distance between the first and the second plate.

4. The surgical implant assembly of claim 1 wherein the handle assembly seats a portion of the implant pusher member.

5. The surgical implant assembly of claim 1 wherein the implant delivery track further comprises features that align the implant with the first longitudinal axis as it is advances along the implant delivery track.

6. The surgical implant assembly of claim 1 wherein at least one surface of the implant comprises features that align the implant with the first longitudinal axis as it is advances along the implant delivery track.

7. The surgical implant assembly of claim 1 wherein the implant pusher member, when fully extended, positions the implant adjacent to the distraction assembly.

* * * * *